(12) United States Patent
Wen et al.

(10) Patent No.: US 11,447,485 B2
(45) Date of Patent: Sep. 20, 2022

(54) CLASS OF BIFUNCTIONAL COMPOUNDS WITH QUANTERNARY AMMONIUM SALT STRUCTURE

(71) Applicant: Beijing Showby Pharmaceutical Co., Ltd., Beijing (CN)

(72) Inventors: Shouming Wen, Beijing (CN); Zejun Gao, Beijing (CN); Junyi Wang, Beijing (CN); Xiaoping Chen, Beijing (CN)

(73) Assignee: Beijing Showby Pharmaceutical Co., Ltd., Beijing (CN)

( * ) Notice: Subject to any disclaimer, the term of this patent is extended or adjusted under 35 U.S.C. 154(b) by 0 days.

(21) Appl. No.: 16/469,457

(22) PCT Filed: Dec. 13, 2017

(86) PCT No.: PCT/CN2017/115807
§ 371 (c)(1),
(2) Date: Jun. 13, 2019

(87) PCT Pub. No.: WO2018/108089
PCT Pub. Date: Jun. 21, 2018

(65) Prior Publication Data
US 2020/0002329 A1    Jan. 2, 2020

(30) Foreign Application Priority Data
Dec. 14, 2016 (CN) .......................... 201611150752.1

(51) Int. Cl.
*C07D 453/02* (2006.01)
*A61P 11/08* (2006.01)
*A61K 9/00* (2006.01)

(52) U.S. Cl.
CPC .......... *C07D 453/02* (2013.01); *A61K 9/0075* (2013.01); *A61P 11/08* (2018.01)

(58) Field of Classification Search
CPC ..................................................... A61P 11/08
See application file for complete search history.

(56) References Cited

U.S. PATENT DOCUMENTS

| | | | |
|---|---|---|---|
| 5,679,693 A | 10/1997 | Emonds-Alt et al. | |
| 2012/0010236 A1 | 1/2012 | Zhao | |
| 2014/0088097 A1 | 3/2014 | Hamprecht et al. | |

FOREIGN PATENT DOCUMENTS

| CN | 1088582 A | 6/1994 | |
|---|---|---|---|
| CN | 1784400 A | 6/2006 | |
| CN | 102459231 A | 5/2012 | |
| IN | 200502848 P4 | 9/2007 | |
| JP | 2006517971 A | 8/2006 | |
| JP | 2007501862 A | 2/2007 | |
| JP | 2008513380 A | 5/2008 | |
| JP | 2011527672 A | 11/2011 | |
| JP | 2014519508 A | 8/2014 | |
| RU | 2120436 C1 | 10/1998 | |
| WO | 9807722 A1 | 2/1998 | |
| WO | 9816200 A1 | 4/1998 | |
| WO | 2004/106333 A1 | 12/2004 | |
| WO | 2014/086927 A1 | 6/2014 | |
| WO | 2016128456 A1 | 8/2016 | |
| WO | WO-2016128456 A1 * | 8/2016 | ........... C07D 403/12 |

OTHER PUBLICATIONS

Jan. 15, 2020, Office Action of Russian Application No. 2019121119/04 (041270).
Aug. 13, 2019 (EP) European Search Report of Application No. EP17880998.
Jan. 1, 2009, Ray Nicholas C. et al.; Muscarinic antagonist-beta-adrenergic agonist dual pharmacology molecules as bronchodilators; a patent review. Expert Opinion on Therapeutic Patents, vol. 19, No. 1, pp. 1-12.
Feb. 26, 2018, International Search Report of PCT/CN2017/115807.
Jul. 22, 2020, (JP), Japanese office action of Application No. 2019-533093.
July 2, 2020, (CA), Canadian Office Action of Application No. 3,047,023.
May 19, 2021 (CN) Chinese office action of Application No. 201780076957.6.

* cited by examiner

*Primary Examiner* — John S Kenyon
(74) *Attorney, Agent, or Firm* — Banner & Witcoff, Ltd.

(57) ABSTRACT

The invention provides a class of compounds represented by formula (I), having bifunctional active quaternary ammonium salt structure of a β₂-adrenoreceptor agonist and an M receptor antagonist, a pharmaceutically acceptable salt, solvate, and optical isomer thereof. A pharmaceutical composition comprising such a compound with quaternary ammonium salt structure, a method for preparing such a compound with quaternary ammonium salt structure and an intermediate thereof, and uses thereof in treating pulmonary disorders are also provided. The compounds of the invention have high selectivity to the M receptor subtype, and have less adverse reaction and lower toxic and side effects in the treatment of pulmonary diseases such as COPD and asthma.

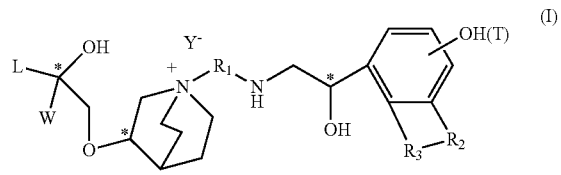

19 Claims, No Drawings

CLASS OF BIFUNCTIONAL COMPOUNDS WITH QUANTERNARY AMMONIUM SALT STRUCTURE

TECHNICAL FIELD

The invention relates to a class of compounds with a bifunctional active quaternary ammonium salt structure of a $\beta_2$-adrenoceptor agonist and a muscarinic receptor (M receptor) antagonist. The invention also relates to pharmaceutical compositions including such quaternary ammonium salt compounds, methods for preparing such quaternary ammonium salt compounds and intermediates thereof, and uses of treating pulmonary disorders.

BACKGROUND ART

Asthma and chronic obstructive pulmonary disease (COPD) are the most common diseases in pulmonary disorders, in which COPD is the fourth fatal disease worldwide and is projected to be the third by 2020. COPD is generally associated with cigarette smoking, and may also easily suffered by other environmental pollutions such as occupational harmful dust, gas, fume, and smog.

Bronchodilators are the first choice of treating asthma and COPD. The common bronchodilators include a $\beta_2$-adrenoceptor agonist (e.g., albuterol, formoterol, salmeterol and indacaterol) and an M receptor antagonist (e.g., glycopyrronium bromide, ipratropium bromide, tiotropium bromide, etc.). In addition to a single preparation, a compound preparation consisting of a $\beta_2$-adrenoceptor agonist and an M receptor antagonist is also used for the treatment of lung diseases such as asthma and COPD, and has better therapeutic effect. For example, U.S. Pat. No. 6,433,027 discloses a therapeutic composition including M receptor antagonist tiotropium bromide and $\beta_2$-adrenoceptor agonist formoterol fumarate.

In addition, the compounds having both $\beta_2$-adrenoceptor agonistic activity and M receptor antagonistic activity were reported to be used for the treatment of asthma and COPD in many literatures, such as WO2004074246, WO2009098448, WO2010004517, WO2008096127, WO2008149110, WO2008017827, WO2010126025, WO2010015792, WO2005111004, WO2010015792, WO2008041095, WO2005051946, WO2011012896, WO2010123766, etc. The chemical structure of these compounds having both $\beta_2$-adrenoceptor agonistic activity and M receptor antagonistic activity (abbreviated as MABA) consists of three moieties, that is, an M receptor antagonistic activity moiety, $\beta_2$-adrenoceptor agonistic activity moiety and a linker moiety. A typical MABA compound has the following structural formula:

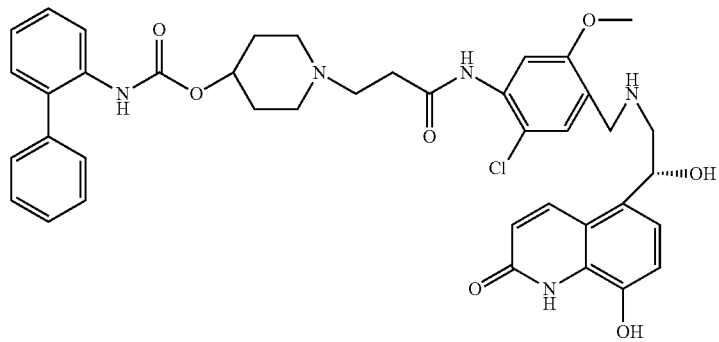

TD5959

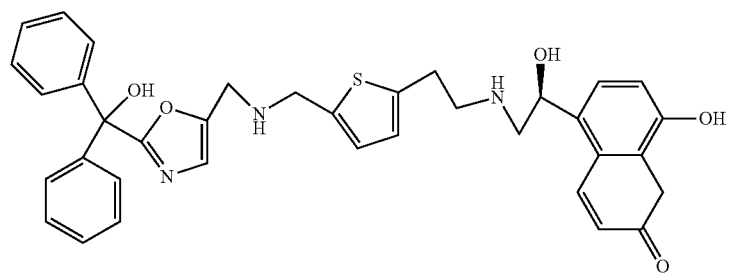

WO2010015792 (Argenta/Astra Zeneca)

-continued

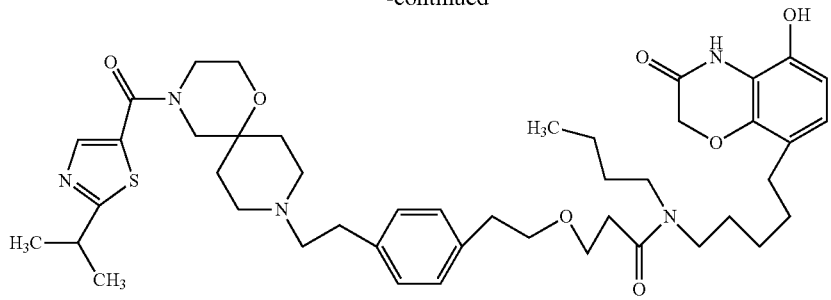

WO2011012896(Pulmagen/AstraZeneca)

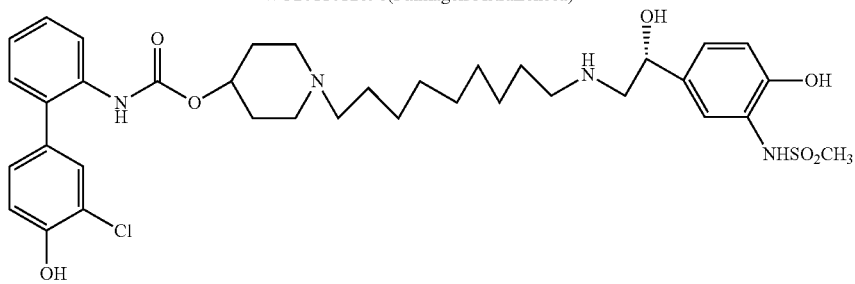

WO2008041095(PF4348235, Pfizer)

Such bifunctional compounds are capable of producing bronchodilation effect via two separate modes of action and have a single molecular pharmacokinetic. A phase II clinical study of the representative compound TD5959 has shown that the compound has a good effect on moderate and severe COPD. However, such bifunctional compounds reported in the literature are currently less selective for the M receptor subtype. The shortcoming of the prior art is that the vast majority of such bifunctional compounds in the literature are tertiary amine-type structural compounds, which may pass through the blood-brain barrier, produce other central side effects, and have no obvious selectivity for the $M_3$ receptor subtype, block the $M_2$ receptor to produce many adverse reactions such as increased heart rate, elevated blood pressure, and aggravation of asthma. Quaternary ammonium salts are not easily passed through the blood-brain barrier, and swallowed part of inhalation preparations are of low bioavailability. Therefore, it is an ideal choice to design and synthesize a MABA compound with a quaternary ammonium salt structure. However the literatures WO2004074246 and WO2008017827 reported a plurality of compounds prepared through linking groups to link the N atoms of two active units of a known active M receptor antagonist and $\beta_2$ adrenoceptor agonist, but the screened biological activity results are not ideal. WO2004074246 shows the activity of the M receptor antagonistic moiety is significantly reduced by 100 times. WO2008017827 shows the activity of the $\beta_2$ adrenoceptor agonistic moiety significantly reduced by more than 100 times, and such MABA do not achieve the desired results, leading to the abandonment of a similar method to find the ideal MABA quaternary ammonium salt, no similar study has been reported since then.

SUMMARY OF THE INVENTION

It is an object of the invention to provide a quaternary ammonium salt compound having $\beta_2$ adrenoceptor agonistic activity and M receptor antagonistic activity, and pharmaceutically acceptable salt, solvate, optical isomer and precursor thereof. In view of this, through continuous changes in M receptor antagonists and $\beta_2$ adrenoceptor agonist active units and linking groups, through extensive research and screening, a new class of an ideal MABA compound with a quaternary ammonium salt structure has been surprisingly discovered in the invention. Preliminary animal experiments have proved that the activity of such compounds reach the requirement of designing more prominent advantages than MABA of the prior art: (1) compared with the prior art, the dose that intravenous injection of the compound of the invention causes the heart rate to increase is more than 10 times that of the prior art compound; (2) the compound of the invention has a hepatic strong first-pass effect, but is stable in the lung, and cannot accumulate sufficient toxic dose even if it enters the circulatory system; and (3) the matching degree between antagonistic activity of the M receptor and agonistic activity of the $\beta_2$ receptor of the compound of the invention is very ideal. Compared with the prior art, the compound of the invention has high selectivity to the M receptor subtype, has the characteristics of fast action, long action time, lower toxic and side effects, and due to the quaternary ammonium salt structure, it is difficult to pass the blood-brain barrier, easily metabolized and less prone to cardiovascular-related side effects. The structure of this class of compounds is shown as formula I:

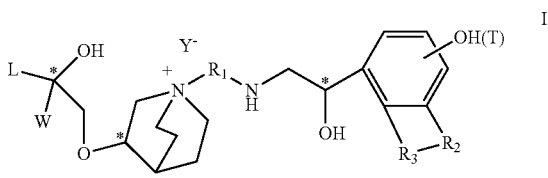

Carbons marked with * in the formula I are all (R) configuration.

L is (4-10C) aryl or heteroaryl, wherein the hetero atom of the heteroaryl is selected from N, O, and S, and the above groups may be unsubstituted or optionally substituted with one or more substituents selected from halogen, —$OR^1$, —$SR^1$, —$NR^1R^2$, —$NHCOR^1$, —$CONR^1R_2$, —CN, —$NO_2$, —$COOR^1$, —$CF_3$, and $C_1$-$C_4$ linear or branched hydrocarbyl.

$R^1$, $R^2$ may be hydrogen atom, $C_1$-$C_4$ linear or branched hydrocarbyl.

L is preferably unsubstituted phenyl group, pyridyl group, furyl group or thienyl group.

W is independently selected from substituted or unsubstituted (3-7C)cycloalkyl, the substituent is selected from halogen, (1-4C)alkyl, (1-4C)alkoxy, alkoxyhydrocarbyl, and heterocycle. Preferably, W is unsubstituted (3-7C)cycloalkyl, and most preferably W is cyclobutyl, cyclopentyl and cyclohexyl.

$R_1$ is a divalent group —$(R_{1a})_d$-$(A_1)_e$-$(R_{1b})_f$—, wherein d, e, and f are each independently selected from 0, 1, 2 or 3, and the number of adjoining atoms in the shortest chain between two nitrogen atoms to which $R_1$ is attached is in the range of 3 to 14.

$R_{1a}$ and $R_{1b}$ are each independently selected from (1-10C) alkylene, (2-10C)alkenylene, (1-4C)alkyleneoxy, alkyleneoxyalkyl, alkyleneamido, alkyleneacyloxy, alkyleneamino, etc., wherein each of alkylene, alkenylene, alkyleneoxy, alkyleneoxyalkyl, alkyleneamino, alkyleneacyloxy, alkyleneamido is unsubstituted or substituted with substituents independently selected from (1-4C)alkyl, chloro, fluoro, hydroxy, phenyl and substituted phenyl, $R_{1a}$ and $R_{1b}$ may be the same or different.

$A_1$ is independently selected from (3-7C)cycloalkylene, (2-7C)alkylene, (6-10C)arylene, (4-9C)heteroarylene, and (3-8C)heterocycloalkylene, etc., wherein cycloalkylene may be unsubstituted or substituted with 1-4 substituents independently selected from (1-6C)alkyl. Each of arylene, heteroarylene, and heterocycloalkylene may be unsubstituted or substituted with 1-3 substituents independently selected from halogen, (1-6C)alkyl, (1-6C)alkoxy, —S-(1-4C)alkyl, —S(O)-(1-4C)alkyl, —S(O)$_2$-(1-4C)alkyl, —C(O)—O-(1-4C)alkyl, —NH-(1-4C)alkyl, —N=[(1-4C)alkyl]$_2$, carboxy, nitro, cyano, amido, ester group, trifluoromethyl, and trifluoromethoxy.

In particular, $R_{1a}$ and $R_{1b}$ in the divalent group $R_1$ are each independently selected from (1-10C)alkylene, (1-4C)alkyleneoxy, alkyleneamido, etc. $A_1$ is independently selected from (6-10C)arylene, etc., wherein the arylene may be unsubstituted or substituted with 1-2 substituents independently selected from halogen, (1-6C)alkyl, (1-6C)alkoxy, carboxy, nitro, cyano, amido, or ester group.

$R_1$ is further selected from: —$(CH_2)_3$—, —$(CH_2)_4$—, —$(CH_2)_8$—, —$(CH_2)_9$—, —$(CH_2)_{10}$—, —$(CH_2)_2O(CH_2)_2$—, —$(CH_2)_2O(CH_2)_4$—, —$(CH_2)_3O(CH_2)_4$—, —$(CH_2)_4O(CH_2)_4$—, —$(CH_2)_5O(CH_2)_4$—, —$(CH_2)_2O(CH_2)_2O(CH_2)_2$—, —$(CH_2)_2O(CH_2)_3O(CH_2)_2$—, —$CH_2O(CH_2)_5OCH_2$—, —$(CH_2)_2O(CH_2)_2O(CH_2)_2O(CH_2)_2$—, —$(CH_2)_2O$(phen-1,4-ylene)$(CH_2)_2$—, —$(CH_2)_3O$(phen-1,4-ylene)$CH_2$—, —$(CH_2)_3O$(3, 5-dichloro-phen-1,4-ylene)$CH_2$—, —$(CH_2)_2CONH$(2-methoxy-5-chloro-phen-1,4-ylene)$CH_2$—, —$(CH_2)_2CONH$(3-methyl-phen-1,4-ylene)$CH_2$—, —$(CH_2)_2CONH$(2-methoxy-phen-1,4-ylene)$CH_2$—, —$(CH_2)_2CONH$(phen-1,4-ylene)$CH_2$—, —$(CH_2)_3CONH$(phen-1,4-ylene)$CH(CH_3)$—, —$(CH_2)_3OCH_2$(3-methoxy-phen-1,4-ylene)$CH(CH_3)$—, —$(CH_2)_3O$(phen-1,4-ylene)$C(CH_3)_2$—, —$(CH_2)_3O$(phen-1,4-ylene)$CH(CH_2CH_3)$—, —$(CH_2)_3O$(phen-1,4-ylene)$(CH_2)_2$—, —$(CH_2)_3O$(phen-1,4-ylene)$(CH_2)_3$—, —$(CH_2)_3O$(phen-1,4-ylene)$CH_2CH(CH_3)$—, —$(CH_2)_2OCH_2$(phen-1,4-ylene)$CH_2O(CH_2)_2$—, —$(CH_2)_2OCH_2$(phen-1,4-ylene)$CH(CH_3)$—, —$(CH_2)_2O$(phen-1,4-ylene)$O(CH_2)_2$—, —$(CH_2)_3O$(2-methoxy-phen-1,4-ylene)$O(CH_2)_3$—, —$(CH_2)_3O$(phen-1,4-ylene)$O(CH_2)_3$—, —$(CH_2)_3O$(phen-1,4-ylene)$CH_2C(CH_3)_2$—, —$(CH_2)_2O$(phen-1,4-ylene)$CH_2C(CH_3)_2$—, —$(CH_2)_2O$(phen-1,4-ylene)$CH_2CH(CH_3)$—, —$(CH_2)_2O$(phen-1,4-ylene)$(CH_2)_2$—, and —$(CH_2)_2O(CH_2)_3O(CH_2)_2$—.

$R_2$ is selected from —$N(R_{2a})C(R_{2b})(O)$, —$C(R_{2c})(R_{2d})OR_{2e}$, —$N(R_{2f})$—, —O—, etc. $R_3$ is selected from hydrogen, —$C(R_{3a})$=$C(R_{3b})$—$C(O)$—, —$OC(R_{3c})(R_{3d})C(O)$—, —$N(R_{3e})CH(R_{3f})C(O)$—, —$C(R_{3g})(R_{3h})S(O)_2$—, —SCO—, etc., with the proviso that when $R_3$ is hydrogen, $R_2$ is selected from —$N(R_{2a})C(R_{2b})(O)$ and —$C(R_{2c})(R_{2d})OR_{2e}$, and when $R_3$ is selected from —$C(R_{3a})$=$C(R_{3b})$—$C(O)$—, —$OC(R_{3c})(R_{3d})C(O)$—, —$N(R_{3e})CH(R_{3f})C(O)$—, —$C(R_{3g})(R_{3h})S(O)_2$— and —SCO—, $R_2$ is selected from —$N(R_{2f})$— and —O—.

$R_{2a-2f}$ and $R_{3a-3h}$ are each independently selected from hydrogen or (1-4C)alkyl.

$R_2$ is preferably selected from —NHCHO, —$CH_2OH$, —NH—, and —O—.

$R_3$ is preferably selected from: hydrogen, —CH=CH—C(O)—, —$OCH_2C(O)$—, —$NHCH_2C(O)$—, —$CH_2S(O)_2$—, and —SCO—.

T represents a position of hydroxy on the benzene ring, and is selected from the ortho or meta position of $R_2$ on the benzene ring.

$Y^-$ is selected from pharmaceutically acceptable acid radicals, including inorganic acid radicals such as $Br^-$, $Cl^-$, $I^-$, bicarbonate, carbonate, bisulfate, sulfate, nitrate, phosphate, hydrogen phosphate, dihydrogen phosphate and phosphite; and organic acid radicals such as formate, acetate, propionate, isobutyrate, methanesulfonate, p-toluenesulfonate, benzoate, oxalate, tartrate, fumarate, malonate, succinate, suberate, mandelate, phthalate, benzene sulfonate, citrate, glucuronate, galactonate and amino acid radical. Preferably $Y^-$ is $Br^-$ or $Cl^-$.

The invention also includes compounds represented by the following structural formulae Ia-Id:

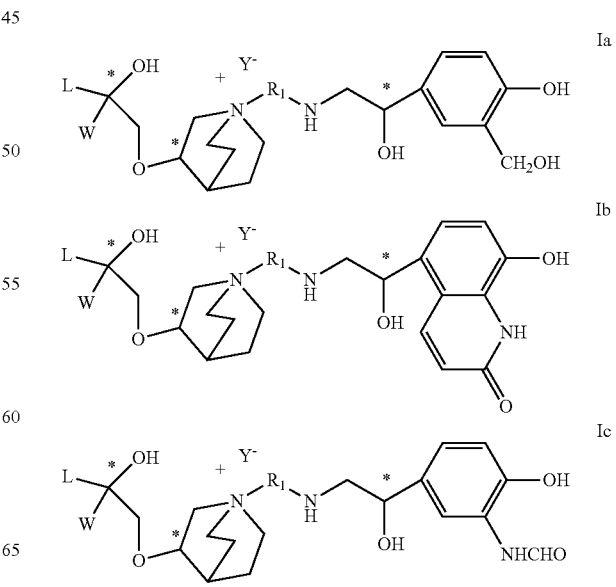

-continued

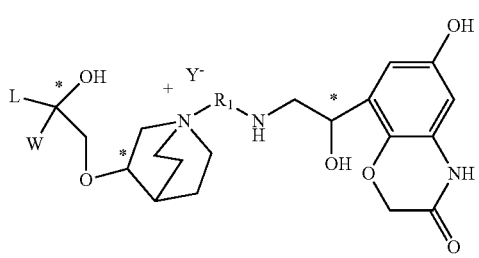

Id

In the formulae Ia-Id: carbons marked with * are (R) configuration, and L, W, $R_1$, Y are consistent with the groups defined above.

The quaternary ammonium salt compounds of the invention have M receptor antagonism and $β_2$ adrenoceptor agonism. They readily access raw materials from the market, are prepared by the general methods described below, and may also be prepared by the application of other information readily available to those skilled in the art. Specific embodiments and related methods are described herein, and the corresponding compounds can not only be prepared by using the methods of the invention to those skilled in the art, but also be prepared by using other reagents, methods, and starting materials. Unless otherwise stated, in addition to the conditions of the general or preferred methods (i.e., reaction temperature, pressure, time, solvent used, molar ratio of reactants, etc.) given in the invention, other methods and conditions may be employed. While the optimum reaction conditions vary with the particular reactants or solvents, those skilled in the art can readily determine these reaction conditions by conventional optimization procedures.

Furthermore, it will be apparent to those skilled in the art that conventional protecting groups are necessary to prevent unwanted chemical reactions of specific functional groups from interfering with the achievement of the target reaction. Suitable protecting groups for specific functional groups, as well as suitable conditions for the protection and deprotection of such functional groups, are well known in the art. If necessary, protecting groups other than these herein can also be used. The conditions for protection and deprotection of the protecting groups of various functional groups are described in detail in various literatures.

The invention relates to a method of preparing a compound of formula I, and a pharmaceutically acceptable salt, solvate thereof, or mixtures thereof, and to use of novel intermediates in the preparation of these compounds. The method of preparing a compound of formula I, or a pharmaceutically acceptable salt, solvate, or optical isomer thereof includes:

(a) reacting an intermediate 1 or salt thereof with $X_1$—$R_1$—$X_2$ to generate an intermediate 2;

(b) reacting the intermediate 2 with an intermediate 3 to generate an intermediate 4 with protecting groups;

(c) de-protecting groups from the intermediate 4 or other compound of formula I with protecting groups to obtain the compound of formula I; and (d) exchanging the compound of formula I with a basic anion exchange resin to produce a hydroxide of formula I, and then reacting with various acids to prepare quaternary ammonium salts with various acid radicals; or exchanging the compound of formula I with a specific anion exchange resin to prepare a quaternary ammonium salt with a specific acid radical; or reacting a halide of the formula I with silver oxide to generate a hydroxide of the formula I and then reacting with other acids to generate quaternary ammonium salts with various acid radicals; or reacting a halide of the formula I with a silver salt to produce a quaternary ammonium salt with a corresponding acid radical.

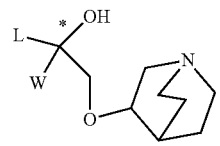

1

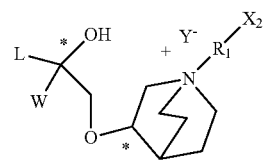

2

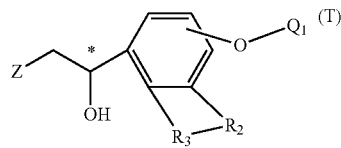

3

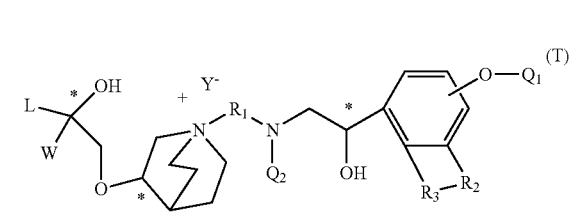

4

In the intermediates 1, 2, 3, 4, carbons marked with * are designated as R configurations, hereinafter is the same as defined above.

T represents a position of the group on the phenyl ring, and is selected from the ortho and meta position of $R_2$ on the benzene ring.

$Q_1$ is hydrogen or a hydroxy protecting group which is selected from silyl ethers such as trimethylsilyl, tert-butyldimethylsilyl, tert-butyldiphenylsilyl, etc., esters (acyl groups) such as formyl, acetyl, etc., and arylmethyl groups such as benzyl, p-methoxybenzyl, 9-fluorenylmethyl, benzhydryl, etc. $Q_2$ is hydrogen or an amino protecting group which is selected from benzyl (Bn), tert-butoxycarbonyl (Boc), benzyloxycarbonyl (Cbz), 9-fluorenylmethoxycarbonyl (Fmoc), formyl, acetyl, etc. $X_1$ and $X_2$ in the compound $X_1$—$R_1$—$X_2$ are independently selected from $NHQ_2$, halogen such as chlorine, bromine and iodine, and sulfonates such as methanesulfonate, p-toluenesulfonate and carbonyl. Z is selected from $NHQ_2$, halogen such as chlorine, bromine and iodine, and sulfonates such as methanesulfonate and p-toluenesulfonate, with the proviso that when $X_2$ is halogen or sulfonate, Z is —$NHQ_2$, when $X_2$ is —$NHQ_2$, Z is halogen or sulfonate, and when $X_2$ is carbonyl, Z is —$NQ_2$ and $Q_2$ is hydrogen. R is (1-6C)alkyl, phenyl or substituted phenyl, preferably methyl, ethyl, p-tolyl or phenyl. $R_1$, $R_2$, $R_3$, Y are the same as defined above.

In the above method, when one of the raw materials is salt, the salt is usually neutralized before or during the reaction, and such neutralization is usually carried out with a base of which molar equivalent is equal to that of the salt.

When $Q_1$ and $Q_2$ are protecting groups, they can be removed by methods well known to those skilled in the art.

The reaction between the compound 1 and $X_1$—$R_1$—$X_2$ in the step (a) is a substitution reaction in which a nucleophilic nitrogen atom in the compound 1 is substituted for $X_1$ in $X_1$—$R_1$—$X_2$ to form a quaternary ammonium salt.

The step (a) is usually carried out in a protic solvent, a dipolar solvent or an inert solvent such as methanol, ethanol, acetonitrile, acetone, N,N-dimethylformamide, N,N-dimethylacetamide, dimethylsulfoxide, and the like. The reaction is usually carried out in the range of 10-100° C. until the reaction is substantially completed. The separation of the product is carried out by a usual purification method, that is, extraction, recrystallization, column chromatography, and the like.

The preparation of intermediate 1 was carried out by the method reported in the literature (WO2015007073A1), that is, was prepared by the intermediate 5 and intermediate 6 in the presence of a strong base.

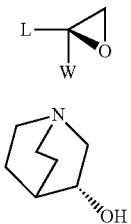

5

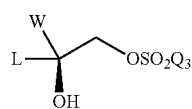

6

The molar ratio of the two intermediates is intermediate 5:intermediate 6=1:1-2, preferably 1:1.2. The reaction is carried out in a dipolar solvent, an aprotic solvent, or an inert solvent, and the usual solvent is usually acetonitrile, acetone, N,N-dimethylformamide, N,N-dimethylacetamide, dimethylsulfoxide, and the like. The reaction temperature is in the range of 10-100° C., preferably 70-100° C. The strong base is selected from sodium hydride, sodium amide, and the like. The molar ratio of the strong base to the intermediate 6 is 1-2:1, preferably 1.2:1. The reaction time is 2-10 hours, preferably 5-8 hours.

The intermediate 6 can be commercially available.

The intermediate 5 can be prepared by the intermediate 7:

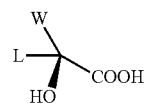

7

In the intermediate 7, $Q_3$ is selected from methyl, phenyl, p-tolyl, and the like. The intermediate 7 removes one molecule of sulfonic acid in the molecule under alkaline condition to generate epoxy compound intermediate 5, and the reaction solvent is selected from methanol, ethanol, acetone, N,N-dimethylformamide, N,N-dimethyl acetamide, dimethylsulfoxide, and the like. The base is selected from sodium hydroxide, potassium hydroxide, sodium carbonate, potassium carbonate, and the like. The reaction time is 2-10 hours, preferably 3-6 hours. The reaction temperature is 10-100° C., preferably 20-50° C.

The preparation of the intermediate 7 is derived from the intermediate 8:

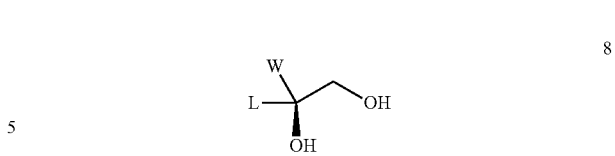

The intermediate 8 is reacted with sulfonyl chloride under alkaline condition to generate the intermediate 7. The solvent used in the reaction is an inert solvent such as dichloromethane, chloroform, acetonitrile, acetone, N,N-dimethylformamide, N,N-dimethylacetamide, dimethylsulfoxide, and the like. The base is selected from sodium hydroxide, potassium hydroxide, sodium carbonate, potassium carbonate, pyridine, triethylamine, N-methylmorpholine, and the like. The reaction time is 2-10 hours, preferably 3-6 hours. The reaction temperature is 10-100° C., preferably 20-50° C.

The intermediate 8 is prepared by the intermediate 9 in the R configuration:

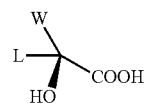

9

The intermediate 9 is reduced with a reducing agent such as sodium borohydride in the presence of a Lewis acid to obtain intermediate 8 directly. The reaction solvent is an inert solvent such as dichloromethane, chloroform, acetonitrile, acetone, N,N-dimethylformamide, N,N-dimethylacetamide, or a mixture thereof. The Lewis acid is aluminum trichloride, tin tetrachloride, titanium tetrachloride, or the like. The reaction time is 2-10 hours, preferably 3-6 hours. The reaction temperature is 10-100° C., preferably 20-50° C.

The intermediate 9 is obtained by chiral resolution of its racemate, the used resolution method may be with reference to Patent WO9942460, and CN100408549C.

The preparation methods of the various types of compounds represented by the formula $X_1$—$R_1$—$X_2$ are described in detail in the preparation and examples.

In step (b), intermediate 2 and intermediate 3 are subjected to nucleophilic substitution reaction to generate the intermediate 4, i.e., an amino nitrogen atom substituted the leaving group. The reaction is usually carried out in a protic solvent, a dipolar solvent or an inert solvent such as methanol, ethanol, acetonitrile, acetone, N,N-dimethylformamide, N,N-dimethylacetamide, dimethyl sulfoxide, and the like. The reaction is usually carried out at a temperature in the range of 10-100° C., preferably 60-100° C., until the reaction is substantially completed.

When $X_2$ in the intermediate 2 is —$OSO_2R$, R is as defined above, and the structural formula of the intermediate 2 is formula 10:

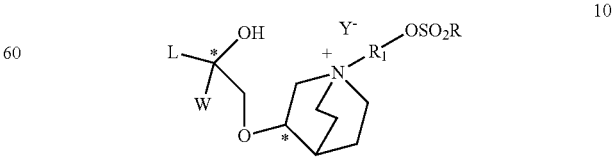

10

The preparation of formula 10 is prepared by reacting formula 11 with a sulfonyl chloride under alkaline condition.

The reaction solvent is dichloromethane, tetrahydrofuran, ethyl ether, isopropyl ether, acetonitrile, acetone, or a mixture thereof. The reaction temperature is room temperature. The base is selected from potassium carbonate, sodium carbonate, sodium hydroxide, sodium bicarbonate, potassium bicarbonate, triethylamine, N-methylmorpholine, diisopropylamine, and the like. The sulfonyl chloride is selected from methanesulfonyl chloride and p-toluenesulfonyl chloride. The molar ratio of the formula 11 to the sulfonyl chloride is 1:1-2, preferably 1:1.05. The molar ratio of the intermediate 2 to the base is 1:1-2, preferably 1:1.2.

11

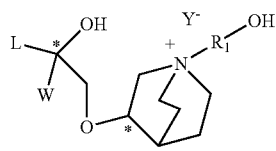

In the intermediate 3, Z is —$NHQ_2$, $Q_1$ and $Q_2$ are as defined above, the structural formula of the intermediate 3 is formula 12:

12

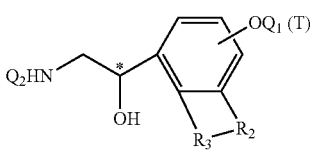

In the intermediate 3, when Z is a leaving group such as Br⁻, and $Q_1$ is as defined above, the structural formula of the intermediate 3 is formula 13:

13

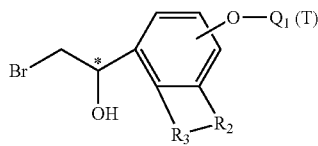

In the formula 12, when $R_3$ is hydrogen, $R_2$ is —$CH_2OQ_4$, and T is at the ortho position. Q, and $Q_2$ are respectively as described above. $Q_4$ is hydrogen or a hydroxy protecting group which is selected from silyl ethers such as trimethylsilyl, tert-butyldimethylsilyl, tert-butyldiphenylsilyl and the like, esters (acyl groups) such as formyl, acetyl and the like, and arylmethyl groups such as benzyl, p-methoxybenzyl, 9-fluorenylmethyl, benzhydryl and the like. The structural formula of the compound of formula 12 is formula 14:

14

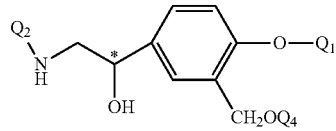

The preparation of the formula 14 is carried out by reacting the formula 15 with $Q_2NH_2$ under alkaline condition under pressure or heating. The reaction solvent is alcohol, water or $Q_2NH_2$. The reaction temperature is 50-120° C., preferably 80-110° C. The reaction time is 1-10 hours, preferably 4-6 hours.

15

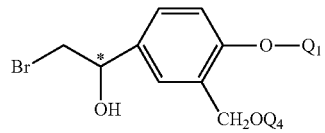

In formula 15, $Q_4$ is as described above. Formula 15 is the R configuration product obtained by the chiral reduction of formula 16 using borane dimethyl sulfide or tetrahydrofuran solution in the presence of a chiral catalyst. The reaction solvent is selected from tetrahydrofuran, dioxane, ethyl ether, dichloromethane, and the like. The reaction time is 1-6 hours. The reaction temperature is −5-50° C., preferably 0 to 40° C.

16

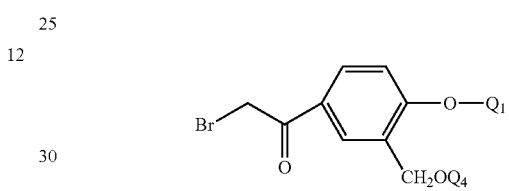

In formula 16, $Q_1$ and $Q_4$ are the same as defined above, and the preparation method thereof is carried out by reacting formula 17 with bromine in a solution. The reaction solvent is selected from tetrahydrofuran, dioxane, ethyl ether, isopropyl ether, dichloromethane, chloroform, and a mixture thereof. The reaction time is 1-6 hours. The reaction temperature is −5-50° C., preferably −5-30° C.

17

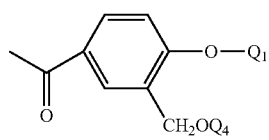

In formula 17, $Q_1$ and $Q_4$ are the same as defined above, and the preparation method thereof is carried out by reacting 4-hydroxy-3-hydroxymethylacetophenone with a hydroxy protecting group-containing compound under alkaline condition, for example, with benzyl bromide.

In formula 12, when $R_3$ is hydrogen, $R_2$ is —NHCHO, and T is at ortho position, $Q_1$ and $Q_2$ are respectively as described above, and the structural formula thereof is formula 18:

18

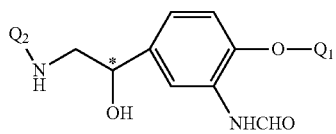

Formula 18 is prepared by reacting formula 19 with $Q_2NH_2$ under pressure or heating. The reaction solvent is selected from alcohols, water, tetrahydrofuran, dioxane or $Q_2NH_2$. The reaction temperature is 50-120° C., preferably 80-110° C. The reaction time is 1-10 hours.

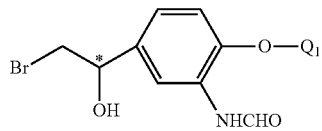

19

In formula 19, $Q_1$ is the same as defined above, and its preparation is carried out by chiral reduction of formula 20 using borane dimethyl sulfide or tetrahydrofuran solution in the presence of a chiral catalyst to give the R configuration. The reaction conditions are the same as those for the preparation of Compound 15.

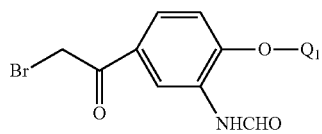

20

In the formula 20, $Q_1$ is the same as defined above, a compound of the formula 20 is prepared from a compound of formula 21 and anhydrous formic acid. The reaction condensing agent is selected from 1,3-dicyclohexylcarbodiimide (DCC), diisopropylcarbodiimide (DIC), 1-(3-dimethylaminopropyl)-3-ethylcarbodiimide (EDCI), and the like. A compound of the formula 20 may also be prepared by reacting a mixed anhydride prepared by acetic anhydride and formic acid with formula 21. The reaction solvent is selected from dichloromethane, tetrahydrofuran, anhydrous formic acid, or a mixture thereof. The reaction time is 2-8 hours. The reaction temperature is 5-50° C., preferably the temperature is 5-30° C.

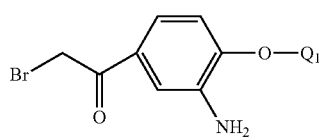

21

In the compound of formula 21, $Q_1$ is the same as defined above, and the compound of formula 21 is prepared by reducing the compound of formula 22 with a metal and ammonium chloride. The reaction solvent is selected from water, alcohols such as methanol, ethanol, and the like. The metal is selected from reductive iron powder, zinc powder, and the like.

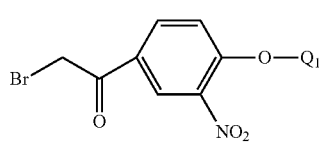

22

In the formula 22, $Q_1$ is the same as defined above, and the formula 22 is prepared by reacting formula 23 with bromine in a solution. The reaction solvent is tetrahydrofuran, dioxane, ethyl ether, isopropyl ether, dichloromethane, chloroform, or the like. The reaction time is 1-6 hours. The reaction temperature is −5-50° C., preferably the temperature is 5-30° C.

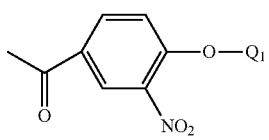

23

In the formula 23, $Q_1$ is the same as defined above, and the formula 23 is prepared by reacting 4-hydroxy-3-nitroacetophenone with a hydroxy protecting group-containing compound under alkaline condition, for example, by reacting with benzyl bromide.

In the formula 12, $Q_1$ and $Q_2$ are the same as defined above. When $R_2$ is —NH—, $R_3$ is —CH=CH—CO—, and T is at ortho position, the compound represented by formula 12 is formula 24:

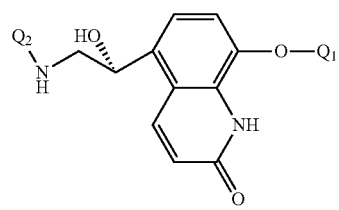

24

The preparation method of formula 24 is carried out by a nucleophilic addition reaction of the formula 25 and $Q_2NH_2$, and the reaction solvent is selected from methanol, ethanol, acetonitrile, tetrahydrofuran, dioxane, ethyl ether, isopropyl ether, and a mixture thereof, preferably methanol, ethanol, acetonitrile, tetrahydrofuran, dioxane. The reaction temperature is 10-100° C. The reaction time 2-8 hours. $Q_1$ and $Q_2$ are respectively as described above.

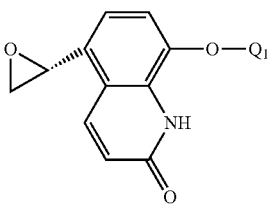

25

In the formula 25, $Q_1$ is the same as defined above, and a compound of the formula 25 is cyclized from a compound of formula 26 under alkaline condition. The base is selected from potassium carbonate, sodium carbonate, sodium hydroxide, potassium hydroxide, and the like. The reaction solvent is water, methanol, ethanol, acetonitrile, acetone, butanone, or the like, preferably methanol, ethanol, acetone or water. The reaction temperature is 10-100° C., preferably, the temperature is 10-30° C. The reaction time is 1-5 hours.

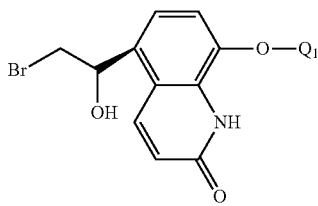

26

In the structural formula of formula 26, $Q_1$ is the same as defined above. The preparation thereof is carried out by selective reduction of formula 27 with borane in the presence of a chiral catalyst to form an alcohol in the R configuration. The catalyst used in the reaction is (1R, 2S)-(+)-indanol. The reaction solvent is selected from N,N-dimethylformamide, N,N-diethylacetamide, dimethylsulfoxide, dichloromethane, chloroform, tetrahydrofuran, ethyl ether or isopropyl ether, and the like, preferably tetrahydrofuran or ethyl ether. The molar ratio of formula 27 to (1R, 2S)-(+)-indanol is 1:0.01-0.2. The molar ratio of formula 27 to borane is 1:1.1-2.5. The reaction temperature is 0-50° C., preferably the temperature is 0-30° C. The reaction time is 4-10 hours.

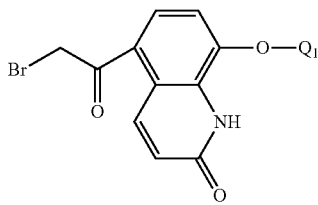

27

In formula 27, $Q_1$ is the same as defined above. The preparation method thereof is carried out by reacting formula 28 with bromine in a solution. The reaction solvent is selected from tetrahydrofuran, dioxane, ethyl ether, isopropyl ether, dichloromethane, chloroform, and the like. The reaction time is 1-6 hours. The reaction temperature is −5-50° C., preferably the temperature is 0 to 30° C.

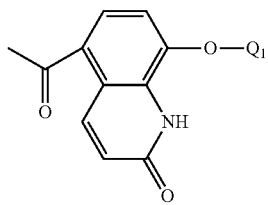

28

The preparation of formula 28 takes 5-acetyl-8-hydroxyquinoline as the starting material which is reacted with $Q_1X$ under alkaline condition to generate formula 28. X is a leaving group, selected from halogen such as chlorine, bromine and iodine, sulfonate such as methanesulfonate and p-toluenesulfonate. The base is selected from potassium carbonate, sodium carbonate, and the like. The reaction solvent is selected from methanol, ethanol, acetone, butanone, tetrahydrofuran, dioxane, dichloromethane, chloroform, ethyl ether, isopropyl ether, acetonitrile, and the like, preferably acetone, tetrahydrofuran or acetonitrile.

In the formula 12, $Q_1$ and $Q_2$ are the same as defined above. When $R_2$ is —NH—, $R_3$ is —O—$CH_2$—CO—, and T is at a meta position, the compound represented by formula 12 is formula 29:

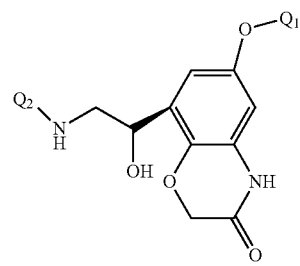

29

The preparation method is carried out by a nucleophilic addition reaction of that formula 30 and $Q_2NH_2$, and the reaction conditions are similar to those of formula 24. $Q_1$ and $Q_2$ are respectively as described above.

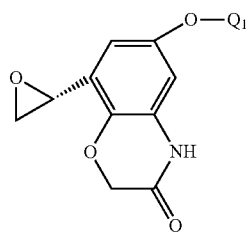

30

Formula 30 is prepared from formula 31, and its preparation method is similar to that of formula 25, wherein $Q_1$ is the same as defined above.

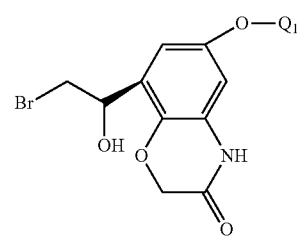

31

Formula 31 is prepared from formula 32, and its preparation method is similar to that of formula 26, wherein $Q_1$ is the same as defined above.

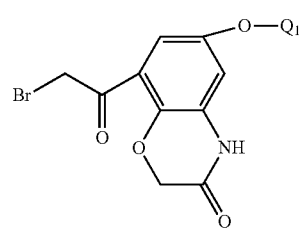

32

Formula 32 is prepared from formula 33, and its preparation method refers to preparation method of formula 27, wherein $Q_1$ is the same as defined above.

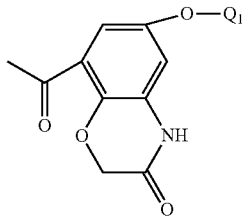

33

Formula 33 is prepared by reacting formula 34 with chloroacetyl chloride under alkaline condition. The preparation conditions are that: the molar ratio of formula 34 to chloroacetyl chloride is 1:1-2, preferably 1:1.05. The base is selected from potassium carbonate, sodium carbonate, potassium bicarbonate, sodium bicarbonate or low-concentration sodium hydroxide solution, and the like, and the molar ratio of formula 34 to base is 1:1-3, preferably 1:1.5. The reaction temperature is 10-100° C., preferably 20-60° C.

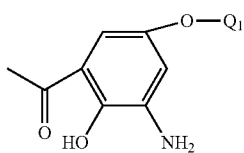

34

Formula 34 is obtained from formula 35 in which a nitro group is reduced to an amino group. The preparation method can adopt a hydrogenation method, and platinum oxide is used as a catalyst for selective hydrogenation. The reaction solvent is selected from methanol, ethanol, tetrahydrofuran and a mixture thereof. The temperature is 10-50° C., preferably 20-30° C. The pressure is 0.5-4 MPa. Optionally, reductive iron powder is used for selective reduction with in ammonium chloride aqueous solution so that a nitro group is reduced to an amino group. The solvent is selected from methanol, ethanol, tetrahydrofuran, and mixture thereof. The molar ratio of formula 34 to ammonium chloride is 1:1-4, preferably 1:2. The molar ratio of formula 35 to reductive iron powder is 1:1-5, preferably 1:2.

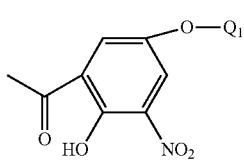

35

Formula 35 is prepared by nitration of formula 36. The reaction solvent is glacial acetic acid, and the reaction temperature is -5-50° C., preferably 0-30° C.

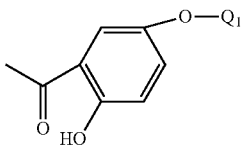

36

Formula 36 is prepared by reacting 2,4-dihydroxyacetophenone with $Q_1X$ under weak alkaline condition, and $Q_1X$ is the same as defined above. The base is selected from sodium bicarbonate, potassium bicarbonate, mixture thereof, and the like. The molar ratio of 2,4-dihydroxyacetophenone to base is 1:1. The molar ratio of 2,4-dihydroxyacetophenone to $Q_1X$ is 1:1. The reaction temperature is 10-50° C., and the reaction time is 2-5 hours.

In step (c), the intermediate 4 or other target compound with a protecting group is reduced to generate the target compound. Any suitable reducing agent can be used in the reaction, for example, in catalytic hydrogenation. The catalyst is selected from Pd/C, Raney nickel, platinum oxide and a mixture thereof, and a metal hydride reagent such as sodium triacetyl borohydride and the like. The reaction solvent is selected from methanol, ethanol, and a mixture thereof.

In step (d), the compound of formula I is exchanged with a basic anion exchange resin to produce a hydroxide of formula I, such as $OH^-$ resin, and then is reacted with various acids to prepare quaternary ammonium salts with various acid radicals, including various salts of acid radicals as mentioned above. Optionally, the compound of formula I is exchanged with a specific anion exchange resin to produce a quaternary ammonium salt with a specific acid radical. Optionally, a halide of the formula I is reacted with silver oxide to generate a hydroxide of the formula I and then reacted with other acids to generate quaternary ammonium salts with various acid radicals. Optionally, a halide of the formula I is reacted with a silver salt such as silver sulfate or silver nitrate to produce a quaternary ammonium salt with a corresponding acid radical.

In specific embodiments, certain specific compounds of formula I are prepared by method (a1)-(d1). The method includes compounds having the following structural formula or optional pharmaceutically acceptable salts or solvates thereof or optical isomers thereof, and mixtures thereof.

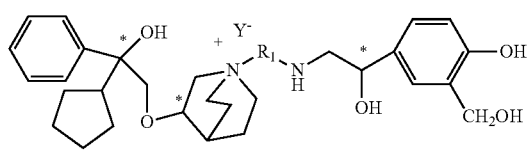

Ia1

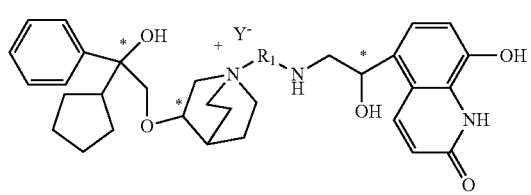

Ib1

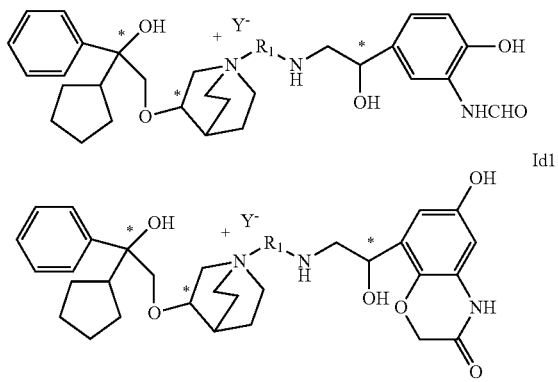

On the other hand, the invention relates to a pharmaceutical composition of a compound of formula I, which includes an acceptable pharmaceutical carrier, and the pharmaceutical composition can selectively contain other therapeutic ingredients, such as steroidal anti-inflammatory drug, phosphodiesterase inhibitor (PDE-4) and their pharmaceutically acceptable salts, solvates and therapeutically effective amount of optical isomers.

The compound of formula I of the invention is generally used in the form of compositions or preparations for patients. These compositions can be applied to patients by any acceptable route of administration, including but not limited to inhalational, oral, nasal, topical (including transdermal) and parenteral administration. That is, any form of the compound of the invention suitable for any particular mode of administration (including free base, pharmaceutically acceptable salts or solvates thereof, etc.) can be used in the pharmaceutical composition of the invention.

The pharmaceutical composition of the invention generally contains a therapeutically effective amount of a compound of the invention or a pharmaceutically acceptable salt or solvate thereof. Generally, such pharmaceutical composition contains from about 0.001% to about 100% by weight of the active ingredient.

Any conventional carriers or excipients can be used in the invention, and the selection of a particular carrier or excipient, or a combination of carrier and excipient, depends on the mode of administration or medical condition or disease type for treating a particular patient. The preparation technology of the pharmaceutical composition for a specific mode is within the knowledge of those skilled in the art. In addition, the carrier or excipient or the combination of the carrier and excipient can be commercially purchased.

Representative examples as pharmaceutically acceptable carriers include but are not limited to: (1) saccharides such as glucose, lactose, sucrose, etc.; (2) starches, such as corn starch; (3) cellulose and its derivatives, such as sodium carboxymethyl cellulose, cellulose acetate, etc.; (4) talc; (5) excipients, such as cocoa butter and waxes; (6) oils, such as olive oil, soybean oil, etc.; (7) alcohols, such as ethanol, propylene glycol, glycerol, sorbitol, polyethylene glycol, mannitol, etc.; (8) esters, such as ethyl oleate and ethyl laurate; (9) pyrogen-free water; (10) isotonic saline; (11) phosphate buffer solution; (12) compressed propellant gases, such as chlorofluorocarbons, hydrofluorocarbons, etc.; and (13) other non-toxic miscible substances used in pharmaceutical compositions.

The composition of the invention is generally prepared by thoroughly mixing the compound of the invention with optional one or more carriers. If necessary, the homogeneous mixture obtained in the invention can be plasticized or loaded into tablets, capsules, pills, cans or cartridges using conventional equipments and methods.

The pharmaceutical composition of the invention is suitable for inhalation administration. Compositions for inhalation administration are usually in the form of an aerosols or a powder inhalation. Such compositions are generally administered using well-known administration devices, such as nebulizer, metered dose inhaler (MDI) or dry powder inhaler (DPI) or other similar inhalation devices.

The composition containing the active ingredient of the invention is atomized and administered by nebulizer. Atomization devices can usually generate high-speed air flow to atomize the pharmaceutical composition containing active ingredient to be inhaled into respiratory tract by patients. Therefore, the active ingredient is usually dissolved in a suitable solvent to make a solution and placed in the nebulizer. Optionally, the active ingredient is micronized and is in combination with a suitable carrier to form a suspension of micronized particles suitable for inhalation. Micronization is generally defined as more than or equal to 90% of particles with a diameter of less than 10 μm. Suitable atomization devices are commercially available.

Representative pharmaceutical compositions using nebulizer include isotonic aqueous solution or ethanol solution containing 0.05 μg/ml to 10 mg/ml of compound of formula I or pharmaceutically acceptable salt, or solvate, or optical isomers thereof.

The pharmaceutical composition contained in the invention is administered by inhalation using a dry powder inhaler. Dry powder inhalers are usually administered in such a way that the active ingredient forms a free-flowing powder in the patient's airflow during inhalation. Therefore, the active ingredient is usually formulated together with a suitable excipient to obtain a free flowing powder, e.g. lactose as an excipient.

Representative pharmaceutical compositions for dry powder inhalers include dry lactose having a particle size between about 1 μm to 100 μm and the above-mentioned micronized particles of a compound of formula I, or a pharmaceutically acceptable salt or solvate or optical isomer thereof.

The dry powder formulation may be prepared by dry mixing the active ingredient with the excipient, or without the excipient, and then the pharmaceutical composition is loaded into a dry powder dispenser or into an inhalation cartridge or capsule for use with a dry powder administration device.

Dry powder administration devices are commercially available.

The pharmaceutical composition containing the active ingredient of the present invention is administered by inhalation using a metered dose inhaler. Such metered-dose inhalation device uses compressed propellant gas to discharge a measured amount of active ingredients or pharmaceutically acceptable salts thereof. Therefore, the pharmaceutical composition administered by the metered dose inhaler is contained in a solution or suspension propelled by liquefaction.

Representative pharmaceutical compositions for metered-dose inhalers include 0.001% to about 3% by weight of a compound of formula I or a pharmaceutically acceptable salt or solvate or optical isomer thereof, about 0% to about 40% of cosolvent ethanol or diols, preferably 5% to about 30%, and about 0% to 3% by weight of a surfactant. The rest is hydrofluoroalkane (HFA) propellant.

Such composition is usually prepared by adding chilled or pressurized hydrofluoroalkanes into a suitable container containing the active ingredient, ethanol (if present) and surfactant (if present). To prepare the suspension, the active ingredient is micronized and then mixed with the propellant. The preparation is then placed in an aerosol can to form a part of a metered dose inhaler. The suspension preparation can also be prepared by a spray drying method to form a surfactant coating on the surface of active ingredient microparticles.

Methods and preparations for preparing inhalable particles and other examples suitable for inhalation administration are discussed in the literatures.

The composition of the invention is suitable for oral administration. The pharmaceutical composition for oral administration can be capsule, tablet, pill, powder, granule, flat capsule and sugar-coated pill, or can be made into aqueous or non-aqueous solution or suspension, or made into water-in-oil or oil-in-water emulsion, or made into syrup. They all contain a predetermined amount of the active ingredient of the compound of the invention.

When the solid dosage form is administered, the composition of the invention includes the compound of the invention as an active ingredient and one or more pharmaceutically acceptable drug carriers as appropriate, for example, (1) fillers or extenders, such as starch, sucrose, silicic acid, etc.; (2) adhesives, such as carboxymethyl cellulose, polyvinylpyrrolidone, etc.; (3) humectants, such as glycerol; (4) disintegrants, such as calcium carbonate, starch, etc.; (5) lubricants, such as magnesium stearate, talc, solid polyethylene glycol or mixtures thereof; and (6) absorbent, such as kaolin, etc.

Releasing agents, humectants, coating agents, sweeteners, antioxidants, perfume agents, flavoring agents and preservatives may also be present in the composition of the invention. Pharmaceutically acceptable antioxidants include, but are not limited to, the following substances: water soluble antioxidants, such as sodium sulfite, ascorbic acid, cysteine hydrochloride, etc.; fat-soluble antioxidants, such as propyl gallate, alpha-tocopherol, etc.; and metal chelating agent, such as citric acid, sorbitol, and ethylenediamine tetraacetic acid (EDTA), etc.

Coating agents for tablets, capsules and pills include, but are not limited to, cellulose acetate phthalate (CAP), carboxymethyl ethyl cellulose (CMEC), and the like.

The composition of the invention can also be formulated into a slow release agent to control the slow release of active ingredients, for example, carboxymethyl cellulose or other polymer matrices, liposomes or microspheres in different proportions are used to make the slow-controlled agent.

Suitable liquid dosage forms for oral administration include suspensions, syrups, emulsions, microemulsions, and solutions, etc. Liquid dosage forms contain active ingredients and inert diluents, such as water and other solvents, solubilizers and emulsifiers, etc. Typical representatives are as follows: oils (olive oil, etc.), glycerin, polyethylene glycol, fatty acid esters of sorbitan, or mixtures thereof.

The pharmaceutical composition of the invention can also be a mixture formed by a compound of formula I or a pharmaceutically acceptable salt, solvate or optical isomer thereof and mixtures thereof with other drugs for co-administration therapy. For example, the pharmaceutical composition of the invention includes: one or more other bronchodilators such as $PDE_3$ inhibitor, $\beta_2$ adrenoceptor agonist, etc.; anti-inflammatory agents such as steroidal anti-inflammatory agents, non-steroidal anti-inflammatory agents, $PDE_4$ inhibitors, etc.; M receptor antagonists; anti-infective agents such as Gram-negative and Gram-positive antibiotics, antiviral drugs, etc.; antihistamine; protease inhibitor; and afferent blockers such as $D_2$ agonists. Other therapeutic agents can be applied in the form of pharmaceutically acceptable salts or solvates. In addition, other therapeutic agents can also be applied in the form of optical isomers.

Representative $\beta_2$ adrenoceptor agonist that can be used in combination with the compound of the invention (in addition to the compounds of the present invention) includes, but are not limited to, salmeterol, salbutamol, levalbuterol, formoterol, indacaterol, wielandt, arformoterol, salmefamol, fenoterol, isoetharine, metaproterenol, bitolterol, pirbuterol, etc., or pharmaceutically acceptable salts thereof.

Representative steroidal anti-inflammatory agents (other than the compound of the invention) that can be used in combination with the compound of the invention include, but are not limited to, methylprednisolone, prednisolone, dexamethasone, fluticasone propionate, beclomethasone ester, budesonide, flunisolide, mometasone ester, triamcinolone, rofleponide, ciclesonide, etc., or pharmaceutically acceptable salt thereof. When in use, the steroidal anti-inflammatory agents will be present in the composition in a therapeutically effective amount, usually the amount of steroid is between 0.05 μg and 500 μg.

Other suitable compositions include compositions formed by the compound represented by formula I of the invention and other anti-inflammatory drugs. For example, the typical representative drugs of the non-steroidal anti-inflammatory drugs are as follows: NSAIDs such as sodium nedocromil, sodium cromoglycate, etc., phosphodiesterase (PDE) inhibitors such as theophylline, $PDE_4$ inhibitors, mixed $PDE_3$/$PDE_4$ inhibitors, etc, leukotriene antagonists such as montelukast, protease inhibitors, cytokine antagonists, and cytokine synthesis inhibitors.

Representative M receptor antagonists that can be used in combination with the compounds of the present invention (in addition to the compounds of the invention) include, but are not limited to, glycopyrrolate, ipratropium bromide, tiotropium bromide, atropine, atropine sulfate, atropine oxide, methyl atropine nitrate, homatropine hydrobromide, scopolamine hydrobromide, oxitropium bromide, methantheline bromide, propantheline bromide, anisotropine methyl bromide, clidinium bromide, isopropamide iodide, mepenzolate bromide, pirenzepine, telenzepine, methoctramine, etc., or pharmaceutically acceptable salts thereof.

Antihistamine drugs that can be used in combination with the compounds of the invention include, but are not limited to, ethanolamines such as clemastine fumarate, carbinoxamine maleate, diphenhydramine hydrochloride, dimenhydrinate, etc., ethylenediamines such as pyrilamine maleate, tripelennamine hydrochloride and tripelennamine citrate, etc., alkylamines such as chlorpheniramine, acrivastine, etc., piperazines such as hydroxyzine hydrochloride, acid-resistant hydroxyzine, cyclizine hydrochloride, cyclizine lactate, meclizine hydrochloride, cetirizine hydrochloride, etc., piperidines such as astemizole, levocabastine hydrochloride, loratadine and its analogues, terfenadine, fexofenadine hydrochloride, azelastine hydrochloride, etc., and pharmaceutically acceptable salts thereof.

Effective therapeutic doses of other drugs administered in combination with the compounds of the invention are in the range of about 0.005 mg to about 10 mg each time.

The invention also relates to the use of a compound of formula I, or a pharmaceutically acceptable salt, solvate, optical isomer thereof, or a mixture thereof, for preparing a medicament for treating respiratory diseases, including COPD, asthma, rhinitis and the like.

The compound of the invention have both $\beta_2$-adrenoceptor agonistic and M-receptor antagonistic activities, so they are suitable for treating diseases mediated by $\beta_2$-adrenoceptor and M-receptor. That is, diseases that can be alleviated by using $\beta_2$-adrenoceptor agonists and M receptor antagonists. Such disease includes pulmonary disorders or diseases related to reversible airway obstruction, such as COPD, asthma, pulmonary fibrosis, etc.

The invention relates to a method for treating lung diseases, which includes administering an effective dose of a compound of formula I or a pharmaceutically acceptable salt or solvate or optical isomer thereof to a patient in need of treatment. In the treatment of diseases, the compound of the invention is usually administered by inhalation in the form of daily multiple doses, daily single doses or weekly single doses. The dosage is about 1.0 μg to about 200 μg each time.

When administered by inhalation, the compound of the invention has bronchiectasis, so the invention relates to a method of providing bronchiectasis to a patient, including administering an effective dose of a compound of formula I or a pharmaceutically acceptable salt or solvate or optical isomer thereof to the patient in need of treatment. The dosage is about 1.0 μg to about 200 μg each time.

The invention relates to a method for treating chronic obstructive pulmonary disease or asthma, which includes administering an effective dose of a compound of formula I or a pharmaceutically acceptable salt or solvate or optical isomer thereof to a patient in need of treatment. In the treatment of COPD or asthma, it is administered in a daily multi-dose and single-dose manner, with the dosage ranging from about 1.0 μg to about 200 μg each time.

When the compound of the invention is used in the treatment of lung diseases, the compound of the present invention may optionally be administered in combination with other therapeutic agents. Especially when the compound of the invention is combined with steroidal anti-inflammatory drugs, the two active ingredient compositions of the invention can provide triple therapy, namely $\beta_2$-adrenoceptor agonistic effect, M receptor antagonistic effect and anti-inflammatory effect. The composition containing two active ingredients of the invention is generally easier to prepare as compared with the composition containing three active ingredients. Therefore, the two-component composition is superior to the three-component composition. The pharmaceutical composition of the invention may contain a therapeutically effective amount of a steroidal anti-inflammatory agent.

The compound of the invention shows $\beta_2$-adrenoceptor agonistic activity and M receptor antagonistic activity. Among other properties, compounds that are of special interest are compounds with Ki value of $M_3$ receptor subtype inhibition constant and EC50 of $\beta_2$-adrenoceptor agonistic activity activity less than 100 nm, especially compounds with both values less than 10 nm. In addition, in vitro experiments or similar experiments, those compounds with similar Ki value of $M_3$ receptor subtype inhibition constant and EC50 value of $\beta_2$-adrenoceptor agonistic activity must also be paid attention to. For example, attention may be paid to compounds of which a ratio of Ki value of $M_3$ receptor subtype inhibition constant to $EC_{50}$ value of $\beta_2$-adrenoceptor agonistic activity is about 1:30 to about 30:1, particularly 1:20 to 20:1, more particularly about 1:10 to about 10:1, and far more particularly 1:5 to about 5:1.

The invention also provides a method of treating COPD, including administering an effective dose of a compound having $M_3$ receptor antagonistic activity and $\beta_2$-adrenoceptor agonistic activity to a patient in need of treatment.

In certain specific examples, the compound of the invention may have weak M receptor antagonistic activity or $\beta_2$-adrenoceptor agonist receptor binding activity, but they may still be used alone as M receptor antagonist or $\beta_2$-adrenoceptor agonist receptors.

When describing the compound, composition, method and process of the invention, unless otherwise indicated, the following terms have the following meanings.

The term "alkyl" refers to linear or branched unsubstituted saturated hydrocarbons. Unless otherwise defined, such alkyl groups generally contain 1 to 10 carbon atoms. Representative alkyl groups include methyl, ethyl, n-propyl, isopropyl, n-butyl, isobutyl, tert-butyl, and the like.

The term "alkoxy" refers to a monovalent group of formula (alkyl)-O—, wherein alkyl is as defined herein. Representative alkoxy groups include methoxy, ethoxy, n-propoxy, isopropoxy, n-butoxy, isobutoxy, tert-butoxy, and the like.

The term "arylene" refers to a divalent group of an aromatic ring, including substituted and unsubstituted aromatic rings. Representative arylene groups include 1,4-phenylene, 2-methoxy-1,4-phenylene, 2,5-furylidene, and the like.

The term "heterocyclylene" refers to a divalent group of heteroatom cyclic hydrocarbons, including substituted and unsubstituted heterocycloalkanes. Representative examples include 2,3-tetrahydrofurylidene, 2,4-tetrahydropyrrolyliene, and the like.

The term "alkylene amide group" refers to a divalent group containing both alkyl and amide groups, including substituted and unsubstituted alkylene amide groups. Representative alkylene amide groups include 2-oxopropylamine-1,4-ylidene, 2-oxoethylamine-1,3-ylidene, and the like.

The term "halogen" refers to fluorine, chlorine, bromine and iodine.

The term "pharmaceutically acceptable salt" refers to a salt that can be used to administer to a patient. This salt can be derived from pharmaceutically acceptable inorganic and organic bases, and can also be derived from pharmaceutically acceptable inorganic and organic acids, including salts of active compounds prepared with relatively non-toxic acids or bases according to the specific substituents present on the compound described herein. Examples of salts derived from pharmaceutically acceptable inorganic base include, but are not limited to, ammonium, calcium, potassium, sodium, and the like. Salts derived from pharmaceutically acceptable organic bases include salts of primary, secondary and tertiary amines including substituted amines, cyclic amines, natural amines, and the like, such as but not limited to betaine, caffeine, choline, and the like. When the compound of the invention contain relatively basic functional groups, salts can be obtained by contacting such compound in free form with a sufficient amount of the desired acid alone or in a suitable inert solvent. Examples of pharmaceutically acceptable acid addition salts include those derived from inorganic acids such as, but not limited to, nitrates, carbonates, bicarbonates, phosphates, sulfates, bisulfates, hydrochlorides, hydrobromates, and the like; and salts derived from relatively nontoxic organic acids such as, but not limited to, acetic acid, succinic acid, fumaric acid, mandelic acid, benzenesulfonic acid, p-toluenesulfonic acid, citric acid, tartaric acid, methanesulfonic acid, and the like.

The forms of the compound involved in the invention and salt thereof can be converted to each other by conventional methods in the art. For example, ammonium salts can be separated into free forms by contacting the salts with bases or acids in a conventional manner. The compound in free form is added to acid or base to obtain other salt forms. Some physical properties of the free form of the compound, such as solubility in polar solvents, are different from those of various salt forms, but for the purposes of the invention, the salt has the same therapeutic effect as the parent form of the compound.

In addition to the salt form, the invention provides compounds in the form of prodrug esters. The "prodrugs" of the compounds described herein are those compounds that are susceptible to chemical changes under physiological environment to obtain the compounds of the present invention.

"Precursor group" refers to a type of protecting group that can transform a drug to a prodrug when the functional group used to mask the active drug is formed into a "precursor moiety". Precursor groups are usually linked to functional groups of drugs via bonds that can be cleaved under specific conditions of use. Therefore, the precursor group is a part of a precursor portion that is cleaved under specific use conditions to release functional groups.

Specific examples of suitable precursor groups and their corresponding precursor moieties will be apparent to those skilled in the art.

Certain compounds of the invention have asymmetric carbon atom (optical rotation center) or double bond. Its racemate, diastereomer, geometric isomer and optical isomer are all included in the scope of the invention. These isomers can be resolved or asymmetrically synthesized by conventional methods to make the isomers "optically pure", i.e. substantially free of its other isomers. For example, if a specific enantiomer of the compound of the invention is required, it can be prepared by asymmetric synthesis or by derivatization with chiral auxiliary reagent, wherein the resulting mixture of diastereomers is separated and the auxiliary group is cleaved to obtain the pure desired enantiomer. Optionally, the different diastereoisomers formed according to its multiple chiral center is separated by a preparation column, for example, compounds 61, 70, 82, 98 and other compounds have chiral carbon in their R1 structures, i.e. separation is carried out by this method. Alternatively, when the molecule contains a basic functional group such as an amino group or an acidic functional group such as a carboxyl group, a salt of the asymmetric isomer is formed with an appropriate rotatory active acid or base, and then the diastereomer thus formed is separated by fractional crystallization or chromatography methods well-known in the art, and then the pure enantiomer is recovered.

The term "solvate" refers to a composite or a polymer formed by one or more molecules of a compound in formula I or a pharmaceutically acceptable salt thereof and one or more molecules of a solvent. This solvate is usually a crystal of solute and solvent with a fixed molar ratio. Representative solvents include, such as, ethanol, acetic acid, isopropanol, N, N-dimethylformamide, tetrahydrofuran, dimethyl sulfoxide and water. In general, solvated forms are equivalent to non-solvated forms and are included within the scope of the invention.

The term "therapeutically effective amount" refers to an amount sufficient to achieve treatment by administering to a patient in need of treatment.

The term "leaving group" refers to a functional group or atom substituted by another group or atom in a substitution reaction, such as a nucleophilic substitution reaction. Representative leaving group includes, for example, chlorine, bromine, iodine, etc.; sulfonate groups such as methanesulfonate, p-toluenesulfonate, p-bromobenzenesulfonate, p-nitrobenzenesulfonate, etc.; and acyloxy groups such as acetyloxy, trifluoroacetyloxy, etc.

The term "amino protecting group" refers to a suitable amino group to prevent an unnecessary irreversible reaction of the amino group in the reaction process, and the protecting group can be removed afterwards without affecting other parts of the molecular structure. Representative amino protecting groups include, but are not limited to, benzyl (Bn), tert-butyloxycarbonyl(Boc), benzyloxycarbonyl (Cbz), 9-fluorenylmethoxycarbonyl (Fmoc), formyl, acetyl, etc.

The term "hydroxy protecting group" refers to a protecting group suitable for hydroxy groups to prevent unnecessary reactions from occurring. Representative hydroxy protecting group includes, but not limited to, silyl ethers such as trimethylsilyl, tert-butyldimethylsilyl, tert-butyldiphenylsilyl, etc.; esters (acyl groups) such as formyl, acetyl, etc.; and arylmethyl groups such as benzyl, p-methoxybenzyl, 9-fluorenylmethyl, benzhydryl, etc. In addition, the two hydroxy groups can be protected by protecting groups, such as propylene glycol ether formed by the reaction of acetone and diol.

DETAILED DESCRIPTION OF THE PREFERRED EMBODIMENT

The following preparation and examples illustrate specific embodiments of the invention, which are not intended to limit the scope of the invention in any way unless otherwise specified.

Preparation 1

(R)-1-[(4-benzyloxy-3-benzyloxymethyl)phenyl]-2-benzylaminoethanol (a) 4-hydroxy-3-chloromethyl acetophenone 360 g (2.637 mol) of 4-hydroxyacetophenone was placed in a 5000 mL three-necked flask, 775.5 g (10.34 mol) of formaldehyde aqueous solution was added, and 3216 g of concentrated hydrochloric acid was added with stirring. The solid was completely dissolved, the temperature of the reaction mixture was set to be 20° C. by a cold water bath, and HCl was introduced. The reaction was continued with stirring, the reaction solution turned red, and the solid was precipitated. The reaction was continued with stirring for 5 hours. The reaction mixture was poured into ice water, stirred for 30 minutes, filtered to collect the solid, washed with water 5 times, 1000 mL for each time, and then washed with petroleum ether 2 times. The solid was dried in an oven at 50° C. to obtain 400 g of 4-hydroxy-3-chloromethyl acetophenone red solid with a yield of 82.1%.

(b) 4-hydroxy-3-acetyloxymethyl acetophenone 397.5 g (2.153 mol) of 4-hydroxy-3-chloromethyl acetophenone was placed in a 2000 mL three-necked flask, 1000 mL glacial acetic acid was added, and 215 g (2.62 mol) of sodium acetate was added with stirring. The reaction mixture was heated to 100° C., the reaction solution was brown, the reaction was continued with stirring at this temperature for 3 hours, and the reaction was terminated. The reaction was cooled to room temperature. The reaction mixture was poured into ice water, and extracted with dichloromethane 3 times, 600 mL for each time. The organic phase was combined, and washed with water 3 times. The organic phase was dried over anhydrous magnesium sulfate. The desiccant was filtered and removed. The dichloromethane was removed under reduced pressure. The residual solid was dissolved with 200 mL ethyl acetate by heating, cooled and crystallized. The solid was filtered and collected to obtain 211 g of 4-hydroxy-3-acetyloxymethyl acetophenone as a white solid with a yield of 47%.

(c) 4-benzyloxy-3-acetyloxymethyl acetophenone 315 g (1.51 mol) of 4-hydroxy-3-acetyloxymethyl acetophenone was placed in a 3000 mL three-necked flask, and 1800 mL DMF (N,N-dimethylformamide) was added for dissolution. The reaction was cooled to the internal temperature of 10° C., 215 g of anhydrous potassium carbonate was added, 291 g (1.65 mol) of benzyl bromide was added dropwise at this temperature, and the dropwise addition was completed within 2 hours. The temperature of the reaction mixture was increased to 30° C., and the reaction was continued for 10 hours. Potassium carbonate was removed by filtration, and N,N-dimethylformamide was removed under reduced pressure from the solution. The residue was added with 1500 mL of water, and extracted with ethyl ether 3 times, 1000 mL for each time. The ethyl ether extract solution was combined. The ethyl ether layer was washed with water 3 times, 1000 mL for each time, and the ethyl ether layer was dried over anhydrous magnesium sulfate. The desiccant was removed by filtration, and ethyl ether was removed. The residue was dissolved by heating with 150 mL of ethanol, and left to cool for crystallization. The solid was filtered and collected to obtain 334 g of 4-benzyloxy-3-acetyloxymethyl acetophenone as a white solid with a yield of 74%.

(d) 4-benzyloxy-3-hydroxymethyl acetophenone 238 g (0.798 mol) of 4-benzyloxy-3-acetyloxymethyl acetophenone was placed in a 3000 mL three-necked flask, 1900 mL of methanol was added, and the raw materials were dissolved by heating and stirring. Then 83.11 g (1.995 mol) of sodium hydroxide was added. The reaction was heated and refluxed for 1 hour. The reaction was stopped, the solvent was removed under reduced pressure, 1000 mL of water was added, and the mixture was extracted with dichloromethane 3 times, 800 mL for each time. The dichloromethane layers were combined and dried over anhydrous magnesium sulfate. Magnesium sulfate was removed by filtration. The solution was concentrated under reduced pressure. A part of dichloromethane was removed, then the equal volume of ethyl acetate was added, and the solution was placed in a refrigerator for crystallization. The solid was filtered and collected to obtain 172.56 g of 4-benzyloxy-3-hydroxymethyl acetophenone as a white solid with a yield of 84.4%.

(e) 4-benzyloxy-3-benzyloxymethyl acetophenone 172.56 g (0.673 mol) of 4-benzyloxy-3-hydroxymethyl acetophenone was dissolved in 1000 mL of tetrahydrofuran placed in a 2 L three-necked flask, and heated to the internal temperature of 30° C. Sodium hydride was added in batches, totally 34.65 g (1.0 mol). After addition. The reaction was continued with stirring for 20 minutes, and benzyl bromide 176.28 g (1.0 mol) was added dropwise at this temperature for about 1 hour. After the addition, the reaction was continued with stirring for 10 hours. The solvent was removed under reduced pressure. The residue was added with 800 mL of water, and extracted with ethyl acetate 3 times, 600 mL for each time. The extracted solution were combined, dried over anhydrous magnesium sulfate, then concentrated to dryness under reduced pressure after removing the desiccant by filtration. The residue was dissolved with ethanol for crystallization, and the solid was filtered and collected to obtain 164.15 g of white 4-benzyloxy-3-benzyloxymethyl acetophenone with a yield of 70.4%.

(f) 4-benzyloxy-3-benzyloxymethylbromoacetophenone 178.5 g (500.1 mmol) of 4-benzyloxy-3-benzyloxymethyl acetophenone was placed in a 3 L three-necked flask. 2200 mL of dichloromethane was added and stirred for 30 min. 88 g (510 mmol) of bromine was added dropwise at the internal temperature of 20-25° C. The dropwise addition was completed within 2 hours, and the reaction was carried out for 30 min, so that a large amount of solid products were obtained. TLC analysis showed that the raw materials were slightly unreacted completely. The solid was removed by filtration. The solid was dissolved in a mixed solvent of 2000 mL dichloromethane, and washed with saturated aqueous sodium bicarbonate solution (1000 mL×3 times). The organic layer was dried over anhydrous magnesium sulfate. The desiccant was removed by filtration, and the solvent was exhausted under reduced pressure (20° C.) by a water pump to obtain a solid. The solid was recrystallized with absolute ethanol, and cooled to dryness to obtain 180.5 g of the product with a yield of 83.1%.

(g) (R)-1-[(4-benzyloxy-3-benzyloxymethyl)phenyl]-2-bromoethanol 0.360 g (2.37 mmol) of (1R,2S)-(+)-1-amino-2-indenol was placed in a 2 L three-necked flask. 145 mL of THF was added, and stirred at 20-25° C. 3.3 mL (34.8 mmol) of borane dimethyl sulfide was added and stirred for 20 min, at the same time 130.72 g (300.0 mmol) of 4-benzyloxy-3-benzyloxymethylbromoacetophenone in 1396 mL THF solution and 24.54 mL (258.8 mmol) of borane dimethyl sulfide in 364 mL THF solution were added dropwise at 20-25° C. The dropwise addition was completed within 3 hours. The reaction was kept at the temperature of 20-25° C. and reacted for 30 min under nitrogen protection. TLC analysis showed that the reaction was complete. With external ice bath cooling (<10° C.), 145.4 mL of methanol was added dropwise, and the reaction was kept in an ice bath (<10° C.) and stirred for minutes after dropwise addition. The solvent was exhausted at 40° C. under reduced pressure by a water pump. 500 mL of water and 500 mL of ethyl acetate were added and stirred at room temperature until bubbles were generated. The solution was stirred at room temperature for 5 minutes, and transferred to a separatory funnel. The organic layer was separated out, the water layer was further extracted with ethyl acetate (150 mL×3 times). The organic layers were combined and dried over anhydrous magnesium sulfate.

The desiccant was removed by filtration, and the solvent was exhausted at 40° C. under reduced pressure by a water pump to obtain a crude product. 113.1 g of oily viscous product was obtained by crude column chromatography with a yield of 86.0%.

$^1$HNMR (ppm): (CD$_3$Cl), 7.52-7.38 (5H), 7.36-7.29 (5H), 7.27-7.19 (2H), 6.88 (d, 1H), 5.19 (s, 2H), 5.10 (s, 2H), 4.92

(t, 1H), 3.86-3.79 (m, 1H), 3.66-3.52 (m, 1H), 2.18 (Br, 1H) HPLC analysis (chiral column, Daicel AD-H column, 4.6 mm*250 mm), 96.831% (R-configuration), 2.54% (S-configuration)

(h) (R)-1-[(4-benzyloxy-3-benzyloxymethyl)phenyl]-2-benzylaminoethanol 87.4 g (200.0 mmol) of intermediate (R)-1-[(4-benzyloxy-3-benzyloxymethyl)phenyl]-2-bromoethanol was placed into a 500 mL three-necked flask. 162.3 g (1.517 mol) of benzylamine and 100 mL of dioxane were added. The reaction was carried out for 3 hours at 100-110° C. in an oil bath. TLC analysis showed that the intermediate was reacted completely. The solvent was removed at 45° C. under reduced pressure by a water pump. 500 mL of ethyl acetate and 500 mL of water were added and stirred, sodium bicarbonate was added to adjust the water layer with the pH 8-9, the water layer was transferred into a separatory funnel to separate out the organic layer, and the water layer was further extracted with ethyl acetate (300 mL×3 times). The organic layers were combined and dried over anhydrous magnesium sulfate. The desiccant was removed by filtration, and the solvent was removed at 45° C. under reduced pressure by a water pump to obtain an oily product.

160 mL of ethyl acetate was added into the abovementioned oily product, stirred for dissolution, cooled and crystallized in an ice bath. The white solid was filtered and washed with a small amount of ethyl acetate. The product was air dried at 60° C. for 2 hours to obtain 64.8 g of crystallized product with a reaction yield of 75.5%.

$^1$HNMR (ppm, DMSO (d$_6$)): 7.52-7.38 (5H), 7.36-7.09 (10H), 7.27-7.19 (2H), 6.88 (d, 1H), 5.19 (s, 2H), 5.10 (s, 2H), 4.92 (t, 1H), 3.86-3.79 (m, 1H), 3.66-3.52 (m, 1H), 2.18 (Br, 1H)

Preparation 2

(R)-(−)-3-[(R)-2-hydroxy-2-cyclopentyl-2-phenyl] ethoxy-1-azabicyclo[2,2,2]octane (a) R-cyclopentylmandelic acid In a 5 L three-necked flask, 320 g (1.453 mol) of cyclopentylmandelic acid racemate, 2670 mL of acetonitrile and 211 mL of water were added, stirred and heated for dissolution. The temperature of the reaction mixture was 40-45° C., at which time the solid was completely dissolved. 141.53 g (0.725 mol) of D-tyrosine methyl ester was added at this temperature to precipitate a solid. A heating was performed until the reaction mixture was refluxed and the solid was completely dissolved so that a clear and transparent solution is obtained. The heating was stopped, the reaction mixture was cooled to 0° C. in an ice bath, and the reaction was continued with stirring for 4 hours to precipitate a large amount of crystals. The solid was collected by filtration, washed with acetonitrile three times (3×150 mL), and dried to obtain 230.69 g of R-cyclopentylmandelic acid D-tyrosine methyl ester salt with a yield of 76.6%. 230.69 g of the above R-cyclopentylmandelic acid D-tyrosine methyl ester salt was added to a 5 L three-necked flask, and 2000 mL of toluene and 1000 mL of water were added. 66 mL of concentrated hydrochloric acid was added with stirring, heated to 40° C. in a water bath until the solid was completely dissolved, and cooled. The aqueous phase and organic phase were separated with a separatory funnel. 20 mL of concentrated hydrochloric acid was added to the aqueous phase and extracted twice (2×250 mL) with toluene. The organic phases were combined and dried over anhydrous magnesium sulfate. The desiccant was removed by filtration, the solvent was removed under reduced pressure, and the residue was added with 500 mL of n-hexane and stirred to produce a large amount of solid. The solid was filtered and dried at 45° C. for 3 hours to obtain 134.4 g of R-cyclopentylmandelic acid white solid with a yield of 83.4%.

(b) (R)-2-hydroxy-2-phenyl-2-cyclopentyl ethanol

In a 10 L reaction kettle, 134 g (0.608 mol) of R-cyclopentylmandelic acid and 2 L of glycol dimethyl ether were added to and stirred for dissolution. The reaction mixture was cooled to −5° C., 243.21 g (1.824 mol) of aluminum trichloride was slowly added, the temperature was maintained, 92 g (2.43 mol) of sodium borohydride was added in batches, and the addition was completed within half an hour. The temperature of the reaction mixture was increased to 50° C., and the reaction was continuously stirred for 4 hours. After the reaction was completed, the mixture was cooled to about 10° C. and 1.1 L of 2 mol/L hydrochloric acid was added dropwise to control the temperature of the reaction mixture unchanged. After the addition was completed, isopropyl ether was used to extract 3 times (3×500 mL). The organic phases were combined, washed with saturated sodium bicarbonate solution 3 times (3×200 mL), and dried over anhydrous magnesium sulfate. The desiccant was removed by filtration, the solvent was removed under reduced pressure, petroleum ether was added to grind the residue, and the solid was filtered and collected to obtain 99.88 g of (R)-2-hydroxy-2-phenyl-2-cyclopentylethanol with a yield of 79.6%.

(c) (R)-2-hydroxy-2-phenyl-2-cyclopentylethanol p-toluenesulfonate 350 mL of dichloromethane was placed in a 2 L three-necked flask. 98.88 g (0.479 mol) of (R)-2-hydroxy-2-phenyl-2-cyclopentyl ethanol was added, and stirred for dissolution. The reaction mixture was cooled to −5° C., 121.17 g (1.198 mol) of N-methylmorpholine was added, and 400 mL of dichloromethane solution containing 91.32 g (0.479 mol) of paratoluensulfonyl chloride was added dropwise. The dropwise addition was completed within 1 hour, and the reaction was continued at this temperature for 4 hours. The reaction mixture was washed with water 3 times (3×500 mL) to separate the organic phase, and the organic phase was dried over anhydrous magnesium sulfate. The desiccant was removed by filtration, the solvent was removed under reduced pressure, isopropyl ether was added to grind the residue, and the solid was filtered and collected to obtain 140 g of (R)-2-hydroxy-2-phenyl-2-cyclopentyl ethanol p-toluenesulfonate with a yield of 81.1%.

(d) (R)-1-phenyl-1-cyclopentyl-ethylene oxide 700 mL dimethyl sulfoxide was placed in a 2 L three-necked flask, 139 g (0.386 mol) of (R)-2-hydroxy-2-phenyl-2-cyclopentylethanol p-toluenesulfonate was added, the temperature of the reaction mixture was increased to 30° C., and the solid was completely dissolved by stirring. 20.07 g (0.502 mol) of solid sodium hydride (60%) was added. After the addition, the temperature of the reaction mixture was increased to 50° C. and the reaction was continued for 3 hours, the raw materials were completely disappeared. The reaction solution was cooled to 10° C., 300 mL of water was added dropwise, and isopropyl ether was added to extract three times (3×500 mL). The organic phases were combined and dried over anhydrous magnesium sulfate. The desiccant was removed by filtration, and the solvent was removed under reduced pressure to obtain 70 g of (R)-1-phenyl-1-cyclopentyl-ethylene oxide solid with a yield of 96.3%.

(e) (R)-(−)-3-[(R)-2-hydroxy-2-cyclopentyl-2-phenyl]ethoxy-1-azabicyclo[2,2,2]octane 500 mL of dimethyl sulfoxide was placed in a 2 L reaction kettle. 47.5 g (0.373 mol) of R-(−)-3-quinine alcohol was added and stirred, but the solid was insoluble. 7.5 g (0.313 mol) of sodium hydride (60%) was added until bubbles were generated. The reaction mixture was heated to 80° C., and the reaction was stirred at this temperature for 1 hour. 100 mL of dimethyl sulfoxide solution containing 70 g (0.372 mol) of (R)-1-phenyl-1-cyclopentyl-ethylene oxide was added dropwise for about 1 hour. After the addition was completed, the reaction was continued at this temperature for 2 hours. The reaction mixture was cooled to 20° C., and 785 mL of water was added dropwise. The addition was completed, the mixture was extracted with ethyl acetate 3 times (3×500 mL), the organic phases were combined, and the organic phases were washed with water 3 times (3×200 mL). The organic phases were separated out and dried over anhydrous magnesium sulfate. The desiccant was removed by filtration, and the solvent was removed under reduced pressure to obtain 88.5 g of solid (R)-(−)-3-[(R)-2-hydroxy-2-cyclopentyl-2-phenyl]ethoxy-1-azabicyclo[2,2,2]octane with a yield of 75.2%.

Preparation 3

8-benzyloxy-5-[(R)-2-benzylamino-1-hydroxyethyl]-1H-quinolin-2-one (a) 8-acetyloxy-(1H)-quinolin-2-one 80 g (0.5 mol) of 8-hydroxyquinoline nitrogen oxide was added to a 500 mL three-necked flask. 300 mL (3.15 mol) of acetic anhydride was added, stirred and heated to 90-100° C. The reaction was continued with stirring for 4 hours while maintaining such temperature, and the reaction mixture was cooled in an ice bath to precipitate a solid. The solid was collected by filtration, washed with ice-cold acetic anhydride twice (2×50 mL), and dried under vacuum to obtain 82.2 g of 8-acetyloxy-(1H)-quinolin-2-one solid with a yield of 81.0%.

(b) 5-acetyl-8-hydroxy-(1H)-quinolin-2-one

In a 500 mL three-necked flask, 200 mL of 1,2-dichloroethane was added, then 61 g (0.30 mol) of 8-acetyloxy-(1H)-quinolin-2-one was added to suspend in a solvent, the reaction mixture was heated to 80° C., 120 g (0.90 mol) of aluminum trichloride was added in batches, and the reaction was continued at this temperature for 1.5 hours to completely convert it into 5-acetyl-8-hydroxy-(1H)-quinolin-2-one. Then, the reaction mixture was poured into 1 liter of hot water with 80° C., and maintained at this temperature for 30 minutes. Then, the reaction mixture was thermally filtered. The solid was ground, washed with water, and dried under vacuum at 80° C. 50.3 g of light yellow 5-acetyl-8-hydroxy-(1H)-quinolin-2-one was obtained with a yield of 82.6%.

(c) 5-acetyl-8-benzyloxy-(1H)-quinolin-2-one 32.52 g (0.16 mol) of 5-acetyl-8-hydroxy-(1H)-quinolin-2-one was added to a 500 mL reaction flask, 200 mL of N,N-dimethylformamide was added for dissolution, 27.2 g (0.20 mol) of anhydrous potassium carbonate was added, 27.4 g (0.16 mol) of benzyl bromide was added dropwise with stirring, and the reaction was stirred at room temperature for 4 hours. Potassium carbonate was removed by filtration. The residue was dissolved in 1500 mL of dichloromethane, washed with water 3 times (3×300 mL) and dried over anhydrous magnesium sulfate. Dichloromethane was removed by filtration and concentrating, the residue was ground with acetone, and the solid was filtered and washed with acetone/water (1/1, 2×35 mL) to obtain 42.8 g of 5-acetyl-8-benzyloxy-(1H)-quinolin-2-one with a yield of 91.5%.

(d) 8-benzyloxy-5-bromoacetyl-(1H)-quinolin-2-one 40.0 g (0.137 mol) of 5-acetyl-8-benzyloxy-(1H)-quinolin-2-one was added to a 1 liter three-necked flask, and 500 mL of dichloromethane was added and stirred for dissolution. The reaction solution was cooled to about 0° C. in an ice bath, and 0.267 g (0.002 mol) of anhydrous aluminum trichloride was added. Then 20 g (0.15 mol) of bromine was added dropwise, the addition was completed within about 30 minutes, and the reaction mixture was increased to room temperature. At this temperature, the reaction was continued with stirring for 4 hours, and the thin layer chromatography detection showed that the reaction was complete. The reaction mixture was washed with saturated sodium bicarbonate solution three times (3×100 mL), and the organic phase was dried over anhydrous magnesium sulfate for 3 hours. Magnesium sulfate was removed by filtration, and the solvent was removed by concentrating under reduced pressure to obtain 42.2 g of 8-benzyloxy-5-(2-bromoacetyl)-(1H)-quinolin-2-one solid with a yield of 82.9%.

(e) 8-benzyloxy-5-[(R)-2-bromo-1-hydroxyethyl]-1H-quinolin-2-one 0.12 g (0.79 mmol) of (1R,2S)-(+)-1-amino-2-indenol was placed in a 500 mL three-necked flask. 50 mL of THF was added and stirred at 20-25° C. 1.1 ml (11.6 mmol) of borane dimethyl sulfide was added and stirred for 20 min. At the same time, 37.2 g (100.0 mmol) of 8-benzyloxy-5-(2-bromoacetyl)-(1H)-quinolin-2-one and 500 ml of THF solution and 8.1 ml (86.3 mmol) of borane dimethyl sulfide and 120 ml of THF solution were added dropwise at 20-25° C. for 3 hours. The reaction was kept at the temperature of 20-25° C. and reacted for 30 min under nitrogen protection. TLC analysis showed that the reaction was complete. With external ice bath cooling (<10° C.), 50 mL of methanol was added dropwise, and the reaction was kept in the ice bath (<10° C.) and stirred for 10 minutes after dropwise addition. The solvent was removed below 45° C. under reduced pressure by a water pump. 200 mL of water and 200 ml of ethyl acetate were added and stirred at room temperature until bubbles were generated, stirred at room temperature for 5 minutes, and transferred into a separatory funnel. The organic layer was separated out. The water layer was further extracted with ethyl acetate (50 ml×3 times). The organic layers were combined and dried over anhydrous magnesium sulfate. The desiccant was removed by filtration, and the solvent was removed below 45° C. under reduced pressure by a water pump to obtain a crude product. The crude product was thermally dissolved with 400 mL acetonitrile. 3 g of activated carbon was added. Reflux was performed for 5 minutes, filtration was performed when it was hot, and crystals were precipitated by cooling. The solid was filtered and collected to obtain 31.8 g of 8-benzyloxy-5-[(R)-2-bromo-1-hydroxyethyl]-1H-quinolin-2-one with a yield of 85.5%.

(f) 8-benzyloxy-5-[(R)-2-benzylamino-1-hydroxyethyl]-(1H)-quinolin-2-one 29.9 g (80.0 mmol) of intermediate 8-benzyloxy-5-[(R)-2-bromo-1-hydroxyethyl]-(1H)-quinolin-2-one was placed into a 500 ml three-necked flask. 40.3 g (0.51 mol) of benzylamine and 30 mL of dioxane were added. The reaction was carried out for 3 hours at 100-110° C. in an oil bath. TLC analysis showed that the intermediate was reacted completely. The solvent was removed below 45° C. under reduced pressure by a water pump. 150 ml of ethyl acetate and 200 ml of water were added and stirred, sodium bicarbonate was added to adjust the water layer with pH 8-9, the water layer was transferred into a separatory funnel to separate out the organic layer, and the water layer was further extracted with ethyl acetate (100 ml×3 times. The organic layers were combined and dried over anhydrous magnesium sulfate. The desiccant removed by filtration, the solvent was removed below 45° C. under reduced pressure by a water pump to obtain an oily product. 160 ml of ethyl acetate was added to the above oily product and stirred for dissolution, cooled and crystallized in an ice bath. White solid was filtered and washed with a small amount of ethyl acetate. The product was air dried at 60° C. for 2 hours to obtain 25 g of crystalline product with a reaction yield of 81.2%.

Preparation 4

(R)-2-benzylamino-1-[(4-benzyloxy-3-formamido)phenyl]ethanol (a) (R)-2-bromo-1-[(4-benzyloxy-3-nitro)phenyl]ethanol 0.132 g (0.87 mmol) of (1R,2S)-(+)-1-amino-2-indenol was placed in 2 L of three-necked flask. 180 mL of THE was added, and stirred at about 10° C. 9.2 ml (97.0 mmol) of borane dimethyl sulfide was added and stirred for 25 min. the temperature of the reaction mixture was kept at 5-10° C., at the same time, 63.6 g (180.16 mmol) of 4-benzyloxy-3-nitro-bromoacetophenone and 600 ml of THF solution and 8.1 ml (86.3 mmol) of borane dimethyl sulfide and 120 ml of THE solution were added dropwise. The dropwise addition was completed within 3 hours. The reaction mixture was kept at 5-10° C. and reacted for 30 min under nitrogen protection. TLC analysis showed that the reaction was complete. With external ice bath cooling (<10° C.), 50 mL of methanol was added dropwise, and the reaction was kept in an ice bath (<10° C.) and stirred for 10 minutes after dropwise addition. The solvent was pumped out at 45° C. under reduced pressure by a water pump. 200 ml of water and 200 ml of ethyl acetate were added to the residue, stirred at room temperature until bubbles were generated, stirred at room temperature for 5 minutes, and transferred into a separatory funnel. The organic layer was separated out. The water layer was further extracted with ethyl acetate (100 ml×3 times). The organic layers were combined and dried over anhydrous magnesium sulfate. The desiccant was removed by filtration, and the solvent was exhausted below 45° C. under reduced pressure by a water pump to obtain an oily product. The oily product was ground with n-hexane and cooled to separate out the solid. The solid was filtered and collected to obtain 57.9 g of (R)-2-bromo-1-[(4-benzyloxy-3-nitro)phenyl]ethanol with a yield of 90.5%.

(b) (R)-2-bromo-1-[(4-benzyloxy-3-amino)phenyl]ethanol 55 g (156.15 mmol) of (R)-2-bromo-1-[(4-benzyloxy-3-nitro)phenyl]ethanol was placed into a 1 L hydrogenation reaction kettle. 600 mL of methanol was added, stirred and dissolved. after that, 5 g of 10% palladium carbon was added, hydrogen is introduced, the pressure is maintained at 0.4 MPa, and the reaction temperature was maintained to be no more than 5° C. Under these conditions, the reaction was carried out for 12 hours. The reaction mixture was filtered. Palladium carbon was washed with methanol three times (3×100 mL) and the solvent was removed under reduced pressure. The residue was dissolved with ethyl acetate/petroleum ether (1/1), cooled and crystallized at 0° C., filtered to collect the solid, and dried to obtain 41.9 g of (R)-2-bromo-1-[(4-benzyloxy-3-amino)phenyl]ethanol with a yield of 83.3%.

(c) (R)-2-bromo-1-[(4-benzyloxy-3-formylamino)phenyl]ethanol

In a 500 mL three-necked flask, 88 g of anhydrous formic acid was added, cooled to 0-5° C. 19.6 g (18.7 mmol) of acetic anhydride was added dropwise with stirring, the reaction temperature was kept at 0-5° C., the reaction solution was stirred for 15 minutes, 40.0 g (12.4 mmol) of (R)-2-bromo-1-[(4-benzyloxy-3-amino)phenyl]ethanol was added to the reaction solution, and the reaction was continued at this temperature for 10 hours, so that the raw material (R)-2-bromo-1-[(4-benzyloxy-3-amino)phenyl]ethanol was completely reacted. Excess formic acid was removed under reduced pressure. The residue was dissolved with 400 mL of dichloromethane. The dichloromethane layer was washed with water three times (3×100 mL). The organic phase was dried over anhydrous magnesium sulfate. The desiccant was removed by filtration. The solvent was removed under reduced pressure. The residue was dissolved with 300 mL of methanol by heating. cooling was performed for crystallization, and the solid was filtered and collected to obtain 30.2 g of (R)-2-bromo-1-[(4-benzyloxy-3-formylamino)phenyl]ethanol with a yield of 72.8%.

(d) (R)-2-benzylamino-1-[(4-benzyloxy-3-formylamino)phenyl]ethanol 30.0 g (85.7 mmol) of intermediate (R)-2-bromo-1-[(4-benzyloxy-3-formylamino)phenyl]ethanol was added into a 500 ml three-necked flask with 40.3 g (0.51 mol) of benzylamine and 30 mL of dioxane. The reaction was carried out for 3 hours at 100-110° C. in an oil bath. TLC analysis showed that the intermediate was reacted completely. The solvent was exhausted under reduced pressure (45° C., −0.095 MPa) by a water pump. 250 ml of ethyl acetate and 200 ml of water were added and stirred, sodium bicarbonate was added to adjust the water layer with pH 8-9, and the water layer was transferred into a separatory funnel to separate out the organic layer. The water layer was further extracted with ethyl acetate (100 ml×3 times). The organic layers were combined and dried over anhydrous magnesium sulfate. The desiccant was removed by filtration, the solvent was removed below 45° C. under reduced pressure by a water pump to obtain an oily product. 260 ml of ethyl acetate was added to the above-mentioned oily product and stirred for dissolution, cooled and crystallized in an ice bath. The white solid was filtered and washed with a small amount of ethyl acetate. The product was air dried at 60° C. for 2 hours to obtain 19.65 g of crystalline product with a reaction yield of 80.1%.

Preparation 5

8-[(1R)-1-hydroxy-2-benzylamine]ethyl-5-benzyloxy-2H-1,4-benzoxazin-3(4H)-one (formula 28)

(a) 2-hydroxy-5-benzyloxy acetophenone 152 g (1.0 mol) of 2,5-dihydroxy acetophenone was added to a 1 L three-necked flask. 400 mL of absolute ethanol was added, stirred for dissolution. 92.4 g (1.1 mol) of sodium bicarbonate was added at room temperature and stirred for 5 minutes. The temperature of the reaction mixture was kept at 0-10° C. 180 g (1.05 mol) of benzyl bromide was added dropwise, and the addition was completed within 20 minutes. At this temperature, the reaction was continued with stirring for 3 hours, and thin layer detection showed that the raw material 2,5-dihydroxyacetophenone was reacted completely. The solvent was removed under reduced pressure. The residue was dissolved with 400 mL of dichloromethane, and washed with saturated citric acid aqueous solution 3 times (3×150 mL). The dichloromethane solution was dried over anhydrous magnesium sulfate. Anhydrous magnesium sulfate was removed by filtration. Dichloromethane was removed from the solution under reduced pressure. The residue was dissolved in 300 mL of absolute ethanol which is cooled and crystallized to obtain 213.7 g of 2-hydroxy-5-benzyloxy acetophenone as a white solid with a yield of 88.3%. The chemical purity was 99.0% (HPLC).

(b) 2-hydroxy-3-nitro-5-benzyloxy acetophenone 210 g (0.868 mol) of 2-hydroxy-5-benzyloxy acetophenone and 900 mL of glacial acetic acid were added into a 2 L three-necked flask for dissolution, the reaction mixture was cooled to 10-20° C., 64.3 mL (0.90 mol) of 63% concentrated nitric acid was added dropwise, and the addition was completed within 20 minutes. The reaction was continued with stirring at this temperature for 1 hour, and the reaction was completed. The reaction mixture was poured into 900 mL of ice water, and continually stirred for 1 hour to precipitate crystals. The solid was filtered, washed with ice water three times, and dried under vacuum at 50° C. to obtain 224 g of 2-hydroxy-3-nitro-5-benzyloxyacetophenone solid with a yield of 89.9%. The chemical purity was 99.2% (HPLC).

(c) 2-hydroxy-3-amino-5-benzyloxy acetophenone 220 g (0.767 mol) of 2-hydroxy-3-nitro-5-benzyloxy acetophenone solid was placed in a 2 L hydrogenation reaction kettle, 800 mL of dioxane was added, and 11 g of platinum oxide was added. At room temperature, hydrogen was introduced and the pressure was maintained at 3 MPa until hydrogen absorption was stopped. The catalyst was removed by filtration and directly used for the next reaction without treatment.

(d) 8-acetyl-6-benzyloxy-2H-1,4-benzoxazin-3(4H)-one 272 g (2.0 mol) of anhydrous potassium carbonate was added into a 3 L three-necked flask, and the filtrate of the above step (c) was added and stirred. 112.5 g (0.90 mol) chlorine acetyl chloride dissolved in 800 mL of dioxane was added dropwise at room temperature, and the addition was completed within 30 minutes. The reaction mixture was heated to 70° C. and the reaction was continued with stirring for 2 hours. The solvent was removed under reduced pressure, the residue was added with 1 L of water, and dissolved with 1 L of dichloromethane. The aqueous phase was extracted to separate the organic phase. The aqueous phase is extracted with dichloromethane twice (2×500 mL). The organic phases were combined, and washed with water three times (3×500 mL). The organic phase was dried over anhydrous magnesium sulfate. The desiccant was removed by filtration. A part of dichloromethane was removed under reduced pressure until a volume of the organic phases was about 500 mL. By adding 1500 mL of petroleum ether and stirring, the organic phases precipitated crystals. The crystals were filtered and dried at 50° C. to obtain 156.7 g of 8-acetyl-6-benzyloxy-2H-1,4-benzoxazin-3(4H)-one solid with a total yield of 68.8% in two steps. The chemical purity was 99.1% (HPLC).

(e) 8-(bromoacetyl)-6-benzyloxy-2H-1,4-benzoxazin-3(4H)-one 148.5 g (0.50 mol) of 8-acetyl-6-benzyloxy-2H-1,4-benzoxazin-3(4H)-one solid was added to a 2-liter three-necked flask, and 1000 mL of dioxane was added and stirred for dissolution. The reaction solution was cooled to about 0° C. in an ice bath, and 1.0 g (0.01 mol) of anhydrous aluminum trichloride was added. Then 176 g (0.55 mol) of bromine was added dropwise, and the addition was completed within about 30 minutes. The reaction mixture was increased to room temperature. At this temperature, the reaction was continued with stirring for 4 hours, and the thin layer chromatography detection showed that the reaction was complete. The solvent was removed from the reaction mixture under reduced pressure. The residue was dissolved in 1000 mL of dichloromethane, and washed with saturated sodium bicarbonate solution three times (3×100 ml). The organic phase was dried over anhydrous magnesium sulfate for 3 hours. Magnesium sulfate was removed by filtration, the filtrate was concentrated under reduced pressure to remove solvent, and the obtained oily product was ground with petroleum ether to obtain 161.2 g of 8-(bromoacetyl)-6-benzyloxy-2H-1,4-benzoxazin-3(4H)-one solid with a yield of 85.7%. The chemical purity was 98.3% (HPLC).

(f) 8-[(1R)-1-hydroxy-2-bromo]ethyl-6-benzyloxy-2H-1,4-benzoxazin-3(4H)-one 0.308 g (2.61 mmol) of (1R,2S)-(+)-1-amino-2-indenol was placed in a 3 L three-necked flask. 380 mL of THF was added and stirred at about 10° C. 21.4 ml (0.226 mol) of borane dimethyl sulfide was added and stirred for 25 min. The temperature of the reaction mixture was kept at 5-10° C., at the same time, 158.2 g (0.42 mol) of 8-(bromoacetyl)-6-benzyloxy-2H-1,4-benzoxazin-3(4H)-one solid in 1200 ml THF solution and 18.9 ml (0.20 mol) of borane dimethyl sulfide in 120 ml THF solution were added dropwise, and the dropwise addition was completed within 3 hours. The reaction mixture was kept at 5-10° C. and reacted for 30 min under nitrogen protection. TLC analysis showed that the reaction was complete. With external ice bath cooling (<10° C.), 120 mL of methanol was added dropwise, and the reaction mixture was kept in an ice bath (<10° C.) and stirred for 10 minutes after dropwise addition. The solvent was removed below 45° C. under reduced pressure by a water pump. 500 ml of water and 500 ml of ethyl acetate were added to the residue and stirred at room temperature until bubbles were generated. The mixture was stirred at room temperature for 5 min and transferred to a separatory funnel to separate out the organic layer. The water layer was further extracted with ethyl acetate (100 ml×3 times), the organic layers were combined and dried over anhydrous magnesium sulfate. The desiccant was removed by filtration, the solvent was removed below 45° C. under reduced pressure by a water pump to obtain an oily product. The oily product was ground with n-hexane and cooled to precipitate a solid. The solid was filtered and collected to obtain 144.5 g of 8-[(1R)-1-hydroxy-2-bromo]ethyl-6-benzyloxy-2H-1,4-benzoxazin-3(4H)-one with a yield of 91.0%. The chemical purity is 98.5% (HPLC) and the ee value is 95%.

(g) 8-[(1R)-1-hydroxy-2-benzylamine]ethyl-6-benzyloxy-2H-1,4-benzoxazin-3(4H)-one 143.6 g (0.38 mol) of intermediate (8-[(1R)-1-hydroxy-2-bromo]ethyl-5-benzyloxy-2H-1,4-benzoxazin-3(4H)-one was placed into a 1000 ml three-necked flask. 321.0 g (3.0 mol) of benzylamine and 120 mL of dioxane were added. The reaction was carried out for 3.5 h at 100-110° C. in an oil bath. TLC analysis showed that the intermediate was reacted completely. The solvent was exhausted under reduced pressure (45° C., −0.095 MPa) by a water pump. 1050 ml of dichloromethane and 400 ml of water were added and stirred, sodium bicarbonate was added to adjust the water layer with the pH 8-9, and the water layer was transferred into a separatory funnel to separate out the organic layer. The water layer was further extracted with dichloromethane (200 ml×3 times). The organic layers were combined, and dried over anhydrous magnesium sulfate. The desiccant was removed by filtration, the solvent was removed below 45° C. under reduced pressure by a water pump to obtain an oily product.
460 ml of ethyl acetate was added to the above-mentioned oily product and stirred for dissolution. The reaction mixture was cooled and crystallized in an ice bath. The white solid was filtered and washed with a small amount of ethyl acetate. The product was air dried at 60° C. for 2 hours to obtain 123.6 g of 8-[(1R)-1-hydroxy-2-benzylamine]ethyl-6-benzyloxy-2H-1,4-benzoxazin-3(4H)-one crystallized product with a reaction yield of 83.6%. The purity of isomer was 98.5%.

Example 1

(R)-(−)-3-[(R)-2-hydroxy-2-cyclopentyl-2-phenyl]ethoxy-1-{3-[(R)-2-(3-hydroxymethyl-4-hydroxy)phenyl-2-hydroxyethylamino]propyl}-1-azabicyclo[2,2,2]octylonium bromide

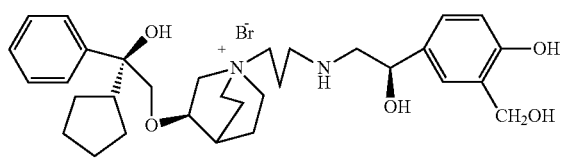

(a) (R)-(−)-3-[(R)-2-hydroxy-2-cyclopentyl-2-phenyl]ethoxy-1-(3-bromopropyl)-1-azabicyclo[2,2,2]octylonium bromide In a 250 mL three-necked flask, 30 mL of absolute ethanol, and 6.0 g (19.02 mmol) (R)-(−)-3-[(R)-2-hydroxy-2-cyclopentyl-2-phenyl]ethoxy-1-azabicyclo[2,2,2]octane (Preparation 2) were added, stirred and dissolved, and then 153.6 g (760.8 mmol) of 1,3-dibromopropane was added, stirred and reacted at room temperature for 12 hours. Ethanol and excess 1,3-dibromopropane were removed under reduced pressure, and the residue was crystallized with dichloromethane and n-hexane (1/2) to obtain 9.5 g of (R)-(−)-3-[(R)-2-hydroxy-2-cyclopentyl-2-phenyl]ethoxy-1-(3-bromopropyl)-1-azabicyclo[2,2,2]octylonium bromide solid with a yield of 96.1%. MS(m/z) 436.3, 438.3.

(b) (R)-(−)-3-[(R)-2-hydroxy-2-cyclopentyl-2-phenyl]ethoxy-1-{3-[(R)-2-(3-benzyloxymethyl-4-benzyloxy)phenyl-2-hydroxyethylbenzylamino]propyl}-1-azabicyclo[2,2,2]octylonium bromide 2.396 g (5.283 mmol) of (R)-1-[(4-benzyloxy-3-benzyloxymethyl)phenyl]-2-benzylaminoethanol (preparation 1) and 2.733 g (5.283 mmol) of (a) were added to a 50 mL reaction flask. 20 mL of dioxane was added. After the reaction mixture was stirred for 10 minutes, 1.475 g (10.566 mmol) of anhydrous potassium carbonate was added, the temperature of the reaction mixture was increased to 80° C., and the reaction was carried out at this temperature for 5 hours. Thin layer detection showed that the reaction was complete. The reaction was stopped, and the reaction mixture was cooled to room temperature and filtered to remove insoluble substances. The solvent was removed from the filtrate under reduced pressure, 5 mL isopropanol was added to the residue for freeze crystallization, and the solid was filtered and collected to obtain 3.0 g of the target product. The yield was 63.8%. MS(m/z) 809.9.

(c) (R)-(−)-3-[(R)-2-hydroxy-2-cyclopentyl-2-phenyl]ethoxy-1-{(3-[(R)-2-(3-hydroxymethyl-4-hydroxy)phenyl-2-hydroxyethylamino]propyl}-1-azabicyclo[2,2,2]octylonium bromide 2.5 g (4.83 mmol) of the product (b) was placed in a hydrogenation reaction kettle, 30 mL of methanol was added for dissolution, 0.5 g of 10% Pd—C was added, hydrogen was introduced, the pressure was kept at 0.43 MPa, and the temperature was room temperature. After 10 hours, the reaction was stopped, the catalyst was removed by filtration, the filtrate was concentrated to dryness under reduced pressure, and the residue was crystallized with ethanol. 1.6 g of the target compound solid was obtained with a yield of 53.5%. $^1$HNMR (δ ppm) (DMSO-$d_6$) 7.19-7.24 (m, 5H), 6.95-7.01 (m, 3H), 5.0 (s, 1H), 4.80 (s, 2H), 4.74 (m, 1H), 3.93 (s, 2H), 3.68 (d, 2H), 3.15 (m, 1H), 2.90 (m, 1H), 2.84 (m, 1H), 2.55 (m, 2H), 2.43 (S, 1H), 2.36 (m, 2H), 2.21 (S, 1H), 2.10 (s, 1H), 2.0 (m, 3H), 1.79-1.81 (m, 3H), 1.75 (m, 1H), 1.69 (m, 2H), 1.56-1.60 (m, 6H), 1.34-1.46 (m, 6H); Calculated for MS(m/z) of $C_{32}H_{47}BrN_2O_5$: 619.63, found: 539.27 (M+Br).

Example 2

(R)-(−)-3-[(R)-2-hydroxy-2-cyclopentyl-2-phenyl]ethoxy-1-(3-{(R)-[2-hydroxy-2-(8-hydroxy-2-oxo-1,2-dihydroquinolin-5-yl)]ethylamino}propyl)-1-azabicyclo[2,2,2]octylonium bromide

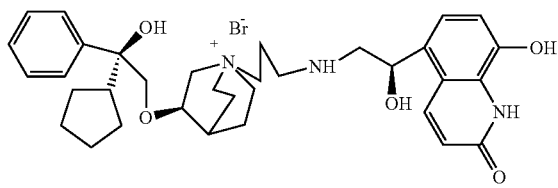

(a) (R)-(−)-3-[(R)-2-hydroxy-2-cyclopentyl-2-phenyl]ethoxy-1-(3-bromopropyl)-1-azabicyclo[2,2,2]octylonium bromide The above compound was prepared according to the method of Example 1(a).

(b) (R)-(−)-3-[(R)-2-hydroxy-2-cyclopentyl-2-phenyl]ethoxy-1-(3-{(R)-[2-hydroxy-2-(8-benzyloxy-2-oxo-1,2-dihydroquinolin-5-yl)]ethylbenzylamino}propyl)-1-azabicyclo[2,2,2]octylonium bromide The above compound was prepared according to the method of Example 1(b).

2.0 g (5.0 mmol) of 8-benzyloxy-5-[(R)-2-benzylamino-1-hydroxyethyl]-[1H]-quinolin-2-one (preparation 2) and 2.587 g (5.0 mmol) of (a) were added to a 50 mL reaction flask. 20 mL dioxane was added. After the reaction mixture was stirred for 10 minutes, 1.475 g (10.566 mmol) of anhydrous potassium carbonate was added, the temperature of the reaction mixture was increased to 80° C. The reaction was carried out at this temperature for 5 hours. Thin layer detection showed that the reaction is complete. The reaction was stopped, and the reaction mixture was cooled to room temperature and filtered to remove insoluble substances. The solvent was removed from the filtrate under reduced pressure, 5 mL isopropanol was added to the residue for freeze crystallization, and the solid was filtered and collected to obtain 2.3 g of the target product. The yield was 54.9%. MS(m/z) 758.65.

(c) (R)-(−)-3-[(R)-2-hydroxy-2-cyclopentyl-2-phenyl]ethoxy-1-(3-{(R)-[2-hydroxy-2-(8-hydroxy-2-oxo-1,2-dihydroquinolin-5-yl)]ethylamino}propyl)-1-azabicyclo[2,2,2]octylonium bromide The above compound was prepared according to the method of Example 1(c). 2.2 g (2.62 mmol) of the product (b) was placed in a hydrogenation reaction kettle, 20 mL of methanol was added for dissolution, 0.4 g of 10% Pd—C was added, hydrogen was introduced, the pressure was kept at 0.43 MPa, and the temperature was room temperature. After 10 hours, the reaction was stopped, the catalyst was removed by filtration, the filtrate was concentrated to dryness under reduced pressure, and the residue was crystallized with isopropanol. 1.3 g of the target compound solid was obtained with a yield of 90.0%.

$^1$HNMR (δ ppm) (DMSO-$d_6$) 8.0 (s, 1H), 7.36 (d, 1H), 7.19-7.24 (m, 5H), 6.71 (d, 1H) 6.57 (d, 1H), 6.52 (d, 1H), 5.01 (s, 1H), 4.79 (s, 2H), 4.73 (m, 1H), 3.93 (s, 2H), 3.68 (d, 2H), 3.15 (m, 1H), 2.90 (m, 1H), 2.84 (m, 1H), 2.54 (m, 2H), 2.43 (S, 1H), 2.36 (m, 2H), 2.10 (s, 1H), 2.0 (m, 3H), 1.79-1.82 (m, 3H), 1.75 (m, 1H), 1.68 (m, 2H), 1.55-1.61 (m, 6H), 1.35-1.46 (m, 6H).

Calculated for MS(m/z) of $C_{34}H_6BrN_3O_5$: 656.65, found: 576.26 (M+Br).

Example 3

(R)-(−)-3-[(R)-2-hydroxy-2-cyclopentyl-2-phenyl]ethoxy-1-{4-[(R)-2-(3-hydroxymethyl-4-hydroxy)phenyl-2-hydroxyethylamino]butyl}-1-azabicyclo[2,2,2]octylonium bromide

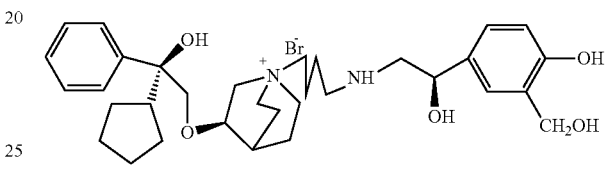

(a) (R)-(−)-3-[(R)-2-hydroxy-2-cyclopentyl-2-phenyl]ethoxy-1-(4-bromobutyl)-1-azabicyclo[2,2,2]octylonium bromide The above compound was prepared according to the method of Example 1(a).

In a 250 mL three-necked flask, 25 mL of absolute ethanol and 0.5 g of (R)-(−)-3-[(R)-2-hydroxy-2-cyclopentyl-2-phenyl]ethoxy-1-azabicyclo[2,2,2]octane (15.85 mmol) (preparation 2) were added, stirred and dissolved. Then 78.4 mL (634.0 mmol) of 1,4-dibromobutane was added, stirred and reacted at room temperature for 18 hours. Ethanol and excess 1,4-dibromobutane were removed under reduced pressure, and the residue was crystallized with dichloromethane and n-hexane (1/2) to obtain 8.1 g of (R)-(−)-3-[(R)-2-hydroxy-2-cyclopentyl-2-phenyl]ethoxy-1-(4-bromobutyl)-1-azabicyclo[2,2,2]octylonium bromide solid with a yield of 96.1%. MS(m/z) 450.3, 452.3.

(b) (R)-(−)-3-[(R)-2-hydroxy-2-cyclopentyl-2-phenyl]ethoxy-1-{4-[(R)-2-(3-benzyloxymethyl-4-benzyloxy)phenyl-2-hydroxyethylbenzylamino]butyl}-1-azabicyclo[2,2,2]octylonium bromide 4.096 g (7.253 mmol) of (R)-1-[(4-benzyloxy-3-benzyloxymethyl)phenyl]-2-benzylaminoethanol (preparation 1) and 3.854 g (7.253 mmol) of (a) were added to a 50 mL reaction bottle. 30 ml of N, N-dimethylformamide was added. After the reaction mixture was stirred for 10 minutes, 3.038 g (21.759 mmol) of anhydrous potassium carbonate was added, the temperature of the reaction mixture was increased to 55-60° C., and the reaction was carried out at this temperature for 12 hours. The thin layer detection showed that the reaction was complete. The reaction was stopped, and the reaction mixture was cooled to room temperature and filtered to remove insoluble substances. The solvent was removed from the filtrate under reduced pressure, 5 mL isopropanol was added to the residue for freeze crystallization, and the solid was filtered and collected to obtain 3.24 g of the target product. The yield was 48.0%. MS(m/z) 823.811.

(c) (R)-(−)-3-[(R)-2-hydroxy-2-cyclopentyl-2-phenyl]ethoxy-1-{4-[(R)-2-(3-hydroxymethyl-4-hydroxy)phenyl-2-hydroxyethylamino]butyl}-1-azabicyclo[2,2,2]octylonium bromide 2.8 g (3.11 mmol) of product (b) was placed in a hydrogenation reactor kettle, 30 mL of methanol was added for dissolution, 0.7 g of 10% Pd—C was added, hydrogen was introduced, the pressure was kept at 0.43 MPa, and the temperature was room temperature. After 12 hours, the reaction was stopped, the catalyst was removed by filtration, the filtrate was concentrated to dryness under reduced pressure, and the residue was crystallized with ethanol. 1.5 g of the target compound solid was obtained with a yield of 76.5%. $^1$HNMR (δ ppm) (DMSO-$d_6$) 7.18-7.23 (m, 5H), 6.96-7.01 (m, 3H), 5.0 (s, 1H), 4.80 (s, 2H), 4.74 (m, 1H), 3.93 (s, 2H), 3.68 (d, 2H), 3.15 (m, 1H), 2.90 (m, 1H), 2.83 (m, 1H), 2.55 (m, 2H), 2.43 (S, 1H), 2.35 (m, 2H), 2.21 (S, 1H), 2.10 (s, 1H), 2.0 (m, 3H), 1.79-1.81 (m, 3H), 1.75 (m, 1H), 1.69 (m, 2H), 1.55-1.61 (m, 8H), 1.34-1.46 (m, 6H); Calculated for MS(m/z) of $C_{33}H_{49}BrN_2O_5$: 633.66, found: 553.38 (M+Br).

Example 4

(R)-(−)-3-[(R)-2-hydroxy-2-cyclopentyl-2-phenyl]ethoxy-1-(4-{(R)-[2-hydroxy-2-(3-formamido-4-hydroxy)phenyl]ethylamino}butyl-1-azabicyclo[2,2,2]octylonium bromide

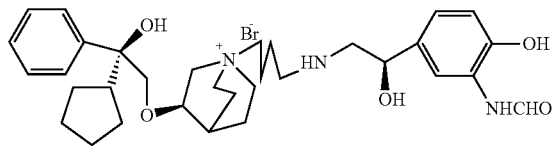

(a) (R)-(−)-3-[(R)-2-hydroxy-2-cyclopentyl-2-phenyl]ethoxy-1-(4-bromobutyl)-1-azabicyclo[2,2,2]octylonium bromide The above compound was prepared according to the method of Example 3(a).

(b) (R)-(−)-3-[(R)-2-hydroxy-2-cyclopentyl-2-phenyl]ethoxy-1-(4-{(R)-[2-hydroxy-2-(3-formamido-4-benzyloxy)phenyl]ethylbenzylamino}butyl-1-azabicyclo[2,2,2]octylonium bromide The above compound was prepared according to the method of Example 3(b).

1.882 g (5.0 mmol) of (R)-2-benzylamino-1-[(4-benzyloxy-3-formamido)phenyl]ethanol (preparation 4) and 2.66 g (5.0 mmol) of (a) were added to a 50 mL reaction flask, 30 mL of acetonitrile was added. After the reaction mixture was stirred for 10 minutes, 1.5 g (11.0 mmol) of anhydrous potassium carbonate was added, the temperature of the reaction mixture was increased to 55-60° C., and the reaction was carried out at this temperature for 12 hours. The thin layer detection showed that the reaction was complete. The reaction was stopped, and the reaction mixture was cooled to room temperature and filtered to remove insoluble substances. The solvent was removed from the filtrate under reduced pressure, 5 mL of ethanol was added to the residue for freeze crystallization, and the solid was filtered and collected to obtain 3.04 g of the target product. The yield was 73.6%. MS(m/z) 746.911.

(c) (R)-(−)-3-[(R)-2-hydroxy-2-cyclopentyl-2-phenyl]ethoxy-1-(4-{(R)-[2-hydroxy-2-(3-formamido-4-hydroxy)phenyl]ethylamino}butyl-1-azabicyclo[2,2,2]octylonium bromide The above compound was prepared according to the method of Example 3(c).

2.9 g (3.42 mmol) of the product (b) was placed in a hydrogenation reaction kettle, 30 mL of methanol was added for dissolution, 0.6 g of 10% Pd—C was added, hydrogen was introduced, the pressure was maintained at 0.4-0.43 MPa and the temperature was room temperature. After 15 hours, the reaction was stopped, the catalyst was removed by filtration, the filtrate was concentrated to dryness under reduced pressure, and the residue was crystallized with ethanol. 1.5 g of the target compound solid was obtained with a yield of 67.8%.

$^1$HNMR (δ ppm) (DMSO-$d_6$) 8.21 (s, 1H), 7.40 (m, 1H), 7.18-7.23 (m, 5H), 6.66-6.71 (m, 2H), 5.0 (s, 1H), 4.74 (m, 1H), 4.0 (s, 1H), 3.92 (s, 2H), 3.68 (d, 2H), 3.15 (m, 1H), 2.91 (m, 1H), 2.83 (m, 1H), 2.54 (m, 2H), 2.42 (S, 1H), 2.35 (m, 2H), 2.10 (s, 1H), 2.0 (m, 3H), 1.79-1.81 (m, 3H), 1.75 (m, 1H), 1.69 (m, 2H), 1.55-1.61 (m, 8H), 1.34-1.46 (m, 6H); Calculated for MS(m/z) of $C_{33}H_{48}BrN_3O_5$: 646.65, found: 566.28.

Example 5

(R)-(−)-3-[(R)-2-hydroxy-2-cyclopentyl-2-phenyl]ethoxy-1-(9-{-[(R)-2-hydroxy-2-(6-hydroxy-2H-1,4-benzoxazin-3(4H)-one-8-yl)]ethylamino}nonyl)-1-azabicyclo[2,2,2]octylonium bromide (R)-(−)-3-[(R)-2-hydroxy-2-cyclopentyl-2-phenyl]ethoxy-1-(9-{-[(R)-2-hydroxy-2-(6-hydroxy-2H-1,4-benzoxazin-3(4H)-one-8-yl)]ethylamino}nonyl)-1-azabicyclo[2,2,2]octylonium methanesulfonate

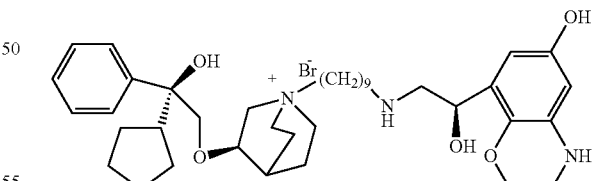

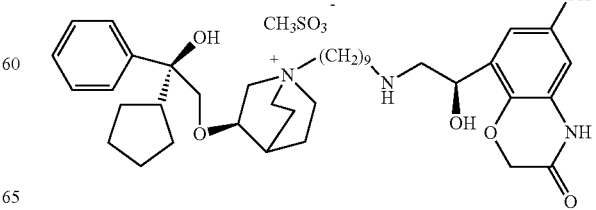

(a) (R)-(−)-3-[(R)-2-hydroxy-2-cyclopentyl-2-phenyl]ethoxy-1-(9-bromononyl)-1-azabicyclo[2,2,2]octylonium bromide The above compound was prepared according to the method of Example 1(a).

In a 250 mL three-necked flask, 35 mL of absolute ethanol and 5.0 g (15.85 mmol) (R)-(−)-3-[(R)-2-hydroxy-2-cyclopentyl-2-phenyl]ethoxy-1-azabicyclo[2,2,2]octane (preparation 2) was added, stirred and dissolved. Then 60.69 g (212.2 mmol) of 1,9-dibromononane was added, stirred and reacted at room temperature for 18 hours. Ethanol and excess 1,9-dibromononane were removed under reduced pressure, and the residue was crystallized with dichloromethane and petroleum ether (1/3) to obtain 9.1 g of the target product with a yield of 95.4%. MS(m/z) 520.18, 522.18.

(b) (R)-(−)-3-[(R)-2-hydroxy-2-cyclopentyl-2-phenyl]ethoxy-1-9-{(R)-[2-hydroxy-2-(5-benzyloxy-2H-1,4-benzoxazin-3(4H)-one-8-yl)]ethylbenzylamino}nonyl)-1-azabicyclo[2,2,2]octylonium bromide 2.02 g (5.0 mmol) of 8-[(1R)-1-hydroxy-2-benzylamine]ethyl-6-benzyloxy-2H-1,4-benzoxazin-3(4H)-one (preparation 5) and 3.0 g (5.0 mmol) of (a) were added to a 50 mL reaction flask, 30 mL dioxane was added. After the reaction mixture was stirred for 10 minutes, 1.0 g (7.35 mmol) of anhydrous potassium carbonate was added. The temperature of the reaction mixture was increased to 65-70° C. The reaction was carried out at this temperature for 12 hours. Thin layer detection showed that the reaction was complete. The reaction was stopped, and the reaction mixture was cooled to room temperature and filtered to remove insoluble substances. The solvent was removed from the filtrate under reduced pressure, 5 mL isopropanol was added to the residue for freeze crystallization, and the solid was filtered and collected to obtain 3.56 g of the target product. The yield was 77.0%. MS(m/z) 844.35 (M+Br).

(c) (R)-(−)-3-[(R)-2-hydroxy-2-cyclopentyl-2-phenyl]ethoxy-1-(9-{-[(R)-[2-hydroxy-2-(6-hydroxy-2H-1,4-benzoxazin-3(4H)-one-8-yl)]ethylamino}nonyl)-1-azabicyclo[2,2,2]octylonium bromide 3.4 g (3.67 mmol) of the product (b) was placed in a hydrogenation reaction kettle, 30 mL of methanol was added for dissolution, 0.6 g of 10% Pd—C was added, hydrogen was introduced, the pressure was kept at 0.43 MPa, and the temperature was room temperature. After 15 hours of reaction, hydrogen absorption was stopped, the reaction was stopped, the catalyst was removed by filtration, the filtrate was concentrated to dryness under reduced pressure, and the residue was crystallized with isopropanol. 1.5 g of the target compound solid was obtained with a yield of 54.8%. $^1$HNMR (δ ppm) (DMSO-d$_6$) 8.0 (s, 1H), 7.15-7.20 (m, 5H), 6.60 (d, 1H), 6.20 (d, 1H), 5.0 (s, 1H), 4.88 (s, 2H), 4.73 (m, 1H), 3.93 (s, 1H), 3.68 (d, 1H), 3.14 (m, 1H), 2.91 (m, 1H), 2.84 (m, 1H), 2.55 (m, 2H), 2.36 (m, 2H), 2.21 (S, 1H), 2.10 (s, 1H), 2.0 (m, 2H), 1.96 (m, 1H), 1.79-1.80 (m, 3H), 1.75 (m, 1H), 1.69 (m, 2H), 1.55-1.61 (m, 6H), 1.34-1.46 (m, 10H), 1.27-1.29 (m, 10H); Calculated for MS(m/z) of $C_{39}H_{58}BrN_3O_6$: 744.80, found: 664.35 (M+Br).

(d) (R)-(−)-3-[(R)-2-hydroxy-2-cyclopentyl-2-phenyl]ethoxy-1-(9-{-[(R)-[2-hydroxy-2-(6-hydroxy-2H-1, 4-benzoxazin-3(4H)-one-8-yl)]ethylamino}nonyl)-1-azabicyclo[2,2,2]octylonium methanesulfonate 0.56 g (0.75 mmol) of product (c) was dissolved in 10 mL of methanol water (v/v 1:1), 0.10 g of silver oxide was added, stirred at room temperature for 30 minutes, the resulted solid was removed by filtration, the solid was washed with 5 mL of water, the filtrates were combined, concentrated under reduced pressure to remove part of the solvent, 82 mg of methanesulfonic acid was added, stirred for 10 minutes, 0.2 g of activated carbon was added to the solution, continually stirred for 5 minutes, filtered, the filtrate was concentrated to dryness, and the residue was crystallized with 3 mL of isopropanol to obtain 0.45 g of the target product, with a yield of 59.2%. $C_{40}H_{61}N_3O_9S$ elemental analysis (%) (calculated value) C, 63.10 (63.21), H, 7.97 (8.09), N, 5.36 (5.53).

The following compounds can be synthesized using similar methods and raw materials described above.

| Example No. | Name of compounds | Molecular formula | MS (m/z) Measured value (Calculated Value) |
|---|---|---|---|
| 6 | (structure with cyclopropyl, (CH$_2$)$_8$ linker) | $C_{35}H_{53}BrN_2O_5$ | 581.35 (661.71) |
| 7 | (structure with cyclopentyl, (CH$_2$)$_9$ linker) | $C_{38}H_{59}BrN_2O_5$ | 623.36 (703.59) |

-continued
| Example No. | Name of compounds | Molecular formula | MS (m/z) Measured value (Calculated Value) |
|---|---|---|---|
| 8 | 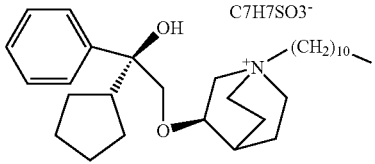 C7H7SO3⁻ | $C_{46}H_{68}N_2O_8S$ | 637.38 (809.11) |
| 9 | 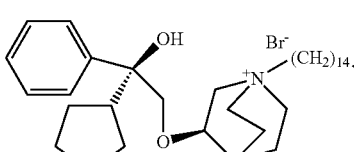 | $C_{43}H_{69}BrN_2O_5$ | 693.39 (773.92) |
| 10 | 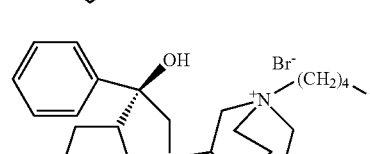 | $C_{35}H_{48}BrN_3O_5$ | 590.28 (670.68) |
| 11 | 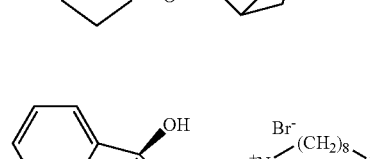 | $C_{38}H_{54}BrN_3O_5$ | 632.34 (712.76) |
| 12 | 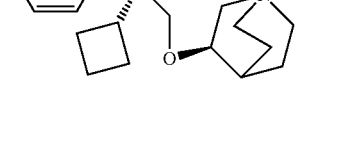 | $C_{40}H_{58}BrN_3O_5$ | 660.36 (740.81) |
| 13 | 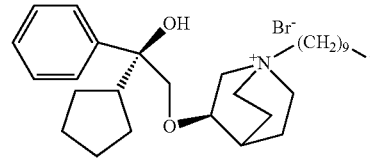 | $C_{41}H_{60}BrN_3O_5$ | 674.37 (754.84) |
| 14 | 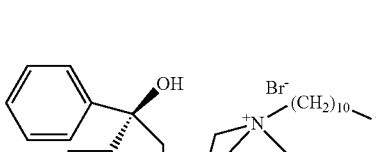 | $C_{42}H_{62}BrN_3O_5$ | 688.39 (768.86) |

-continued

| Example No. | Name of compounds | Molecular formula | MS (m/z) Measured value (Calculated Value) |
|---|---|---|---|
| 15 | | $C_{33}H_{48}BrN_3O_5$ | 556.26 (646.66) |
| 16 | | $C_{37}H_{56}BrN_3O_5$ | 622.34 (702.76) |
| 17 | | $C_{38}H_{58}BrN_3O_5$ | 716.79 (636.36) |
| 18 | | $C_{39}H_{60}BrN_3O_5$ | 650.37 (730.82) |
| 19 | | $C_{40}H_{62}BrN_3O_5$ | 664.39 (744.84) |
| 20 | | $C_{33}H_{46}BrN_3O_6$ | 580.26 (660.64) |
| 21 | | $C_{34}H_{48}BrN_3O_6$ | 594.27 (674.67) |

-continued

| Example No. | Name of compounds | Molecular formula | MS (m/z) Measured value (Calculated Value) |
|---|---|---|---|
| 22 | 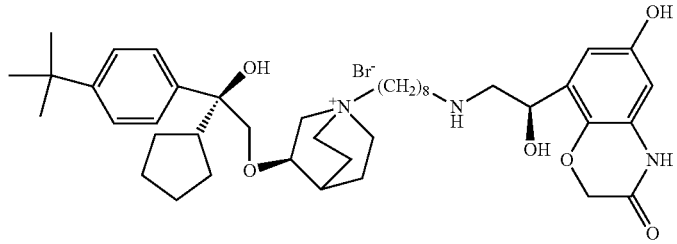 | $C_{42}H_{64}BrN_3O_6$ | 706.34 (786.88) |
| 23 | 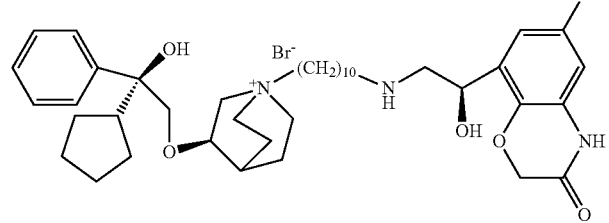 | $C_{40}H_{60}BrN_3O_6$ | 678.37 (758.83) |
| 24 | 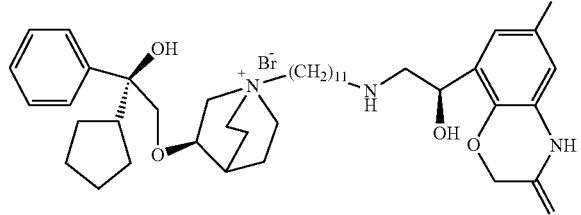 | $C_{41}H_{62}BrN_3O_6$ | 692.38 (772.85) |

Preparation 6

4-tert-butoxyformylamino-1-butanol 318 g (3.0 mol) of sodium carbonate were placed in a 3 L three-necked flask. 500 mL of dioxane and 500 mL of water were added and dissolved. 178 g (2.0 mol) of 4-amino-1-butanol was added to the reaction flask once, and stirred evenly. The temperature of the reaction mixture was maintained at about 10° C., and 500 mL of dioxane solution containing 545 g (2.50 mol) of di-tert-butyl dicarbonate was added dropwise. The reaction temperature was maintained and stirring was continued for 4 hours. The dioxane was removed under reduced pressure. The aqueous phase was extracted with dichloromethane three times (3×1000 mL), dried over anhydrous magnesium sulfate, and the solvent was removed under reduced pressure to obtain 343 g of the target product with a yield of 90.7%.

Preparation 7

4-tert-butoxyformylaminobutyl-2-bromoethyl ether

In a 500 mL three-necked flask, 37.8 g (0.20 mol) of 4-tert-butoxyformylamino-1-butanol was added and dissolved in 200 mL tetrahydrofuran. 8.0 g (0.20 mol) of sodium hydride (60%) was added, stirred for 15 minutes. 75.2 g (0.40 mol) of 1,2-dibromoethane was added dropwise. After the addition, the temperature of the reaction mixture was increased to 50° C., and the reaction was continued for 4 hours. The solvent and excess 1,2-dibromoethane were removed under reduced pressure. The residue was dissolved in 300 mL of ethyl acetate, washed with water three times (3×100 mL), and dried over anhydrous magnesium sulfate. The desiccant was removed by filtration, and the solvent was removed under reduced pressure to obtain 48.5 g of the target product with a yield of 77.2%.

Example 25

(R)-(−)-3-[(R)-2-hydroxy-2-cyclopentyl-2-phenyl] ethoxy-1-[2-(4-{(R)-[2-hydroxy-2-(3-formamido-4-hydroxy)phenyl]ethylamino}butoxy)ethyl]-1-azabicyclo[2,2,2]octylonium bromide

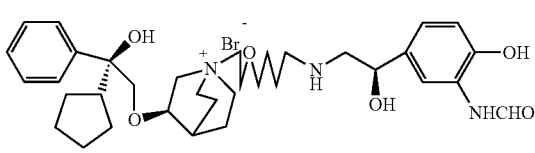

(a) (R)-(−)-3-[(R)-2-hydroxy-2-cyclopentyl-2-phenyl]ethoxy-1-[2-(4-tert-butoxyformamidobutoxy)ethyl]-1-azabicyclo[2,2,2]octylonium bromide In a 250 mL three-necked flask, 25 mL of absolute ethanol, and 5.0 g (15.85 mmol) of (R)-(−)-3-[(R)-2-hydroxy-2-cyclopentyl-2-phenyl]ethoxy-1-azabicyclo[2,2,2]octane (Preparation 2) were added, stirred and dissolved. Then 16.2 g (50.0 mmol) of 4-tert-butoxyformylaminobutyl-2-bromoethyl ether (Preparation 7) was added, stirred and reacted at room temperature for 24 hours. Ethanol was removed under reduced pressure, and the residue was crystallized with dichloromethane and n-hexane (2/1) to obtain 6.1 g of the target product solid with a yield of 63.1%. MS(m/z) 531.3 (M+Br).

(b) (R)-(−)-3-[(R)-2-hydroxy-2-cyclopentyl-2-phenyl]ethoxy-1-[2-(4-aminobutoxy)ethyl]-1-azabicyclo[2,2,2]octylonium bromide 5.9 g (8.92 mmol) of product (a) was placed in a 50 mL single-necked flask. 30 mL of 2 mol HBr dioxane solution was added, stirred at room temperature for 2 hours. The solvent was removed under reduced pressure, and the remaining solid was neutralized with N-methylmorpholine and subjected to column chromatography to obtain 3.3 g of the target product with a yield of 72.3%. MS(m/z) 431.3 (M+Br).

(c) (R)-(−)-3-[(R)-2-hydroxy-2-cyclopentyl-2-phenyl]ethoxy-1-[2-(4-{(R)-[2-hydroxy-2-(3-formamido-4-benzyloxy)phenyl]ethylamino}butoxy)ethyl]-1-azabicyclo[2,2,2]octylonium bromide 3.20 g (9.39 mmol) of the intermediate (R)-2-bromo-1-[(4-benzyloxy-3-formylamino)phenyl]ethanol (Preparation 4) was placed in a 50 ml three-necked flask. 3.20 g (6.26 mmol) of (b), 2.76 g (20 mmol) of anhydrous potassium carbonate and 5 mL of dioxane were added. The reaction was carried out in an oil bath at 100-110° C. for 3 hours. TLC analysis showed that the intermediate was reacted completely. The solvent was exhausted under reduced pressure by a water pump (45° C., −0.095 MPa). The residue was ground with a mixed solvent of petroleum ether and dichloromethane (3/1) to obtain a solid. The solid was crystallized with isopropanol to obtain 3.8 g of the target product with a yield of 77.7%. MS(m/z) 700.3 (M+Br)

(d) (R)-(−)-3-[(R)-2-hydroxy-2-cyclopentyl-2-phenyl]ethoxy-1-[2-(4-{(R)-[2-hydroxy-2-(3-formamido-4-hydroxy)phenyl]ethylamino}butoxy)ethyl]-1-azabicyclo[2,2,2]octylonium bromide 3.50 g (4.48 mmol) of product (c) was placed in a hydrogenation reaction kettle, 30 mL of methanol was added for dissolution, 0.5 g of 10% Pd—C was added, hydrogen was introduced, the pressure was maintained at 0.4-0.43 MPa, and the temperature was room temperature. After 10 hours of reaction, the reaction was stopped, the catalyst was removed by filtration, the filtrate was concentrated to dryness under reduced pressure, and the residue was crystallized with ethanol. 1.8 g of the target compound solid was obtained with a yield of 58.2%.

$^1$HNMR (δ ppm) (DMSO-d$_6$) 8.20 (s, 1H), 7.40 (m, 1H), 7.18-7.23 (m, 5H), 6.64-6.71 (m, 2H), 5.0 (s, 1H), 4.74 (m, 1H), 4.0 (s, 1H), 3.93 (s, 1H), 3.67 (d, 1H), 3.37-3.47 (m, 4H), 3.15 (m, 1H), 2.91 (m, 1H), 2.83 (m, 1H), 2.53-2.55 (m, 4H), 2.25 (m, 2H), 2.10 (s, 1H), 1.96-2.0 (m, 3H), 1.75-1.81 (m, 3H), 1.69 (m, 2H), 1.56-1.60 (m, 6H), 1.34-1.46 (m, 6H); Calculated for MS(m/z) of $C_{35}H_{52}BrN_3O_6$: 690.71, found: MS(m/z) 610.30 (M+Br).

Preparation 8

4-tert-butoxyformamidebutyl-5-bromopentyl ether

The above compound was prepared according to the method of Preparation 7.

Preparation 9

4-tert-butoxyformamidebutyl-4-bromobutyl ether

The above compound was prepared according to the method of Preparation 7.

Preparation 10

4-tert-butoxyformamidebutyl-3-bromopropyl ether

The above compound was prepared according to the method of Preparation 7.

Preparation 11

2-tert-butoxyformamideethyl-2-bromoethyl ether

The above compound was prepared according to the method of Preparation 7.

Example 26

(R)-(−)-3-[(R)-2-hydroxy-2-cyclopentyl-2-phenyl]ethoxy-1-[5-(4-{(R)-[2-hydroxy-2-(6-hydroxy-2H-1,4-benzoxazin-3(4H)-one-8-yl)]ethylamino}butoxy)pentyl]-1-azabicyclo[2,2,2]octylonium bromide

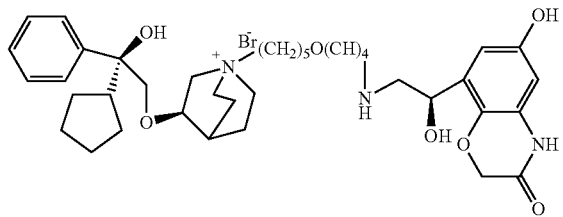

(a) (R)-(−)-3-[(R)-2-hydroxy-2-cyclopentyl-2-phenyl]ethoxy-1-[5-(4-tert-butoxyformamidobutoxy)pentyl]-1-azabicyclo[2,2,2]octylonium bromide In a 250 mL three-necked flask, 25 mL of absolute ethanol and 5.0 g (15.85 mmol) of (R)-(−)-3-[(R)-2-hydroxy-2-cyclopentyl-2-phenyl]ethoxy-1-azabicyclo[2,2,2]octane (Preparation 2) were added, stirred for dissolution. Then 17.58 g (52.0 mmol) of 4-tert-butoxyformamidobutyl-5-bromopentyl ether (Preparation 8) was added. The reaction mixture was stirred to react at 40° C. for 4 hours. Ethanol was removed under reduced pressure, and the residue was crystallized with dichloromethane and n-hexane (2/1) to obtain 6.0 g of the target product solid with a yield of 60.1%. MS(m/z) 573.3 (M+Br).

53

(b) (R)-(−)-3-[(R)-2-hydroxy-2-cyclopentyl-2-phenyl]ethoxy-1-[2-(4-aminobutoxy)pentyl]-1-azabicyclo[2,2,2]octylonium bromide 5.9 g (9.02 mmol) of the product (a) was placed in a 50 mL single-necked flask, and 30 mL of 2 mol HBr dioxane solution was added and stirred at room temperature for 2 hours. The solvent was removed under reduced pressure, and the remaining solid was neutralized with N-methylmorpholine and subjected to column chromatography to obtain 3.2 g of the target product with a yield of 64.2%. MS(m/z) 473.3 (M+Br).

(c) (R)-(−)-3-[(R)-2-hydroxy-2-cyclopentyl-2-phenyl]ethoxy-1-[5-(4-{(R)-[2-hydroxy-2-(6-benzyloxy-2H-1,4-benzoxazin-3(4H)-one-8-yl)]ethylamino}butoxy)pentyl]-1-azabicyclo[2,2,2]octylonium bromide 4.20 g (11.2 mmol) of intermediate 8-[(1R)-1-hydroxy-2-bromo]ethyl-5-benzyloxy-2H-1,4-benzoxazin-3(4H)-one (Preparation 5(f)) was placed in a 50 ml three-necked flask. 3.10 g (5.60 mmol) of (b), 2.76 g (20 mmol) of potassium carbonate, and 5 mL of dioxane were added. The reaction was carried out in an oil bath at 100-110° C. for 3 h. TLC analysis showed that the intermediate was reacted completely. The solvent was exhausted below 45° C. under reduced pressure by a water pump. The residue was ground with a mixed solvent of petroleum ether and dichloromethane (3/1) to obtain a solid. The solid was crystallized with isopropanol to obtain 3.9 g of the target product with a yield of 81.8%. MS(m/z) 770.4 (M+Br).

(d) (R)-(−)-3-[(R)-2-hydroxy-2-cyclopentyl-2-phenyl]ethoxy-1-[5-(4-{(R)-[2-hydroxy-2-(6-hydroxy-2H-1,4-benzoxazin-3(4H)-one-8-yl)]ethylamino}butoxy)pentyl]-1-azabicyclo[2,2,2]octylonium bromide 3.80 g (4.47 mmol) of the product (c) was placed in a hydrogenation reaction kettle, 30 mL of methanol was added for dissolution, 0.5 g of 10% Pd—C was added, hydrogen was introduced, the pressure was maintained at 0.4-0.43 MPa, and the temperature was room temperature. After 10 hours of reaction, the reaction was stopped, the catalyst was removed by filtration, the filtrate was concentrated to dryness under reduced pressure, and the residue was crystallized with isopropanol. 1.9 g of the target compound solid was obtained with a yield of 55.8%. $^1$HNMR (δ ppm) (DMSO-d$_6$) 8.0 (s, 1H), 7.18-7.20 (m, 5H), 6.65 (d, 1H), 6.20 (d, 1H), 5.0 (s, 1H), 4.88 (s, 2H), 4.74 (m, 1H), 3.93 (d, 1H), 3.68 (d, 1H), 3.37-3.40 (m, 4H), 3.15 (m, 1H), 2.91 (m, 1H), 2.84 (m, 1H), 2.55 (m, 2H), 2.36 (t, 2H), 2.10 (s, 1H), 1.98-2.0 (m, 3H), 1.75-1.81 (m, 4H), 1.69 (m, 2H), 1.56-1.60 (m, 6H), 1.34-1.46 (m, 12H), 1.29 (m, 2H); Calculated for MS(m/z) of C$_{39}$H$_{58}$BrN$_3$O$_7$: 760.80, found: MS(m/z) 680.35 (M+Br).

54

Example 27

(R)-(−)-3-[(R)-2-hydroxy-2-cyclopentyl-2-phenyl]ethoxy-1-[4-(4-{(R)-[2-(3-hydroxymethyl-4-hydroxy)phenyl-2-hydroxy]ethylamino}butoxy)butyl-1-azabicyclo[2,2,2]octylonium bromide

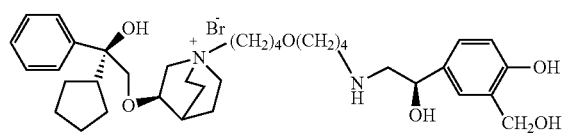

(a) (R)-(−)-3-[(R)-2-hydroxy-2-cyclopentyl-2-phenyl]ethoxy-1-[4-(4-tert-butoxyformamidobutoxy)butyl-1-azabicyclo[2,2,2]octylonium bromide The above compound was prepared according to the method of Example 25(a).

(b) (R)-(−)-3-[(R)-2-hydroxy-2-cyclopentyl-2-phenyl]ethoxy-1-[4-(4-aminobutoxy)butyl-1-azabicyclo[2,2,2]octylonium bromide The above compound was prepared according to the method of Example 25(b).

(c) (R)-(−)-3-[(R)-2-hydroxy-2-cyclopentyl-2-phenyl]ethoxy-1-[4-(4-{(R)-[2-(3-benzyloxyhydroxymethyl-4-benzyloxy)phenyl-2-hydroxy]ethylamino}butoxy)butyl-1-azabicyclo[2,2,2]octylonium bromide 3.50 g (8.19 mmol) of intermediate (R)-1-[(4-benzyloxy-3-benzyloxymethyl)phenyl]-2-bromoethanol (Preparation 1(g)) was placed in a 50 ml three-necked flask. 3.20 g (5.09 mmol) of (b), 2.76 g (20 mmol) of potassium carbonate and 5 mL of dioxane were added. The reaction was carried out for 3 hours at 100-110° C. in an oil bath. TLC analysis showed that the intermediate was reacted completely. The solvent was exhausted below 45° C. under reduced pressure by a water pump. The residue was ground with a mixed solvent of petroleum ether and dichloromethane (3/1) to obtain a solid. The solid was crystallized with isopropanol to obtain 4.1 g of the target product with a yield of 93.8%. MS(m/z) 777.4 (M+Br).

(d) (R)-(−)-3-[(R)-2-hydroxy-2-cyclopentyl-2-phenyl]ethoxy-1-[4-(4-{(R)-[2-(3-hydroxymethyl-4-hydroxy)phenyl-2-hydroxy]ethylamino}butoxy)butyl-1-azabicyclo[2,2,2]octylonium bromide 4.0 g (4.10 mmol) of the product (c) was placed in a hydrogenation reaction kettle, 30 mL of methanol was added for dissolution, 0.8 g of 10% Pd—C was added, hydrogen was introduced, the pressure was maintained at 0.4-0.43 MPa, and the temperature was room temperature. After 20 hours of reaction, the reaction was stopped, the catalyst was removed by filtration, the filtrate was concentrated to dryness under reduced pressure, and the residue was crystallized with ethanol. 1.6 g of the target compound solid was obtained with a yield of 55.4%.

¹HNMR (δ ppm) (DMSO-d₆) 7.17-7.20 (m, 5H), 6.95 (m, 2H), 6.64 (d, 1H), 5.0 (s, 1H), 4.79 (s, 2H), 4.74 (m, 1H), 3.93 (d, 1H), 3.67 (d, 1H), 3.37-3.47 (t, 41H), 3.14 (m, 1H), 2.90 (m, 1H), 2.84 (m, 1H), 2.53-2.55 (m, 2H), 2.36 (m, 2H), 1.96-2.0 (m, 5H), 1.74-1.81 (m, 4H), 1.69 (m, 2H), 1.56-1.60 (m, 6H) 1.34-1.46 (m, 14H); Calculated for MS(m/z) of $C_{37}H_{57}BrN_2O_6$: 705.76, found: 625.34 (M+Br).

The following compounds can be prepared from the above raw materials according to the above methods.

| Example No. | Name of compounds | Molecular formula | MS (m/z) Measured value (Calculated Value) |
|---|---|---|---|
| 28 | | $C_{35}H_{53}BrN_2O_6$ | 597.31 (677.71) |
| 29 | | $C_{38}H_{59}BrN_2O_6$ | 639.36 (719.79) |
| 30 | | $C_{36}H_{55}BrN_2O_6$ | 611.32 (691.74) |
| 31 | | $C_{34}H_{51}BrN_2O_7$ | 599.28 (679.68) |
| 32 | | $C_{37}H_{52}BrN_3O_6$ | 634.30 (714.73) |
| 33 | | $C_{44}H_{66}BrN_3O_6$ | 732.35 (812.92) |

-continued

| Example No. | Name of compounds | Molecular formula | MS (m/z) Measured value (Calculated Value) |
|---|---|---|---|
| 34 | | $C_{38}H_{54}BrN_3O_6$ | 648.32 (728.76) |
| 35 | | $C_{39}H_{56}BrN_3O_6$ | 662.34 (742.78) |
| 36 | | $C_{36}H_{51}BrN_3O_6$ | 621.30 (701.71) |
| 37 | | $C_{38}H_{58}BrN_3O_6$ | 652.35 (732.79) |
| 38 | | $C_{38}H_{58}BrN_3O_7$ | 668.31 (748.79) |
| 39 | | $C_{37}H_{56}BrN_3O_6$ | 638.34 (718.76) |
| 40 | | $C_{33}H_{48}BrN_3O_6$ | 582.27 (662.66) |

-continued

| Example No. | Name of compounds | Molecular formula | MS (m/z) Measured value (Calculated Value) |
|---|---|---|---|
| 41 | 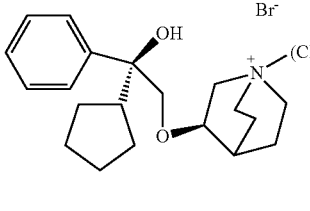 | $C_{36}H_{52}BrN_3O_7$ | 638.30 (718.72) |
| 42 | 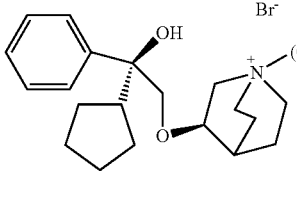 | $C_{37}H_{54}BrN_3O_7$ | 652.32 (732.75) |
| 43 | 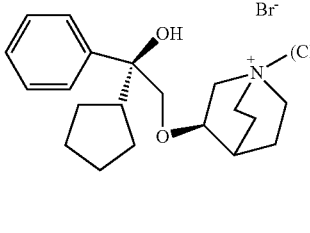 | $C_{38}H_{56}BrN_3O_7$ | 666.33 (746.77) |
| 44 | 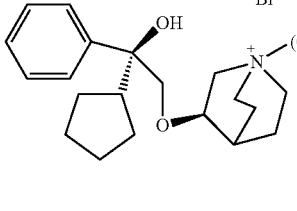 | $C_{34}H_{48}BrN_3O_7$ | 610.27 (690.67) |

Preparation 12

1,3-bis(2-bromoethoxy)propane 38 g (0.50 mol) of 1,3-propanediol was dissolved in 500 mL of tetrahydrofuran. 40 g (1.0 mol) of sodium hydride (60%) was added. The reaction mixture was stirred at room temperature for 15 minutes. 752 g (4.0 mol) of 1,2-dibromoethane was added dropwise. After the addition, reflux reaction was carried out for 3 hours, the solvent and excess 1,2-dibromoethane were removed under reduced pressure. The residue was dissolved in 500 mL of dichloromethane, washed with water three times (3×200 mL), and dried over anhydrous magnesium sulfate. The desiccant was removed by filtration, and the solvent was removed under reduced pressure to obtain 80 g of the target product with a yield of 61%.

Preparation 13

Bis(2-bromoethoxyethyl)ether 42.4 g (0.40 mol) of bis(2-hydroxyethyl)ether was dissolved in 400 mL of tetrahydrofuran. 33.6 g (1.05 mol) of sodium hydride (60%) was added. The reaction mixture was stirred at room temperature for 25 minutes. 752 g (4.0 mol) of 1,2-dibromoethane was added dropwise. After the addition, reflux reaction was carried out for 5 hours, the solvent and excess 1,2-dibromoethane were removed under reduced pressure. The residue was dissolved in 400 mL of dichloromethane, washed with water three times (3×200 mL), and dried over anhydrous magnesium sulfate. The desiccant was removed by filtration, and the solvent was removed under reduced pressure to obtain 70 g of the target product with a yield of 54.7%.

Example 45

(R)-(−)-3-[(R)-2-hydroxy-2-cyclopentyl-2-phenyl]ethoxy-1-(2-{2-[2-(2-{(R)-[2-(3-hydroxymethyl-4-hydroxy)phenyl-2-hydroxy]ethylamino}ethoxy)ethoxy]ethoxy}ethyl)-1-azabicyclo[2,2,2]octylonium bromide

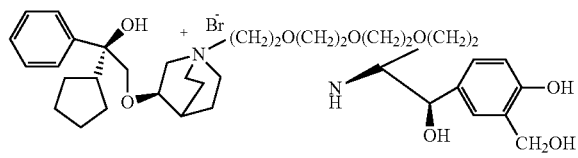

(a) (R)-(−)-3-[(R)-2-hydroxy-2-cyclopentyl-2-phenyl]ethoxy-1-(2-{2-[2-(2-ethoxy)ethoxy]ethoxy}bromoethyl)-1-azabicyclo[2,2,2]octylonium bromide In a 250 mL three-necked flask, 30 mL of absolute ethanol, 6.0 g (19.02 mmol) of (R)-(−)-3-[(R)-2-hydroxy-2-cyclopentyl-2-phenyl]ethoxy-1-azabicyclo[2,2,2]octane (preparation 2) were added, stirred and dissolved. Then 243.6 g (760.8 mmol) of bis(2-bromoethoxyethyl) ether (Preparation 13) were added. The reaction mixture was stirred to react at room temperature for 10 hours. The ethanol was removed under reduced pressure, the excess bis(2-bromoethoxyethyl)ether in the residue was removed by column chromatography, and the crude product was crystallized with dichloromethane and n-hexane (1/1) to obtain 9.3 g of the target product with a yield of 76.9%. MS(m/z) 654.2, 656.2.

(b) (R)-(−)-3-[(R)-2-hydroxy-2-cyclopentyl-2-phenyl]ethoxy-1-(2-{2-[2-(2-{(R)-[2-(3-benzyloxymethyl-4-benzyloxy)phenyl-2-hydroxy]ethylamino}ethoxy)ethoxy]ethoxy}ethyl)-1-azabicyclo[2,2,2]octylonium bromide 2.396 g (5.283 mmol) of (R)-1-[(4-benzyloxy-3-benzyloxymethyl)phenyl]-2-benzylamino ethanol (Preparation 1) and 3.46 g (5.283 mmol) of (a) was added to a 50 mL reaction flask. 20 mL of dioxane was added. After the reaction mixture was stirred for 10 minutes, 1.475 g (10.566 mmol) of anhydrous potassium carbonate was added, the temperature of the reaction mixture was increased to 80° C., and the reaction was carried out at this temperature for 3 hours. Thin layer detection showed that the reaction is complete. The reaction was stopped, and the reaction mixture was cooled to room temperature and filtered to remove insoluble substances. The solvent was removed from the filtrate under reduced pressure, 5 mL isopropanol was added to the residue for freeze crystallization, and the solid was filtered and collected to obtain 2.8 g of the target product. The yield was 57.7%. Calculated for MS(m/z) of $C_{51}H_{69}BrN_2O$: 918.0, found: 838.4 (M+Br).

(c) (R)-(−)-3-[(R)-2-hydroxy-2-cyclopentyl-2-phenyl]ethoxy-1-(2-{2-[2-(2-{(R)-[2-(3-hydroxymethyl-4-hydroxy)phenyl-2-hydroxy]ethylamino}ethoxy)ethoxy]ethoxy}ethyl)-1-azabicyclo[2,2,2]octylonium bromide 2.4 g (2.61 mmol) of product (b) was placed in a hydrogenation reaction kettle, 30 mL of methanol was added for dissolution, 0.5 g of 10% Pd—C was added, hydrogen was introduced, the pressure was kept at 0.43 MPa, and the temperature was room temperature. After 20 hours of reaction, the reaction was stopped, the catalyst was removed by filtration, the filtrate was concentrated to dryness under reduced pressure, and the residue was crystallized with isopropanol. 1.3 g of the target compound solid was obtained with a yield of 67.5%.

$^1$HNMR (δ ppm) (DMSO-de) 7.18-7.21 (m, 5H), 6.59-6.95 (m, 3H), 5.0 (s, 1H), 4.79 (s, 2H), 4.74 (m, 1H), 3.93 (d, 1H), 3.68 (d, 1H), 3.47-3.54 (m, 12H), 3.15 (m, 1H), 2.90 (m, 1H), 2.83 (m, 1H), 2.72 (t, 2H), 2.53 (m, 2H), 2.36 (m, 1H), 2.21 (S, 1H), 2.10 (s, 1H), 1.96-2.0 (m, 3H), 1.79-1.81 (m, 3 H), 1.74 (m, 1H), 1.69 (m, 2H), 1.56-1.60 (m, 6H), 1.33-1.45 (m, 6H); Calculated for MS(m/z) of $C_{37}H_{57}BrN_2O_8$: 737.76, found: 657.3 (M+Br).

Example 46

(R)-(−)-3-[(R)-2-hydroxy-2-cyclopentyl-2-phenyl]ethoxy-1-{2-[2-(2-{(R)-[2-hydroxy-2-(3-formamido-4-hydroxy)phenyl]ethylamino}ethoxy)ethoxy]ethyl}-1-azabicyclo[2,2,2]octylonium chloride

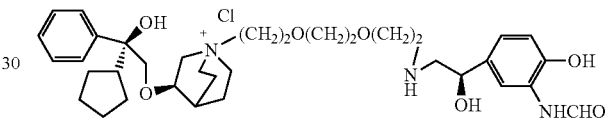

(a) (R)-(−)-3-[(R)-2-hydroxy-2-cyclopentyl-2-phenyl]ethoxy-1-{2-[2-(2-chloroethoxy)ethoxy]ethyl}-1-azabicyclo[2,2,2]octylonium chloride In a 250 mL three-necked flask, 30 mL of absolute ethanol, 6.0 g (19.02 mmol) of (R)-(−)-3-[(R)-2-hydroxy-2-cyclopentyl-2-phenyl]ethoxy-1-azabicyclo[2,2,2]octane (Preparation 2) were added, stirred and dissolved. Then 142.3 g (760.8 mmol) of 1,2-bis(2-chloroethoxy)ethane (Shanghai Hanhong Chemical) was added. The reaction mixture was heated to 45° C., stirred and reacted for 6 hours. Ethanol was removed under reduced pressure, excess 1,2-bis(2-chloroethoxy)ethane in the residue was removed by column chromatography, and the crude product was crystallized with dichloromethane and n-hexane (3/1) to obtain 8.3 g of the target product with a yield of 86.8%. Calculated for MS(m/z) of $C_{26}H_{41}ClNO_4$: 502.51, found: 466.24 (M−Cl), 468.23 (M−Cl).

(b) (R)-(−)-3-[(R)-2-hydroxy-2-cyclopentyl-2-phenyl]ethoxy-1-{2-[2-(2-{(R)-[2-hydroxy-2-(3-formamido-4-benzyloxy)phenyl]ethylamino}ethoxy)ethoxy]ethyl-1-azabicyclo[2,2,2]octylonium chloride 1.882 g (5.0 mmol) of (R)-2-benzylamino-1-[(4-benzyloxy-3-formamido)phenyl]ethanol (Preparation 4) and 2.568 g (5.0 mmol) of (a) was added to a 50 mL reaction flask. 30 mL of acetonitrile was added. After the reaction mixture was stirred for 10 minutes, 1.5 g (11.0 mmol) of anhydrous potassium carbonate was added, the temperature of the reaction mixture was increased to 75-80° C., and the reaction was carried out at this temperature for 8 hours. Thin layer detection showed that the reaction was complete. The reaction was stopped, and the reaction mixture was cooled to room temperature and filtered to remove insoluble substances. The solvent was removed from the filtrate under reduced pressure, 5 mL isopropanol was added to the residue for freeze crystallization, and the solid was filtered and collected to obtain 2.4 g of the target product. The yield was 63.8%. Calculated for MS(m/z) of $C_{42}H_{58}ClN_3O_7$: 752.38, found: 716.84 (M−Cl).

(c) (R)-(−)-3-[(R)-2-hydroxy-2-cyclopentyl-2-phenyl]ethoxy-1-{2-[2-(2-{(R)-[2-hydroxy-2-(3-formamido-4-hydroxy)phenyl]ethylamino}ethoxy)ethoxy]ethyl}-1-azabicyclo[2,2,2]octylonium chloride 2.1 g (2.79 mmol) of the product (b) was placed in a hydrogenation reaction kettle, 25 mL of methanol was added for dissolution, 0.4 g of 10% Pd—C was added, hydrogen was introduced, the pressure was maintained at 0.4-0.43 MPa, and the temperature was room temperature. After 10 hours of reaction, the reaction was stopped, the catalyst was removed by filtration, the filtrate was concentrated to dryness under reduced pressure, and the residue was crystallized with isopropanol. 1.1 g of the target compound solid was obtained with a yield of 59.5%.

$^1$HNMR (δ ppm) (DMSO-$d_6$) 8.20 (s, 1H), 7.40 (dd, 1H), 7.19-7.21 (m, 5H), 6.64-6.76 (m, 2H), 5.01 (s, 1H), 4.73 (m, 1H), 4.0 (s, 1H), 3.93 (d, 2H), 3.68 (d, 2H), 3.47-3.54 (m, 8H), 3.15 (m, 1H), 2.90 (m, 1H), 2.84 (m, 1H), 2.72 (t, 2H), 2.53 (d, 2H), 2.10 (s, 1H), 2.0 (m, 3H), 1.79-1.81 (m, 3H), 1.75 (m, 1H), 1.68 (m, 2H), 1.55-1.61 (m, 6H), 1.34-1.46 (m, 6H); Calculated for MS(m/z) of $C_{35}H_{52}ClN_3O_7$: 662.26, found: 626.74 (M−Cl).

The following compounds can be prepared from the above raw materials according to the methods of Examples 45 and 46:

| Example No | Name of compounds | Molecular formula | MS (m/z) Measured value (Calculated Value) |
|---|---|---|---|
| 47 | | $C_{35}H_{53}ClN_2O_7$ | 613.30 (648.71) |
| 48 | | $C_{36}H_{55}BrN_2O_7$ | 627.32 (707.74) |
| 49 | | $C_{42}H_{62}BrN_3O_8$ | 736.33 (816.86) |
| 50 | | $C_{37}H_{52}ClN_3O_7$ | 650.30 (685.73) |
| 51 | | $C_{38}H_{54}BrN_3O_7$ | 664.32 (744.76) |

| Example No | Name of compounds | Molecular formula | MS (m/z) Measured value (Calculated Value) |
|---|---|---|---|
| 52 | (structure) | $C_{37}H_{56}BrN_3O_8$ | 670.33 (750.76) |
| 53 | (structure) | $C_{41}H_{64}BrN_3O_7$ | 710.32 (790.87) |
| 54 | (structure) | $C_{38}H_{56}BrN_3O_9$ | 698.32 (778.77) |
| 55 | (structure) | $C_{36}H_{52}ClN_3O_8$ | 654.30 (689.72) |
| 56 | (structure) | $C_{37}H_{56}BrN_3O_7$ | 668.32 (748.74) |

Preparation 14

2-[(4-bromoethoxy)phenyl]ethyl alcohol (a) 4-[2-hydroxyethyl]phenol 166 g (1.0 mol) of methyl p-hydroxyphenylacetate was dissolved in 500 mL of methanol, cooled in an ice bath. 56.75 g (1.50 mol) of sodium borohydride was added in batches, and the addition was completed within about 2 hours. The reaction was continued with stirring for 2 hours. The thin layer detection showed that the raw materials were reacted completely. The solvent was removed under reduced pressure. The residue was dissolved in water which is adjusted to be with the pH of 2 by adding 2M hydrochloric acid. The solution was extracted with dichloromethane three times (300 mL×3). The extracts were combined, and dried over anhydrous magnesium sulfate. The desiccant was removed by filtration, the solvent was removed under reduced pressure, and the residue was crystallized with ethyl acetate and petroleum ether (1/5). 120.0 g of the target compound was obtained with a yield of 86.9%.

(b) 2-[(4-bromoethoxy)phenyl]ethylalcohol 30 g (0.217 mol) of the product (a) was dissolved in 300 mL of ethanol. 22.4 (0.26 mol) of sodium bicarbonate was added. 188 g (1.0 mol) of 1,2-dibromoethane was added at the same time. The reaction mixture was heated and stirred. The reaction was carried out at 50° C. for 5 hours. The solvent and excess 1,2-dibromoethane were removed under reduced pressure. The residue was dissolved in 300 mL of dichloromethane, washed with water three times (100 mL×3), and dried over anhydrous magnesium sulfate. The desiccant was removed by filtration. The solvent was removed under reduced pressure to obtain 35.0 g of the target compound with a yield of 65.8%. m/z 245.01, 247.05 (M+H).

Preparation 15

2-[(4-bromopropoxy)phenyl]ethyl alcohol 30 g (0.217 mol) of the product of the Preparation 14(a) was dissolved in 300 mL of ethanol. 22.4 g (0.26 mol) of sodium bicarbonate was added. 202 g (1.0 mol) of 1,3-dibromopropane was added at the same time. The reaction mixture was heated and stirred. The reaction was carried out at 50° C. for 6 hours. The solvent and excess 1,2-dibromopropane were removed under reduced pressure. The residue was dissolved in 300 mL of dichloromethane, washed with water three times (100 mL×3), and dried over anhydrous magnesium sulfate. The desiccant was removed by filtration. The solvent was removed under reduced pressure to obtain 40 g of the target compound with a yield of 71.1%. m/z 259.03, 261.04 (M+H).

Preparation 16

3-(4-bromopropoxyphenyl) propanol (a) 4-(3-hydroxypropyl) phenol 45.0 g (0.25 mol) of methyl p-hydroxyphenylpropionate was dissolved in 200 mL of methanol, cooled in an ice bath. 14.2 g (0.375 mol) of sodium borohydride was added in batches, and the addition was completed within about 1 hour. The reaction was continued with stirring at room temperature for 2 hours. Thin layer detection showed that the raw materials was reacted completely. The solvent was removed under reduced pressure. The residue was dissolved in water which is adjusted to be with the pH 2 by adding 2M hydrochloric acid. The solution was extracted with dichloromethane three times (200 mL×3). The extracts were combined, and dried over anhydrous magnesium sulfate. The desiccant was removed by filtration, the solvent was removed under reduced pressure, and the residue was crystallized with dichloromethane and petroleum ether (1/5). 32.0 g of the target compound was obtained with a yield of 84.2%.

(b) 3-(4-bromopropoxyphenyl)propanol 30 g (0.197 mol) of the product (a) was dissolved in 300 mL of ethanol. 22.4 (0.26 mol) of sodium bicarbonate was added. 161.6 g (0.80 mol) of 1,3-dibromopropane was added at the same time. The reaction mixture was heated and stirred. The reaction was carried out at 50° C. for 5 hours. The solvent and excess 1,3-dibromopropane were removed under reduced pressure. The residue was dissolved in 250 mL of dichloromethane, washed with water three times (100 mL×3), and dried over anhydrous magnesium sulfate. The desiccant was removed by filtration, and the solvent was removed under reduced pressure to obtain 25 g of the target compound with a yield of 46.5%. m/z 273.03, 275.04 (M+H).

Preparation 17

4-bromopropoxybenzylalcohol

The above compound was prepared according to the method of Preparation 16(b), the yield was 75.1%, m/z 245.01, 247.0 (M+H).

Preparation 18

1-(4-bromopropoxyphenyl) acetone 45 g (0.30 mol) of 1-(4-hydroxyphenyl)acetone was dissolved in 300 mL of ethanol. 62.1 g (0.45 mol) of potassium carbonate was added. 161.6 g (0.80 mol) of 1,3-dibromopropane was added at the same time. The reaction mixture was stirred. The reaction was carried out at room temperature for 5 hours, and the solvent and excess 1,3-dibromopropane were removed under reduced pressure. The residue was dissolved in 250 mL of dichloromethane, washed with water three times (100 mL×3), and dried over anhydrous magnesium sulfate. The desiccant was removed by filtration, and the solvent was removed under reduced pressure to obtain 44.8 g of the target compound with a yield of 52.5%. m/z 285.01, 287.02 (M+H).

Preparation 19

1-(4-bromoethoxyphenyl) acetone

The above compound was prepared according to the method of Preparation 18. The yield was 62.3%, m/z 271.03, 273.02 (M+H).

Preparation 20

4-bromopropoxy-3,5-dichlorobenzyl alcohol (a) Methyl 4-hydroxy-3,5-dichlorobenzoate 62.1 g (0.30 mol) of 4-hydroxy-3,5-dichlorobenzoic acid was dissolved in 300 mL of methanol. 3 g of p-toluenesulfonic acid was added. The reaction mixture was heated and refluxed for 6 hours. The solvent was removed under reduced pressure. The residue was dissolved in 500 mL of dichloromethane, washed with water three times (200 mL×3), and dried over anhydrous magnesium sulfate. The desiccant was removed by filtration, and the solvent was removed to obtain 56.3 g of the target product with a yield of 84.9%. m/z 219.01 (M–H).

(b) 4-hydroxy-3,5-dichlorobenzyl alcohol 56 g (0.253 mol) of (a) was dissolved in 300 mL of methanol, cooled in an ice bath. 15.13 g (0.40 mol) of sodium borohydride were added in batches, and the addition was completed within about 1.5 hours. The reaction was continued with stirring for 2 hours, thin layer detection showed that the raw materials were reacted completely. The solvent was removed under reduced pressure. The residue was dissolved in water which is adjusted to be with the pH of 2 by adding 2M hydrochloric acid. The solution was extracted with dichloromethane three times (200 mL×3).

The extracts were combined, and dried over anhydrous magnesium sulfate. The desiccant was removed by filtration, the solvent was removed under reduced pressure, and the residue was crystallized with dichloromethane and petroleum ether (1/5). 30.3 g of the target compound was obtained in 62.0% yield. m/z 192.02 (M–H).

(c) 4-bromopropoxy-3,5-dichlorobenzyl alcohol

The above compound was prepared according to the method of Preparation 16(b), the yield was 68.5%, m/z 311.03 (M–H).

Preparation 21

4-(3-bromopropoxy)acetophenone 40.8 g (0.30 mol) of 4-hydroxyacetophenone was dissolved in 400 mL of methanol. 62.1 g (0.45 mol) of potassium carbonate was added. 161.6 g (0.80 mol) of 1,3-dibromopropane was added at the same time. The reaction mixture was stirred. The reaction was carried out at room temperature for 10 hours. The solvent and excess 1,3-dibromopropane were removed under reduced pressure. The residue was dissolved in 250 mL of dichloromethane, washed with water three times (100 mL×3), and dried over anhydrous magnesium sulfate. The desiccant was removed by filtration, and the solvent was removed under reduced pressure to obtain 44.8 g of the target compound with a yield of 58.1%. m/z 257.01, 259.01 (M+H).

Preparation 22

2-(4-bromopropoxyphenyl)-2-propanol (a) 2-(4-benzyloxyphenyl)-2-propanol 62.3 g (0.25 mol) of 4-benzyloxybromobenzene was dissolved in 300 mL of tetrahydrofuran. 6.3 g (0.263 mol) of magnesium metal was added under the protection of argon. A catalytic amount of iodine was added. The reaction mixture was heated and refluxed for 30 minutes. 58 g (1 mol) of acetone was added dropwise. After the addition, the reflux reaction was continued for 3 hours. The reaction mixture was cooled to room temperature. Under ice bath cooling, 132 mL of 2M hydrochloric acid was added dropwise, and the tetrahydrofuran and excess acetone were removed under reduced pressure. The remaining aqueous phase was extracted 3 times with ethyl ether (200 mL×3) and dried over anhydrous magnesium sulfate overnight. The desiccant was removed by filtration, and the filtrate was concentrated to dryness to obtain 38.8 g of the target product with a yield of 68.0%. m/z 228.11.

(b) 2-(4-hydroxyphenyl)-2-propanol 35 g (0.153 mol) of the product (a) was dissolved in 150 mL of methanol, 2.4 g of 10% Pd—C was added, hydrogen was introduced, the pressure was maintained at 0.4-0.43 MPa, and the temperature was room temperature. After 4 hours of reaction, the reaction was stopped, the catalyst was removed by filtration, and the filtrate was concentrated to dryness under reduced pressure to obtain 18.8 g of the target product with a yield of 80.7%. m/z 152.08.

(c) 2-(4-bromopropoxyphenyl)-2-propanol (b) 15.8 g (0.104 mol) of the product was dissolved in 200 mL of methanol. 31.1 g (0.225 mol) of potassium carbonate was added. 80.8 g (0.40 mol) of 1,3-dibromopropane was added at the same time. The reaction mixture was stirred. The reaction was carried out at room temperature for 20 hours, and the solvent and excess 1,3-dibromopropane were removed under reduced pressure. The residue was dissolved in 250 mL of dichloromethane, washed with water three times (100 mL×3), and dried over anhydrous magnesium sulfate. The desiccant was removed by filtration, and the solvent was removed under reduced pressure to obtain 24.8 g of the target compound with a yield of 87.3%. m/z 272.04, 274.0.

Preparation 23

4-(3-bromopropoxy)propionylbenzene

The above compound was prepared according to the method of Preparation 22(c), the yield was 65.8%, m/z 270.02, 272.02.

Preparation 24

1-[4-(2-bromoethoxy)phenyl]-2-methyl-2-propanol (a) 1-[(4-benzyloxy)phenyl]-2-methyl-2-propanol 131.50 g (0.50 mol) of 4-benzyloxybenzyl bromide was dissolved in 600 mL of tetrahydrofuran. 12.6 g (0.526 mol) of magnesium metal was added under the protection of argon. A catalytic amount of iodine was added. The reaction mixture was stirred at room temperature for 30 minutes. 116 g (2.0 mol) of acetone was added dropwise. After the addition, the reaction was continued with stirring at room temperature for 4 hours. The reaction mixture was cooled with an ice bath, 266 mL of 2M hydrochloric acid was added dropwise, and tetrahydrofuran and excess acetone were removed under reduced pressure. The remaining aqueous phase was extracted with dichloromethane 3 times (400 mL×3) and dried over anhydrous magnesium sulfate overnight. The desiccant was removed by filtration, and the filtrate was concentrated to dryness to obtain 91.2 g of the target product with a yield of 75.28%. m/z 242.31.

(b) 1-[(4-hydroxy)phenyl]-2-methyl-2-propanol 88.0 g (0.363 mol) of the product (a) was dissolved in 400 mL of methanol, 4.4 g of 10% Pd—C was added, hydrogen was introduced, the pressure was maintained at 0.4-0.43 MPa, and the temperature was room temperature. After 5 hours of reaction, the reaction was stopped, the catalyst was removed by filtration, and the filtrate was concentrated to dryness under reduced pressure. The residue was crystallized with dichloromethane/petroleum ether (1:1) to obtain 53.4 g of the target product with a yield of 88.6%. m/z 166.1.

(c) 1-[4-(2-bromoethoxy)phenyl]-2-methyl-2-propanol 20.8 g (0.125 mol) of the product (b) was dissolved in 200 mL of methanol. 31.1 g (0.225 mol) of potassium carbonate was added. 75.2 g (0.40 mol) of 1,2-dibromoethane was added at the same time. The reaction mixture was stirred, heated to 50° C. to react for 20 hours, and filtered. The solvent and excess 1,2-dibromoethane were removed under reduced pressure. The residue was dissolved in 250 mL of dichloromethane, washed with water three times (100 mL×3), and dried over anhydrous magnesium sulfate. The desiccant was removed by filtration, and the solvent was removed under reduced pressure to obtain 21.9 g of the target compound with a yield of 80.3%. m/z 272.04, 274.0.

Preparation 25

1-[4-(2-bromopropoxy)phenyl]-2-methyl-2-propanol

The above compound was prepared according to the method of Preparation 24(b), the yield was 78.9%, m/z 286.05, 288.0.

Preparation 26

3-methyl-4-(3-bromopropoxy)acetophenone 30.38 g (0.20 mol) of 4-hydroxy-3-methylacetophenone was dissolved in 300 mL of methanol. 31.1 g (0.225 mol) of potassium carbonate was added. At the same time 121.2 g (0.60 mol) of 1,3-dibromopropane was added. The reaction mixture was stirred and reacted at room temperature for 20 hours. The solvent and excess 1,3-dibromopropane were removed under reduced pressure. The residue was dissolved in 250 mL of dichloromethane, washed with water three times (100 mL×3), and dried over anhydrous magnesium sulfate. The desiccant was removed by filtration, and the solvent was removed under reduced pressure to obtain 28.3 g of the target compound with a yield of 52.2%. m/z 270.02, 272.0.

Preparation 27

3-methoxy-4-(3-bromopropoxy)acetophenone

The above compound was prepared according to the method of Preparation 26, the yield was 65.8%, m/z 286.02, 288.0.

Preparation 28

(R)-(−)-3-[(R)-2-benzyloxycarboxyl-2-cyclopentyl-2-phenyl]ethoxy-1-azabicyclo[2,2,2]octane 31.45 g (0.10 mol) of the (e) product of Preparation 2 was dissolved in 300 mL of dichloromethane, cooled in an ice bath. 20.0 g of triethylamine was added with stirring for 5 minutes. The reaction temperature was controlled to be below 10° C. 20.40 g (0.12 mol) of benzyloxyformyl chloride was added dropwise. The reaction was carried out at this temperature for 4 hours. The reaction mixture was filtered. The filtrate was diluted by 200 mL of dichloromethane, washed with saturated sodium bicarbonate solution three times (200 mL×3), and dried over anhydrous magnesium sulfate. A part of, about 350 mL of, the solvent was removed under reduced pressure. By adding 200 mL of petroleum ether, the filtrate was cooled and crystallized to obtain 40.50 g of the target compound with a yield of 90.1%. MS 449.26.

Example 57

(R)-(−)-3-[(R)-2-hydroxy-2-cyclopentyl-2-phenyl)]
ethoxy-1-{2-[4-(2-{[(R)-[2-(3-hydroxy methyl-4-hydroxy)phenyl-2-hydroxy]ethylamino}ethyl)phenoxy]ethyl}-1-azabicyclo[2,2,2]octylonium bromide (R)-(−)-3-[(R)-2-hydroxy-2-cyclopentyl-2-phenyl)]
ethoxy-1-{2-[4-(2-{(R)-[2-(3-hydroxymethyl-4-hydroxy)phenyl-2-hydroxy]ethylamino}ethyl)phenoxy]ethyl}-1-azabicyclo[2,2,2]octylonium benzoate

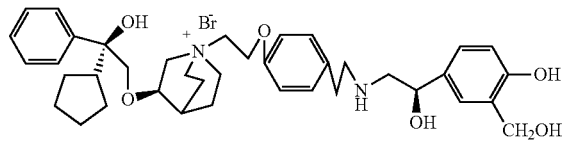

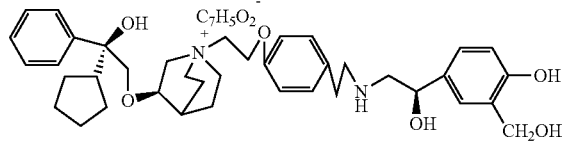

(a) (R)-(−)-3-[(R)-2-benzyloxyformoxy-2-cyclopentyl-2-phenyl)]ethoxy-1-[2-(4-hydroxyeth ylphenoxy) ethyl]-1-azabicyclo[2,2,2]octylonium bromide In a 250 mL three-necked flask, 30 mL of absolute ethanol, and (R)-(−)-3-[(R)-2-benzyloxyformoxy-2-cyclopentyl-2-phenyl]ethoxy-1-azabicyclo[2,2,2]octane (Preparation 28) were added, stirred and dissolved. Then 69.9 g (285.3 mmol) of (4-bromoethoxy)phenylethyl alcohol (Preparation 14) was added. The reaction mixture was stirred and reacted at room temperature for 12 hours. The ethanol was removed under reduced pressure, the excess (4-bromoethoxy)phenethyl alcohol in the residue was removed by column chromatography, and the crude product was crystallized with dichloromethane and n-hexane (2/1) to obtain 20.61 g of the target product with a yield of 75.4%. MS(m/z) 614.23.

(b) (R)-(−)-3-[(R)-2-benzyloxyformoxy-2-cyclopentyl-2-phenyl)]ethoxy-1-[2-(4-methylsulfonyloxyethylphenoxy)ethyl]-1-azabicyclo[2,2,2]octylonium bromide 19.3 g (31.4 mmol) of (a) product was dissolved in 150 mL of dichloromethane. 5.0 g (50.0 mmol) of N-methylmorpholine was added. The reaction mixture is cooled in an ice bath. 5.50 g (48.0 mmol) of methylsulfonyl chloride was added dropwise. The reaction was continued with stirring at this temperature for 4 hours. The solvent was removed under reduced pressure, and 18.8 g of the target product was obtained by column chromatography with a yield of 87.8%, MS(m/z) 682.21.

(c) (R)-(−)-3-[(R)-2-hydroxy-2-cyclopentyl-2-phenyl)]ethoxy-1-{2-[4-(2-{[(R)-[2-(3-benzyl oxymethyl-4-benzyloxy)phenyl-2-hydroxy] ethylamino}ethyl)phenoxy]ethyl}-1-azabicyclo[2,2,2]octylonium bromide 2.396 g (5.283 mmol) of (R)-1-[(4-benzyloxy-3-benzyloxymethyl)phenyl]-2-benzylaminoethanol (Preparation 1)

and 3.57 g (5.283 mmol) of (b) were added to a 50 mL reaction flask. 20 mL of dioxane was added. After the reaction mixture was stirred for 10 minutes, 1.475 g (10.566 mmol) of anhydrous potassium carbonate was added, the temperature of the reaction mixture was increased to 80° C., and the reaction was carried out at this temperature for 5 hours. Thin layer detection showed that the reaction was complete. The reaction was stopped, and the reaction mixture was cooled to room temperature and filtered to remove insoluble substances. The solvent was removed from the filtrate under reduced pressure. 5 mL isopropanol was added to the residue for freeze crystallization, and the solid was filtered and collected to obtain 2.85 g of the target product. The yield was 51.87%. Calculated for MS(m/z) of $C_{61}H_{61}BrN_2O_8$: 1040.0, found: 959.4 (M+Br).

(d) (R)-(−)-3-[(R)-2-hydroxy-2-cyclopentyl-2-phenyl)]ethoxy-1-{2-[4-(2-{[(R)-[2-(3-hydroxymethyl-4-hydroxy)phenyl-2-hydroxy]ethylamino}ethyl)phenoxy]ethyl}-1-azabicyclo[2,2,2]octylonium bromide 2.60 g (2.50 mmol) of the product (c) was placed in a hydrogenation reaction kettle, 18 mL of methanol was added for dissolution, 0.5 g of 10% Pd—C was added, hydrogen was introduced, the pressure was kept at 0.43 MPa, and the temperature was room temperature. After 24 hours of reaction, the reaction was stopped, the catalyst was removed by filtration, the filtrate was concentrated to dryness under reduced pressure, and the residue was crystallized with isopropanol. 1.2 g of the target compound solid was obtained with a yield of 66.0%.

$^1$HNMR (δ ppm) (DMSO-$d_6$) 7.19-7.21 (m, 5H), 7.01 (d, 2H), 6.59-6.95 (m, 5H), 5.0 (s, 1H), 4.79 (s, 2H), 4.74 (m, 1H), 4.04 (t, 2H), 3.93 (d, 1H), 3.68 (d, 1H), 3.15 (m, 1H), 2.67-2.90 (m, 8H), 1.96-2.0 (m, 5H), 1.79-1.81 (m, 3H), 1.74 (m, 1H), 1.69 (m, 2H), 1.56-1.60 (m, 6H), 1.34-1.45 (m, 6H); Calculated for MS(m/z) of $C_{39}H_{53}BrN_2O_6$: 725.75, found: 645.32 (M+Br).

(e) (R)-(−)-3-[(R)-2-hydroxy-2-cyclopentyl-2-phenyl)]ethoxy-1-{2-[4-(2-{(R)-[2-(3-hydroxymethyl-4-hydroxy)phenyl-2-hydroxy]ethylamino}ethyl)phenoxy]ethyl}-1-azabicyclo[2,2,2]octylonium benzoate 0.545 g (0.75 mmol) of product (d) was dissolved in 50 mL of water, adsorbed and eluted with a strong alkaline anion exchange column. The eluent was concentrated to 50 mL under reduced pressure. The reaction mixture was added with 2 mL ethanol solution containing 100 mg benzoic acid, stirred for 5 minutes, and concentrated to dryness under reduced pressure. The residue was crystallized with isopropanol. 0.42 g of the target product was obtained with a yield of 72.9%. Elemental analysis (%) (calculated value) C, 71.98 (72.04), H, 7.52 (7.62), N, 3.61 (3.65).

Example 58

(R)-(−)-3-[(R)-2-hydroxy-2-cyclopentyl-2-phenyl]ethoxy-1-{3-[4-(1-{(R)-[2-hydroxy-2-(8-hydroxy-2-oxo-1,2-dihydroquinolin-5-yl)]ethylamino}methyl)phenoxy]propyl}-1-azabicyclo[2,2,2]octylonium bromide

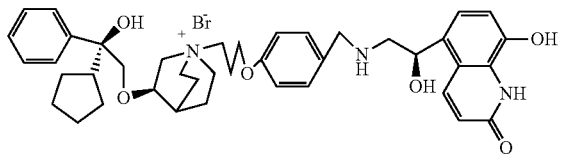

(a) (R)-(−)-3-[(R)-2-benzyloxyformoxy-2-cyclopentyl-2-phenyl)]ethoxy-1-[3-(4-hydroxymethylphenoxy)propyl]-1-azabicyclo[2,2,2]octylonium bromide The above compound was prepared according to the method of Example 57(a).

(b) (R)-(−)-3-[(R)-2-benzyloxyformoxy-2-cyclopentyl-2-phenyl)]ethoxy-1-[3-(4-methylsulfonyloxymethylphenoxy)propyl]-1-azabicyclo[2,2,2]octylonium bromide The above compound was prepared according to the method of Example 57(b).

(c) (R)-(−)-3-[(R)-2-benzyloxyformoxy-2-cyclopentyl-2-phenyl]ethoxy-1-{3-[4-(1-{(R)-[2-hydroxy-2-(8-benzyloxy-2-oxo-1,2-dihydroquinolin-5-yl)]ethylamino}methyl)phenoxy]propyl}-1-azabicyclo[2,2,2]octylonium bromide 2.0 g (5.0 mmol) of 8-benzyloxy-5-[(R)-2-benzylamino-1-hydroxyethyl]-(1H)-quinolin-2-one (Preparation 2) and 3.20 g (5.0 mmol) of (b) were added to a 50 mL reaction flask. 20 mL dioxane was added. After the reaction mixture was stirred for 10 minutes, 1.475 g (10.566 mmol) of anhydrous potassium carbonate was added. The temperature of the reaction mixture was increased to 80° C. The reaction was carried out at this temperature for 5 hours. Thin layer detection showed that the reaction was complete. The reaction was stopped, and the reaction mixture was cooled to room temperature and filtered to remove insoluble substances. The solvent was removed from the filtrate under reduced pressure, 5 mL isopropanol was added to the residue for freeze crystallization, and the solid was filtered and collected to obtain 2.6 g of the target product. The yield was 52.6%. Calculated for MS(m/z) of $C_{56}H_{64}BrN_3O_8$: 986.89, found: 906.35 (M+Br).

(d) (R)-(−)-3-[(R)-2-hydroxy-2-cyclopentyl-2-phenyl]ethoxy-1-{3-[4-(1-{(R)-[2-hydroxy-2-(8-hydroxy-2-oxo-1,2-dihydroquinolin-5-yl)]ethylamino}methyl)phenoxy]propyl}-1-azabicyclo[2,2,2]octylonium bromide 2.40 g (2.43 mmol) of product (c) was placed in a hydrogenation reaction kettle, 20 mL of methanol was added for dissolution, 0.5 g of 10% Pd—C was added, hydrogen was introduced, the pressure was maintained at 0.43 MPa, and the temperature was room temperature. After 15 hours of reaction, the reaction was stopped, the catalyst was removed by filtration, the filtrate was concentrated to dryness under reduced pressure, and the residue was crystallized with isopropanol. 1.08 g of the target compound solid was obtained with a yield of 58.2%.

$^1$HNMR (δ ppm) (DMSO-$d_6$) 8.01 (s, 1H), 7.35 (d, 1H), 7.19-7.21 (m, 5H), 6.95 (d, 2H), 6.71 (d, 1H) 6.57-6.65 (m, 3H), 6.52 (d, 1H), 5.01 (s, 1H), 4.74 (m, 1H), 3.94 (m, 3H), 3.81 (t, 2H), 3.68 (d, 1H), 3.15 (m, 1H), 2.90 (m, 1H), 2.84 (m, 1H), 2.36 (m, 2H), 2.10 (s, 1H), 2.0 (m, 4H), 1.79-1.82 (m, 5H), 1.75 (m, 1H), 1.68 (m, 2H), 1.56-1.60 (m, 6H), 1.35-1.46 (m, 6H).

Calculated for MS(m/z) of $C_{41}H_{52}BrN_3O_6$: 762.772, found: 682.30 (M+Br).

Example 59

(R)-(−)-3-[(R)-2-hydroxy-2-cyclopentyl-2-phenyl]ethoxy-1-{3-[(3,5-dichloro-4-(1-{(R)-[2-hydroxy-2-(3-formamido-4-hydroxy)phenyl]ethylamino}methyl)phenoxy)propyl}-1-azabicyclo[2,2,2]octylonium bromide

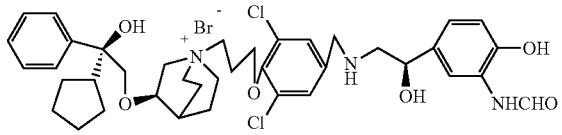

(a) (R)-(−)-3-[(R)-2-benzyloxyformoxy-2-cyclopentyl-2-phenyl)]ethoxy-1-{3-[3,5-dichloro-4-(hydroxymethyl)phenoxy]propyl}-1-azabicyclo[2,2,2]octylonium bromide The above compound was prepared according to the method of Example 57(a).

(b) (R)-(−)-3-[(R)-2-benzyloxyformoxy-2-cyclopentyl-2-phenyl)]ethoxy-1-{3-[3,5-dichloro-4-(methanesulfonyloxymethyl)phenoxy]propyl}-1-azabicyclo[2,2,2]octylonium bromide The above compound was prepared according to the method of Example 57(b).

(c) (R)-(−)-3-[(R)-2-benzyloxyformoxy-2-cyclopentyl-2-phenyl]ethoxy-1-{3-[(3,5-dichloro-4-(1-{(R)-[2-hydroxy-2-(3-formamido-4-benzyloxy)phenyl]ethylamino}methyl)phenoxy)propyl}-1-azabicyclo[2,2,2]octylonium bromide 1.882 g (5.0 mmol) of (R)-2-benzylamino-1-[(4-benzyloxy-3-formamido)phenyl]ethanol (Preparation 4) and 3.69 g (5.0 mmol) of (b) were added to a 50 mL reaction flask, 30 mL acetonitrile was added. After the reaction mixture was stirred for 10 minutes, 1.5 g (11.0 mmol) of anhydrous potassium carbonate was added, the temperature of the reaction mixture was increased to 65-70° C. The reaction was carried out at this temperature for 10 hours. Thin layer detection showed that the reaction was complete. The reaction was stopped, and the reaction mixture was cooled to room temperature and filtered to remove insoluble substances. The solvent was removed from the filtrate under reduced pressure, 5 mL isopropanol was added to the residue for freeze crystallization, and the solid was filtered and collected to obtain 2.92 g of the target product. The yield was 56.6%. Calculated for MS(m/z) of $C_{54}H_{62}BrCl_2N_3O$: 1031.76, found: 950.27 (M+Br).

(d) (R)-(−)-3-[(R)-2-hydroxy-2-cyclopentyl-2-phenyl]ethoxy-1-{3-[(3,5-dichloro-4-(1-{(R)-[2-hydroxy-2-(3-formamido-4-hydroxy)phenyl]ethylamino}methyl)phenoxy)propyl}-1-azabicyclo[2,2,2]octylonium bromide 2.80 g (2.71 mmol) of the product (c) was placed in a hydrogenation reaction kettle, 30 mL of methanol was added for dissolution, 0.8 g of 10% Pd—C was added, hydrogen was introduced, the pressure was maintained at 0.4-0.43 MPa, and the temperature was room temperature. After 15 hours of reaction, the reaction was stopped, the catalyst was removed by filtration, the filtrate was concentrated to dryness under reduced pressure, and the residue was crystallized with isopropanol. 1.38 g of the target compound solid was obtained with a yield of 63.1%.

$^1$HNMR (δ ppm) (DMSO-$d_6$) 8.20 (s, 1H), 7.40 (m, 1H), 7.18-7.21 (m, 5H), 6.84 (d, 2H) 6.64-6.76 (m, 2H), 5.01 (s, 1H), 4.73 (m, 1H), 4.01 (s, 1H), 3.93 (m, 3H), 3.81 (d, 2H), 3.68 (d, 1H), 3.15 (m, 1H), 2.90 (m, 1H), 2.83 (m, 1H), 2.36 (m, 2H), 2.10 (s, 2H), 1.98-2.0 (m, 3H), 1.79-1.81 (m, 5H), 1.75 (m, 1H), 1.69 (m, 2H), 1.55-1.61 (m, 6H), 1.34-1.46 (m, 6H); Calculated for MS(m/z) of $C_{39}H_{50}BrCl_2N_3O_6$: 807.64, found: 726.22 (M+Br).

Example 60

(R)-(−)-3-[(R)-2-hydroxy-2-cyclopentyl-2-phenyl]ethoxy-1-{2-[4-(2-{(R)[-2-hydroxy-2-(6-hydroxy-2H-1,4-benzoxazin-3(4H)-one-8-yl)]ethylamino}isobutyl)phenoxy]ethyl}-1-azabicyclo[2,2,2]octylonium bromide

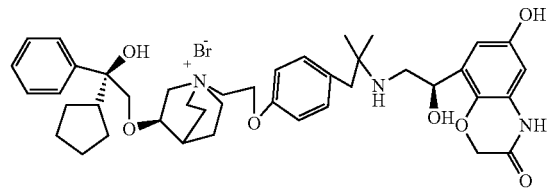

(a) (R)-(−)-3-[(R)-2-benzyloxyformoxy-2-cyclopentyl-2-phenyl)]ethoxy-1-{2-[4-(2-hydroxy-2-methyl)propylphenoxy]ethyl}-1-azabicyclo[2,2,2]octylonium bromide The above compound was prepared according to the method of Example 57(a).

(b) (R)-(−)-3-[(R)-2-benzyloxyformoxy-2-cyclopentyl-2-phenyl)]ethoxy-1-{2-[4-(2-methylsulfonyloxy-2-methyl)propylphenoxy]ethyl)-1-azabicyclo[2,2,2]octylonium bromide The above compound was prepared according to the method of Example 57(b).

(c) (R)-(−)-3-[(R)-2-benzyloxyformoxy-2-cyclopentyl-2-phenyl)]ethoxy-1-{2-[4-(2-{(R)-[2-hydroxy-2-[(6-benzyloxy-2H-1,4-benzoxazin-3(4H)-one-8-yl)]ethylamino}isobutyl)phenoxy]ethyl}-1-azabicyclo[2,2,2]octylonium bromide 2.02 g (5.0 mmol) of 8-[(1R)-1-hydroxy-2-benzylamine]ethyl-6-benzyloxy-2H-1,4-benzoxazin-3(4H)-one (Preparation 5) and 3.57 g (5.0 mmol) of (b) were added to a 50 mL reaction flask. 30 mL dioxane was added. After the reaction mixture was stirred for 10 minutes, 1.0 g (7.35 mmol) of anhydrous potassium carbonate was added. The temperature of the reaction mixture was increased to 55-60° C. The reaction was carried out at this temperature for 10 hours. Thin layer detection showed that the reaction was complete. The reaction was stopped, and the reaction mixture was cooled to room temperature and filtered to remove insoluble substances. The solvent was removed from the filtrate under reduced pressure, 10 mL of isopropanol was added to the residue for freeze crystallization, and the solid was filtered and collected to obtain 2.98 g of the target product. The yield was 58.5%.

Calculated for MS(m/z) of $C_{57}H_{68}BrN_3O_9$: 1018.93, found: 938.38 (M+Br).

(d) (R)-(−)-3-[(R)-2-hydroxy-2-cyclopentyl-2-phenylethoxy]-1-{2-[4-(2-{(R)-2-hydroxy-2-[(6-hydroxy-2H-1,4-benzoxazin-3(4H)-one-8-yl)]ethylamino}isobutyl)phenoxy]ethyl}-1-azabicyclo[2,2,2]octylonium bromide 2.80 g (2.75 mmol) of product (c) was placed in a hydrogenation reaction kettle, 20 mL of methanol was added for dissolution, 0.8 g of 10% Pd—C was added, hydrogen was introduced, the pressure was kept at 0.43 MPa, and the temperature was room temperature. After 12 hours of reaction, hydrogen absorption was stopped, the reaction was stopped, the catalyst was removed by filtration, the filtrate was concentrated to dryness under reduced pressure, and the residue was crystallized with isopropanol. 1.46 g of the target compound solid was obtained with a yield of 66.8%. $^1$HNMR (δ ppm) (DMSO-$d_6$) 8.01 (s, 1H), 7.18-7.20 (m, 5H), 7.01 (d, 2H), 6.72 (d, 2H), 6.65 (d, 1H), 6.20 (d, 1H), 5.01 (s, 1H), 4.87 (s, 2H), 4.74 (m, 1H), 4.04 (t, 2H), 3.93 (s, 1H), 3.68 (d, 1H), 3.14 (m, 1H), 2.91 (m, 1H), 2.84 (m, 1H), 2.78 (t, 2H), 2.59 (s, 2H), 2.10 (m, 2H), 2.0 (m, 2H), 1.96 (m, 1H), 1.79-1.81 (m, 3H), 1.75 (m, 1H), 1.69 (m, 2H), 1.56-1.60 (m, 6H), 1.34-1.46 (m, 6H), 1.15 (s, 6H).

Calculated for MS(m/z) of $C_{42}H_{56}BrN_3O_7$: 794.93, found: 714.33 (M+Br).

Preparation 29

(R)-1-[(4-hydroxy-3-hydroxymethyl)phenyl]-2-aminoethanol 44 g (0.10 mol) of the product (g) of preparation 1 was dissolved in 300 mL of methanol in a hydrogenation reaction kettle, 6.6 g of 10% Pd—C was added, hydrogen was introduced, the pressure was maintained at 0.43 MPa, hydrogen absorption was stopped after the hydrogenation reaction was carried out at room temperature for 20 hours, the reaction was stopped, the catalyst was removed by filtration, the filtrate was concentrated to dryness under reduced pressure, and the residue was crystallized with isopropanol. 15.6 g of the target compound solid was obtained with a yield of 85.1%. MS(m/z) 182.09 (M−H).

Preparation 30

8-hydroxy-5-[(R)-2-amino-1-hydroxyethyl]-1H-quinolin-2-one

The above compound was prepared according to the method of Preparation 29 using the product (f) of Preparation 3.

Preparation 31

(R)-2-amino-1-[(4-hydroxy-3-formamido)phenyl]ethanol

The above compound was prepared according to the method of Preparation 29 using the product (d) of Preparation 4.

Preparation 32

8-[(1R)-1-hydroxy-2-amino]ethyl-6-hydroxy-2H-1,4-benzoxazin-3(4H)-one

The above compound was prepared according to the method of Preparation 29 using the product (g) of Preparation 5.

Example 61

(R)-(−)-3-[(R)-2-hydroxy-2-cyclopentyl-2-phenyl]ethoxy]-1-{2-[4-(2-{(R)-[2-hydroxy-2-(3-formamido-4-hydroxy)phenyl]ethylamino}propyl)phenoxy]ethyl}-1-azabicyclo[2,2,2]octylonium bromide

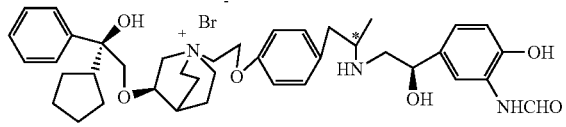

(a) (R)-(−)-3-[(R)-2-hydroxy-2-cyclopentyl-2-phenyl]ethoxy-1-[2-(4-acetonylphenoxy)ethyl]-1-azabicyclo[2,2,2]octylonium bromide The above compound was prepared according to the method of Example 57(a).

(b) (R)-(−)-3-[(R)-2-hydroxy-2-cyclopentyl-2-phenyl]ethoxy]-1-{2-[4-(2-{(R)-[2-hydroxy-2-(3-formamido-4-hydroxy)phenyl]ethylamino}propyl)phenoxy]ethyl}-1-azabicyclo[2,2,2]octylonium bromide The above compound was prepared according to the method of Example 3(b). 0.981 g (5.0 mmol) of (R)-2-amino-1-[(4-hydroxy-3-formamido)phenyl]ethanol (Preparation 31) and 2.86 g (5.0 mmol) OF (a) were added to a 50 mL reaction flask, 50 mL dichloromethane was added. After the reaction mixture was stirred for 10 minutes, 1.27 g (6.0 mmol) of sodium triacetyl borohydride was added, and 1 drop of acetic acid was added for catalysis. The reaction mixture was reacted for 24 hours at room temperature, and thin layer detection showed that the reaction was complete. The reaction was stopped, and the reaction mixture was cooled to room temperature and filtered to remove insoluble substances. The solvent was removed from the filtrate under reduced pressure, 5 mL of ethanol was added to the residue for freeze crystallization, and the solid was filtered and collected to obtain 1.56 g of the target product. The yield was 73.6%. $^1$HNMR (δ ppm) (DMSO-$d_6$) 8.20 (s, 1H), 7.40 (m, 1H), 7.18-7.20 (m, 5H), 7.01 (d, 2H), 6.72 (d, 2H), 6.66-6.71 (m, 2H), 5.0 (s, 1H), 4.74 (m, 1H), 4.04 (t, 2H), 4.0 (s, 1H), 3.92 (d, 1H), 3.67 (d, 1H), 3.15-3.18 (m, 2H), 2.91 (m, 1H), 2.78 (t, 2H), 2.54 (m, 2H), 2.76-2.51 (dd, 2H), 2.10 (s, 1H), 1.96-2.0 (m, 4H), 1.79-1.81 (m, 3H), 1.75 (m, 1H), 1.69 (m, 2H), 1.55-1.61 (m, 6H), 1.34-1.46 (m, 6H), 1.10 (d, 3H); Calculated for MS(m/z) of $C_{40}H_{54}BrN_3O_6$: 752.78, found: 671.32 (M+Br).

(c) Preparation of Compound 61-S and Compound 61-R 0.80 g of product (b) was dissolved in 5 mL of methanol, separated and purified with a preparation column, gradient elution was carried out using the mixed acetonitrile and water, to respectively collect 61-S and 61-R components, the solvent was removed under reduced pressure, and the residue was crystallized with ethanol to obtain 0.28 g of compound (61-S) and 0.31 g of compound (63-R).

Example 62

(R)-(-)-3-[(R)-2-hydroxy-2-cyclopentyl-2-phenyl]ethoxy-1-{3-[4-(1-{(R)-[2-hydroxy-2-(8-hydroxy-2-oxo-1,2-dihydroquinolin-5-yl)]ethylamino}propylidene)phenoxy]propyl}-1-azabicyclo[2,2,2]octylonium bromide

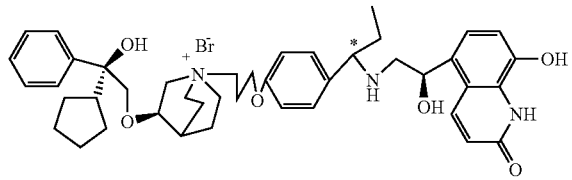

(a) (R)-(-)-3-[(R)-2-hydroxy-2-cyclopentyl-2-phenyl]ethoxy-1-[3-(4-propionylphenoxy)propyl]-1-azabicyclo[2,2,2]octylonium bromide The above compound was prepared according to the method of Example 57(a).

(b) (R)-(-)-3-[(R)-2-hydroxy-2-cyclopentyl-2-phenyl]ethoxy-1-{3-[4-(1-{(R)-[2-hydroxy-2-(8-hydroxy-2-oxo-1,2-dihydroquinolin-5-yl)]ethylamino}propylidene)phenoxy]propyl}-1-azabicyclo[2,2,2]octylonium bromide 1.27 g (6.0 mmol) of sodium triacetyl borohydride was suspended in 50 mL of dichloromethane, 1.10 g (5.0 mmol) of 8-hydroxy-5-[(R)-2-amino-1-hydroxyethyl]-1H-quinolin-2-one (Preparation 30) and 3.0 g (5.0 mmol) of (a) were added, and 1 drop of acetic acid was added for catalysis. The reaction was continued with stirring for 20 hours at room temperature. Thin layer detection showed that the reaction was complete. The reaction was stopped, and the reaction mixture was cooled to room temperature and filtered to remove insoluble substances. The solvent was removed from the filtrate under reduced pressure, 8 mL isopropanol was added to the residue for freeze crystallization, and the solid was filtered and collected to obtain 2.3 g of the target product. The yield was 58.2%.

$^1$HNMR (δ ppm) (DMSO-$d_6$) 8.01 (s, 1H), 7.36 (d, 1H), 7.19-7.21 (m, 5H), 7.02 (d, 2H), 6.71 (m, 3H) 6.56 (d, 1H), 6.52 (d, 1H), 5.01 (s, 1H), 4.74 (m, 1H), 3.94-3.90 (m, 4H), 3.67 (d, 1H), 3.16 (m, 1H), 2.91 (m, 1H), 2.84 (m, 1H), 2.36 (m, 2H), 2.10 (s, 1H), 2.0 (m, 3H), 1.79-1.81 (m, 5H), 1.75-1.74 (m, 3H), 1.69 (m, 2H), 1.55-1.61 (m, 6H), 1.35-1.46 (m, 6H), 0.96 (t, 3H).

Calculated for MS(m/z) of $C_{43}H_{56}BrN_3O_6$: 790.82, found: 719.32 (M+Br).

(c) Preparation of Compound 62-S and Compound 62-R 1.10 g of product (b) was dissolved in 10 mL of methanol, separated and purified with a preparation column. Gradient elution was carried out using the mixed acetonitrile and water to respectively collect eluants of 62-S and 62-R components. The solvent was removed under reduced pressure, and the residue was crystallized with isopropanol to obtain 0.35 g of compound (62-S) and 0.30 g of compound (62-R), respectively.

Example 63

(R)-(-)-3-[(R)-2-hydroxy-2-cyclopentyl-2-phenyl]ethoxy-1-{3-[(4-(3-methyl-1-{(R)-[2-hydroxy-2-(6-hydroxy-2H-1,4-benzoxazin-3(4H)-one-8-yl)]ethylamino}ethylidene)phenoxy]propyl}-1-azabicyclo[2,2,2]octylonium bromide

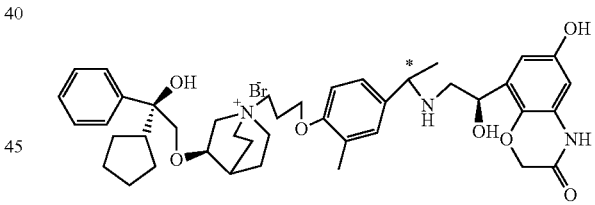

(a) (R)-(-)-3-[(R)-2-hydroxy-2-cyclopentyl-2-phenyl]ethoxy-1-{3-[(4-acetyl-3-methyl)phenoxy]propyl}-1-azabicyclo[2,2,2]octylonium bromide The above compound was prepared according to the method of Example 57(a).

(b) (R)-(-)-3-[(R)-2-hydroxy-2-cyclopentyl-2-phenyl]ethoxy-1-{3-[(4-(3-methyl-1-{(R)-[2-hydroxy-2-(6-hydroxy-2H-1,4-benzoxazin-3(4H)-one-8-yl)]ethylamino ethylidene)phenoxy]propyl}-1-azabicyclo[2,2,2]octylonium bromide 1.27 g (6.0 mmol) of sodium triacetyl borohydride was suspended in 50 mL of dichloromethane, 1.12 g (5.0 mmol) of 8-hydroxy-5-[(R)-2-amino-1-hydroxyethyl]-(1H)-quinolin-2-one (Preparation 32) and 2.93 g (5.0 mmol) of (a) were added, and 1 drop of acetic acid was added for catalysis. The reaction was continued with stirring for 18 hours at room temperature. Thin layer detection showed that the reaction was complete. The reaction was stopped, and the reaction mixture was cooled to room temperature and filtered to remove insoluble substances. The solvent was removed from the filtrate under reduced pressure, the residue was added with 6 mL of ethanol for freeze crystallization, and the solid was filtered and collected to obtain 1.86 g of the target product. The yield was 46.8%.

$^1$HNMR (δ ppm) (DMSO-d$_6$) 8.02 (s, 1H), 7.19-7.21 (m, 5H), 6.82 (m, 2H), 6.65-6.60 (m, 2H), 6.20 (d, 1H), 5.0 (s, 1H), 4.88 s, 2H), 4.74 (m, 1H), 4.08 (q, 1H), 3.94 (m, 3H), 3.68 (d, 1H), 3.15 (m, 1H), 2.91 (m, 1H), 2.84 (m, 1H), 2.35 (m, 4H), 2.09 (m, 1H), 2.0 (m, 2H), 1.96 (m, 1H), 1.79-1.81 (m, 5H), 1.75 (m, 1H), 1.69 (m, 2H), 1.56-1.60 (m, 6H), 1.34-1.46 (m, 9H).

Calculated for MS(m/z) of $C_{42}H_{56}BrN_3O_7$: 794.81, found: 714.30 (M+Br).

(c) Preparation of Compound 63-S and Compound 63-R 0.60 g of product (b) was dissolved in 3 mL of methanol, separated and purified with a preparation column. Gradient elution was carried out using the mixed acetonitrile and water to collect 63-S and 63-R components. The solvent was removed under reduced pressure, and the residue was crystallized with isopropanol to obtain 0.146 g of compound 63-S and 0.187 g of compound 63-R, respectively.

The following compounds can be synthesized using raw materials described above and similar methods.

| Example No. | Name of compounds | Molecular formula | MS (m/z) Measured value (Calculated Value) |
|---|---|---|---|
| 64 | | $C_{39}H_{53}BrN_2O_6$ | 645.31 (725.75) |
| 65 | | $C_{38}H_{53}BrN_2O_6S$ | 665.32 (745.81) |
| 66 | | $C_{41}H_{57}BrN_2O_6$ | 673.34 (753.81) |
| 67 | | $C_{45}H_{65}BrN_2O_6$ | 729.34 (809.91) |
| 67-S | | $C_{45}H_{65}BrN_2O_6$ | 729.34 (809.91) |

-continued

| Example No. | Name of compounds | Molecular formula | MS (m/z) Measured value (Calculated Value) |
|---|---|---|---|
| 67-R | | $C_{45}H_{65}BrN_2O_6$ | 729.34 (809.91) |
| 68 | | $C_{39}H_{51}BrCl_2N_2O_6$ | 713.23 (794.64) |
| 69 | | $C_{40}H_{55}BrN_2O_6$ | 659.32 (739.79) |
| 69-S | | $C_{40}H_{55}BrN_2O_6$ | 659.32 (739.79) |
| 69-R | | $C_{40}H_{55}BrN_2O_6$ | 659.32 (739.79) |
| 70 | | $C_{41}H_{57}BrN_2O_7$ | 689.34 (769.80) |
| 70-S | | $C_{41}H_{57}BrN_2O_7$ | 689.34 (769.80) |

-continued

| Example No. | Name of compounds | Molecular formula | MS (m/z) Measured value (Calculated Value) |
|---|---|---|---|
| 70-R | | $C_{41}H_{57}BrN_2O_7$ | 689.34 (769.80) |
| 71 | | $C_{41}H_{57}BrN_2O_6$ | 673.34 (753.81) |
| 72 | | $C_{41}H_{57}BrN_2O_6$ | 673.33 (753.80) |
| 72-S | | $C_{41}H_{57}BrN_2O_6$ | 673.33 (753.80) |
| 72-R | | $C_{41}H_{57}BrN_2O_6$ | 673.33 (753.80) |
| 73 | | $C_{42}H_{59}BrN_2O_6$ | 687.35 (767.85) |
| 74 | | $C_{41}H_{57}BrN_2O_6$ | 673.34 (753.81) |

| Example No. | Name of compounds | Molecular formula | MS (m/z) Measured value (Calculated Value) |
|---|---|---|---|
| 75 | | $C_{40}H_{55}BrN_2O_6$ | 659.31 (739.78) |
| 75-S | | $C_{40}H_{55}BrN_2O_6$ | 659.31 (739.78) |
| 75-R | | $C_{40}H_{55}BrN_2O_6$ | 659.31 (739.78) |
| 76 | | $C_{40}H_{55}BrN_2O_6$ | 659.32 (739.79) |
| 76-S | | $C_{40}H_{55}BrN_2O_6$ | 659.32 (739.79) |
| 76-R | | $C_{40}H_{55}BrN_2O_6$ | 659.32 (739.79) |
| 77 | | $C_{43}H_{55}N_3O_8$ | 682.30 (741.91) |

-continued

| Example No. | Name of compounds | Molecular formula | MS (m/z) Measured value (Calculated Value) |
|---|---|---|---|
| 78 | | $C_{42}H_{53}BrClN_3O_6$ | 731.32 (811.24) |
| 79 | | $C_{43}H_{56}BrN_3O_6$ | 710.34 (790.83) |
| 80 | | $C_{43}H_{56}BrN_3O_6$ | 710.34 (790.83) |
| 80-S | | $C_{43}H_{56}BrN_3O_6$ | 710.34 (790.83) |
| 80-R | | $C_{43}H_{56}BrN_3O_6$ | 710.34 (790.83) |
| 81 | | $C_{39}H_{50}BrN_3O_7$ | 672.30 (752.73) |

-continued

| Example No. | Name of compounds | Molecular formula | MS (m/z) Measured value (Calculated Value) |
|---|---|---|---|
| 82 | | $C_{43}H_{56}BrN_3O_6$ | 710.34 (790.83) |
| 82-S | | $C_{43}H_{56}BrN_3O_6$ | 710.34 (790.83) |
| 82-R | | $C_{43}H_{56}BrN_3O_6$ | 710.34 (790.83) |
| 83 | | $C_{42}H_{54}BrN_3O_6$ | 696.32 (776.80) |
| 83-S | | $C_{42}H_{54}BrN_3O_6$ | 696.32 (776.80) |
| 83-R | | $C_{42}H_{54}BrN_3O_6$ | 696.32 (776.80) |

-continued

| Example No. | Name of compounds | Molecular formula | MS (m/z) Measured value (Calculated Value) |
|---|---|---|---|
| 84 | | $C_{43}H_{56}BrN_3O_6$ | 710.34 (790.83) |
| 85 | | $C_{44}H_{58}BrN_3O_6$ | 724.35 (804.86) |
| 86 | | $C_{43}H_{56}BrN_3O_6$ | 710.34 (790.83) |
| 87 | | $C_{42}H_{54}BrN_3O_6$ | 696.32 (776.80) |
| 87-S | | $C_{42}H_{54}BrN_3O_6$ | 696.32 (776.80) |

-continued

| Example No. | Name of compounds | Molecular formula | MS (m/z) Measured value (Calculated Value) |
|---|---|---|---|
| 87-R | | $C_{42}H_{54}BrN_3O_6$ | 696.32 (776.80) |
| 88 | | $C_{42}H_{54}BrN_3O_6$ | 696.31 (776.81) |
| 88-S | | $C_{42}H_{54}BrN_3O_6$ | 696.31 (776.81) |
| 88-R | | $C_{42}H_{54}BrN_3O_6$ | 696.31 (776.81) |
| 89 | | $C_{39}H_{52}BrN_3O_6$ | 658.30 (738.75) |
| 90 | | $C_{39}H_{52}BrN_3O_6$ | 658.31 (738.76) |

-continued

| Example No. | Name of compounds | Molecular formula | MS (m/z) Measured value (Calculated Value) |
|---|---|---|---|
| 91 | | $C_{40}H_{54}BrN_3O_6$ | 672.32 (752.78) |
| 92 | | $C_{41}H_{56}BrN_3O_6$ | 686.34 (766.80) |
| 93 | | $C_{41}H_{56}BrN_3O_6$ | 686.33 (766.81) |
| 93-S | | $C_{41}H_{56}BrN_3O_6$ | 686.33 (766.81) |
| 93-R | | $C_{41}H_{56}BrN_3O_6$ | 686.33 (766.81) |
| 94 | | $C_{40}H_{54}BrN_3O_6$ | 672.32 (752.78) |
| 94-S | | $C_{40}H_{54}BrN_3O_6$ | 672.32 (752.78) |

-continued

| Example No. | Name of compounds | Molecular formula | MS (m/z) Measured value (Calculated Value) |
|---|---|---|---|
| 94-R | | $C_{40}H_{54}BrN_3O_6$ | 672.32 (752.78) |
| 95 | | $C_{41}H_{56}BrN_3O_7$ | 702.33 (782.80) |
| 95-S | | $C_{41}H_{56}BrN_3O_7$ | 702.33 (782.80) |
| 95-R | | $C_{41}H_{56}BrN_3O_7$ | 702.33 (782.80) |
| 96 | | $C_{41}H_{56}BrN_3O_6$ | 686.33 (766.81) |
| 97 | | $C_{41}H_{56}BrN_3O_6$ | 686.34 (766.80) |
| 97-S | | $C_{41}H_{56}BrN_3O_6$ | 686.34 (766.80) |

-continued

| Example No. | Name of compounds | Molecular formula | MS (m/z) Measured value (Calculated Value) |
|---|---|---|---|
| 97-R | | $C_{41}H_{56}BrN_3O_6$ | 686.34 (766.80) |
| 98 | | $C_{42}H_{58}BrN_3O_6$ | 700.34 (780.82) |
| 99 | | $C_{41}H_{56}BrN_3O_6$ | 700.32 (780.83) |
| 100 | | $C_{41}H_{56}BrN_3O_6$ | 686.33 (766.81) |
| 100-S | | $C_{41}H_{56}BrN_3O_6$ | 686.33 (766.81) |
| 100-R | | $C_{41}H_{56}BrN_3O_6$ | 686.33 (766.81) |

-continued

| Example No. | Name of compounds | Molecular formula | MS (m/z) Measured value (Calculated Value) |
|---|---|---|---|
| 101 | | $C_{40}H_{52}BrN_3O_7$ | 686.30 (766.76) |
| 102 | | $C_{40}H_{52}BrN_3O_7$ | 686.31 (766.75) |
| 103 | | $C_{41}H_{54}BrN_3O_7$ | 700.32 (780.79) |
| 104 | | $C_{42}H_{56}BrN_3O_7$ | 714.33 (794.81) |
| 105 | | $C_{42}H_{56}BrN_3O_7$ | 714.32 (794.80) |

-continued

| Example No. | Name of compounds | Molecular formula | MS (m/z) Measured value (Calculated Value) |
|---|---|---|---|
| 105-S | | $C_{42}H_{56}BrN_3O_7$ | 714.32 (794.80) |
| 105-R | | $C_{42}H_{56}BrN_3O_7$ | 714.32 (794.80) |
| 106 | | $C_{39}H_{49}BrCl_2N_4O_7$ | 756.22 (836.645) |
| 107 | | $C_{41}H_{54}BrN_3O_7$ | 700.32 (780.79) |
| 107-S | | $C_{41}H_{54}BrN_3O_7$ | 700.32 (780.79) |

| Example No. | Name of compounds | Molecular formula | MS (m/z) Measured value (Calculated Value) |
|---|---|---|---|
| 107-R | | $C_{41}H_{54}BrN_3O_7$ | 700.32 (780.79) |
| 108 | | $C_{42}H_{56}BrN_3O_8$ | 730.33 (810.81) |
| 108-S | | $C_{42}H_{56}BrN_3O_8$ | 730.33 (810.81) |
| 108-R | | $C_{42}H_{56}BrN_3O_8$ | 730.33 (810.81) |
| 109 | | $C_{42}H_{56}BrN_3O_7$ | 714.32 (794.80) |

-continued

| Example No. | Name of compounds | Molecular formula | MS (m/z) Measured value (Calculated Value) |
|---|---|---|---|
| 110 | | $C_{42}H_{56}BrN_3O_7$ | 714.31 (794.82) |
| 110-S | | $C_{42}H_{56}BrN_3O_7$ | 714.31 (794.82) |
| 110-R | | $C_{42}H_{56}BrN_3O_7$ | 714.31 (794.82) |
| 111 | | $C_{45}H_{62}BrN_3O_7$ | 756.33 (836.89) |
| 112 | | $C_{42}H_{56}BrN_3O_8$ | 730.33 (810.81) |

| Example No. | Name of compounds | Molecular formula | MS (m/z) Measured value (Calculated Value) |
|---|---|---|---|
| 112-S | | $C_{42}H_{56}BrN_3O_8$ | 730.33 (810.81) |
| 112-R | | $C_{42}H_{56}BrN_3O_8$ | 730.33 (810.81) |

Preparation 33

1,4-bis(3-bromopropoxy)benzene 110.1 g (1.0 mol) of 1,4-hydroquinone was dissolved in 800 mL of methanol, 606 g (3.0 mol) of 1,3-dibromopropane and 276 g (2.0 mol) of anhydrous potassium carbonate were added. The reaction mixture was refluxed for 6 hours, and the reaction was stopped. The solid was removed by filtration, and the solvent was removed from the solution to dryness under reduced pressure. 500 mL of ethyl acetate was added for dissolution, and washed with water three times (200 mL×3). The organic phase was dried over anhydrous magnesium sulfate. The desiccant was removed by filtration, and the filtrate was concentrated to dryness. 209 g of the target product was obtained with a yield of 59.4%, m/z 351.95.

Preparation 34

2-methoxy-1,4-bis(3-bromopropoxy)benzene 98.1 g (0.70 mol) of 2-methoxy-1,4-hydroquinone was dissolved in 600 mL of methanol. 404 g (2.0 mol) of 1,3-dibromopropane and 207 g (1.50 mol) of anhydrous potassium carbonate were added. The reaction mixture was refluxed for 8 hours, and the reaction was stopped. The solid was removed by filtration. Methanol and excess 1,3-dibromopropane were removed from the solution to dryness under reduced pressure. 400 mL of ethyl acetate was added for dissolution, washed with water three times (200 mL×3). The organic phase was dried over anhydrous magnesium sulfate overnight. The desiccant was removed by filtration, and the filtrate was concentrated to dryness. 189 g of the target product was obtained with a yield of 49.5%, m/z 381.96.

Preparation 35

1,4-bis(2-bromoethoxy) benzene

The above compound was prepared according to the method of Preparation 32.

Preparation 36

2-methoxy-5-chloro-4-(3-bromopropionamido)benzylalcohol (a) Methyl 2-methoxy-5-chloro-4-amino benzoate hydrochloride 500 mL of absolute methanol was placed in a 1000 mL three-necked flask, cooled to about −5° C. in an ice salt bath. 130 mL of thionyl chloride was added dropwise. After the dropwise addition was completed, 100.5 g (0.50 mol) of 2-methoxy-5-chloro-4-aminobenzoic acid was added with stirring, the solid was not completely dissolved, the reaction mixture was naturally heated to room temperature, the reaction was continued with stirring for 24 hours, and the solid was filtered and collected. The solid was dissolved by heating with 250 mL methanol, frozen for crystallization, filtered to collect the solid, and dried to obtain 94.9 g of the target product with a yield of 75.7%.

(b) Methyl 2-methoxy-5-chloro-4-(3-bromopropionamido) benzoate 94.0 g (0.373 mol) of the product (a) was dissolved in 300 mL DMF. 37.4 g (0.373 mol) of N-methylmorpholine was added. The reaction mixture was cooled and stirred for 10 minutes in an ice bath. 57.1 g (0.373 mol) of 3-bromopropionic acid and 103 g (0.50 mol) of dicyclohexylcarbodiimide were added. The reaction mixture was heated up to room temperature after the addition was completed. The reaction was continued with stirring for 24 hours, and the solvent was removed under reduced pressure. The residue was dissolved in 300 mL of ethyl acetate, the solid was removed by filtration, and the solid was washed with 200 mL of ethyl acetate three times. The ethyl acetate solutions were combined, washed with saturated sodium bicarbonate solution three times (150 mL×3), washed with water three times (150 mL×3), and dried over anhydrous magnesium sulfate. The desiccant was removed by filtration, and the filtrate was concentrated to dryness to obtain 108.3 g of the target product with a yield of 82.8%, m/z 348.97, 350.97.

(c) 2-methoxy-5-chloro-4-(3-bromopropionamido)benzyl alcohol 107 g (0.306 mol) of the product (b) was dissolved in 400 mL of methanol, cooled in an ice bath. 18.9 g (0.50 mol) of sodium borohydride was added in batches, and the addition was completed within about 1 hour. After the addition was completed, the reaction was continued with stirring at this temperature for 2 hours. The reaction mixture was gradually heated up to room temperature, and kept on reaction for 4 hours. The solvent was removed under reduced pressure. The residue was dissolved in 500 mL of dichloromethane, washed with water 3 times (150 mL×3), and dried over anhydrous magnesium sulfate. The desiccant was removed by filtration, and the filtrate was concentrated to dryness to obtain 77.9 g of the target product with a yield of 78.9%. m/z 320.98, 322.97.

Preparation 37

2-methoxy-4-(3-bromopropionamido)benzyl alcohol

The above compound was prepared according to the method of Preparation 36.

Preparation 38

3-methyl-4-(3-bromopropionamido)benzyl alcohol

The above compound was prepared according to the method of Preparation 36.

Preparation 39

4-(3-bromopropionamido)benzyl alcohol

The above compound was prepared according to the method of Preparation 36.

Preparation 40

1,1-dimethoxy-1-[4-(2-bromoethoxymethyl)phenyl] ethane (a) 1,1-dimethoxy-1-(4-methoxyformyl)phenyl ethane 89 g (0.50 mol) of methyl 4-acetylbenzoate was dissolved in 400 mL of methanol. 20 g of hydrogen chloride was introduced. The reaction mixture were heated to 50° C. and reacted for 4 hours, and the reaction was terminated. Excess methanol and hydrogen chloride gas were removed under reduced pressure. The residue was dissolved in 400 mL of dichloromethane, washed with saturated sodium bicarbonate solution 3 times (150 mL×3), washed with water 3 times (150 mL×3), and dried over anhydrous magnesium sulfate. The desiccant was removed by filtration, the solvent was removed under reduced pressure to obtain 100.80 g of the target product, with a yield of 90.0%, m/z 224.1.

(b) 1,1-dimethoxy-1-(4-hydroxymethyl)phenyl ethane 98.0 g (0.437 mol) of the product (a) was dissolved in 300 mL of methanol, cooled in an ice bath. 37.6 g (1.0 mol) of sodium borohydride was added in batches, and the addition was completed within 2 hours. After the addition was completed, the reaction mixture was heated up to room temperature, and the reaction was continued with stirring for 2 hours. Methanol was removed under reduced pressure, the residue was dissolved with 400 mL of dichloromethane, the dichloromethane layer was washed with water three times (150 mL×3), the organic phase was dried over anhydrous magnesium sulfate, the desiccant was removed by filtration, and the solvent was removed under reduced pressure to obtain 68.80 g of the target product, with a yield of 80.2%, m/z 196.1.

(c) 1,1-dimethoxy-1-[4-(2-bromoethoxymethyl)phenyl]ethane 67.0 g (0.341 mol) of the product (b) was dissolved in 300 mL of tetrahydrofuran. 15.0 g (0.375 mol) of sodium hydride (60%) was added. The reaction mixture was stirred at room temperature for 15 minutes. 263.2 g (1.40 mol) of 1,2-dibromoethane was added dropwise. The reaction mixture was refluxed for 4 hours after the addition was completed. The solvent was removed under reduced pressure, the residue was dissolved with 400 mL of dichloromethane, and the dichloromethane layer was washed with water three times (150 mL×3). The organic phase was dried over anhydrous magnesium sulfate, the desiccant was removed by filtration, and the solvent was removed under reduced pressure to obtain 88.90 g of the target product with a yield of 86.0%, m/z 302.0 (M–H).

Preparation 41

1,4-bis(2-bromoethoxymethyl) benzene (a) 1,4-bis(hydroxymethyl) benzene 138.0 g (0.75 mol) of dimethyl terephthalate was dissolved in 400 mL of methanol, cooled in an ice bath. 75.20 g (2.0 mol) of sodium borohydride was added in batches, and the addiction was completed within 2 hours. After addition, the reaction mixture was heated and refluxed for 4 hours. Methanol was removed under reduced pressure, the residue was dissolved with 500 mL of dichloromethane, the dichloromethane layer was washed with water three times (150 mL×3), the organic phase was dried over anhydrous magnesium sulfate, the desiccant was removed by filtration, and the solvent was removed under reduced pressure to obtain 80.80 g of the target product, with a yield of 77.9%, m/z 138.07.

(b) 1,4-bis(2-bromoethoxymethyl) benzene 78.0 g (0.565 mol) of the product (a) was dissolved in 500 mL of tetrahydrofuran. 24.86 g (0.622 mol) of sodium hydride was added, stirred at room temperature for 15 minutes. 526.4 g (2.80 mol) of 1,2-dibromoethane was added dropwise. The reaction mixture was refluxed for 8 hours after the addition was completed. The solvent and excess 1,2-dibromoethane were removed under reduced pressure, and the residue was dissolved in 800 mL of dichloromethane. The dichloromethane layer was washed with water three times (250 mL×3), the organic phase was dried over anhydrous magnesium sulfate, the desiccant was removed by filtration, and the solvent was removed under reduced pressure to obtain 138.80 g of the target product with a yield of 69.8%, m/z 352.0.

Example 113

(R)-(−)-3-[(R)-2-hydroxy-2-cyclopentyl-2-phenyl] ethoxy-1-{3-[4-(3-{(R)-[2-hydroxy-2-(3-formamido-4-hydroxy)phenyl]ethylamino}propoxy)phenoxy]propyl}-1-azabicyclo[2,2,2]octylonium bromide

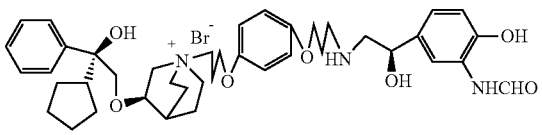

(a) (R)-(−)-3-[(R)-2-hydroxy-2-cyclopentyl-2-phenyl]ethoxy-1-{3-[4-(3-bromopropoxy)phenoxy]propyl}-1-azabicyclo[2,2,2]octylonium bromide The above compound was prepared according to Example 3(a).

(b) (R)-(−)-3-[(R)-2-hydroxy-2-cyclopentyl-2-phenyl]ethoxy-1-{3-[4-(3-{(R)-[2-hydroxy-2-(3-formamido-4-benzyloxy)phenyl]ethylbenzylamino}propoxy)phenoxy]propyl}-1-azabicyclo[2,2,2]octylonium bromide 1.882 g (5.0 mmol) of (R)-2-benzylamino-1-[(4-benzyloxy-3-formamido)phenyl]ethanol (Preparation 4) and 3.38 g (5.0 mmol) of (a) were added to a 50 mL reaction flask, 30 mL of dioxane was added. After the reaction mixture was stirred for 10 minutes, 1.5 g (11.0 mmol) of anhydrous potassium carbonate was added, the temperature of the reaction mixture was increased to 55-60° C., and the reaction was carried out at this temperature for 12 hours. Thin layer detection showed that the reaction was complete. The reaction was stopped, and the reaction mixture was cooled to room temperature and filtered to remove insoluble substances. The solvent was removed from the filtrate under reduced pressure, the residue was added with 10 mL isopropanol for freeze crystallization, and the solid was filtered and collected to obtain 3.26 g of the target product. The yield was 67.7%. Calculated for MS(m/z) of $C_{55}H_{68}BrN_3O_7$: 963.0, found: 883.4 (M+Br).

(c) (R)-(−)-3-[(R)-2-hydroxy-2-cyclopentyl-2-phenyl]ethoxy-1-{3-[4-(3-{(R)-[2-hydroxy-2-(3-formamido-4-hydroxy)phenyl]ethylamino}propoxy)phenoxy]propyl}-1-azabicyclo[2,2,2]octylonium bromide 3.10 g (3.22 mmol) of the product (b) was placed in a hydrogenation reaction kettle, 30 mL of methanol was added for dissolution, 0.6 g of 10% Pd—C was added, hydrogen was introduced, the pressure was maintained at 0.4-0.43 MPa, and the temperature was room temperature. After 20 hours of reaction, the reaction was stopped, the catalyst was removed by filtration, the filtrate was concentrated to dryness under reduced pressure, and the residue was crystallized with isopropanol. 1.38 g of the target compound solid was obtained with a yield of 54.7%.

$^1$HNMR (δ ppm) (DMSO-$d_6$) 8.21 (s, 1H), 7.40 (m, 1H), 7.18-7.23 (m, 5H), 6.66-6.71 (m, 2H), 5.0 (s, 1H), 4.74 (m, 1H), 4.0 (s, 1H), 3.92 (s, 2H), 3.68 (d, 2H), 3.15 (m, 1H), 2.91 (m, 1H), 2.83 (m, 1H), 2.54 (m, 2H), 2.42 (S, 1H), 2.35 (m, 2H), 2.10 (s, 1H), 2.0 (m, 3H), 1.79-1.81 (m, 3H), 1.75 (m, 1H), 1.69 (m, 2H), 1.55-1.61 (m, 8H), 1.34-1.46 (m, 6H); Calculated for MS(m/z) of $C_{41}H_{56}BrN_3O_7$: 782.8, found: 702.3 (M+Br).

Example 114

(R)-(−)-3-[(R)-2-hydroxy-2-cyclopentyl-2-phenyl]ethoxy-1-{2-[4-(2-{(R)-[2-(3-hydroxymethyl-4-hydroxy)phenyl-2-hydroxy]ethylamino}ethyoxyl)phenoxy]ethyl}-1-azabicyclo[2,2,2]octylonium bromide

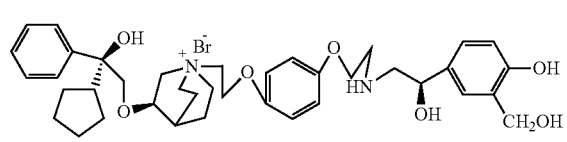

(a) (R)-(−)-3-[(R)-2-hydroxy-2-cyclopentyl-2-phenyl]ethoxy-1-{2-[4-(2-bromoethyoxyl)phenoxy]ethyl}-1-azabicyclo[2,2,2]octylonium bromide The above compound was prepared according to the method of Example 1(a)

(b) (R)-(−)-3-[(R)-2-hydroxy-2-cyclopentyl-2-phenyl]ethoxy-1-{2-[4-(2-{(R)-[2-(3-benzyloxymethyl-4-benzyloxy)phenyl-2-hydroxy]ethylbenzylamino}ethyoxy)phenoxy]ethyl}-1-azabicyclo[2,2,2]octylonium bromide 2.40 g (5.28 mmol) of (R)-1-[(4-benzyloxy-3-benzyloxymethyl)phenyl]-2-benzylamino ethanol (Preparation 1) and 3.38 g (5.28 mmol) of (a) were added to a 50 mL reaction flask, 20 mL of dioxane was added. After the reaction mixture was stirred for 10 minutes, 1.475 g (10.60 mmol) of anhydrous potassium carbonate was added, the temperature of the reaction mixture was increased to 65-70° C., and the reaction was carried out at this temperature for 8 hours. Thin layer detection showed that the reaction was complete. The reaction was stopped, and the reaction mixture was cooled to room temperature and filtered to remove insoluble substances. The solvent was removed from the filtrate under reduced pressure, the residue was dissolved in isopropanol and frozen for crystallization, and the solid was filtered and collected to obtain 3.42 g of the target product. The yield was 64.0%. Calculated for MS(m/z) of $C_{60}H_{71}BrN_2O_7$: 1012.1, found: 932.4 (M+Br).

(c) (R)-(−)-3-[(R)-2-hydroxy-2-cyclopentyl-2-phenyl]ethoxy-1-{2-[4-(2-{(R)-[2-(3-hydroxy methyl-4-hydroxy)phenyl-2-hydroxy]ethylamino}ethyoxyl)phenoxy]ethyl}-1-azabicyclo[2,2,2]octylonium bromide 3.30 g (3.26 mmol) of product (b) was placed in a hydrogenation reaction kettle, 20 mL of methanol was added for dissolution, 0.8 g of 10% Pd—C was added, hydrogen was introduced, the pressure was kept at 0.43 MPa, and the temperature was room temperature. After 10 hours of reaction, the reaction was stopped. The catalyst was removed by filtration. The filtrate was concentrated to dryness under reduced pressure. The residue was dissolved with isopropanol, and frozen for crystallization. 1.38 g of the target compound solid was obtained with a yield of 57.1%.
$^1$HNMR (δ ppm) (DMSO-d$_6$) 7.19-7.22 (m, 5H), 6.95-7.01 (m, 2H), 6.66 (d, 2H), 6.63-6.59 (m, 3H), 5.0 (s, 1H), 4.79 (s, 2H), 4.74 (m, 1H), 4.04 (t, 2H), 4.06 (t, 2H), 3.93 (d, 1H), 3.68 (d, 1H), 3.15 (m, 1H), 2.97 (t, 2H), 2.90 (m, 1H), 2.74 (m, 1H), 2.78 (t, 2H), 2.21 (S, 1H), 2.10 (s, 1H), 2.0 (m, 3H), 1.79-1.81 (m, 3H), 1.75 (m, 1H), 1.69 (m, 2H), 1.56-1.60 (m, 6H), 1.34-1.46 (m, 6H); Calculated for MS(m/z) of $C_{39}H_{53}BrN_2O_7$: 741.8, found: 661.3 (M+Br).

Example 115

(R)-(−)-3-[(R)-2-hydroxy-2-cyclopentyl-2-phenyl] ethoxy-1-{3-[5-chloro-2-methoxy-4-({(R)-[2-hydroxy-2-(8-hydroxy-2-oxo-1,2-dihydroquinolin-5-yl)]ethylamino}methyl)anilino]oxopropyl}-1-azabicyclo[2,2,2]octylonium bromide

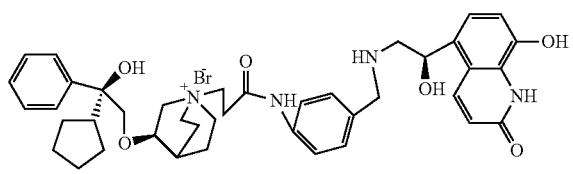

(a) (R)-(−)-3-[(R)-2-benzyloxyformoxy-2-cyclopentyl-2-phenyl)]ethoxy-1-{3-[(5-chloro-2-methoxy-4-hydroxymethyl)anilino]oxopropyl}-1-azabicyclo[2,2,2]octylonium bromide The above compound was prepared according to the method of Example 57(a).

(b) (R)-(−)-3-[(R)-2-benzyloxyformoxy-2-cyclopentyl-2-phenyl]ethoxy-1-{2-[5-chloro-2-methoxy-4-methanesulfonyloxymethyl)anilino]oxopropyl}-1-azabicyclo[2,2,2]octylonium bromide The above compound was prepared according to the method of Example 57(b).

(c) (R)-(−)-3-[(R)-2-benzyloxyformoxy-2-cyclopentyl-2-phenyl]ethoxy-1-{2-[5-chloro-2-methoxy-4-({(R)-[2-hydroxy-2-(8-benzyloxy-2-oxo-1,2-dihydroquinolin-5-yl)]ethylbenzylamino}methyl)anilino]oxopropyl)-1-azabicyclo[2,2,2]octylonium bromide 2.0 g (5.0 mmol) of 8-benzyloxy-5-[(R)-2-benzylamino-1-hydroxyethyl]-(1H)-quinolin-2-one (Preparation 2) and 4.28 g (5.0 mmol) of (b) were added to a 50 mL reaction flask, 30 mL dioxane was added. After the reaction mixture was stirred for 10 minutes, 1.475 g (10.57 mmol) of anhydrous potassium carbonate was added, the temperature of the reaction mixture was increased to 65-70° C. The reaction was carried out at this temperature for 5 hours. Thin layer detection showed that the reaction was complete. The reaction was stopped, and the reaction mixture was cooled to room temperature and filtered to remove insoluble substances. The solvent was removed from the filtrate under reduced pressure. The residue was dissolved in 10 mL of ethanol, frozen and crystallized. The solid was filtered and dried to obtain 2.96 g of the target product. The yield was 51.2%. Calculated for MS(m/z) of $C_{64}H_{70}BrClN_4O_9$: 1154.49, found: 1073.86 (M+Br).

(d) (R)-(−)-3-[(R)-2-hydroxy-2-cyclopentyl-2-phenyl]ethoxy-1-{3-[5-chloro-2-methoxy-4-({(R)-[2-hydroxy-2-(8-hydroxy-2-oxo-1,2-dihydroquinolin-5-yl)]ethylamino}methyl)anilino]oxo propyl}-1-azabicyclo[2,2,2]octylonium bromide 2.88 g (2.49 mmol) of product (c) was placed in a hydrogenation reaction kettle, 20 mL of methanol was added for dissolution, 0.7 g of 10% Pd—C was added, hydrogen was introduced, the pressure was kept at 0.43 MPa, and the temperature was at room temperature. After 18 hours of reaction, hydrogen absorption was stopped, the catalyst was removed by filtration, the filtrate was concentrated to dryness under reduced pressure, and the residue was dissolved and crystallized with ethanol. 1.48 g of the target compound solid was obtained with a yield of 70.7%.
$^1$HNMR (δ ppm) (DMSO-d$_6$) 8.10 (s, 1H), 8.01 (s, 1H), 7.36 (d, 1H), 7.18-7.21 (m, 5H), 6.97 (d, 1H), 6.94 (d, 1H), 6.71 (d, 1H), 6.52 (d, 1H), 5.0 (s, 1H), 4.74 (m, 1H), 3.93 (m, 1H), 3.81 (d, 2H), 3.73 (s, 3H), 3.68 (d, 1H), 3.15 (m, 1H), 2.90 (m, 1H), 2.84 (m, 1H), 2.74 (t, 2H), 2.33 (t, 2H), 2.05 (s, 1H), 2.0 (m, 4H), 1.79-1.81 (m, 3H), 1.75 (m, 1H), 1.68 (m, 2H), 1.56-1.60 (m, 6H), 1.35-1.46 (m, 6H).
Calculated for MS(m/z) of $C_{42}H_{52}BrClN_4O_7$: 840.24, found: 759.77 (M+Br).

Example 116

(R)-(−)-3-[(R)-2-hydroxy-2-cyclopentyl-2-phenyl] ethoxy-1-{3-[4-({(R)-[2-hydroxy-2-(6-hydroxy-2H-1,4-benzoxazin-3(4H)-one-8-yl)]ethylamino}methyl) anilino]oxopropyl}-1-azabicyclo[2,2,2]octylonium bromide

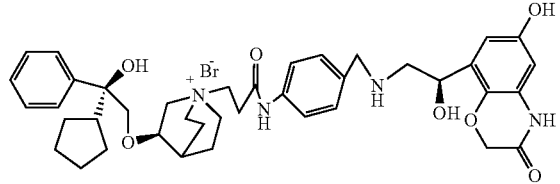

(a) (R)-(−)-3-[(R)-2-benzyloxyformoxy-2-cyclopentyl-2-phenyl]ethoxy-1-[3-(4-hydroxymethylanilino) oxopropyl]-1-azabicyclo[2,2,2]octylonium bromide The above compound was prepared according to the method of Example 57(a).

(b) (R)-(−)-3-[(R)-2-benzyloxyformoxy-2-cyclopentyl-2-phenyl]ethoxy-1-[3-(4-methylsulfonyloxymethylanilino)oxopropyl]-1-azabicyclo[2,2,2]octylonium bromide The above compound was prepared according to the method of Example 57(b).

(c) (R)-(−)-3-[(R)-2-benzyloxyformoxy-2-cyclopentyl-2-phenyl]ethoxy-1-{2-[4-({(R)-[2-hydroxy-2-(6-benzyloxy-2H-1,4-benzoxazin-3(4H)-one-8-yl)]ethylbenzylamino}methyl)anilinoformyl]ethyl}-1-azabicyclo[2,2,2]octylonium bromide 2.02 g (5.0 mmol) of 8-[(R)-1-hydroxy-2-benzylamine]ethyl-6-benzyloxy-2H-1,4-benzoxazin-3(4H)-one (Preparation 5) and 3.96 g (5.0 mmol) were added to a 50 mL reaction flask, 30 ml dioxane was added. After the reaction mixture was stirred for 10 minutes, 1.0 g (7.35 mmol) of anhydrous potassium carbonate was added, the temperature of the reaction mixture was increased to 65-70° C. The reaction was carried out at this temperature for 10 hours. Thin layer detection showed that the reaction was complete. The reaction was stopped, and the reaction mixture was cooled to room temperature and filtered to remove insoluble substances. The solvent was removed from the filtrate under reduced pressure, the residue was added with 10 mL isopropyl alcohol for freeze crystallization, and the solid was filtered and collected to obtain 2.88 g of the target product. The yield was 60.0%.

Calculated for MS(m/z) of $C_{62}H_{69}BrN_4O_9$: 1094.0, found: 1014.38 (M+Br).

(d) (R)-(−)-3-[(R)-2-hydroxy-2-cyclopentyl-2-phenyl]ethoxy-1-{3-[4-({(R)-[2-hydroxy-2-(6-hydroxy-2H-1,4-benzoxazin-3(4H)-one-8-yl)]ethylamino}methyl)anilino]oxopropyl}-1-azabicyclo[2,2,2]octylonium bromide 2.70 g (2.47 mmol) of the product (c) was placed in a hydrogenation reaction kettle, 20 mL of methanol was added for dissolution, 0.6 g of 10% Pd—C was added, hydrogen was introduced, and the pressure was maintained at 0.43 MPa. After the reaction was carried out at room temperature for 16 hours, hydrogen absorption was stopped, and the reaction was stopped. The catalyst was removed by filtration, the filtrate was concentrated to dryness, and the residue was crystallized with isopropanol. 1.26 g of the target compound solid was obtained with a yield of 65.4%.

$^1$HNMR (δ ppm) (DMSO-$d_6$) 8.05 (s, 1H), 8.0 (s, 1H), 7.52 (d, 2H), 7.19-7.21 (m, 5H), 7.04 (d, 2H), 6.65 (d, 1H), 6.20 (d, 1H), 5.0 (s, 1H), 4.88 (s, 2H), 4.74 (m, 1H), 3.93 (d, 1H), 3.81 (d, 2H), 3.68 (d, 1H), 3.15 (m, 1H), 2.91 (m, 1H), 2.84 (m, 1H), 2.74 (t, 2H), 2.33 (t, 2H), 2.10 (m, 2H), 2.0 (m, 2H), 1.96 (m, 1H), 1.79-1.81 (m, 3H), 1.75 (m, 1H), 1.69 (m, 2H), 1.56-1.60 (m, 6H), 1.34-1.46 (m, 6H).

Calculated for MS(m/z) of $C_{40}H_{51}BrN_4O_7$: 779.76, found: 700.33 (M+Br).

Example 117

(R)-(−)-3-[(R)-2-hydroxy-2-cyclopentyl-2-phenyl]ethoxy-1-{2-[4-(2-{(R)-[2-hydroxy-2-(3-formamido-4-hydroxy)phenyl]ethylamino}ethylidene)benzyloxy]ethyl}-1-azabicyclo[2,2,2]octylonium bromide

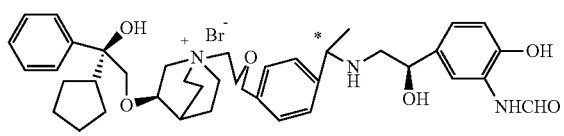

(a) (R)-(−)-3-[(R)-2-hydroxy-2-cyclopentyl-2-phenyl]ethoxy-1-{2-[4-(1,1-dimethoxyethyl) benzyloxy]ethyl}-1-azabicyclo[2,2,2]octylonium bromide The above compound was prepared according to the method of Example 1(a).

(b) (R)-(−)-3-[(R)-2-hydroxy-2-cyclopentyl-2-phenyl]ethoxy-1-{2-[4-(2-{(R)-[2-hydroxy-2-(3-formamido-4-hydroxy)phenyl]ethylamino}ethylidene)benzyloxy]ethyl}-1-azabicyclo[2,2,2]octylonium bromide 0.981 g (5.0 mmol) of (R)-2-amino-1-[(4-hydroxy-3-formamido)phenyl]ethanol (Preparation 30) and 3.09 g (5.0 mmol) of (a) were added to a 250 mL reaction flask, 50 mL dichloromethane was added. After the reaction mixture was stirred for 10 minutes, 2.54 g (12.0 mmol) of sodium triacetyl borohydride was added, and 1 drop of acetic acid was added for catalysis. The reaction mixture was reacted for 24 hours at room temperature, and thin layer detection showed that the reaction was complete. The reaction was stopped, and the reaction mixture was filtered to remove insoluble substances. The solvent was removed from the filtrate under reduced pressure, 5 mL of ethanol was added to the residue for freeze crystallization, and the solid was filtered and collected to obtain 1.62 g of the target product. The yield was 43.0%.

$^1$HNMR (δ ppm) (DMSO-$d_6$) 8.21 (s, 1H), 7.40 (m, 1H), 7.18-7.20 (m, 5H), 7.14 (d, 2H) 7.05 (d, 2H), 6.76 (dd, 1H), 6.64 (dd, 1H), 5.0 (s, 1H), 4.74 (m, 1H), 4.63 (s, 2H), 4.08 (m, 1H), 4.0 (s, 1H), 3.93 (d, 1H), 3.68 (d, 1H), 3.47 (t, 2H), 3.15 (m, 1H), 2.91 (m, 1H), 2.84 (m, 1H), 2.53 (t, 2H), 2.10 (s, 1H), 1.96-2.0 (m, 3H), 1.79-1.81 (m, 3H), 1.75 (m, 1H), 1.69 (m, 2H), 1.55-1.61 (m, 6H), 1.34-1.46 (m, 6H), 1.38 (d, 3H); Calculated for MS(m/z) of $C_{40}H_{54}BrN_3O_6$: 752.78, found: 672.32 (M+Br).

(c) Resolution of 117-S Isomer and 117-R Isomer

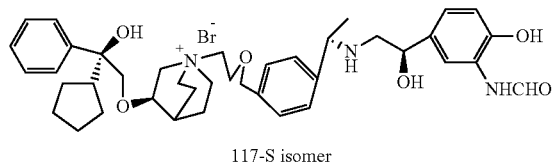

117-S isomer

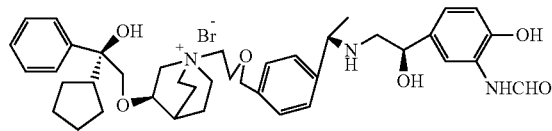

117-R isomer 0.80 g of product (b) was dissolved in methanol, separated with a preparation column, gradient elution was carried out with methanol and water, component peaks of S-isomer and R-isomer were collected respectively, drained under reduced pressure, the residue was recrystallized with ethanol to obtain 0.24 g of S-isomer and 0.28 g of R-isomer.

Example 118

(R)-(-)-3-[(R)-2-hydroxy-2-cyclopentyl-2-phenyl]
ethoxy-1-{2-[4-(2-{(R)-[2-hydroxy-2-(6-hydroxy-
2H-1,4-benzoxazin-3(4H)-one-8-yl)]
ethylamino}ethoxymethyl)benzyloxy]ethyl}-1-
azabicyclo[2,2,2]octylonium bromide

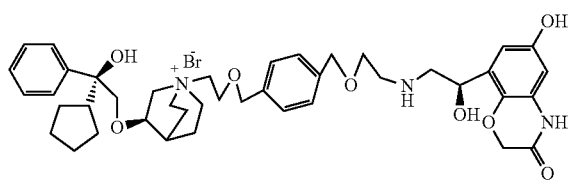

(a) (R)-(-)-3-[(R)-2-hydroxy-2-cyclopentyl-2-phenyl]ethoxy-1-{2-[4-(2-bromoethoxymethyl)benzyloxy]ethy}-1-azabicyclo[2,2,2]octylonium bromide The above compound was prepared according to the method of Example 1(a).

In a 250 mL three-necked flask, 35 mL of absolute ethanol was added, 5.0 g (15.85 mmol) of (R)-(-)-3-[(R)-2-hydroxy-2-cyclopentyl-2-phenyl]ethoxy-1-azabicyclo[2,2,2]octane (Preparation 2) was added. After the reaction mixture was stirred for dissolution, 44.66 g (126.3 mmol) of 1,4-bis(2-bromoethoxymethyl)benzene (preparation 40) was added. The reaction was carried out with stirring at room temperature for 18 hours. Ethanol was removed under reduced pressure, and the residue was subjected to column chromatography to obtain 8.50 g of the target product in a yield of 80.4%. MS(m/z) 686.18, 688.17.

(b) (R)-(-)-3-[(R)-2-hydroxy-2-cyclopentyl-2-phenyl]ethoxy-1-{2-[4-(2-{(R)-2-hydroxy-2-(5-benzyloxy-2H-1,4-benzoxazin-3(4H)-one-8-yl)]
ethylbenzylamino}ethoxymethyl)benzyloxy]ethyl}-1-azabicyclo[2,2,2]octylonium bromide 2.02 g (5.0 mmol) of 8-[(1R)-1-hydroxy-2-benzylamine]ethyl-6-benzyloxy-2H-1,4-benzoxazin-3(4H)-one (Preparation 5) and 3.38 g (5.0 mmol) of (a) were added to a 50 mL reaction flask, 30 mL dioxane was added. After the reaction mixture was stirred for 10 minutes, 1.0 g (7.35 mmol) of anhydrous potassium carbonate was added, and the temperature of the reaction mixture was increased to 75-80° C. The reaction was carried out at this temperature for 12 hours. Thin layer detection showed that the reaction was complete. The reaction was stopped, and the reaction mixture was cooled to room temperature and filtered to remove insoluble substances. The solvent was removed from the filtrate under reduced pressure, the residue was added with 15 mL of ethanol for freeze crystallization, and the solid was filtered and collected to obtain 3.36 g of the target product. The yield was 67.8%. MS(m/z) 901.45.

(c) (R)-(-)-3-[(R)-2-hydroxy-2-cyclopentyl-2-phenyl]ethoxy-1-{2-[4-(2-{(R)-[2-hydroxy-2-(6-hydroxy-2H-1,4-benzoxazin-3(4H)-one-8-yl)]
ethylamino}ethoxymethyl)benzyloxy]ethyl}-1-azabicyclo[2,2,2]octylonium bromide 3.20 g (3.23 mmol) of product (b) was placed into a hydrogenation reaction kettle, 30 mL of methanol was added for dissolution, 0.6 g of 10% Pd—C was added, hydrogen was introduced, the pressure was kept at 0.43 MPa, and the temperature was room temperature. After 18 hours of reaction, hydrogen absorption was stopped, the reaction was stopped, the catalyst was removed by filtration, the filtrate was concentrated to dryness under reduced pressure, and the residue was crystallized with ethanol. 1.48 g of the target compound solid was obtained with a yield of 56.5%. $^1$HNMR (δ ppm) (DMSO-d$_6$) 8.0 (s, 1H), 7.15-7.20 (m, 5H), 7.12 (d, 4H), 6.65 (d, 1H), 6.20 (d, 1H), 5.0 (s, 1H), 4.88 (s, 2H), 4.73 (m, 1H), 4.63 (s, 4H), 3.93 (d, 1H), 3.68 (d, 1H), 3.49 (t, 2H0, 3.47 (t, 2H), 3.15 (m, 1H), 2.91 (m, 1H), 2.84 (m, 1H), 2.72 (t, 2H), 2.53 (t, 2H), 2.10 (s, 1H), 2.0 (m, 2H), 1.96 (m, 1H), 1.79-1.81 (m, 3H), 1.75 (m, 1H), 1.69 (m, 2H), 1.55-1.61 (m, 6H), 1.34-1.46 (m, 6H). Calculated for MS(m/z) of $C_{42}H_{56}BrN_3O_8$: 810.8, found: 730.3 (M+Br).

The following compounds can be prepared using raw materials synthesized above and synthesis methods:

| Example No. | Name of compounds | Molecular formula | MS (m/z) Measured value (Calculated Value) |
|---|---|---|---|
| 119 | | $C_{45}H_{59}BrN_2O_7$ | 739.34 (819.86) |

-continued

| Example No. | Name of compounds | Molecular formula | MS (m/z) Measured value (Calculated Value) |
|---|---|---|---|
| 120 | | $C_{40}H_{55}BrN_2O_6$ | 659.32 (739.78) |
| 120-S | | $C_{40}H_{55}BrN_2O_6$ | 659.32 (739.78) |
| 120-R | | $C_{40}H_{55}BrN_2O_6$ | 659.32 (739.78) |
| 121 | | $C_{42}H_{59}BrN_2O_8$ | 619.35 (799.83) |
| 122 | | $C_{41}H_{57}BrN_2O_7$ | 689.34 (769.80) |
| 123 | | $C_{40}H_{53}BrClN_3O_7$ | 722.77 (803.22) |
| 124 | | $C_{40}H_{54}BrN_3O_8$ | 704.32 (784.78) |

-continued

| Example No. | Name of compounds | Molecular formula | MS (m/z) Measured value (Calculated Value) |
|---|---|---|---|
| 125 | | $C_{40}H_{54}BrN_3O_6$ | 672.31 (752.77) |
| 126 | | $C_{39}H_{52}BrN_3O_6$ | 658.30 (738.75) |
| 127 | | $C_{43}H_{56}BrN_3O_7$ | 726.33 (806.83) |
| 128 | | $C_{42}H_{54}BrN_3O_6$ | 696.32 (776.80) |
| 128-S | | $C_{42}H_{54}BrN_3O_6$ | 696.32 (776.80) |
| 128-R | | $C_{42}H_{54}BrN_3O_6$ | 696.32 (776.80) |
| 129 | | $C_{41}H_{52}BrN_3O_7$ | 698.30 (778.77) |

-continued

| Example No. | Name of compounds | Molecular formula | MS (m/z) Measured value (Calculated Value) |
|---|---|---|---|
| 130 | | C₄₄H₅₈BrN₃O₈ | 756.34 (836.85) |
| 131 | | C₄₃H₅₆BrN₃O₇ | 726.33 (806.83) |
| 132 | | C₄₂H₅₃BrN₄O₇ | 725.31 (805.80) |
| 133 | | C₄₂H₅₃BrN₄O₆ | 709.32 (789.80) |
| 134 | | C₄₁H₅₁BrN₄O₆ | 695.30 (775.77) |
| 135 | | C₄₃H₆₀BrN₃O₇ | 730.33 (810.86) |

-continued

| Example No. | Name of compounds | Molecular formula | MS (m/z) Measured value (Calculated Value) |
|---|---|---|---|
| 136 | | $C_{39}H_{52}BrN_3O_7$ | 674.30 (754.75) |
| 137 | | $C_{42}H_{58}BrN_3O_8$ | 732.34 (812.83) |
| 138 | | $C_{40}H_{52}BrClN_4O_7$ | 735.77 (816.22) |
| 139 | | $C_{40}H_{53}BrN_4O_7$ | 701.31 (781.78) |
| 140 | | $C_{40}H_{53}BrN_4O_6$ | 685.32 (765.78) |
| 141 | | $C_{40}H_{53}BrN_4O_7$ | 701.30 (781.78) |
| 142 | | $C_{40}H_{52}BrN_3O_7$ | 686.30 (766.76) |

-continued
| Example No. | Name of compounds | Molecular formula | MS (m/z) Measured value (Calculated Value) |
|---|---|---|---|
| 142-S | 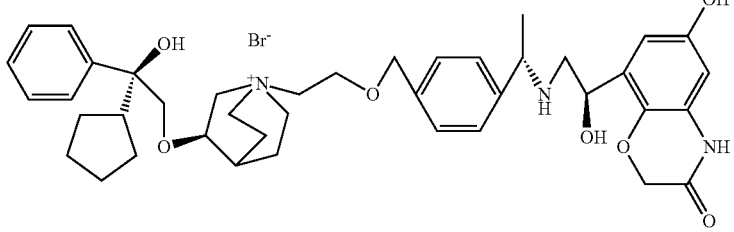 | C₄₀H₅₂BrN₃O₇ | 686.30 (766.76) |
| 142-R | 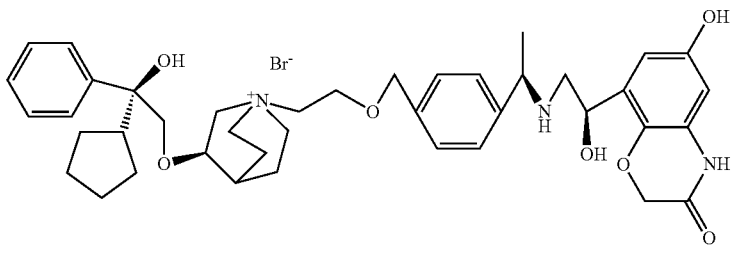 [SMILES: C[C@@H](NC[C@H](O)c1cc(O)cc2c1OCC(=O)N2)c1ccc(COCC[N+]23CCC(CC2)[C@@H](OC[C@@](O)(c2ccccc2)C2CCCC2)C3)cc1 ; [Br-]] | C₄₀H₅₂BrN₃O₇ | 686.30 (766.76) |
| 143 | 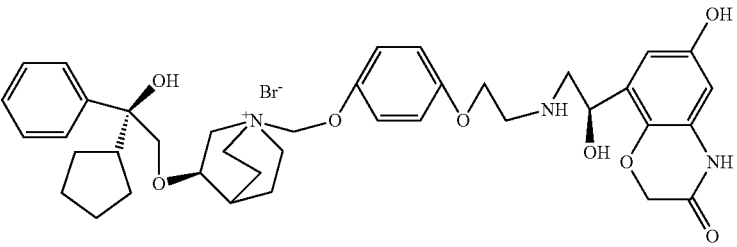 [SMILES: O=C1COc2c(cc(O)cc2[C@@H](O)CNCCOc2ccc(OC[N+]34CCC(CC3)[C@@H](OC[C@@](O)(c3ccccc3)C3CCCC3)C4)cc2)N1 ; [Br-]] | C₄₀H₅₂BrN₃O₈ | 702.29 (782.76) |
| 144 | 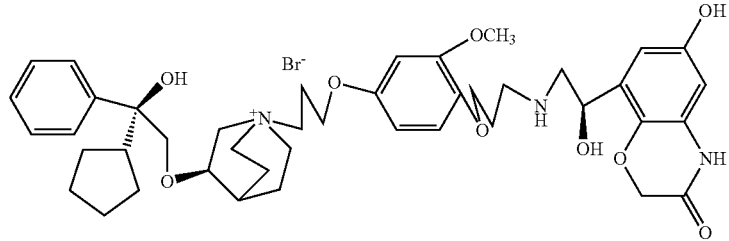 [SMILES: COc1cc(OCCC[N+]23CCC(CC2)[C@@H](OC[C@@](O)(c2ccccc2)C2CCCC2)C3)ccc1OCCCNC[C@H](O)c1cc(O)cc2c1OCC(=O)N2 ; [Br-]] | C₄₃H₅₈BrN₃O₉ | 760.37 (840.84) |
| 145 | 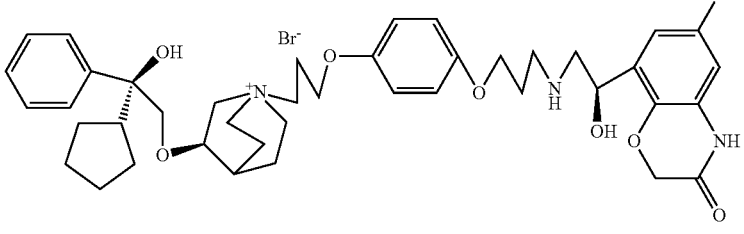 | C₄₂H₅₆BrN₃O₈ | 730.33 (810.81) |

-continued

| Example No. | Name of compounds | Molecular formula | MS (m/z) Measured value (Calculated Value) |
|---|---|---|---|
| 146 | | $C_{40}H_{52}BrClN_4O_8$ | 764.27 (844.23) |
| 147 | | $C_{41}H_{53}BrN_4O_8$ | 729.31 (809.79) |
| 148 | | $C_{41}H_{53}BrN_4O_7$ | 713.31 (793.79) |

Experimental Example 1: Response Intensity of the Constriction of Tracheal Smooth Muscle of Guinea Pig Induced by Antagonizing Carbachol (CCh) According to the Compounds of the Invention Preparation of isolated tracheal smooth muscle specimen of guinea pig: After a guinea pig was anaesthetized by urethane, the trachea between the larynx and the carina was quickly taken out and placed in Krebs-Henseleit (K-H) solution (composition (g/L): NaCl 6.92, KCl 0.35, $CaCl_2$ 0.28, $KH_2PO_4$ 0.16, $MgSO_4$ $7H_2O$ 0.4568, $NaHCO_3$ 2.1, Glucose 2.0) with mixture gas of 5% $CO_2$ and 95% $O_2$ added. After loose connective tissue and fat around the trachea were separated, the trachea was isolated to be a trachea flake with a width of about 3 mm and a length of 20 mm and with two ligated ends, and placed into a 37° C. constant temperature bath (pH 7.4) containing 5 mL of K—H solution, with the mixture gas containing 5% $CO_2$ and 95% $O_2$ continuously added. The upper end was connected with a muscle tension transducer, and the specimen was given a resting tension of 1.0 g. Muscle tension changes were recorded, nutrient solution was changed every 20 min, and the experiment was started after 60 min of equilibrium.

Administration Method: After the trachea flake were stabilized, $3\times10^{-6}$ mol/L CCh was added to the bath. When the constriction tension of the trachea flake reached a peak level, the example compounds, ipratropium bromide and tiotropium bromide were added into a Magnus bath by a cumulative dosing regimen with a dosage of $10^{-9}$~$10^{-5}$ mol, respectively. Diastolic condition of the trachea flake was observed. If no response occurred (below the threshold concentration), the next dosage was continued to be added in the order. If any response occurred, the next dosage was added until its diastolic platform was reached. The above operation was repeated until the shrink curve reached the minimum. Finally, $10^{-6}$ mol/L isoproterenol was added to establish maximum relaxation, and the curve was recorded.

Statistical Methods: Statistics was performed using the Sigma Stat statistical software package, the data was analyzed by using the variance analysis. Student-Newman-Keuls (SNK) test was used in comparison among multiple sample averages number. The statistical test level was α=0.05 (bilateral). $EC_{50}$ (95% confidence limit) was calculated by POMS version 2.0 software from Shanghai Science and Technology Press.

$3\times10^{-6}$ mol/L CCh can make guinea pig tracheal smooth muscle to produce a sustained and stable constriction response. In the cumulative dosing regimen, the compounds to be tested and the control drugs of ipratropium bromide and tiotropium bromide were added into the Magnus bath, and each of the example compounds and each of the control drugs were capable of relaxing the constriction of the tracheal smooth muscle induced by CCh. The results were shown in Table 1.

TABLE 1

The tracheal smooth muscle constriction $EC_{50}$ (μM) of guinea pig induced by some compounds of the invention antagonizing CCh with a concentration of $3 \times 10^{-6}$ mol/L in vitro

| Compound | $EC_{50}$ (μM) ± SD | Onset time (min) ± SD | Time for eliminating inhibition effect (min) |
|---|---|---|---|
| Compound 1 | 0.767 ± 0.18 | 6.82 ± 0.30 | more than 300 |
| Compound 2 | 0.756 ± 0.26 | 6.68 ± 0.36 | more than 300 |
| Compound 3 | 0.355 ± 0.10 | 5.38 ± 0.68 | more than 300 |
| Compound 4 | 0.0358 ± 0.011 | 6.23 ± 0.23 | more than 300 |
| Compound 25 | 0.822 ± 0.27 | 6.86 ± 0.22 | more than 300 |
| Compound 26 | 0.0870 ± 0.021 | 6.56 ± 0.65 | more than 300 |
| Compound 27 | 0.152 ± 0.086 | 5.54 ± 0.43 | more than 300 |
| Compound 45 | 0.0278 ± 0.0091 | 6.39 ± 0.56 | more than 300 |
| Compound 46 | 0.136 ± 0.068 | 6.75 ± 0.33 | more than 300 |
| Compound 48 | 0.0154 ± 0.012 | 6.32 ± 0.49 | more than 300 |
| Compound 50 | 0.0135 ± 0.0092 | 6.76 ± 0.32 | more than 300 |
| Compound 57 | 0.0265 ± 0.016 | 6.03 ± 0.18 | more than 300 |
| Compound 58 | 0.0131 ± 0.0088 | 5.56 ± 0.24 | more than 300 |
| Compound 59 | 0.0165 ± 0.0075 | 6.53 ± 0.66 | more than 300 |
| Compound 60 | 0.0523 ± 0.018 | 6.59 ± 0.43 | more than 300 |
| Compound 62 | 0.0351 ± 0.010 | 7.02 ± 0.22 | more than 300 |
| Compound 63 | 0.0155 ± 0.0078 | 6.19 ± 0.12 | more than 300 |
| Compound 70 | 0.0183 ± 0.0087 | 7.15 ± 0.31 | more than 300 |
| Compound 71 | 0.0190 ± 0.0061 | 6.92 ± 0.26 | more than 300 |
| Compound 75 | 0.1762 ± 0.031 | 6.38 ± 0.35 | more than 300 |
| Compound 78 | 0.0137 ± 0.0078 | 6.48 ± 0.38 | more than 300 |
| Compound 84 | 0.0251 ± 0.0086 | 6.78 ± 0.18 | more than 300 |
| Compound 97 | 0.0167 ± 0.0062 | 6.36 ± 0.22 | more than 300 |
| Compound 99 | 0.0172 ± 0.0072 | 7.35 ± 0.33 | more than 300 |
| Compound 102 | 0.0371 ± 0.019 | 5.78 ± 0.23 | more than 300 |
| Compound 104 | 0.0106 ± 0.0079 | 6.67 ± 0.17 | more than 300 |
| Compound 106 | 0.0183 ± 0.0086 | 6.26 ± 0.24 | more than 300 |
| Compound 114 | 0.0227 ± 0.0080 | 6.24 ± 0.13 | more than 300 |
| Compound 115 | 0.0237 ± 0.010 | 6.82 ± 0.36 | more than 300 |
| Compound 116 | 0.0267 ± 0.0072 | 6.28 ± 0.56 | more than 300 |
| Compound 117 | 0.0217 ± 0.0081 | 5.96 ± 0.21 | more than 300 |
| Compound 118 | 0.0241 ± 0.012 | 6.24 ± 0.41 | more than 300 |
| Compound 128 | 0.0252 ± 0.0021 | 6.08 ± 0.51 | more than 300 |
| Compound 138 | 0.0186 ± 0.0033 | 6.56 ± 0.23 | more than 300 |
| Compound 140 | 0.0235 ± 0.0054 | 6.18 ± 0.18 | more than 300 |
| Compound 141 | 0.0363 ± 0.0095 | 5.88 ± 0.26 | more than 300 |
| Compound 143 | 0.0379 ± 0.012 | 6.85 ± 0.35 | more than 300 |
| Ipratropium bromide | 0.0361 ± 0.0046 | 6.82 ± 0.28 | 185 |
| Tiotropium bromine | 0.0142 ± 0.0022 | 30.37 ± 0.50 | more than 300 |

The results in Table 1 show that all the compounds designed by the invention have the effect of blocking the constriction of tracheal smooth muscle of guinea pig induced by carbachol, a considerable number of compounds have stronger blocking effect than the positive control agent ipratropium bromide, and some compounds have the comparable action intensity as the positive control agent tiotropium bromide. The onset time of the compound of the invention and the ipratropium bromide are shorter than that of tiotropium bromide, on the contrary, the onset time of tiotropium bromide is slow. The compounds of the present invention and tiotropium bromide have a long duration of action, but ipratropium bromide has a short duration of action.

Experimental Example 2: Determination of Antagonistic Intensity and Duration of Action of Bronchoconstriction Response in the Trachea of Guinea Pig Induced by the Compound of the Invention Antagonizing Methacholine (Mch)

Determination of tidal volume, airway flow rate, and transpulmonary pressure: 1.5 g/kg of urethane was intraperitoneally injected to anaesthetize the guinea pig. The guinea pig was fixed supinely, subjected to tracheal intubation, and inserted with an indwelling needle while the external jugular vein was separated. The guinea pig was enclosed into a body plethysmograph, a blunt needle for intubation into thoracic cavity was inserted between ribs 4~5 of the prothorax of the guinea pig, and the intrathoracic pressure could be measured (with a negative value of a water column of a water manometer and a fluctuation with the breath of the guinea pig as marks). After stabilization, the values of the tidal volume, airway flow rate and transpulmonary pressure of the guinea pig prior to administration of Mch were recorded by a MedLab biological signal collection and processing system as base values. 10 μg/kg body weight of Mch was intravenously injected. The changes of the airway flow rate, tidal volume and transpulmonary pressure of the guinea pig within 5 minutes were observed. Calculation of $R_{aw}$ and $C_{dyn}$: the changes of the increased percentage of Raw value and the decreased percentage of $C_{dyn}$ after inhalation of Mch were calculated.

Calculation formulas of $R_{aw}$ and $C_{dyn}$ were respectively:

$$\text{Increased \% of } R_{aw} = \frac{R_{aw} \text{ after inhalation of } Mch - R_{aw} \text{ prior to inhalation (base value)}}{R_{aw} \text{ prior to inhalation (base value)}} \times 100\%$$

-continued

Decreased % of $C_{dyn}$ =

$$\frac{R_{aw} \text{ prior to inhalation of } Mch \text{ (base value)} - R_{aw} \text{ after inhalation}}{R_{aw} \text{ prior to inhalation of } Mch \text{ (base value)}} \times 100\%$$

Dose-effect relationship: For each of example Compounds, 27 guinea pigs were randomly divided into three groups: a group of 0.1 μg/kg of compounds [48, 70, 99, 138] of the invention, a group of 0.3 μg/kg of compounds [48, 70, 99, 138] of the invention, and a group of 1 μg/kg group of compounds [48, 70, 99, 138] of the invention, and there are 15 guinea pigs of a vehicle control group. The airway resistance (Raw) and pulmonary dynamic compliance (Cdyn) were measured within 5 minutes after airway dripping the above concentration of drugs for 30 min, and intravenous injection of 10 μg/kg body weight of Mch for excitation.

Time-effect relationship: After the guinea pigs were anesthetized, 0.5 μg/kg and 1 μg/kg of compounds [48, 70, 99, 138] of the invention were dripped into the airway. Separately at 0.25 h, 0.5 h, 1 h, 1.5 h, 2 h, 4 h, 6 h, 12 h and 24 h after administration, Mch of 10 μg/kg of body weight was intravenously injected for excitation, and the airway resistance (Raw) and pulmonary dynamic compliance ($C_{dyn}$) within 5 min were measured.

Dose-effect relationship: The administration dosages of compounds [48, 70, 99, and 138] of the invention were 0.1 μg/kg, 0.3 μg/kg and 1 μg/kg respectively. 30 min after the airway dripping, Mch of 10 μg/kg of body weight was intravenously injected for excitation, and the airway resistance (Raw) and pulmonary dynamic compliance ($C_{dyn}$) within 5 min were measured. The results were shown in Table 2 below:

After intravenous injection of Mch 10 μg/kg, guinea pig airway resistance was increased by 320%, pulmonary dynamic compliance was decreased by 71%. 0.1 μg/kg, 0.3 μg/kg, and 1 μg/kg of compounds [48, 70, 99, 138] were dripped into guinea pig airway respectively, which inhibited the increase of airway resistance and the decrease of lung dynamic compliance in a dose-dependent manner. The inhibitory rates of compound 48 on airway resistance increase in the three dosage groups were 66.2% ($p<0.01$), 88.3% ($p<0.001$) and 91.6% ($p<0.001$), respectively. The inhibitory rates of lung dynamic compliance decrease were 32.2% ($p>0.05$), 48.9% ($p<0.001$) and 50.1% ($p<0.001$), respectively. The inhibitory rates of compound 70 on airway resistance increase in three dosage groups were 69.6% ($p<0.01$), 86.5% ($p<0.001$) and 92.1% ($p<0.001$), respectively. The inhibitory rates of lung dynamic compliance decrease were 34.2% ($p>0.05$), 47.8% ($p<0.001$) and 49.3% ($p<0.001$), respectively. The inhibitory rates of compound 99 on airway resistance increase in three dosage groups were 73.5% ($p<0.01$), 86.8% ($p<0.001$) and 91.9% ($p<0.001$), respectively. The inhibitory rates of lung dynamic compliance were 35.0% ($p>0.05$), 48.8% ($p<0.001$) and 49.7% ($p<0.001$), respectively. The inhibitory rates of compound 138 on airway resistance increase in three dosage groups were 74.8% ($p<0.01$), 88.9% ($p<0.001$) and 92.6% ($p<0.001$), respectively. The inhibitory rates of lung dynamic compliance decrease were 31.0% ($p>0.05$), 48.2% ($p<0.001$) and 49.9% ($p<0.001$), respectively.

Time-effect relationship: After intravenous injection of Mch 10 μg/kg, the airway resistance of guinea pigs was increased by 328%. After 1 μg/kg of the compounds [48, 70, 99, 138] were dripped into the airway of guinea pigs for 0.25 h, the inhibitory rate on the airway resistance increase was 80% or more. The maximum inhibitory rate can reach 90% or more after 1 hour. With the extension of time, the

TABLE 2

Bronchial contraction response in guinea pigs induced by Example compounds 48, 70, 99, 138 of the invention antagonizing Mch-dose-effect (Mean ± S.E.M) relationship

| Group | Number of animals (n) | Mch 10 μg/kg iv | |
|---|---|---|---|
| | | $R_{aw}$ (cmH$_2$O/ml/s) | $C_{dyn}$ (ml/cmH$_2$O) |
| Vehicle control group | 10 | 1.863 ± 0.406 | 0.079 ± 0.008 |
| 0.1 μg/kg of Example compound 48 | 9 | 0.712 ± 0.065 | 0.115 ± 0.011 |
| 0.3 μg/kg of Example compound 48 | 8 | 0.523 ± 0.032 | 0.139 ± 0.012** |
| 1 μg/kg of Example compound 48 | 8 | 0.493 ± 0.071* | 0.207 ± 0.016*** |
| 0.1 μg/kg of Example compound 70 | 9 | 0.702 ± 0.098 | 0.218 ± 0.013 |
| 0.3 μg/kg of Example compound 70 | 8 | 0.613 ± 0.107* | 0.357 ± 0.087** |
| 1 μg/kg of Example compound 70 | 8 | 0.431 ± 0.095* | 0.345 ± 0.076*** |
| 0.1 μg/kg of Example compound 99 | 8 | 0.778 ± 0.073 | 0.120 ± 0.017 |
| 0.3 μg/kg of Example compound 99 | 9 | 0.528 ± 0.082* | 0.158 ± 0.021** |
| 1 μg/kg of Example compound 99 | 8 | 0.421 ± 0.069* | 0.223 ± 0.035*** |
| 0.1 μg/kg of Example compound 138 | 9 | 0.687 ± 0.079 | 0.124 ± 0.019 |
| 0.3 μg/kg of Example compound 138 | 8 | 0.508 ± 0.093* | 0.158 ± 0.036** |
| 1 μg/kg of Example compound 138 | 9 | 0.418 ± 0.086* | 0.231 ± 0.022*** |

Statistical methods: one-way ANOVA. Comparison between groups was tested by Bonferroni method. The comparison with vehicle control group were *P <0.05, P <0.01, *P <0.001.

inhibitory rate of airway resistance increase after 24 hours was still 85% or more, and there were statistical differences compared with vehicle control group (p<0.01~0.001). In order to confirm the correctness of the results, the administration dosage of compounds [48, 70, 99, 138] were reduced to 0.5 μg/kg. The results showed that after 0.5 μg/kg of the compounds [48, 70, 99, 138] were dripped into the airway of guinea pigs for 12 h, the inhibitory rate on the airway resistance was 85% or more (p<0.001), after 24 h, the inhibitory rate on the airway resistance was 75% or more (p<0.01). There was no significant difference in the inhibitory rate on the airway resistance between 1 μg/kg of compounds [48, 70, 99, 138] and 0.5 μg/kg of the same after 12 hours. However, after 24 h, there was no significant difference in the inhibitory rate on the airway resistance between 1 μg/kg of compounds [48, 70, 99, 138] and 0.5 μg/kg of the same (p<0.05). The above results suggested that 1 μg/kg of compounds [48, 70, 99, 138] and 0.5 μg/kg of the same were long-acting tracheal dilators, of which the acting time after administration of dripping by airway was more than 24 hours.

Experimental Example 3: Study on Activity and Selectivity of the Compounds of the invention to Human Recombinant $\beta_1$ and $\beta_2$ Adrenoceptors Expressed in HEK and CHO Cells In order to measure the activity and selectivity of agonists to human $\beta_1$ and $\beta_2$ adrenoceptors, the cAMP accumulation of expressed receptors in each recombinant cell line was measured. cAMP was determined by homology radioimmunoassay, that is, cells were washed with PSB buffer solution and suspended in the buffer solution at room temperature to grow to 30000-40000 cells per well. The test compound was diluted with PSB buffer solution containing 0.1% BSA and tested at 11 gradient concentrations ranging from 100 uM to 0.1 pM. For the analysis of $\beta_1$-adrenoceptor, 10 nM of ICI118551 was added to block the expression of $\beta_2$-adrenoceptor in HEK293 cells. After the compound was added to the suspended cells, the scintillation plate was incubated at 37° C. for 10 minutes, the reaction was terminated with ice-cold detection buffer solution, and its radioactivity was measured after storage at 4° C. overnight.

The agonistic activity (pEC$_{50}$ value) was analyzed by regression using S-type dose response model of software package (GraphPad Software, San Diego, Calif.). Selectivity was calculated from the ratio of measured cAMP of $\beta_1$ and $\beta_2$ adrenoceptors, which was expressed as sel. $\beta_1/\beta_2$=(EC$_{50}$ ($\beta_1$)/EC$_{50}$ ($\beta_2$)).

TABLE 3

Study results on activity and selectivity of some compounds of the invention to $\beta_1$ and $\beta_2$ adrenoceptors

| Example compound | EC50 ($\beta$1) nM | EC50 ($\beta$2) nM | sel ($\beta$1/$\beta$2) |
|---|---|---|---|
| Compound 1 | 197 ± 87 | 12.8 ± 4.2 | 15.4 |
| Compound 2 | 210 ± 89 | 32 ± 15 | 7.8 |
| Compound 3 | 160 ± 72 | 10.3 ± 2.4 | 15.6 |
| Compound 4 | 43 ± 16 | 1.2 ± 0.38 | 36.8 |
| Compound 25 | 33 ± 15 | 1.1 ± 0.35 | 30.8 |
| Compound 26 | 8.6 ± 2.1 | 0.46 ± 0.23 | 18.8 |
| Compound 27 | 252 ± 112 | 3.2 ± 1.4 | 78.9 |
| Compound 45 | 216 ± 87 | 8.2 ± 78 | 120.3 |
| Compound 46 | 52 ± 21 | 0.75 ± 0.21 | 68.9 |
| Compound 48 | 284 ± 105 | 0.67 ± 0.12 | 423.8 |
| Compound 50 | 256 ± 101 | 4.5 ± 1.3 | 56.9 |
| Compound 57 | 172 ± 64 | 2.5 ± 0.9 | 68.8 |

TABLE 3-continued

Study results on activity and selectivity of some compounds of the invention to $\beta_1$ and $\beta_2$ adrenoceptors

| Example compound | EC50 ($\beta$1) nM | EC50 ($\beta$2) nM | sel ($\beta$1/$\beta$2) |
|---|---|---|---|
| Compound 58 | 246 ± 81 | 2.7 ± 1.2 | 89.8 |
| Compound 59 | 83 ± 31 | 0.32 ± 0.12 | 213.4 |
| Compound 60 | 9.7 ± 2.3 | 0.79 ± 0.32 | 12.3 |
| Compound 62 | 251 ± 87 | 1.98 ± 0.31 | 126.7 |
| Compound 63 | 17 ± 5.8 | 0.41 ± 0.18 | 80.8 |
| Compound 70 | 156 ± 78 | 0.41 ± 0.11 | 379.8 |
| Compound 71 | 150 ± 64 | 0.32 ± 0.09 | 468.2 |
| Compound 75 | 238 ± 73 | 4.1 ± 1.4 | 56.8 |
| Compound 78 | 201 ± 79 | 1.9 ± 0.6 | 108.6 |
| Compound 84 | 196 ± 81 | 0.82 ± 0.31 | 238.8 |
| Compound 97 | 678 ± 201 | 12.0 ± 3.1 | 56.7 |
| Compound 99 | 117 ± 45 | 0.30 ± 0.13 | 389 |
| Compound 102 | 224 ± 103 | 2.2 ± 1.2 | 102.6 |
| Compound 104 | 39 ± 18 | 1.32 ± 0.56 | 29.6 |
| Compound 106 | 63 ± 28 | 0.22 ± 0.08 | 288.9 |
| Compound 114 | 227 ± 104 | 2.3 ± 1.5 | 98.9 |
| Compound 115 | 201 ± 78 | 2.36 ± 0.87 | 85.5 |
| Compound 116 | 56 ± 24 | 0.82 ± 0.31 | 68.8 |
| Compound 117 | 70 ± 33 | 1.75 ± 0.64 | 39.8 |
| Compound 118 | 23 ± 9 | 0.98 ± 0.33 | 23.8 |
| Compound 128 | 108 ± 51 | 0.42 ± 0.11 | 258.8 |
| Compound 138 | 94 ± 32 | 0.41 ± 0.10 | 228.3 |
| Compound 140 | 76 ± 26 | 0.88 ± 0.23 | 86.9 |
| Compound 141 | 91 ± 33 | 0.67 ± 0.22 | 135.9 |
| Compound 143 | 12 ± 3 | 1.2 ± 0.56 | 9.8 |
| Formotero | 46 ± 3.6 | 0.22 ± 0.10 | 209 |

Result analysis: The compounds of the invention have good agonistic activity and functional selectivity to $\beta_2$ adrenoceptor.

Experimental Example 4: Study on Activity Determination and Selectivity In Vitro of the Compounds of the Invention to Human Recombinant $M_1$, $M_2$, $M_3$ Receptor Subtypes Expressed in CHO Cells Transfected CHOm$_1$, CHOm$_2$, and CHOm$_3$ cells were cultured in DMEM medium (containing 15% fetal bovine serum, 4 mML-glutamine, 1% nonessential amino acid, and 1% antibiotic/antifungal) at 37° C. and 5% $CO_2$ incubator, respectively.

Referring to the literature [Hu Ya 'er, Shi Ju, Xia Zongqin; Some pharmacological and biological properties of CHOm$_2$ cells transfected with $M_2$ receptor cDNA [J]. Nuclear Science and Technology, 1999, 11(22): 642-646], when the cells in the culture flask grew and proliferated to form monolayer cells, and the bottom of the flask was covered by about 90% (about 48 h after inoculation), the medium was discarded, and washed twice with PBS (pH 7.4) buffer solution. Then the cells were scraped with an icy phosphate buffer solution (pH 7.7, containing 5 mmol/L MgCl$_2$). The collected cells were homogenized with a Teflon glass homogenizer, the homogenate was centrifuged at 20000r×20 min at low temperature, and the precipitate was homogenized with a reaction buffer solution to form a membrane protein suspension. The amount of protein added into each of reaction tubes was: m1 (about 0.05 mg), m2 (0.05 mg), m3 (0.1 mg), respectively, Concentration of [$^3$H]-QNB was 0.1-2.16 nmol/L. 1 μmol/L of atropine was added into non-specific binding tube. The total reaction volume was 300 μL. The resulting solution was then reacted at 25° C. for 5 h and quenched with an icy reaction buffer solution, and collected on a glass fiber membrane by using a multihead cell collector. After drying at 80° C., the filter membrane sheet was placed into a liquid scintillation vial, followed by the addition of 5 ml of liquid scintillation agent, and then kept in dark place overnight, with cpm measured by a liquid scintillation spectrometer. Bmax and Kd values were calculated by Graphpad prism software.

$^3$H-QNB, which is non-selective to M receptor, was added to each experimental tube as the labeling ligand, and the final concentration of each tube was m1, m3 (1.042 nmol/L), m2 (1.81 nmol/L). At the same time, different concentrations of tiotropium bromide, ipratropium bromide and each test compound were added, the final concentration was $10^{-10} \sim 10^{-4}$ mol/L, totaling 11 dosages. The same amount of membrane protein sample (same as the saturation experiment mentioned above) was added. The total volume of the reaction was 300 μL, and competitive binding reaction was carried out. Another nonspecific binding tube was set up to measure nonspecific binding with a large amount of atropine (final concentration of 1 μmol/L). After the reaction was carried out at 25° C. for 5 h and terminated with ice-cold reaction buffer solution, the reaction product was collected on glass fiber filter membrane using multi-head cell collector. After drying at 80° C., the filter membrane was placed into a liquid scintillation vial, added with 5 ml of liquid scintillation agent, and kept in dark place overnight. Cpm was measured with a liquid scintillation meter. Ki values of each compound to three M receptor subtypes were calculated by Graphpad prism software. The selectivity of M receptor subtype was compared among tiotropium bromide, ipratropium bromide and each test compound.

TABLE 4

Experimental results of activity determination and selectivity of some compounds of the invention to M receptor antagonist

| Example compound | hM$_1$Ki (nM) | hM$_2$Ki (nM) | hM$_3$Ki (nM) | M$_1$/M$_2$* | M$_1$/M$_3$ | M$_2$/M$_3$ |
|---|---|---|---|---|---|---|
| Tiotropium | 0.029 ± 0.009 | 0.035 ± 0.005 | 0.0193 ± 0.005 | 1.2069 | 0.6655 | 0.5514 |
| Ipratropium | 1.41 ± 0.45 | 0.81 ± 0.12 | 0.692 ± 0.21 | 0.5745 | 0.4908 | 0.8543 |
| Compound 1 | 0.733 ± 0.32 | 0.968 ± 0.15 | 0.561 ± 0.22 | 1.3206 | 0.7653 | 0.5795 |
| Compound 2 | 0.326 ± 0.15 | 0.838 ± 0.31 | 0.128 ± 0.013 | 2.5706 | 0.3926 | 0.1527 |
| Compound 3 | 0.767 ± 0.16 | 0.938 ± 0.40 | 0.451 ± 0.18 | 1.2229 | 0.5880 | 0.4808 |
| Compound 4 | 1.789 ± 0.40 | 1.986 ± 0.51 | 0.879 ± 0.32 | 1.1101 | 0.4913 | 0.4426 |
| Compound 25 | 1.852452 ± 0.20 | 1.846 ± 0.62 | 0.933 ± 0.23 | 0.9965 | 0.5037 | 0.5054 |
| Compound 26 | 0.298 ± 0.11 | 0.598 ± 0.19 | 0.103 ± 0.013 | 2.0067 | 0.3456 | 0.1722 |
| Compound 27 | 0.392 ± 0.24 | 0.878 ± 0.36 | 0.172 ± 0.025 | 2.2398 | 0.4388 | 0.1959 |
| Compound 45 | 0.0668 ± 0.017 | 0.325 ± 0.21 | 0.0288 ± 0.012 | 4.8653 | 0.4311 | 0.0886 |
| Compound 46 | 0.169 ± 0.067 | 0.868 ± 0.38 | 0.0735 ± 0.034 | 5.1361 | 0.4349 | 0.0847 |
| Compound 48 | 0.873 ± 0.091 | 4.376 ± 1.2 | 0.386 ± 0.13 | 5.0126 | 0.4422 | 0.0882 |
| Compound 50 | 0.513 ± 0.24 | 0.973 ± 0.33 | 0.232 ± 0.056 | 1.8967 | 0.4522 | 0.2384 |
| Compound 57 | 0.0783 ± 0.026 | 0.287 ± 0.12 | 0.0376 ± 0.016 | 3.6654 | 0.4802 | 0.1310 |
| Compound 58 | 0.164 ± 0.083 | 0.289 ± 0.087 | 0.0795 ± 0.021 | 1.7622 | 0.4848 | 0.2751 |
| Compound 59 | 0.283 ± 0.018 | 1.998 ± 0.89 | 0.131 ± 0.022 | 7.0601 | 0.4629 | 0.0656 |
| Compound 60 | 0.183 ± 0.013 | 0.216 ± 0.15 | 0.0866 ± 0.012 | 1.1803 | 0.4732 | 0.4009 |
| Compound 62 | 0.465 ± 0.19 | 0.975 ± 0.31 | 0.198 ± 0.016 | 2.0968 | 0.4258 | 0.2031 |
| Compound 63 | 0.0493 ± 0.021 | 0.323 ± 0.17 | 0.0198 ± 0.012 | 6.5517 | 0.4016 | 0.0613 |
| Compound 70 | 0.2188 ± 0.019 | 1.379 ± 0.45 | 0.0831 ± 0.031 | 6.3026 | 0.3798 | 0.0603 |
| Compound 71 | 0.153 ± 0.016 | 0.812 ± 0.35 | 0.0628 ± 0.023 | 5.3072 | 0.4105 | 0.0773 |
| Compound 75 | 1.527 ± 0.29 | 0.988 ± 0.32 | 0.737 ± 0.28 | 0.6470 | 0.4826 | 0.7460 |
| Compound 78 | 0.172 ± 0.14 | 0.316 ± 0.12 | 0.0786 ± 0.039 | 1.8372 | 0.4570 | 0.2487 |
| Compound 84 | 0.886 ± 0.11 | 1.936 ± 0.75 | 0.398 ± 0.11 | 2.1851 | 0.4492 | 0.2056 |
| Compound 97 | 0.243 ± 0.17 | 0.205 ± 0.078 | 0.0923 ± 0.019 | 0.8436 | 0.3798 | 0.4502 |
| Compound 99 | 0.463 ± 0.13 | 2.412 ± 0.87 | 0.155 ± 0.023 | 5.2095 | 0.3348 | 0.0643 |
| Compound 102 | 0.243 ± 0.11 | 0.307 ± 0.16 | 0.0943 ± 0.021 | 1.2634 | 0.3881 | 0.3072 |
| Compound 104 | 0.524 ± 0.14 | 0.531 ± 0.31 | 0.202 ± 0.066 | 1.0134 | 0.3855 | 0.3804 |
| Compound 106 | 0.231 ± 0.18 | 0.559 ± 0.25 | 0.116 ± 0.052 | 2.4199 | 0.5022 | 0.2075 |
| Compound 114 | 1.296 ± 0.12 | 0.884 ± 0.33 | 0.478 ± 0.097 | 0.6821 | 0.3688 | 0.5407 |
| Compound 115 | 0.478 ± 0.13 | 0.835 ± 0.27 | 0.156 ± 0.067 | 1.7469 | 0.3264 | 0.1868 |
| Compound 116 | 0.371 ± 0.23 | 0.406 ± 0.26 | 0.164 ± 0.086 | 1.0943 | 0.4420 | 0.4039 |
| Compound 117 | 0.128 ± 0.009 | 0.387 ± 0.23 | 0.0578 ± 0.026 | 3.0234 | 0.4516 | 0.1494 |
| Compound 118 | 0.658 ± 0.11 | 1.213 ± 0.58 | 0.323 ± 0.078 | 1.8435 | 0.4909 | 0.2663 |
| Compound 128 | 0.278 ± 0.023 | 1.877 ± 0.73 | 0.123 ± 0.069 | 6.7518 | 0.4424 | 0.0655 |
| Compound 138 | 0.217 ± 0.008 | 1.480 ± 0.59 | 0.091 ± 0.038 | 6.8203 | 0.4194 | 0.0615 |
| Compound 140 | 0.356 ± 0.16 | 0.988 ± 0.21 | 0.176 ± 0.082 | 2.7753 | 0.4944 | 0.1781 |
| Compound 141 | 0.252 ± 0.11 | 0.847 ± 0.27 | 0.116 ± 0.056 | 3.3611 | 0.4603 | 0.1370 |
| Compound 143 | 1.322 ± 0.15 | 1.302 ± 0.90 | 0.635 ± 0.27 | 0.9849 | 0.4803 | 0.4877 |

*M$_x$/M$_y$ = Ki(y)/Ki(x)

Experimental results show that the compounds of the invention have the highest selectivity to $M_3$ receptor, followed by $M_1$ receptor and the lowest selectivity to $M_2$ receptor, and the compounds have strong effect on $M_3$ and $M_1$ receptors. Compared with the prior art, the invention has obvious advantages in treating rhinitis, airway hyperresponsiveness, chronic bronchitis, COPD and other diseases.

Experimental Example 5: Activity at MABA, M Receptor and $\beta_2$ Adrenoceptor Determined in Guinea Pig Isolated Trachea (1) The Constriction Effect of Tracheal Smooth Muscle of Guinea Pig Induced by the Example Compounds Antagonizing Carbachol (CCh)

Preparation of an isolated tracheal smooth muscle specimen of a guinea pig: same as Experiment Example 1.

Administration Method: After the trachea flake were stabilized, carbachol with a final concentration of $3 \times 10^{-6}$ mol/L was added, and administration was started when the pressure value of the trachea flake was increased to a stable platform. The experiments were divided into blank group and each test sample administration group. DMSO solution prepared from K—H solution and 50 μl of each test sample solution were added to each group respectively. The test sample administration group was added with $10^{-9}$, $0.3 \times 10^{-8}$, $10^{-8}$, $0.3 \times 10^{-7}$, $10^{-7}$, $0.3 \times 10^{-6}$ and $10^{-6}$ mol/L of test compound and control substance at cumulative concentration. The blank group was added with corresponding diluted DMSO solution. Medlab was used to record the relaxation degree of smooth muscle of the trachea flake. Finally, isoproterenol with a final concentration of $10^{-5}$ mol/L was added as 100% relaxation. The results were shown in Table 5.

(2) Blocking Effect of Example Compounds on M Receptor of Guinea Pig Tracheal Smooth Muscle Preparation of an isolated tracheal smooth muscle specimen of a guinea pig: same as Experiment Example 1.

Administration method: After trachea flake was stabilized, propranolol hydrochloride solution with a final concentration of $10^{-5}$ mol/L was added to block β receptor for 10 min, carbachol with a final concentration of $3 \times 10^{-6}$ mol/L was added (observing M receptor antagonism of compound after propranolol blocks β receptor), and administration was started when the pressure value of the trachea flake was increased to a stable platform. The experiments were divided into a blank group, a propranolol+blank group, each test sample administration group and a propranolol+each test sample administration group. DMSO solution prepared by K—H solution and 50 μl of test sample solution were added to each group of the blank group and each test sample administration group respectively. The propranolol+blank group and propranolol+each test sample administration group were added with 50 μl propranolol solution for 10 min respectively, and then added with DMSO solution prepared from K—H solution and 50 μl of test sample solution. The test sample administration group was added with the compounds to be tested with final concentrations of $10^{-9}$, $0.3 \times 10^{-8}$, $10^{-8}$, $0.3 \times 10^{-7}$, $10^{-7}$, $0.3 \times 10^{-6}$ and $10^{-6}$ mol/L at cumulative concentration, and the blank group was added with corresponding diluted DMSO solution. The propranolol+each test sample administration group was added with propranolol for 10 min, and then added with the compounds to be tested with final concentrations of $10^{-9}$, $0.3 \times 10^{-8}$, $10^{-8}$, $0.3 \times 10^{-7}$, $10^{-7}$, $0.3 \times 10^{-6}$ and $10^{-6}$ mol/L at cumulative concentration. After the propranolol+blank group was added with propranolol for 10 min, corresponding diluted DMSO solution was added. Medlab was used to record the relaxation degree of tracheal smooth muscle, finally sodium nitroprusside with a final concentration of $2 \times 10^{4}$ mol/L was added as 100% relaxation. The results were shown in table 5.

(3) The Antagonism of the Example Compounds on $\beta_2$ Receptor in Guinea Pig Tracheal Smooth Muscle Preparation of an isolated tracheal smooth muscle specimen of a guinea pig: same as Experiment Example 1.

Administration Method: After the trachea flake was stabilized, histamine solution with a final concentration of $3 \times 10^{-5}$ mol/L was added for 10 min, carbachol with a final concentration of $3 \times 10^{-6}$ mol/L was added (observing β receptor antagonism), and administration was started when the pressure value of the trachea flake was increased to a stable platform. The experiments were divided into a blank group, a histamine+blank group, each test sample administration group and a histamine+each test sample administration group. DMSO solution prepared by K—H solution and 50 μl of test sample solution were added to each group of the blank group and each test sample administration group respectively. The histamine+blank group and histamine+each test sample administration group were added with 50 μl histamine solution for 10 min respectively, then added with DMSO solution prepared by K—H solution and 50 μl test sample solution. The test sample administration group was added with the compounds to be tested with final concentrations of $10^{-9}$, $0.3 \times 10^{-8}$, $10^{-8}$, $0.3 \times 10^{-7}$, $10^{-7}$, $0.3 \times 10^{-6}$ and $10^{-6}$ mol/L at cumulative concentration, and the blank group was added with corresponding diluted DMSO solution. The histamine+each test sample administration group was added with histamine for 10 min, and then added with the test compounds with final concentrations of $10^{-9}$, $0.3 \times 10^{-8}$, $10^{-8}$, $0.3 \times 10^{-7}$, $10^{-7}$, $0.3 \times 10^{-6}$ and $10^{-6}$ mol/L at cumulative concentration. After the histamine+blank group was added with histamine for 10 m, corresponding diluted DMSO solution was added. Medlab was used to record the relaxation degree of smooth muscle of the trachea flake. Finally theophylline with a final concentration of $2 \times 10^{-4}$ mol/L was added as 100% relaxation. The results were shown in table 5.

TABLE 5

Experiment results of pharmacodynamic activity of some compounds of the invention in pre-constricted isolated tracheal M receptor antagonists (MA), $\beta_2$ receptor agonists (BA) and bifunctional (MABA)

| Compound | MA ($EC_{50}$, nM) | BA ($EC_{50}$, nM) | MABA ($EC_{50}$, nM) |
|---|---|---|---|
| Compound 7 | 289.7 ± 12.3 | 162.5 ± 9.8 | 72.3 ± 14.6 |
| Compound 12 | 20.1 ± 2.8 | 13.8 ± 2.3 | 5.8 ± 1.4 |
| Compound 61 | 20.6 ± 1.8 | 12.9 ± 1.8 | 5.0 ± 1.1 |
| Compound 69 | 27.7 ± 3.4 | 18.7 ± 2.8 | 7.6 ± 1.8 |
| Compound 94 | 43.5 ± 4.2 | 33.5 ± 5.7 | 19.8 ± 5.4 |
| Compound 113 | 15.6 ± 2.6 | 17.6 ± 1.9 | 7.2 ± 1.4 |
| Compound 122 | 56.7 ± 6.6 | 36.8 ± 4.1 | 15.6 ± 3.6 |
| Compound 131 | 30.2 ± 8.1 | 9.2 ± 1.6 | 4.0 ± 1.0 |
| Compound 80 | 13.3 ± 1.2 | 9.9 ± 1.7 | 3.3 ± 0.9 |
| Compound 82 | 24.3 ± 2.5 | 7.9 ± 1.3 | 2.8 ± 1.1 |
| Tiotropium Bromide | 12.2 ± 0.8 | *NA | *NA |
| Salmeterol | *NA | 93.8 ± 6.8 | *NA |

*NA means not applicable.

The results show that the compounds of the invention have simultaneously strong M receptor blocking function and R receptor agonistic function, and these two functions of a large number of compounds have a matching degree MA:BA which substantially reaches 1-1.5:1. The matching degree of the Example compound 113 almost reaches 1:1.

Experiment Example 6: Acute Toxicity Test of the Compounds of the Invention in Beagle Dogs by Single Gavage Test Compounds:
Example compounds 7, 12, 61, 69, 80, 82, 94, 113, 122, and 131 of the invention
Control Compounds:
(1) The compound of Example 1 in WO2010126025: 4-({[5-(2-{[4-({[(2R)-2-hydroxy-2-(8-hydroxy-2-oxo-1,2-dihydroquinolin-5-yl)ethyl]amino}methyl)phenyl]carbamoyl}ethyl)-2-phenylphenyl]carbamoyl}oxy)-1,1-dimethylpiperidin-1-onium trifluoroacetate (prepared according to the literature method).
(2) The compound of Example 1 in WO2010004517: 5-[(1R)-2-({9-[4-({3-[(R)-cyclohexyl(hydroxy)benzyl)-1H-1,2,4-triazol-1-yl}methyl)piperidin-1-yl]nonyl}amino)-1-hydroxyethyl]-8-hydroxyquinolin-2 (1H)-one (prepared according to the literature method).
Test Method:
Beagle dogs were randomly divided into two groups, half male and half female, and were intravenously injected (iv) with 7.5% ethanol solution of compounds of the invention and control compound. Each compound was set up in two dosage groups of 0.01 mg/kg and 0.10 mg/kg. Heart rate changes were observed after administration (30 min-4 h after administration), and the results were shown in Table 6.

TABLE 6

Heart rate changes after iv administration of the compounds of the invention in Beagle dogs

| Test compound | 0.5-4 h area increase under heart rate curve (%) | |
|---|---|---|
| | 0.01 mg/kg | 0.10 mg/kg |
| compound 7 | −0.5 | 0 |
| compound 12 | 1.2 | 3.6 |
| compound 61 | 0 | 2.1 |
| compound 69 | −5.1 | −3.4 |
| compound 80 | 4 | −5.1 |
| compound 82 | 3.3 | 4.8 |
| compound 94 | −2.8 | 4.6 |
| compound 113 | −3.4 | 3.3 |
| compound 122 | 6.6 | 0 |
| compound 131 | 10 | 2.9 |
| The compound of Example 1 in WO2010126025 | 35.2 | 109 |
| The compound of Example 1 in WO2010004517 | 69.7 | 152 |

As can be seen from Table 6, the heart rate of the Beagle dogs are not changed significantly after the iv administration of the compounds of the present invention at the dosage of 0.1 mg/kg, while the control compound significantly increases the heart rate of the Beagle dogs at the dosage of 0.01 mg/kg. Thus, the compounds of the invention have lower toxicity and side effects.

Experiment Example 7: Stability Tests of the Compounds of the Invention in Liver Microsomes and Lung Homogenate In Vitro 1. Test Compound in Liver Microsomal Test:
Example compounds 7, 12, 61, 69, 80, 82, 94, 113, 122, and 131 of the invention
Control Compound:
(1) the compound of Example 1 in WO2010126025, (2) the compound of Example 1 in WO2010004517.

Experiment Method: the Example compounds of the invention and the control compound were respectively incubated with the liver microsomes of SD rats and Beagle dogs at 37° C. for 0, 2, 5, 10, 15, 20, 30 min, and the samples were analysed respectively by the LC-MS/MS when the reaction was terminated. The area ratio of the 0 min sample was taken as 100%, and the remaining percentage of the compound after incubation at different times was obtained at each time point by comparison with the sample. With the natural logarithm of this percentage on the ordinate and time on the abscissa, a scatter plot was drawn to simulate a straight line with a negative slope of k. The parameters were calculated according to the formula.

$$t_{1/2}(\min) = 0.693/k$$

$$Cl_{int}(\text{mL/min/kg}) = \frac{0.693 \times \text{Liver weight (g/kg)} \times P450 \text{ (mg/g)}}{0.5 \text{ (mg/mL)} \times t_{1/2} \text{ (min)}}$$

Liver weight indicates the liver weight (g) per kilogram of body weight, and P450 indicates the amount (mg) of P450 enzyme per gram of liver.
The values of the different species are shown in the table below:

| Species | Liver weight (g/kg) | P450 protein/liver (mg/g) | Qh (mL/min/kg) |
|---|---|---|---|
| Dog | 32 | 45 | 30 |
| Rat | 40 | 45 | 55 |

$$Cl_{hep}(\text{mL/min/kg}) = \frac{Cl_{int}(\text{mL/min/kg}) \times Qh(\text{mL/min/kg})}{Cl_{int}(\text{mL/min/kg}) + Qh(\text{mL/min/kg})}$$

Qh represents hepatic blood flow, and the values of different species are shown in the table above.
The liver extraction rate (ERh) was calculated according to ERh=$Cl_{hep}$/Qh, and the results are shown in table 7.

TABLE 7

Metabolic stability conditions of the compound liver microsomes in vitro

| Test compound | liver extraction rate (*ERh) | | |
|---|---|---|---|
| | Human | SD rat | Beagle dog |
| compound 7 | 0.94 | 0.97 | 0.98 |
| compound 12 | 0.96 | 0.98 | 0.93 |
| compound 61 | 0.98 | 0.95 | 0.97 |
| compound 69 | 0.95 | 0.96 | 0.94 |
| compound 80 | 0.92 | 0.92 | 0.91 |
| compound 82 | 0.93 | 0.95 | 0.93 |
| compound 94 | 0.93 | 0.94 | 0.94 |
| compound 113 | 0.97 | 0.96 | 0.96 |
| compound 122 | 0.93 | 0.97 | 0.98 |
| compound 131 | 0.99 | 0.93 | 0.93 |
| The compound of Example 1 in WO2010126025 | 0.36 | 0.48 | 0.43 |
| The compound of Example 1 in WO2010004517 | 0.62 | 0.42 | 0.36 |

*The criteria for microsomal stability are as follows: ERh < 0.3 belongs to a compound with better liver metabolic stability, 0.3 < ERh < 0.7 belongs to a compound with medium liver metabolic stability, and ERh > 0.7 belongs to a compound with poor liver metabolic stability.

As is shown in Table 7, the compounds of the invention have poor metabolic stability in SD rat and Beagle dog liver microsomes, metabolized fasterly, and are difficult to accumulate in vivo, whereas the control compound has better metabolic stability and is easier to accumulate in vivo.

2. Lung Homogenate Test Compounds:

Example compounds 7, 12, 61, 69, 80, 82, 94, 113, 122, and 131 of the invention

The compounds of the invention were respectively incubated with the lung homogenate of Beagle dogs for 8 hours in a water bath at 37° C., and sample was analysed by LC-MS/MS when the reaction was terminated. The area ratio of the 0 min sample was taken as 100%, and the remaining percentage of the compounds after incubation for 8 hours was obtained by the comparison with the sample after 8 hours. The results were shown in Table 8.

TABLE 8

Metabolic stability conditions of the compounds of the invention in lung homogenate in vitro (8 h)

| Test compound | Residual rate after incubation of human lung homogenate (%) | Residual rate after incubation of dog lung homogenate (%) |
| --- | --- | --- |
| compound 7 | 93 | 95 |
| compound 12 | 98 | 91 |
| compound 61 | 92 | 89 |
| compound 69 | 94 | 90 |
| compound 80 | 92 | 92 |
| compound 82 | 98 | 97 |
| compound 94 | 91 | 96 |
| compound 113 | 93 | 93 |
| compound 122 | 95 | 92 |
| compound 131 | 90 | 94 |

Conclusion: The above tests demonstrate that the compounds of the invention are stable in lung and thus have long-acting effect in the lung. As can be seen from Table 7, the compounds of the invention have poor metabolic stability in SD rat and Beagle dog liver microsomes, are metabolized fasterly, and are difficult to accumulate in vivo, whereas the control compound has better metabolic stability and is easier to accumulate. It shows that the compounds of the invention cannot accumulate effective toxic dosage.

Preparation Example 1

Dry powder preparation for inhalation administration was prepared by the following method:

Each component and amount thereof in the composition were:

| Compound 59 of the invention | 0.20 mg |
| --- | --- |
| Lactose | 30 mg |

The compound of the invention was micronized, sufficiently mixed with the micronized lactose, and the mixture was loaded into a gelatin suction cartridge and administered by a powder inhaler.

Preparation Example 2

Dry powder preparation for use in dry powder inhalation device was prepared by the following method:

The compound 70 of the invention was micronized, and mixed with the micronized lactose uniformly to form a preparation. The combination ratio of the preparation was 1:200, and the preparation composition was loaded into a dry powder inhalation device capable of transferring 10 μg to 100 μg of the compound of the invention.

Preparation Example 3

Dry powder preparation for use in inhalation administration in metered dose inhaler was prepared by the following method:

10 g of the micronized compound 99 of the invention having an average particle size of less than 10 μm was dispersed in a 200 mL softened aqueous solution containing 0.2 g of lecithin to form a suspension containing 5 wt % of compound of the invention and 0.1 wt % of lecithin, and the suspension was spray dried to form particles having an average particle size of less than 1.5 μm. The particles were loaded into pressurized 1,1,1,2-tetrafluoroethane cartridges.

Preparation Example 4

The pharmaceutical composition for use in metered dose inhaler was prepared by the following method:

5 g of the micronized compound 138 of the invention having an average particle size of less than 10 μm was dispersed in 100 mL of a softened aqueous colloid containing 0.5 g of trehalose and 0.5 g of lecithin to form a suspension containing 5 wt % of the compound of the invention, 0.5% trehalose and 0.5 wt % of lecithin. The suspension was spray dried to form particles having an average particle size of less than 1.5 μm. The particles were loaded into pressurized 1,1,1,2-tetrafluoroethane cartridges.

What we claim is:

1. A compound represented by formula I, or a pharmaceutically acceptable salt, solvate, optical isomer thereof:

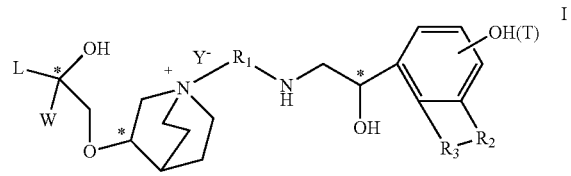

in formula I, carbons marked with * being all (R) configuration, wherein:

L is (4-10C) aryl or heteroaryl wherein the hetero atom of the heteroaryl is selected from N, O, and S, the (4-10C) aryl or heteroaryl is unsubstituted or substituted with one or more substituents selected from halogen, —OR$^1$, —SR$^1$, —NR$^1$R$^2$, —NHCOR$^1$, —CONR$^1$R$^2$, —CN, —NO$_2$, —COOR$^1$, —CF$_3$, and C$_1$-C$_4$ linear or branched hydrocarbyl, each of R and R$^2$ independently is hydrogen atom, C$_1$-C$_4$ linear or branched hydrocarbyl;

W is independently selected from substituted or unsubstituted (3-6C)cycloalkyl, the substituent is selected from halogen, (1-4C)alkyl, (1-4C)alkoxy, alkoxyhydrocarbyl, and heterocycle;

R$_1$ is a divalent group —(R$_{1a}$)$_d$-(A$_1$)$_e$-(R$_{1b}$)$_f$—; wherein d, e, and f are each independently selected from 0, 1, 2 or 3, and the number of adjoining atoms in the shortest chain between two nitrogen atoms to which R$_1$ is attached is in the range of 3 to 14;

R$_{1a}$ and R$_{1b}$ are each independently selected from (1-10C) alkylene, (2-10C)alkenylene, (1-4C)alkyleneoxy, alkyleneoxyalkyl, alkyleneamido, alkyleneacyloxy, and alkyleneamino, wherein each of alkylene, alkenylene, alkyleneoxy, alkyleneoxyalkyl, alkyleneamino, alkyleneacyloxy, alkyleneamido is unsubstituted or substituted with substituents independently selected from (1-4C)alkyl, chloro, fluoro, hydroxy, phenyl and substituted phenyl, $R_{1a}$ and $R_{1b}$ may be the same or different;

$A_1$ is independently selected from (3-7C)cycloalkylene, (2-7C)alkylene, (6-10C)arylene, (4-9C)heteroarylene, and (3-8C)heterocycloalkylene, wherein cycloalkylene may be unsubstituted or substituted with 1-4 substituents independently selected from (1-6C)alkyl; each of arylene, heteroarylene, and heterocycloalkylene may be unsubstituted or substituted with 1-3 substituents independently selected from halogen, (1-6C)alkyl, (1-6C)alkoxy, —S-(1-4C)alkyl, —S(O)-(1-4C)alkyl, —S(O)$_2$-(1-4C)alkyl, —C(O)—O-(1-4C)alkyl, —NH-(1-4C)alkyl, —N=[(1-4C)alkyl]$_2$, carboxy, nitro, cyano, amido, ester group, trifluoromethyl, and trifluoromethoxy;

$R_2$ is independently selected from —N($R_{2a}$)C($R_{2b}$)(O), —C($R_{2c}$)($R_{2d}$)O$R_{2e}$, —N($R_{2f}$)—, —O—; $R_3$ is independently selected from —H, —C($R_{3a}$)=C($R_{3b}$)—C(O)—, —OC($R_{3c}$)($R_{3d}$)C(O)—, —N($R_{3e}$)CH($R_{3f}$)C(O)—, —C($R_{3g}$)($R_{3h}$)S(O)$_2$—, —SCO—; with the provision that $R_2$ is independently selected from —N($R_{2a}$)C($R_{2b}$)(O), —C($R_{2c}$)($R_{2d}$)O$R_{2e}$ when $R_3$ is —H; with the provision that $R_2$ is —N($R_{2f}$)— or —O— when $R_3$ is independently selected from —C($R_{3a}$)=C($R_{3b}$)—C(O)—, —OC($R_{3c}$)($R_{3d}$)C(O)—, —N($R_{3e}$)CH($R_{3f}$)C(O)—, —C($R_{3g}$)($R_{3h}$)S(O)$_2$—, —SCO—, and $R_2$, $R_3$ and their connected carbon atoms join together to form a ring; $R_{2a-2f}$ and $R_{3a-3h}$ are each independently selected from hydrogen and (1-4C)alkyl;

$Y^-$ is selected from $Br^-$, $Cl^-$, $I^-$, bicarbonate, carbonate, bisulfate, sulfate, nitrate, phosphate, hydrogen phosphate, dihydrogen phosphate, phosphite, formate, acetate, propionate, isobutyrate, methanesulfonate, p-toluenesulfonate, benzoate, oxalate, tartrate, fumarate, malonate, succinate, suberate, mandelate, phthalate, benzene sulfonate, citrate, glucuronate, galactonate and amino acid radical; and T represents a position of hydroxy on the benzene ring, and is selected from the ortho or meta position of $R_2$ on the benzene ring.

2. The compound according to claim 1, or the pharmaceutically acceptable salt, solvate, optical isomer thereof, wherein L is an unsubstituted phenyl, pyridyl, furyl or thienyl.

3. The compound according to claim 1, or the pharmaceutically acceptable salt, solvate, optical isomer thereof, wherein W is unsubstituted (3-6C)cycloalkyl.

4. The compound according to claim 3, or the pharmaceutically acceptable salt, solvate, optical isomer thereof, wherein W is cyclobutyl, cyclopentyl or cyclohexyl.

5. The compound according to claim 1, or the pharmaceutically acceptable salt, solvate, optical isomer thereof, wherein $R_{1a}$ and $R_{1b}$ are each independently selected from (1-10C)alkylene, -(1-4C)alkyleneoxy, alkyleneamido; and $A_1$ is independently selected from (6-10C)arylene, wherein the arylene may be unsubstituted or substituted with 1-2 substituents independently selected from halogen, (1-6C)alkyl, (1-6C)alkoxy, carboxy, nitro, cyano, amido, and ester group.

6. The compound according to claim 1, or the pharmaceutically acceptable salt, solvate, optical isomer thereof, wherein $R_1$ is selected from: —(CH$_2$)$_3$—, —(CH$_2$)$_4$—, —(CH$_2$)$_8$—, —(CH$_2$)$_9$—, —(CH$_2$)$_{10}$—, —(CH$_2$)$_2$O(CH$_2$)$_2$—, —(CH$_2$)$_2$O(CH$_2$)$_4$—, —(CH$_2$)$_3$O(CH$_2$)$_4$—, —(CH$_2$)$_4$O(CH$_2$)$_4$—, —(CH$_2$)$_5$O(CH$_2$)$_4$—, —(CH$_2$)$_2$O(CH$_2$)$_2$O(CH$_2$)$_2$—, —(CH$_2$)$_2$O(CH$_2$)$_3$O(CH$_2$)$_2$—, —CH$_2$O(CH$_2$)$_5$OCH$_2$—, —(CH$_2$)$_2$O(CH$_2$)$_2$O(CH$_2$)$_2$O(CH$_2$)$_2$—, —(CH$_2$)$_2$O(phen-1,4-ylene)(CH$_2$)$_2$—, —(CH$_2$)$_3$O(phen-1,4-ylene)CH$_2$—, —(CH$_2$)$_3$O(3,5-dichloro-phen-1,4-ylene)CH$_2$—, —(CH$_2$)$_2$CONH(2-methoxy-5-chloro-phen-1,4-ylene)CH$_2$—, —(CH$_2$)$_2$CONH(3-methyl-phen-1,4-ylene)CH$_2$—, —(CH$_2$)$_2$CONH(2-methoxy-phen-1,4-ylene)CH$_2$—, —(CH$_2$)$_2$CONH(phen-1,4-ylene)CH$_2$—, —(CH$_2$)$_3$CONH(phen-1,4-ylene)CH(CH$_3$)—, —(CH$_2$)$_3$OCH$_2$(3-methoxy-phen-1,4-ylene)CH(CH$_3$)—, —(CH$_2$)$_3$O(phen-1,4-ylene)C(CH$_3$)$_2$—, —(CH$_2$)$_3$O(phen-1,4-ylene)CH(CH$_2$CH$_3$)—, —(CH$_2$)$_3$O(phen-1,4-ylene)(CH$_2$)$_2$—, —(CH$_2$)$_3$O(phen-1,4-ylene)(CH$_2$)$_3$—, —(CH$_2$)$_3$O(phen-1,4-ylene)CH$_2$CH(CH$_3$)—, —(CH$_2$)$_2$OCH$_2$(phen-1,4-ylene)CH$_2$O(CH$_2$)$_2$—, —(CH$_2$)$_2$OCH$_2$(phen-1,4-ylene)CH(CH$_3$)—, —(CH$_2$)$_2$O(phen-1,4-ylene)O(CH$_2$)$_2$—, —(CH$_2$)$_3$O(2-methoxy-phen-1,4-ylene)O(CH$_2$)$_3$—, —(CH$_2$)$_3$O(phen-1,4-ylene)O(CH$_2$)$_3$—, —(CH$_2$)$_3$O(phen-1,4-ylene)CH$_2$C(CH$_3$)$_2$—, —(CH$_2$)$_2$O(phen-1,4-ylene)CH$_2$C(CH$_3$)$_2$—, —(CH$_2$)$_2$O(phen-1,4-ylene)CH$_2$CH(CH$_3$)—, and —(CH$_2$)$_2$O(phen-1,4-ylene)(CH$_2$)$_2$—, —(CH$_2$)$_2$O(CH$_2$)$_3$O(CH$_2$)$_2$—.

7. The compound according to claim 1, or the pharmaceutically acceptable salt, solvate, optical isomer thereof, wherein $R_{2a-2f}$ are hydrogen each.

8. The compound according to claim 1, or the pharmaceutically acceptable salt, solvate, optical isomer thereof, wherein $R_{3a-3h}$ are hydrogen each.

9. The compound according to claim 1, or the pharmaceutically acceptable salt, solvate, optical isomer thereof, wherein $Y^-$ is selected from $Br^-$ or $Cl^-$.

10. The compound according to claim 1, or the pharmaceutically acceptable salt, solvate, optical isomer thereof, having a structure of formula Ia, Ib, Ic or Id:

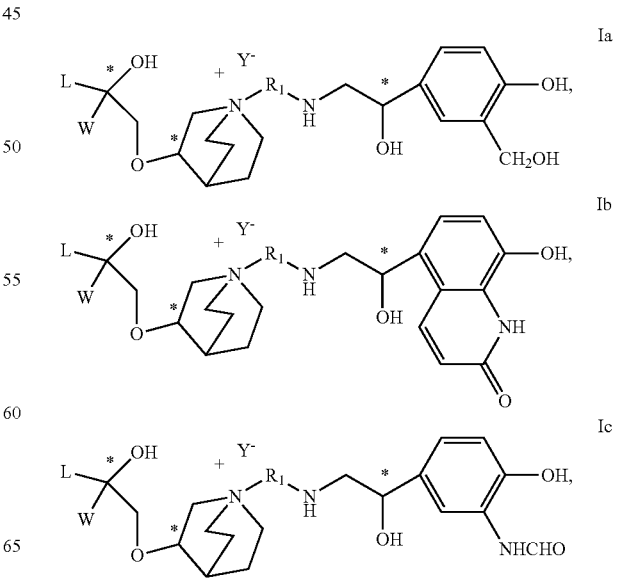

-continued

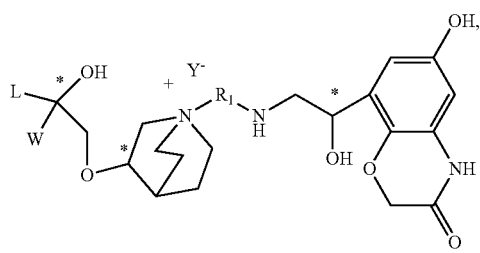

Id wherein: carbons marked with * are (R) configuration, and L, W, R₁ and Y are consistent with those in claim 1.

11. The compound according to claim 1, or the pharmaceutically acceptable salt, solvate, optical isomer thereof, having a structure of formula Ia1, Ib1, Ic1 or Id1:

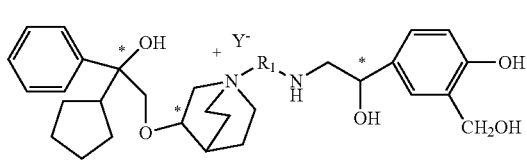

Ia1

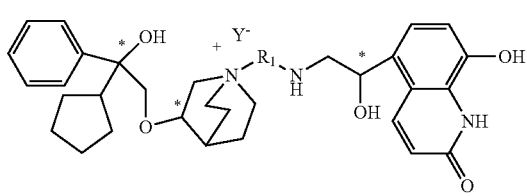

Ib1

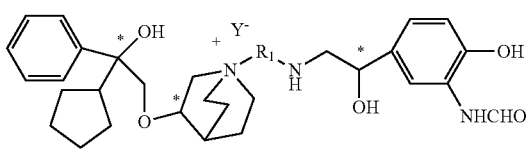

Ic1

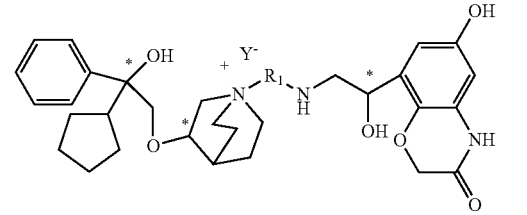

Id1 wherein: carbons marked with * are (R) configuration, and R₁ and Y are consistent with those in claim 1.

12. The compound according to claim 1, or the pharmaceutically acceptable salt, solvate, optical isomer thereof, which is:

(R)-(−)-3-[(R)-2-hydroxy-2-cyclopentyl-2-phenyl]ethoxy-1-{3-[(R)-2-(3-hydroxymethyl-4-hydroxy)phenyl-2-hydroxyethylamino]propyl}-1-azabicyclo[2,2,2]octylonium bromide;

(R)-(−)-3-[(R)-2-hydroxy-2-cyclopentyl-2-phenyl]ethoxy-1-(3-{(R)-[2-hydroxy-2-(8-hydroxy-2-oxo-1,2-dihydroquinolin-5-yl)]ethylamino}propyl)-1-azabicyclo[2,2,2]octylonium bromide;

(R)-(−)-3-[(R)-2-hydroxy-2-cyclopentyl-2-phenyl]ethoxy-1-{4-[(R)-2-(3-hydroxymethyl-4-hydroxy)phenyl-2-hydroxyethylamino]butyl}-1-azabicyclo[2,2,2]octylonium bromide;

(R)-(−)-3-[(R)-2-hydroxy-2-cyclopentyl-2-phenyl]ethoxy-1-(4-{(R)-[2-hydroxy-2-(3-formamido-4-hydroxy)phenyl]ethylamino}butyl-1-azabicyclo[2,2,2]octylonium bromide;

(R)-(−)-3-[(R)-2-hydroxy-2-cyclopentyl-2-phenyl]ethoxy-1-(9-{-[(R)-[2-hydroxy-2-(6-hydroxy-2H-1,4-benzoxazin-3(4H)-one-8-yl)]ethylamino}nonyl)-1-azabicyclo[2,2,2]octylonium bromide;

(R)-(−)-3-[(R)-2-hydroxy-2-cyclopropyl-2-phenyl]ethoxy-1-(8-{(R)-[2-(3-hydroxymethyl-4-hydroxy)phenyl-2-hydroxy]ethylamino}octyl)-1-azabicyclo[2,2,2]octylonium bromide;

(R)-(−)-3-[(R)-2-hydroxy-2-cyclopentyl-2-phenyl]ethoxy-1-(9-{(R)-[2-(3-hydroxymethyl-4-hydroxy)phenyl-2-hydroxy]ethylamino}nonyl)-1-azabicyclo[2,2,2]octylonium bromide;

(R)-(−)-3-[(R)-2-hydroxy-2-cyclopentyl-2-phenyl]ethoxy-1-(10-{(R)-[2-(3-hydroxymethyl-4-hydroxy)phenyl-2-hydroxy]ethylamino}decyl)-1-azabicyclo[2,2,2]octylonium p-toluenesulfonate;

(R)-(−)-3-[(R)-2-hydroxy-2-cyclopentyl-2-phenyl]ethoxy-1-(11-{(R)-[2-(3-hydroxymethyl-4-hydroxy)phenyl-2-hydroxy]ethylamino}tetradecyl)-1-azabicyclo[2,2,2]octylonium bromide;

(R)-(−)-3-[(R)-2-hydroxy-2-cyclopentyl-2-phenyl]ethoxy-1-(4-{(R)-[2-hydroxy-2-(8-hydroxy-2-oxo-1,2-dihydroquinolin-5-yl)]ethylamino}butyl)-1-azabicyclo[2,2,2]octylonium bromide;

(R)-(−)-3-[(R)-2-hydroxy-2-cyclobutyl-2-phenyl]ethoxy-1-(8-{(R)-[2-hydroxy-2-(8-hydroxy-2-oxo-1,2-dihydroquinolin-5-yl)]ethylamino}octyl)-1-azabicyclo[2,2,2]octylonium bromide;

(R)-(−)-3-[(R)-2-hydroxy-2-cyclopentyl-2-phenyl]ethoxy-1-(9-{(R)-[2-hydroxy-2-(8-hydroxy-2-oxo-1,2-dihydroquinolin-5-yl)]ethylamino}nonyl)-1-azabicyclo[2,2,2]octylonium bromide;

(R)-(−)-3-[(R)-2-hydroxy-2-cyclopentyl-2-phenyl]ethoxy-1-(10-{(R)-[2-hydroxy-2-(8-hydroxy-2-oxo-1,2-dihydroquinolin-5-yl)]ethylamino}decyl)-1-azabicyclo[2,2,2]octylonium bromide;

(R)-(−)-3-[(R)-2-hydroxy-2-cyclopentyl-2-phenyl]ethoxy-1-(11-{((R)-[2-hydroxy-2-(8-hydroxy-2-oxo-1,2-dihydroquinolin-5-yl)]ethylamino}hendecyl)-1-azabicyclo[2,2,2]octylonium bromide;

(R)-(−)-3-[(R)-2-hydroxy-2-cyclopentyl-2-(3-methyl)phenyl]ethoxy-1-(3-{(R)-[2-hydroxy-2-(3-formamido-4-hydroxy)phenyl]ethylamino}propyl)-1-azabicyclo[2,2,2]octylonium bromide;

(R)-(−)-3-[(R)-2-hydroxy-2-cyclopentyl-2-phenyl]ethoxy-1-(8-{(R)-[2-hydroxy-2-(3-formamido-4-hydroxy)phenyl]ethylamino}octyl)-1-azabicyclo[2,2,2]octylonium bromide;

(R)-(−)-3-[(R)-2-hydroxy-2-cyclopentyl-2-phenyl]ethoxy-1-(9-{(R)-[2-hydroxy-2-(3-formamido-4-hydroxy)phenyl]ethylamino}nonyl)-1-azabicyclo[2,2,2]octylonium bromide;

(R)-(−)-3-[(R)-2-hydroxy-2-cyclopentyl-2-phenyl]ethoxy-1-(10-{(R)-[2-hydroxy-2-(3-formamido-4-hydroxy)phenyl]ethylamino}decyl)-1-azabicyclo[2,2,2]octylonium bromide;

(R)-(−)-3-[(R)-2-hydroxy-2-cyclopentyl-2-phenyl]
  ethoxy-1-(11-{(R)-[2-hydroxy-2-(3-formamido-4-hy-
  droxy)phenyl]ethylamino}hendecyl)-1-azabicyclo[2,2,
  2]octylonium bromide;
(R)-(−)-3-[(R)-2-hydroxy-2-cyclopentyl-2-phenyl]
  ethoxy-1-(3-{-[(R)-[2-hydroxy-2-(6-hydroxy-2H-1,4-
  benzoxazin-3(4H)-one-8-yl)]ethylamino}propyl)-1-
  azabicyclo[2,2,2]octylonium bromide;
(R)-(−)-3-[(R)-2-hydroxy-2-cyclopentyl-2-phenyl]
  ethoxy-1-(4-{-[(R)-[2-hydroxy-2-(6-hydroxy-2H-1,4-
  benzoxazin-3(4H)-one-8-yl)]ethylamino}butyl)-1-
  azabicyclo[2,2,2]octylonium bromide;
(R)-(−)-3-[(R)-2-hydroxy-2-cyclopentyl-2-(4-isobutyl)
  phenyl]ethoxy-1-(8-{-[(R)-[2-hydroxy-2-(6-hydroxy-
  2H-1,4-benzoxazin-3(4H)-one-8-yl)]
  ethylamino}octyl)-1-azabicyclo[2,2,2]octylonium
  bromide;
(R)-(−)-3-[(R)-2-hydroxy-2-cyclopentyl-2-phenyl]
  ethoxy-1-(10-{-[(R)-[2-hydroxy-2-(6-hydroxy-2H-1,4-
  benzoxazin-3(4H)-one-8-yl)]ethylamino}decyl)-1-
  azabicyclo[2,2,2]octylonium bromide;
(R)-(−)-3-[(R)-2-hydroxy-2-cyclopentyl-2-phenyl]
  ethoxy-1-(11-{(R)-[2-hydroxy-2-(6-hydroxy-2H-1,4-
  benzoxazin-3(4H)-one-8-yl)]ethylamino}hendecyl)-1-
  azabicyclo[2,2,2]octylonium bromide;
(R)-(−)-3-[(R)-2-hydroxy-2-cyclopentyl-2-phenyl]
  ethoxy-1-[2-(4-{(R)-[2-hydroxy-2-(3-formamido-4-
  hydroxy)phenyl]ethylamino}butoxy)ethyl]-1-azabicy-
  clo[2,2,2]octylonium bromide;
(R)-(−)-3-[(R)-2-hydroxy-2-cyclopentyl-2-phenyl]
  ethoxy-1-[5-(4-{(R)-[2-hydroxy-2-(6-hydroxy-2H-1,4-
  benzoxazin-3(4H)-one-8-yl)]ethylamino}butoxy)pen-
  tyl]1-azabicyclo[2,2,2]octylonium bromide;
(R)-(−)-3-[(R)-2-hydroxy-2-cyclopentyl-2-phenyl]
  ethoxy-1-[4-(4-{(R)-[2-(3-hydroxymethyl-4-hydroxy)
  phenyl-2-hydroxy]ethylamino}butoxy)butyl-1-azabi-
  cyclo[2,2,2]octylonium bromide;
(R)-(−)-3-[(R)-2-hydroxy-2-cyclopentyl-2-phenyl]
  ethoxy-1-[2-(4-{(R)-[2-(3-hydroxymethyl-4-hydroxy)
  phenyl-2-hydroxy]ethylamino}butoxy)ethyl]-1-azabi-
  cyclo[2,2,2]octylonium bromide;
(R)-(−)-3-[(R)-2-hydroxy-2-cyclopentyl-2-phenyl]
  ethoxy-1-[5-(4-{(R)-[2-(3-hydroxymethyl-4-hydroxy)
  phenyl-2-hydroxy]ethylamino}butoxy)pentyl]-1-
  azabicyclo[2,2,2]octylonium bromide;
(R)-(−)-3-[(R)-2-hydroxy-2-cyclopentyl-2-phenyl]
  ethoxy-1-[3-(4-{(R)-[2-(3-hydroxymethyl-4-hydroxy)
  phenyl-2-hydroxy]ethylamino}butoxy)propyl]-1-
  azabicyclo[2,2,2]octylonium bromide;
(R)-(−)-3-[(R)-2-hydroxy-2-cyclopentyl-2-(4-methoxy)
  phenyl]ethoxy-1-[2-(2-{(R)-[2-(3-hydroxymethyl-4-
  hydroxy)phenyl-2-hydroxy]ethylamino}ethoxy)ethyl]-
  1-azabicyclo[2,2,2]octylonium bromide;
(R)-(−)-3-[(R)-2-hydroxy-2-cyclopentyl-2-phenyl]
  ethoxy-1-[2-(4-{(R)-[2-hydroxy-2-(8-hydroxy-2-oxo-
  1,2-dihydroquinolin-5-yl)]ethylamino}butoxy)ethyl]-
  1-azabicyclo[2,2,2]octylonium bromide;
(R)-(−)-3-[(R)-2-hydroxy-2-cyclopentyl-2-phenyl]
  ethoxy-1-[5-(4-{(R)-[2-hydroxy-2-(8-hydroxy-2-oxo-
  1,2-dihydroquinolin-5-yl)]ethylamino}heptoxy)
  hexyl]-1-azabicyclo[2,2,2]octylonium bromide;
(R)-(−)-3-[(R)-2-hydroxy-2-cyclopentyl-2-phenyl]
  ethoxy-1-[3-(4-{(R)-[2-hydroxy-2-(8-hydroxy-2-oxo-
  1,2-dihydroquinolin-5-yl)]ethylamino}butoxy)propyl]-
  1-azabicyclo[2,2,2]octylonium bromide;
(R)-(−)-3-[(R)-2-hydroxy-2-cyclopentyl-2-phenyl]
  ethoxy-1-[4-(4-{(R)-[2-hydroxy-2-(8-hydroxy-2-oxo-
  1,2-dihydroquinolin-5-yl)]ethylamino}butoxy)butyl]-
  1-azabicyclo[2,2,2]octylonium bromide;
(R)-(−)-3-[(R)-2-hydroxy-2-cyclopentyl-2-phenyl]
  ethoxy-1-[2-(2-{(R)-[2-hydroxy-2-(8-hydroxy-2-oxo-
  1,2-dihydroquinolin-5-yl)]ethylamino}ethyloxy)
  ethyl]-1-azabicyclo[2,2,2]octylonium bromide;
(R)-(−)-3-[(R)-2-hydroxy-2-cyclopentyl-2-phenyl]
  ethoxy-1-[5-(4-{(R)-[2-hydroxy-2-(3-formamido-4-
  hydroxy)phenyl]ethylamino}butoxy)pentyl]-1-azabi-
  cyclo[2,2,2]octylonium bromide;
(R)-(−)-3-[(R)-2-hydroxy-2-cyclopentyl-2-(3-methyl-4-
  methoxy)phenyl]ethoxy-1-[3-(4-{(R)-[2-hydroxy-2-
  (3-formamido-4-hydroxy)phenyl]ethylamino}butoxy)
  propyl]-1-azabicyclo[2,2,2]octylonium bromide;
(R)-(−)-3-[(R)-2-hydroxy-2-cyclopentyl-2-phenyl]
  ethoxy-1-[4-(4-{(R)-[2-hydroxy-2-(3-formamido-4-
  hydroxy)phenyl]ethylamino}butoxy)butyl]-1-azabicy-
  clo[2,2,2]octylonium bromide;
(R)-(−)-3-[(R)-2-hydroxy-2-cyclopentyl-2-phenyl]
  ethoxy-1-[2-(2-{(R)-[2-hydroxy-2-(3-formamido-4-
  hydroxy)phenyl]ethylamino}ethoxy)ethyl]-1-azabicy-
  clo[2,2,2]octylonium bromide;
(R)-(−)-3-[(R)-2-hydroxy-2-cyclopentyl-2-phenyl]
  ethoxy-1-[2-(4-{(R)-[2-hydroxy-2-(6-hydroxy-2H-1,4-
  benzoxazin-3(4H)-one-8-yl)]ethylamino}butoxy)
  ethyl]-1-azabicyclo[2,2,2]octylonium bromide;
(R)-(−)-3-[(R)-2-hydroxy-2-cyclopentyl-2-phenyl]
  ethoxy-[3-(4-{(R)-[2-hydroxy-2-(6-hydroxy-2H-1,4-
  benzoxazin-3(4H)-one-8-yl)]ethylamino}butoxy)pro-
  pyl]-1-azabicyclo[2,2,2]octylonium bromide;
(R)-(−)-3-[(R)-2-hydroxy-2-cyclopentyl-2-phenyl]
  ethoxy-[4-(4-{(R)-[2-hydroxy-2-(6-hydroxy-2H-1,4-
  benzoxazin-3(4H)-one-8-yl)]ethylamino}butoxy)
  butyl]-1-azabicyclo[2,2,2]octylonium bromide;
(R)-(−)-3-[(R)-2-hydroxy-2-cyclopentyl-2-phenyl]
  ethoxy-[2-(2-{(R)-[2-hydroxy-2-(6-hydroxy-2H-1,4-
  benzoxazin-3(4H)-one-8-yl)]ethylamino}ethoxy)
  ethyl]-1-azabicyclo[2,2,2]octylonium bromide;
(R)-(−)-3-[(R)-2-hydroxy-2-cyclopentyl-2-phenyl]
  ethoxy-1-(2-{2-[2-(2-{(R)-[2-(3-hydroxymethyl-4-hy-
  droxy)phenyl-2-hydroxy]ethylamino}ethoxy)ethoxy]
  ethoxy}ethyl)-1-azabicyclo[2,2,2]octylonium
  bromide;
(R)-(−)-3-[(R)-2-hydroxy-2-cyclopentyl-2-phenyl]
  ethoxy-1-{2-[2-(2-{(R)-[2-hydroxy-2-(3-formamido-
  4-hydroxy)phenyl]ethylamino}ethoxy)ethoxy]ethyl}-
  1-azabicyclo[2,2,2]octylonium chloride;
(R)-(−)-3-[(R)-2-hydroxy-2-cyclopentyl-2-phenyl]
  ethoxy-1-(2-[2-(2-{(R)-[2-(3-hydroxy methyl-4-hy-
  droxy)phenyl-2-hydroxy]ethylamino}ethoxy)ethoxy]
  ethyl}-1-azabicyclo[2,2,2]octylonium chloride;
(R)-(−)-3-[(R)-2-hydroxy-2-cyclopentyl-2-phenyl]
  ethoxy-1-(2-[3-(2-{(R)-[2-(3-hydroxy methyl-4-hy-
  droxy)phenyl-2-hydroxy]ethylamino}ethoxy)propoxy]
  ethyl}-1-azabicyclo[2,2,2]octylonium bromide;
(R)-(−)-3-[(R)-2-hydroxy-2-cyclopentyl-2-phenyl]
  ethoxy-1-(2-{2-[2-(2-{(R)-[2-hydroxy-2-(8-hydroxy-
  2-oxo-1,2-dihydroquinolin-5-yl)]ethylamino}ethoxy)
  propoxy]propoxy}propyl)-1-azabicyclo[2,2,2]
  octylonium bromide;
(R)-(−)-3-[(R)-2-hydroxy-2-cyclopentyl-2-phenyl]
  ethoxy-1-(2-[2-(2-{(R)-[2-hydroxy-2-(8-hydroxy-2-
  oxo-1,2-dihydroquinolin-5-yl)]ethylamino}ethoxy)
  ethoxy]ethyl}-1-azabicyclo[2,2,2]octylonium chloride;
(R)-(−)-3-[(R)-2-hydroxy-2-cyclopentyl-2-phenyl]
  ethoxy-1-(2-[3-(2-{(R)-[2-hydroxy-2-(8-hydroxy-2- oxo-1,2-dihydroquinolin-5-yl)]ethylamino}ethoxy)
propoxy]ethyl}-1-azabicyclo[2,2,2]octylonium
bromide;

(R)-(−)-3-[(R)-2-hydroxy-2-cyclopentyl-2-phenyl]
ethoxy-1-(2-{2-[2-(2-{(R)-[2-hydroxy-2-(3-formamido-4-hydroxy)phenyl]ethylamino}ethoxy)ethoxy]
ethoxy}ethyl)-1-azabicyclo[2,2,2]octylonium
bromide;

(R)-(−)-3-[(R)-2-hydroxy-2-cyclopentyl-2-phenyl]
ethoxy-1-(2-[3-(2-{(R)-[2-hydroxy-2-(3-formamido-4-hydroxy)phenyl]ethylamino}propoxy)pentoxy]butyl}-
1-azabicyclo[2,2,2]octylonium bromide;

(R)-(−)-3-[(R)-2-hydroxy-2-cyclopentyl-2-phenyl]
ethoxy-1-(2-{2-[2-(2-{(R)-[2-hydroxy-2-(6-hydroxy-2H-1,4-benzoxazin-3(4H)-one-8-yl)]
ethylamino}ethoxy)ethoxy]ethoxy}ethyl)-1-
azabicyclo[2,2,2]octylonium bromide;

(R)-(−)-3-[(R)-2-hydroxy-2-cyclopentyl-2-phenyl]
ethoxy-1-{2-[2-(2-{(R)-[2-hydroxy-2-(6-hydroxy-2H-1,4-benzoxazin-3(4H)-one-8-yl)]ethylamino}ethoxy)
ethoxy]ethyl}-1-azabicyclo[2,2,2]octylonium chloride;

(R)-(−)-3-[(R)-2-hydroxy-2-cyclopentyl-2-phenyl]
ethoxy-1-(2-[3-(2-{(R)-[2-hydroxy-2-(6-hydroxy-2H-1,4-benzoxazin-3(4H)-one-8-yl)]ethylamino}ethoxy)
propoxy]ethyl}-1-azabicyclo[2,2,2]octylonium
bromide;

(R)-(−)-3-[(R)-2-hydroxy-2-cyclopentyl-2-phenyl)]
ethoxy-1-{2-[4-(2-{(R)-[2-(3-hydroxymethyl-4-hydroxy)phenyl-2-hydroxy]ethylamino}ethyl)phenoxy]
ethyl]}-1-azabicyclo[2,2,2]octylonium bromide;

(R)-(−)-3-[(R)-2-hydroxy-2-cyclopentyl-2-phenyl)]
ethoxy-1-{2-[4-(2-{(R)-[2-(3-hydroxymethyl-4-hydroxy)phenyl-2-hydroxy]ethylamino}ethyl)phenoxy]
ethyl]}-1-azabicyclo[2,2,2]octylonium benzoate;

(R)-(−)-3-[(R)-2-hydroxy-2-cyclopentyl-2-phenyl]
ethoxy-1-{3-[4-(1-{(R)-[2-hydroxy-2-(8-hydroxy-2-oxo-1,2-dihydroquinolin-5-yl)]ethylamino}methyl)
phenoxy]propyl}-1-azabicyclo[2,2,2]octylonium
bromide;

(R)-(−)-3-[(R)-2-hydroxy-2-cyclopentyl-2-phenyl]
ethoxy-1-{3-[(3,5-dichloro-4-(1-{(R)-[2-hydroxy-2-(3-formamido-4-hydroxy)phenyl]ethylamino}methyl)
phenoxy)propyl}-1-azabicyclo[2,2,2]octylonium
bromide;

(R)-(−)-3-[(R)-2-hydroxy-2-cyclopentyl-2-phenyl]
ethoxy-1-{2-[4-(2-{(R)-[2-hydroxy-2-(6-hydroxy-2H-1,4-benzoxazin-3(4H)-one-8-yl)]ethylamino}isobutyl)
phenoxy]ethyl}-1-azabicyclo[2,2,2]octylonium
bromide;

(R)-(−)-3-[(R)-2-hydroxy-2-cyclopentyl-2-phenyl]
ethoxy]-1-{2-[4-(2-{(R)-[2-hydroxy-2-(3-formamido-4-hydroxy)phenyl]ethylamino}propyl)phenoxy]
ethyl}-1-azabicyclo[2,2,2]octylonium bromide;

(R)-(−)-3-[(R)-2-hydroxy-2-cyclopentyl-2-phenyl]
ethoxy]-1-{2-[4-((R)-2-{(R)-[2-hydroxy-2-(3-formamido-4-hydroxy)phenyl]ethylamino}propyl)phenoxy]
ethyl}-1-azabicyclo[2,2,2]octylonium bromide;

(R)-(−)-3-[(R)-2-hydroxy-2-cyclopentyl-2-phenyl]
ethoxy]-1-{2-[4-((S)-2-{(R)-[2-hydroxy-2-(3-formamido-4-hydroxy)phenyl]ethylamino}propyl)phenoxy]
ethyl}-1-azabicyclo[2,2,2]octylonium bromide;

(R)-(−)-3-[(R)-2-hydroxy-2-cyclopentyl-2-phenyl]
ethoxy-1-{3-[4-(1-{(R)-[2-hydroxy-2-(8-hydroxy-2-oxo-1,2-dihydroquinolin-5-yl)]
ethylamino}propylidene)phenoxy]propyl}-1-azabicyclo[2,2,2]octylonium bromide;

(R)-(−)-3-[(R)-2-hydroxy-2-cyclopentyl-2-phenyl]
ethoxy-1-{3-[4-((R)-1-{(R)-[2-hydroxy-2-(8-hydroxy-2-oxo-1,2-dihydroquinolin-5-yl)]
ethylamino}propylidene)phenoxy]propyl}-1-
azabicyclo[2,2,2]octylonium bromide;

(R)-(−)-3-[(R)-2-hydroxy-2-cyclopentyl-2-phenyl]
ethoxy-1-{3-[4-((S)-1-{(R)-[2-hydroxy-2-(8-hydroxy-2-oxo-1,2-dihydroquinolin-5-yl)]
ethylamino}propylidene)phenoxy]propyl}-1-
azabicyclo[2,2,2]octylonium bromide;

(R)-(−)-3-[(R)-2-hydroxy-2-cyclopentyl-2-phenyl]
ethoxy-1-{3-[(4-(3-methyl-1-{(R)-[2-hydroxy-2-(6-hydroxy-2H-1,4-benzoxazin-3(4H)-one-8-yl)]
ethylamino}ethylidene)phenoxy]propyl}-1-azabicyclo
[2,2,2]octylonium bromide;

(R)-(−)-3-[(R)-2-hydroxy-2-cyclopentyl-2-phenyl]
ethoxy-1-{3-[4-((R)-1-(3-methyl-1-{(R)-[2-hydroxy-2-(6-hydroxy-2H-1,4-benzoxazin-3(4H)-one-8-yl)]
ethylamino}ethylidene)phenoxy]propyl}-1-azabicyclo
[2,2,2]octylonium bromide;

(R)-(−)-3-[(R)-2-hydroxy-2-cyclopentyl-2-phenyl]
ethoxy-1-{3-[4-((S)-1-(3-methyl-1-{(R)-[2-hydroxy-2-(6-hydroxy-2H-1,4-benzoxazin-3(4H)-one-8-yl)]
ethylamino}ethylidene)phenoxy]propyl}-1-azabicyclo
[2,2,2]octylonium bromide;

(R)-(−)-3-[(R)-2-hydroxy-2-cyclopentyl-2-phenyl]
ethoxy-1-{3-[4-(1-{(R)-[2-(3-hydroxymethyl-4-hydroxy)phenyl-2-hydroxy]ethylamino}methyl)phenoxy]propyl}-1-azabicyclo[2,2,2]octylonium bromide;

(R)-(−)-3-[(R)-2-hydroxy-2-cyclopentyl-2-thienyl]
ethoxy-1-{3-[4-(2-{(R)-[2-(3-hydroxymethyl-4-hydroxy)phenyl-2-hydroxy]ethylamino}ethyl)phenoxy]
propyl}-1-azabicyclo[2,2,2]octylonium bromide;

(R)-(−)-3-[(R)-2-hydroxy-2-cyclopentyl-2-phenyl]
ethoxy-1-{3-[4-(3-{(R)-[2-(3-hydroxy methyl-4-hydroxy)phenyl-2-hydroxy]ethylamino}propyl)phenoxy]
propyl}-1-azabicyclo[2,2,2]octylonium bromide;

(R)-(−)-3-[(R)-2-hydroxy-2-cyclopentyl-2-phenyl]
ethoxy-1-{3-[4-(2-{(R)-[2-(3-hydroxymethyl-4-hydroxy)phenyl-2-hydroxy]ethylamino}propyl)phenoxy]
heptanyl}-1-azabicyclo[2,2,2]octylonium bromide;

(R)-(−)-3-[(R)-2-hydroxy-2-cyclopentyl-2-phenyl]
ethoxy-1-{3-[4-((S)-2-{(R)-[2-(3-hydroxymethyl-4-hydroxy)phenyl-2-hydroxy]ethylamino}propyl)phenoxy]heptanyl}-1-azabicyclo[2,2,2]octylonium
bromide;

(R)-(−)-3-[(R)-2-hydroxy-2-cyclopentyl-2-phenyl]
ethoxy-1-{3-[4-((R)-2-{(R)-[2-(3-hydroxymethyl-4-hydroxy)phenyl-2-hydroxy]ethylamino}propyl)phenoxy]heptanyl}-1-azabicyclo[2,2,2]octylonium
bromide;

(R)-(−)-3-[(R)-2-hydroxy-2-cyclopentyl-2-phenyl]
ethoxy-1-{3-[4-(3, 5-dichloro-1-{(R)-[2-(3-hydroxymethyl-4-hydroxy)phenyl-2-hydroxy]
ethylamino}methyl)phenoxy]propyl}-1-azabicyclo[2,
2,2]octylonium bromide;

(R)-(−)-3-[(R)-2-hydroxy-2-cyclopentyl-2-phenyl]
ethoxy-1-{3-[4-({(R)-[2-(3-hydroxymethyl-4-hydroxy)phenyl-2-hydroxyethylamino]
ethylidene}phenoxy)propyl]-1-azabicyclo[2,2,2]
octylonium bromide;

(R)-(−)-3-[(R)-2-hydroxy-2-cyclopentyl-2-phenyl]
ethoxy-1-{3-[4-((S)-1-{(R)-[2-(3-hydroxymethyl-4-hydroxy)phenyl-2-hydroxyethylamino]
ethylidene}phenoxy)propyl]-1-azabicyclo[2,2,2]
octylonium bromide;

(R)-(−)-3-[(R)-2-hydroxy-2-cyclopentyl-2-phenyl]ethoxy-1-{3-[4-((R)-1-{(R)-[2-(3-hydroxymethyl-4-hydroxy)phenyl-2-hydroxyethylamino]ethylidene}phenoxy)propyl]-1-azabicyclo[2,2,2]octylonium bromide;

(R)-(−)-3-[(R)-2-hydroxy-2-cyclopentyl-2-phenyl]ethoxy-1-[3-(3-methoxy-4-{[(R)-2-(3-hydroxymethyl-4-hydroxy)phenyl-2-hydroxyethylamino]ethylidene}phenoxy)propyl]-1-azabicyclo[2,2,2]octylonium bromide;

(R)-(−)-3-[(R)-2-hydroxy-2-cyclopentyl-2-phenyl]ethoxy-1-[3-(3-methoxy-4-{(S)-1-[(R)-2-(3-hydroxymethyl-4-hydroxy)phenyl-2-hydroxyethylamino]ethylidene}phenoxy)propyl]-1-azabicyclo[2,2,2]octylonium bromide;

(R)-(−)-3-[(R)-2-hydroxy-2-cyclopentyl-2-phenyl]ethoxy-1-[3-(3-methoxy-4-{(R)-1-[(R)-2-(3-hydroxymethyl-4-hydroxy)phenyl-2-hydroxyethylamino]ethylidene}phenoxy)propyl]-1-azabicyclo[2,2,2]octylonium bromide;

(R)-(−)-3-[(R)-2-hydroxy-2-cyclopentyl-2-phenyl]ethoxy-1-{3-[4-(2-{(R)-[2-(3-hydroxymethyl-4-hydroxy)phenyl-2-hydroxy]ethylamino}isopropylidene)phenoxy]propyl}-1-azabicyclo[2,2,2]octylonium bromide;

(R)-(−)-3-[(R)-2-hydroxy-2-cyclopentyl-2-phenyl]ethoxy-1-{3-[4-(1-{(R)-2-(3-hydroxy methyl-4-hydroxy)phenyl-2-hydroxy]ethylamino}propylidene)phenoxy]propyl}-1-azabicyclo[2,2,2]octylonium bromide;

(R)-(−)-3-[(R)-2-hydroxy-2-cyclopentyl-2-phenyl]ethoxy-1-{3-[4-((S)-1-{(R)-2-(3-hydroxymethyl-4-hydroxy)phenyl-2-hydroxy]ethylamino}propylidene)phenoxy]propyl}-1-azabicyclo[2,2,2]octylonium bromide;

(R)-(−)-3-[(R)-2-hydroxy-2-cyclopentyl-2-phenyl]ethoxy-1-{3-[4-((R)-1-{(R)-2-(3-hydroxymethyl-4-hydroxy)phenyl-2-hydroxy]ethylamino}propylidene)phenoxy]propyl}-1-azabicyclo[2,2,2]octylonium bromide;

(R)-(−)-3-[(R)-2-hydroxy-2-cyclopentyl-2-phenyl]ethoxy-1-{3-[4-(2-{(R)-[2-(3-hydroxymethyl-4-hydroxy)phenyl-2-hydroxy]ethylamino}isobutyl)phenoxy]propyl}-1-azabicyclo[2,2,2]octylonium bromide;

(R)-(−)-3-[(R)-2-hydroxy-2-cyclopentyl-2-phenyl]ethoxy-1-{2-[4-(2-{(R)-[2-(3-hydroxy methyl-4-hydroxy)phenyl-2-hydroxy]ethylamino}isobutyl)phenoxy]ethyl}-1-azabicyclo[2,2,2]octylonium bromide;

(R)-(−)-3-[(R)-2-hydroxy-2-cyclopentyl-2-phenyl]ethoxy-1-{2-[4-(2-{(R)-[2-(3-hydroxymethyl-4-hydroxy)phenyl-2-hydroxy]ethylamino}propyl)phenoxy]ethyl}-1-azabicyclo[2,2,2]octylonium bromide;

(R)-(−)-3-[(R)-2-hydroxy-2-cyclopentyl-2-phenyl]ethoxy-1-{2-[4-((S)-2-{(R)-[2-(3-hydroxymethyl-4-hydroxy)phenyl-2-hydroxy]ethylamino}propyl)phenoxy]ethyl}-1-azabicyclo[2,2,2]octylonium bromide;

(R)-(−)-3-[(R)-2-hydroxy-2-cyclopentyl-2-phenyl]ethoxy-1-{2-[4-((R)-2-{(R)-[2-(3-hydroxymethyl-4-hydroxy)phenyl-2-hydroxy]ethylamino}propyl)phenoxy]ethyl}-1-azabicyclo[2,2,2]octylonium bromide;

(R)-(−)-3-[(R)-2-hydroxy-2-cyclopentyl-2-phenyl]ethoxy-1-{3-[3-methyl-4-(1-{(R)-[2-(3-hydroxymethyl-4-hydroxy)phenyl-2-hydroxy]ethylamino}ethylidene)phenoxy]propyl-1-azabicyclo[2,2,2]octylonium bromide;

(R)-(−)-3-[(R)-2-hydroxy-2-cyclopentyl-2-phenyl]ethoxy-1-{3-[3-methyl-4-((S)-1-{(R)-[2-(3-hydroxym ethyl-4-hydroxy)phenyl-2-hydroxy]ethylamino}ethylidene)phenoxy]propyl-1-azabicyclo[2,2,2]octylonium bromide;

(R)-(−)-3-[(R)-2-hydroxy-2-cyclopentyl-2-phenyl]ethoxy-1-{3-[3-methyl-4-((R)-1-{(R)-[2-(3-hydroxymethyl-4-hydroxy)phenyl-2-hydroxy]ethylamino}ethylidene)phenoxy]propyl-1-azabicyclo[2,2,2]octylonium bromide;

(R)-(−)-3-[(R)-2-hydroxy-2-cyclopentyl-2-phenyl]ethoxy-1-{2-[4-(2-{(R)-(2-hydroxy-2-(8-hydroxy-2-oxo-1,2-dihydroquinolin-5-yl)]ethylamino}ethyl)phenoxy]ethyl}-1-azabicyclo[2,2,2]octylonium acetate;

(R)-(−)-3-[(R)-2-hydroxy-2-cyclopentyl-2-(4-chloro)phenyl]ethoxy-1-{3-[4-(2-{(R)-(2-hydroxy-2-(8-hydroxy-2-oxo-1,2-dihydroquinolin-5-yl)]ethylamino}ethyl)phenoxy]propyl}-1-azabicyclo[2,2,2]octylonium bromide;

(R)-(−)-3-[(R)-2-hydroxy-2-cyclopentyl-2-phenyl]ethoxy-1-{3-[4-(3-{(R)-(2-hydroxy-2-(8-hydroxy-2-oxo-1,2-dihydroquinolin-5-yl)]ethylamino}propyl)phenoxy]propyl}-1-azabicyclo[2,2,2]octylonium bromide;

(R)-(−)-3-[(R)-2-hydroxy-2-cyclopentyl-2-phenyl]ethoxy-1-{3-[4-(2-{(R)-[2-hydroxy-2-(8-hydroxy-2-oxo-1,2-dihydroquinolin-5-yl)]ethylamino}propyl)phenoxy]propyl}-1-azabicyclo[2,2,2]octylonium bromide;

(R)-(−)-3-[(R)-2-hydroxy-2-cyclopentyl-2-phenyl]ethoxy-1-{3-[4-((S)-2-{(R)-[2-hydroxy-2-(8-hydroxy-2-oxo-1,2-dihydroquinolin-5-yl)]ethylamino}propyl)phenoxy]propyl}-1-azabicyclo[2,2,2]octylonium bromide;

(R)-(−)-3-[(R)-2-hydroxy-2-cyclopentyl-2-phenyl]ethoxy-1-{3-[4-((R)-2-{(R)-[2-hydroxy-2-(8-hydroxy-2-oxo-1,2-dihydroquinolin-5-yl)]ethylamino}propyl)phenoxy]propyl}-1-azabicyclo[2,2,2]octylonium bromide;

(R)-(−)-3-[(R)-2-hydroxy-2-cyclopentyl-2-furyl]ethoxy-1-{3-[3,5-dichloro-(4-{(R)-[2-hydroxy-2-(8-hydroxy-2-oxo-1,2-dihydroquinolin-5-yl)]ethylamino}methyl)phenoxy]propyl}-1-azabicyclo[2,2,2]octylonium bromide;

(R)-(−)-3-[(R)-2-hydroxy-2-cyclopentyl-2-phenyl]ethoxy-1-{3-[4-(1-{(R)-[2-hydroxy-2-(8-hydroxy-2-oxo-1,2-dihydroquinolin-5-yl)]ethylamino}ethylidene)phenoxy]propyl}-1-azabicyclo[2,2,2]octylonium bromide;

(R)-(−)-3-[(R)-2-hydroxy-2-cyclopentyl-2-phenyl]ethoxy-1-{3-[4-((S)-1-{(R)-[2-hydroxy-2-(8-hydroxy-2-oxo-1,2-dihydroquinolin-5-yl)]ethylamino}ethylidene)phenoxy]propyl}-1-azabicyclo[2,2,2]octylonium bromide;

(R)-(−)-3-[(R)-2-hydroxy-2-cyclopentyl-2-phenyl]ethoxy-1-{3-[4-((SR)-1-{(R)-[2-hydroxy-2-(8-hydroxy-2-oxo-1,2-dihydroquinolin-5-yl)]ethylamino}ethylidene)phenoxy]propyl}-1-azabicyclo[2,2,2]octylonium bromide;

(R)-(−)-3-[(R)-2-hydroxy-2-cyclopentyl-2-phenyl]ethoxy-1-{3-[3-methoxy-4-{((R)-2-hydroxy-2-(8-hydroxy-2-oxo-1,2-dihydroquinolin-5-yl)ethylamino]ethylidene}phenoxy)propyl]-1-azabicyclo[2,2,2]octylonium bromide;

(R)-(−)-3-[(R)-2-hydroxy-2-cyclopentyl-2-phenyl]ethoxy-1-{3-[3-methoxy-4-{(S)-1-((R)-2-hydroxy-2-(8-hydroxy-2-oxo-1,2-dihydroquinolin-5-yl)ethylamino]ethylidene}phenoxy)propyl]-1-azabicyclo[2,2,2]octylonium bromide;

(R)-(−)-3-[(R)-2-hydroxy-2-cyclopentyl-2-phenyl]
ethoxy-1-{3-[3-methoxy-4-{(R)-1-((R)-2-hydroxy-2-(8-hydroxy-2-oxo-1,2-dihydroquinolin-5-yl)ethyl-amino]ethylidene}phenoxy)propyl]-1-azabicyclo[2,2,2]octylonium bromide;

(R)-(−)-3-[(R)-2-hydroxy-2-cyclopentyl-2-phenyl]
ethoxy-1-{3-[4-(2-{(R)-[2-hydroxy-2-(8-hydroxy-2-oxo-1,2-dihydroquinolin-5-yl)]ethylamino}isopropylidene)phenoxy]propyl}-1-azabicyclo[2,2,2]octylonium bromide;

(R)-(−)-3-[(R)-2-hydroxy-2-cyclopentyl-2-phenyl]
ethoxy-1-[3-(4-{2-[(R)-2-hydroxy-2-(8-hydroxy-2-oxo-1,2-dihydroquinolin-5-yl)ethylamino]isobutyl}phenoxy)propyl]-1-azabicyclo[2,2,2]octylonium bromide;

(R)-(−)-3-[(R)-2-hydroxy-2-cyclopentyl-2-phenyl]
ethoxy-1-{2-[4-(2-{(R)-[2-hydroxy-2-(8-hydroxy-2-oxo-1,2-dihydroquinolin-5-yl)]ethylamino}isobutyl)phenoxy]ethyl}-1-azabicyclo[2,2,2]octylonium bromide;

(R)-(−)-3-[(R)-2-hydroxy-2-cyclopentyl-2-phenyl]
ethoxy-1-{2-[4-(2-{(R)-[2-hydroxy-2-(8-hydroxy-2-oxo-1,2-dihydroquinolin-5-yl)]ethylamino}propyl)phenoxy]ethyl}-1-azabicyclo[2,2,2]octylonium bromide;

(R)-(−)-3-[(R)-2-hydroxy-2-cyclopentyl-2-phenyl]
ethoxy-1-{2-[4-((S)-2-{(R)-[2-hydroxy-2-(8-hydroxy-2-oxo-1,2-dihydroquinolin-5-yl)]ethylamino}propyl)phenoxy]ethyl}-1-azabicyclo[2,2,2]octylonium bromide;

(R)-(−)-3-[(R)-2-hydroxy-2-cyclopentyl-2-phenyl]
ethoxy-1-{2-[4-((R)-2-{(R)-[2-hydroxy-2-(8-hydroxy-2-oxo-1,2-dihydroquinolin-5-yl)]ethylamino}propyl)phenoxy]ethyl}-1-azabicyclo[2,2,2]octylonium bromide;

(R)-(−)-3-[(R)-2-hydroxy-2-cyclopentyl-2-phenyl]
ethoxy-1-{3-[3-methyl-4-(1-{(R)-[2-hydroxy-2-(8-hydroxy-2-oxo-1,2-dihydroquinolin-5-yl)]ethylamino}ethylidene)phenoxy]propyl}-1-azabicyclo[2,2,2]octylonium bromide;

(R)-(−)-3-[(R)-2-hydroxy-2-cyclopentyl-2-phenyl]
ethoxy-1-{3-[3-methyl-4-((S)-1-{(R)-[2-hydroxy-2-(8-hydroxy-2-oxo-1,2-dihydroquinolin-5-yl)]ethylamino}ethylidene)phenoxy]propyl}-1-azabicyclo[2,2,2]octylonium bromide;

(R)-(−)-3-[(R)-2-hydroxy-2-cyclopentyl-2-phenyl]
ethoxy-1-{3-[3-methyl-4-((R)-1-{(R)-[2-hydroxy-2-(8-hydroxy-2-oxo-1,2-dihydroquinolin-5-yl)]ethylamino}ethylidene)phenoxy]propyl}-1-azabicyclo[2,2,2]octylonium bromide;

(R)-(−)-3-[(R)-2-hydroxy-2-cyclopentyl-2-phenyl]
ethoxy-1-{2-[4-(2-{(R)-[2-hydroxy-2-(3-formamido-4-hydroxy)phenyl]ethylamino}ethyl)phenoxy]ethyl}-1-azabicyclo[2,2,2]octylonium bromide;

(R)-(−)-3-[(R)-2-hydroxy-2-cyclopentyl-2-phenyl]
ethoxy-1-{3-[4-(1-{(R)-[2-hydroxy-2-(3-formamido-4-hydroxy)phenyl]ethylamino}methyl)phenoxy]propyl}-1-azabicyclo[2,2,2]octylonium bromide;

(R)-(−)-3-[(R)-2-hydroxy-2-cyclopentyl-2-phenyl]
ethoxy-1-{3-[4-(2-{(R)-[2-hydroxy-2-(3-formamido-4-hydroxy)phenyl]ethylamino}ethyl)phenoxy]propyl}-1-azabicyclo[2,2,2]octylonium bromide;

(R)-(−)-3-[(R)-2-hydroxy-2-cyclopentyl-2-phenyl]
ethoxy-1-{3-[4-(3-{(R)-[2-hydroxy-2-(3-formamido-4-hydroxy)phenyl]ethylamino}propyl)phenoxy]propyl}-1-azabicyclo[2,2,2]octylonium bromide;

(R)-(−)-3-[(R)-2-hydroxy-2-cyclopentyl-2-phenyl]
ethoxy-1-{3-[4-(2-{(R)-[2-hydroxy-2-(3-formamido-4-hydroxy)phenyl]ethylamino}propyl)phenoxy]propyl}-1-azabicyclo[2,2,2]octylonium bromide;

(R)-(−)-3-[(R)-2-hydroxy-2-cyclopentyl-2-phenyl]
ethoxy-1-{3-[4-((S)-2-{(R)-[2-hydroxy-2-(3-formamido-4-hydroxy)phenyl]ethylamino}propyl)phenoxy]propyl}-1-azabicyclo[2,2,2]octylonium bromide;

(R)-(−)-3-[(R)-2-hydroxy-2-cyclopentyl-2-phenyl]
ethoxy-1-{3-[4-((R)-2-{(R)-[2-hydroxy-2-(3-formamido-4-hydroxy)phenyl]ethylamino}propyl)phenoxy]propyl}-1-azabicyclo[2,2,2]octylonium bromide;

(R)-(−)-3-[(R)-2-hydroxy-2-cyclopentyl-2-phenyl]
ethoxy-1-{3-[4-(1-{(R)-[2-hydroxy-2-(3-formamido-4-hydroxy)phenyl]ethylamino}ethylidene)phenoxy]propyl}-1-azabicyclo[2,2,2]octylonium bromide;

(R)-(−)-3-[(R)-2-hydroxy-2-cyclopentyl-2-phenyl]
ethoxy-1-{3-[4-((S)-1-{(R)-[2-hydroxy-2-(3-formamido-4-hydroxy)phenyl]ethylamino}ethylidene)phenoxy]propyl}-1-azabicyclo[2,2,2]octylonium bromide;

(R)-(−)-3-[(R)-2-hydroxy-2-cyclopentyl-2-phenyl]
ethoxy-1-{3-[4-((R)-1-{(R)-[2-hydroxy-2-(3-formamido-4-hydroxy)phenyl]ethylamino}ethylidene)phenoxy]propyl}-1-azabicyclo[2,2,2]octylonium bromide;

(R)-(−)-3-[(R)-2-hydroxy-2-cyclopentyl-2-phenyl]
ethoxy-1-{3-[3-methoxy-4-(1-{(R)-[2-hydroxy-2-(3-formamido-4-hydroxy)phenyl]ethylamino}ethylidene)phenoxy]propyl}-1-azabicyclo[2,2,2]octylonium bromide;

(R)-(−)-3-[(R)-2-hydroxy-2-cyclopentyl-2-phenyl]
ethoxy-1-{3-[3-methoxy-4-((S)-1-{(R)-[2-hydroxy-2-(3-formamido-4-hydroxy)phenyl]ethylamino}ethylidene)phenoxy]propyl}-1-azabicyclo[2,2,2]octylonium bromide;

(R)-(−)-3-[(R)-2-hydroxy-2-cyclopentyl-2-phenyl]
ethoxy-1-{3-[3-methoxy-4-((R)-1-{(R)-[2-hydroxy-2-(3-formamido-4-hydroxy)phenyl]ethylamino}ethylidene)phenoxy]propyl}-1-azabicyclo[2,2,2]octylonium bromide;

(R)-(−)-3-[(R)-2-hydroxy-2-cyclopentyl-2-phenyl]
ethoxy-1-{3-[4-(2-{(R)-[2-hydroxy-2-(3-formamido-4-hydroxy)phenyl]ethylamino}isopropylidene)phenoxy]propyl}-1-azabicyclo[2,2,2]octylonium bromide;

(R)-(−)-3-[(R)-2-hydroxy-2-cyclopentyl-2-phenyl]
ethoxy-1-{3-[4-(1-{(R)-[2-hydroxy-2-(3-formamido-4-hydroxy)phenyl]ethylamino}propylidene)phenoxy]propyl}-1-azabicyclo[2,2,2]octylonium bromide;

(R)-(−)-3-[(R)-2-hydroxy-2-cyclopentyl-2-phenyl]
ethoxy-1-{3-[4-((S)-1-{(R)-[2-hydroxy-2-(3-formamido-4-hydroxy)phenyl]ethylamino}propylidene)phenoxy]propyl}-1-azabicyclo[2,2,2]octylonium bromide;

(R)-(−)-3-[(R)-2-hydroxy-2-cyclopentyl-2-phenyl]
ethoxy-1-{3-[4-((R)-1-{(R)-[2-hydroxy-2-(3-formamido-4-hydroxy)phenyl]ethylamino}propylidene)phenoxy]propyl}-1-azabicyclo[2,2,2]octylonium bromide;

(R)-(−)-3-[(R)-2-hydroxy-2-cyclopentyl-2-phenyl]
ethoxy-1-{3-[4-(2-{(R)-[2-hydroxy-2-(3-formamido-4-hydroxy)phenyl]ethylamino}isobutyl)phenoxy]propyl}-1-azabicyclo[2,2,2]octylonium bromide;

(R)-(−)-3-[(R)-2-hydroxy-2-cyclohexyl-2-phenyl]
ethoxy-1-{2-[4-(2-{(R)-[2-hydroxy-2-(3-formamido-4-hydroxy)phenyl]ethylamino}isobutyl)phenoxy]ethyl}-1-azabicyclo[2,2,2]octylonium bromide;

(R)-(−)-3-[(R)-2-hydroxy-2-cyclopentyl-2-phenyl]
ethoxy-1-{3-[3-methyl-4-(1-{(R)-[2-hydroxy-2-(3-formamido-4-hydroxy)phenyl]ethylamino}ethylidene)
phenoxy]propyl}-1-azabicyclo[2,2,2]octylonium
bromide;

(R)-(−)-3-[(R)-2-hydroxy-2-cyclopentyl-2-phenyl]
ethoxy-1-{3-[3-methyl-4-((S)-1-{(R)-[2-hydroxy-2-
(3-formamido-4-hydroxy)phenyl]
ethylamino}ethylidene)phenoxy]propyl}-1-azabicyclo
[2,2,2]octylonium bromide;

(R)-(−)-3-[(R)-2-hydroxy-2-cyclopentyl-2-phenyl]
ethoxy-1-{3-[3-methyl-4-((R)-1-{(R)-[2-hydroxy-2-
(3-formamido-4-hydroxy)phenyl]
ethylamino}ethylidene)phenoxy]propyl}-1-azabicyclo
[2,2,2]octylonium bromide;

(R)-(−)-3-[(R)-2-hydroxy-2-cyclopentyl-2-phenyl]
ethoxy-1-{2-[4-(2-{(R)-[2-hydroxy-2-(6-hydroxy-2H-
1,4-benzoxazin-3(4H)-one-8-yl)]ethylamino}ethyl)
phenoxy]ethyl}-1-azabicyclo[2,2,2]octylonium
bromide;

(R)-(−)-3-[(R)-2-hydroxy-2-cyclopentyl-2-phenyl]
ethoxy-1-{3-[4-(1-{(R)-[2-hydroxy-2-(6-hydroxy-2H-
1,4-benzoxazin-3(4H)-one-8-yl)]ethylamino}methyl)
phenoxy]propyl}-1-azabicyclo[2,2,2]octylonium
bromide;

(R)-(−)-3-[(R)-2-hydroxy-2-cyclopentyl-2-phenyl]
ethoxy-1-{3-[4-(2-{(R)-[2-hydroxy-2-(6-hydroxy-2H-
1,4-benzoxazin-3(4H)-one-8-yl)]ethylamino}ethyl)
phenoxy]propyl}1-azabicyclo[2,2,2]octylonium
bromide;

(R)-(−)-3-[(R)-2-hydroxy-2-cyclopentyl-2-phenyl]
ethoxy-1-{3-[4-(3-{(R)-[2-hydroxy-2-(5-hydroxy-2H-
1,4-benzoxazin-3(4H)-one-8-yl)]ethylamino}propyl)
phenoxy]propyl}-1-azabicyclo[2,2,2]octylonium
bromide;

(R)-(−)-3-[(R)-2-hydroxy-2-cyclopentyl-2-phenyl]
ethoxy-1-{3-[4-(2-{(R)-2-hydroxy-2-(6-hydroxy-2H-
1,4-benzoxazin-3(4H)-one-8-yl)]ethylamino}propyl)
phenoxy]propyl}-1-azabicyclo[2,2,2]octylonium
bromide;

(R)-(−)-3-[(R)-2-hydroxy-2-cyclopentyl-2-phenyl]
ethoxy-1-{3-[4-((S)-2-{(R)-2-hydroxy-2-(6-hydroxy-
2H-1,4-benzoxazin-3(4H)-one-8-yl)]
ethylamino}propyl)phenoxy]propyl}-1-azabicyclo[2,
2,2]octylonium bromide;

(R)-(−)-3-[(R)-2-hydroxy-2-cyclopentyl-2-phenyl]
ethoxy-1-{3-[4-((R)-2-{(R)-2-hydroxy-2-(6-hydroxy-
2H-1,4-benzoxazin-3(4H)-one-8-yl)]
ethylamino}propyl)phenoxy]propyl}-1-azabicyclo[2,
2,2]octylonium bromide;

(R)-(−)-3-[(R)-2-hydroxy-2-cyclopentyl-2-pyridyl]
ethoxy-1-{3-[3,5-dichloro-4-(1-[(R)-2-hydroxy-2-(6-
hydroxy-2H-1,4-benzoxazin-3(4H)-one-8-yl)]
ethylamino}methyl)Phenoxy]propyl}-1-azabicyclo[2,
2,2]octylonium bromide;

(R)-(−)-3-[(R)-2-hydroxy-2-cyclopentyl-2-phenyl]
ethoxy-1-{3-[4-(1-{(R)-[2-hydroxy-2-(6-hydroxy-2H-
1,4-benzoxazin-3(4H)-one-8-yl)]
ethylamino}ethylidene)phenoxy]propyl}-1-azabicyclo
[2,2,2]octylonium bromide;

(R)-(−)-3-[(R)-2-hydroxy-2-cyclopentyl-2-phenyl]
ethoxy-1-{3-[4-((S)-1-{(R)-[2-hydroxy-2-(6-hydroxy-
2H-1,4-benzoxazin-3(4H)-one-8-yl)]
ethylamino}ethylidene)phenoxy]propyl}-1-azabicyclo
[2,2,2]octylonium bromide;

(R)-(−)-3-[(R)-2-hydroxy-2-cyclopentyl-2-phenyl]
ethoxy-1-{3-[4-((R)-1-{(R)-[2-hydroxy-2-(6-hydroxy-
2H-1,4-benzoxazin-3(4H)-one-8-yl)]
ethylamino}ethylidene)phenoxy]propyl}-1-azabicyclo
[2,2,2]octylonium bromide;

(R)-(−)-3-[(R)-2-hydroxy-2-cyclopentyl-2-phenyl]
ethoxy-1-{3-[3-methoxy-4-(1-{(R)-[2-hydroxy-2-(6-
hydroxy-2H-1,4-benzoxazin-3(4H)-one-8-yl)]
ethylamino}ethylidene)phenoxy]propyl-1-azabicyclo
[2,2,2]octylonium bromide;

(R)-(−)-3-[(R)-2-hydroxy-2-cyclopentyl-2-phenyl]
ethoxy-1-{3-[3-methoxy-4-((S)-1-{(R)-[2-hydroxy-2-
(6-hydroxy-2H-1,4-benzoxazin-3(4H)-one-8-yl)]
ethylamino}ethylidene)phenoxy]propyl-1-azabicyclo
[2,2,2]octylonium bromide;

(R)-(−)-3-[(R)-2-hydroxy-2-cyclopentyl-2-phenyl]
ethoxy-1-{3-[3-methoxy-4-((R)-1-{(R)-[2-hydroxy-2-
(6-hydroxy-2H-1,4-benzoxazin-3(4H)-one-8-yl)]
ethylamino}ethylidene)phenoxy]propyl-1-azabicyclo
[2,2,2]octylonium bromide;

(R)-(−)-3-[(R)-2-hydroxy-2-cyclopentyl-2-phenyl]
ethoxy-1-{3-[4-(2-{(R)-[2-hydroxy-2-(6-hydroxy-2H-
1,4-benzoxazin-3(4H)-one-8-yl)
ethylamino}isopropylidene)phenoxy]propyl}-1-
azabicyclo[2,2,2]octylonium bromide;

(R)-(−)-3-[(R)-2-hydroxy-2-cyclopentyl-2-phenyl]
ethoxy-1-{3-[4-(1-{(R)-2-hydroxy-2-(6-hydroxy-2H-
1,4-benzoxazin-3(4H)-one-8-yl)]
ethylamino}propylidene)phenoxy]propyl}-1-
azabicyclo[2,2,2]octylonium bromide;

(R)-(−)-3-[(R)-2-hydroxy-2-cyclopentyl-2-phenyl]
ethoxy-1-{3-[4-((S)-1-{(R)-2-hydroxy-2-(6-hydroxy-
2H-1,4-benzoxazin-3(4H)-one-8-yl)]
ethylamino}propylidene)phenoxy]propyl}-1-
azabicyclo[2,2,2]octylonium bromide;

(R)-(−)-3-[(R)-2-hydroxy-2-cyclopentyl-2-phenyl]
ethoxy-1-{3-[4-((R)-1-{(R)-2-hydroxy-2-(6-hydroxy-
2H-1,4-benzoxazin-3(4H)-one-8-yl)]
ethylamino}propylidene)phenoxy]propyl}-1-
azabicyclo[2,2,2]octylonium bromide;

(R)-(−)-3-[(R)-2-hydroxy-2-suberyl-2-phenyl]ethoxy-1-
{3-[4-(2-{(R)-[2-hydroxy-2-(6-hydroxy-2H-1,4-ben-
zoxazin-3(4H)-one-8-yl)]ethylamino}isobutyl)phe-
noxy]propyl-1-azabicyclo[2,2,2] octylonium bromide;

(R)-(−)-3-[(R)-2-hydroxy-2-cyclopentyl-2-phenyl]
ethoxy-1-{2-[4-(2-{(R)-[2-hydroxy-2-(6-hydroxy-2H-
1,4-benzoxazin-3(4H)-one-8-yl)]ethylamino}propyl)
phenoxy]ethyl-1-azabicyclo[2,2,2]octylonium
bromide;

(R)-(−)-3-[(R)-2-hydroxy-2-cyclopentyl-2-phenyl]
ethoxy-1-{2-[4-((S)-2-{(R)-[2-hydroxy-2-(6-hydroxy-
2H-1,4-benzoxazin-3(4H)-one-8-yl)]
ethylamino}propyl)phenoxy]ethyl-1-azabicyclo[2,2,2]
octylonium bromide;

(R)-(−)-3-[(R)-2-hydroxy-2-cyclopentyl-2-phenyl]
ethoxy-1-{2-[4-((R)2-{(R)-[2-hydroxy-2-(6-hydroxy-
2H-1,4-benzoxazin-3(4H)-one-8-yl)]
ethylamino}propyl)phenoxy]ethyl-1-azabicyclo[2,2,2]
octylonium bromide;

(R)-(−)-3-[(R)-2-hydroxy-2-cyclopentyl-2-phenyl]
ethoxy-1-{3-[4-(3-{(R)-[2-hydroxy-2-(3-formamido-
4-hydroxy)phenyl]ethylamino}propoxy)phenoxy]pro-
pyl}-1-azabicyclo[2,2,2]octylonium bromide;

(R)-(−)-3-[(R)-2-hydroxy-2-cyclopentyl-2-phenyl]
ethoxy-1-{2-[4-(2-{(R)-[2-(3-hydroxymethyl-4-hy-
droxy)phenyl-2-hydroxy]ethylamino}ethyoxyl)phe-
noxy]ethyl}-1-azabicyclo[2,2,2]octylonium bromide;

(R)-(−)-3-[(R)-2-hydroxy-2-cyclopentyl-2-phenyl]
ethoxy-1-{3-[5-chloro-2-methoxy-4-({(R)-[2-hy-
droxy-2-(8-hydroxy-2-oxo-1,2-dihydroquinolin-5-yl)]

ethylamino}methyl)anilino]oxopropyl}-1-azabicyclo[2,2,2]octylonium bromide;

(R)-(−)-3-[(R)-2-hydroxy-2-cyclopentyl-2-phenyl]ethoxy-1-{3-[4-({(R)-[2-hydroxy-2-(6-hydroxy-2H-1,4-benzoxazin-3(4H)-one-8-yl]ethylamino}methyl)anilino]oxopropyl}-1-azabicyclo[2,2,2]octylonium bromide;

(R)-(−)-3-[(R)-2-hydroxy-2-cyclopentyl-2-phenyl]ethoxy-1-{2-[4-(2-{(R)-[2-hydroxy-2-(3-formamido-4-hydroxy)phenyl]ethylamino}ethylidene)benzyloxy]ethyl}-1-azabicyclo[2,2,2]octylonium bromide;

(R)-(−)-3-[(R)-2-hydroxy-2-cyclopentyl-2-phenyl]ethoxy-1-{2-[4-((S)-2-{(R)-[2-hydroxy-2-(3-formamido-4-hydroxy)phenyl]ethylamino}ethylidene)benzyloxy]ethyl}-1-azabicyclo[2,2,2]octylonium bromide;

(R)-(−)-3-[(R)-2-hydroxy-2-cyclopentyl-2-phenyl]ethoxy-1-{2-[4-((R)-2-{(R)-[2-hydroxy-2-(3-formamido-4-hydroxy)phenyl]ethylamino}ethylidene)benzyloxy]ethyl}-1-azabicyclo[2,2,2]octylonium bromide;

(R)-(−)-3-[(R)-2-hydroxy-2-cyclopentyl-2-phenyl]ethoxy-1-{2-[4-(2-{(R)-2-hydroxy-2-(6-hydroxy-2H-1,4-benzoxazin-3(4H)-one-8-yl)]ethylamino}ethoxymethyl)benzyloxy]ethyl}-1-azabicyclo[2,2,2]octylonium bromide;

(R)-(−)-3-[(R)-2-hydroxy-2-cyclopentyl-2-naphthyl]ethoxy-1-{2-[4-(2-{(R)-[2-(3-hydroxymethyl-4-hydroxy)phenyl-2-hydroxy]ethylamino}ethoxymethyl)benzyloxy]ethyl}-1-azabicyclo[2,2,2]octylonium bromide;

(R)-(−)-3-[(R)-2-hydroxy-2-cyclopentyl-2-phenyl]ethoxy-1-{2-[4-(1-{(R)-[2-(3-hydroxymethyl-4-hydroxy)phenyl-2-hydroxy]ethylamino}ethylidene)benzyloxy]ethyl}-1-azabicyclo[2,2,2]octylonium bromide;

(R)-(−)-3-[(R)-2-hydroxy-2-cyclopentyl-2-phenyl]ethoxy-1-{2-[4-((S)-1-{(R)-[2-(3-hydroxymethyl-4-hydroxy)phenyl-2-hydroxy]ethylamino}ethylidene)benzyloxy]ethyl}-1-azabicyclo[2,2,2]octylonium bromide;

(R)-(−)-3-[(R)-2-hydroxy-2-cyclopentyl-2-phenyl]ethoxy-1-{2-[4-((R)-1-{(R)-[2-(3-hydroxymethyl-4-hydroxy)phenyl-2-hydroxy]ethylamino}ethylidene)benzyloxy]ethyl}-1-azabicyclo[2,2,2]octylonium bromide;

(R)-(−)-3-[(R)-2-hydroxy-2-cyclopentyl-2-phenyl]ethoxy-1-{3-[2-methoxy-4-(3-{(R)-[2-(3-hydroxymethyl-4-hydroxy)phenyl-2-hydroxy]ethylamino}propoxy)phenoxy]propyl}-1-azabicyclo[2,2,2]octylonium bromide;

(R)-(−)-3-[(R)-2-hydroxy-2-cyclopentyl-2-phenyl]ethoxy-1-{3-[4-(3-{(R)-[2-(3-hydroxy methyl-4-hydroxy)phenyl-2-hydroxy]ethylamino}propoxy)phenoxy]propyl}-1-azabicyclo[2,2,2]octylonium bromide;

(R)-(−)-3-[(R)-2-hydroxy-2-cyclopentyl-2-phenyl]ethoxy-1-{3-[5-chloro-2-methoxy-4-({(R)-[2-(3-hydroxymethyl-4-hydroxy)phenyl-2-hydroxy]ethylamino}methyl)anilino]oxopropyl}-1-azabicyclo[2,2,2]octylonium bromide;

(R)-(−)-3-[(R)-2-hydroxy-2-cyclopentyl-2-(4-hydroxy)phenyl]ethoxy-1-{3-[2-methoy-4-({(R)-[2-(3-hydroxymethyl-4-hydroxy)phenyl-2-hydroxy)]ethylamino}methyl)anilino]oxopropyl}-1-azabicyclo[2,2,2]octylonium bromide;

(R)-(−)-3-[(R)-2-hydroxy-2-cyclopentyl-2-phenyl]ethoxy-1-{3-[3-methyl-4-({(R)-[2-(3-hydroxymethyl-4-hydroxy)phenyl-2-hydroxy]ethylamino}methyl)anilino]oxopropyl}-1-azabicyclo[2,2,2]octylonium bromide;

(R)-(−)-3-[(R)-2-hydroxy-2-cyclopentyl-2-phenyl]ethoxy-1-{3-[4-({(R)-[2-(3-hydroxymethyl-4-hydroxy)phenyl-2-hydroxy]ethylamino}methyl)anilino]oxopropyl}-1-azabicyclo[2,2,2]octylonium bromide;

(R)-(−)-3-[(R)-2-hydroxy-2-cyclopentyl-2-phenyl]ethoxy-1-{2-[4-(2-{(R)-[2-hydroxy-2-(8-hydroxy-2-oxo-1,2-dihydroquinolin-5-yl)]ethylamino}ethoxymethyl)benzyloxy]ethyl}-1-azabicyclo[2,2,2]octylonium bromide;

(R)-(−)-3-[(R)-2-hydroxy-2-cyclopentyl-2-phenyl]ethoxy-1-{2-[4-(1-{(R)-[2-hydroxy-2-(8-hydroxy-2-oxo-1,2-dihydroquinolin-5-yl)]ethylamino}ethylidene)phenoxy]ethyl}-1-azabicyclo[2,2,2]octylonium bromide;

(R)-(−)-3-[(R)-2-hydroxy-2-cyclopentyl-2-phenyl]ethoxy-1-{2-[4-((S)-1-{(R)-[2-hydroxy-2-(8-hydroxy-2-oxo-1,2-dihydroquinolin-5-yl)]ethylamino}ethylidene)phenoxy]ethyl}-1-azabicyclo[2,2,2]octylonium bromide;

(R)-(−)-3-[(R)-2-hydroxy-2-cyclopentyl-2-phenyl]ethoxy-1-{2-[4-((R)-1-{(R)-[2-hydroxy-2-(8-hydroxy-2-oxo-1,2-dihydroquinolin-5-yl)]ethylamino}ethylidene)phenoxy]ethyl}-1-azabicyclo[2,2,2]octylonium bromide;

(R)-(−)-3-[(R)-2-hydroxy-2-cyclopentyl-2-phenyl]ethoxy-1-{2-[4-(2-{(R)-[2-hydroxy-2-(8-hydroxy-2-oxo-1,2-dihydroquinolin-5-yl)yl]ethylamino}ethoxy)phenoxy]ethyl}-1-azabicyclo[2,2,2]octylonium bromide;

(R)-(−)-3-[(R)-2-hydroxy-2-cyclopentyl-2-phenyl]ethoxy-1-{3-[2-methoxy-4-(3-{(R)-[2-hydroxy-2-(8-hydroxy-2-oxo-1,2-dihydroquinolin-5-yl)]ethylamino}propoxy)phenoxy]propyl}-1-azabicyclo[2,2,2]octylonium bromide;

(R)-(−)-3-[(R)-2-hydroxy-2-cyclopentyl-2-phenyl]ethoxy-1-{3-[4-(3-{(R)-[2-hydroxy-2-(8-hydroxy-2-oxo-1,2-dihydroquinolin-5-yl)]ethylamino}propoxy)phenoxy]propyl}-1-azabicyclo[2,2,2]octylonium bromide;

(R)-(−)-3-[(R)-2-hydroxy-2-cyclopentyl-2-phenyl]ethoxy-1-{3-[2-methoxy-4-({(R)-[2-hydroxy-2-(8-hydroxy-2-oxo-1,2-dihydroquinolin-5-yl)]ethylamino}methyl)anilino]oxopropyl}-1-azabicyclo[2,2,2]octylonium bromide;

(R)-(−)-3-[(R)-2-hydroxy-2-cyclopentyl-2-phenyl]ethoxy-1-{3-[3-methyl-4-({(R)-[2-hydroxy-2-(8-hydroxy-2-oxo-1,2-dihydroquinolin-5-yl)]ethylamino}methyl)anilino]oxopropyl}-1-azabicyclo[2,2,2]octylonium bromide;

(R)-(−)-3-[(R)-2-hydroxy-2-cyclopentyl-2-phenyl]ethoxy-1-{2-[4-({(R)-[2-hydroxy-2-(8-hydroxy-2-oxo-1,2-dihydroquinolin-5-yl)]ethylamino}methyl)anilino]oxopropyl}-1-azabicyclo[2,2,2]octylonium bromide;

(R)-(−)-3-[(R)-2-hydroxy-2-(3-ethyl)cyclopentyl-2-phenyl]ethoxy-1-{2-[4-(2-{(R)-[2-hydroxy-2-(3-formamido-4-hydroxy)phenyl]ethylamino}ethoxymethyl)benzyloxy]ethyl}-1-azabicyclo[2,2,2]octylonium bromide;

(R)-(−)-3-[(R)-2-hydroxy-2-cyclopentyl-2-phenyl]ethoxy-1-{2-[4-(2-{(R)-[2-hydroxy-2-(3-formamido-4-hydroxy)phenyl]ethylamino}ethyoxyl)phenoxy]ethyl}-1-azabicyclo[2,2,2]octylonium bromide;

(R)-(−)-3-[(R)-2-hydroxy-2-cyclopentyl-2-phenyl]
ethoxy-1-{3-[2-methoxy-4-(3-{(R)-[2-hydroxy-2-(3-
formamido-4-hydroxy)phenyl]ethylamino}propoxy)
phenoxy]propyl}-1-azabicyclo[2,2,2]octylonium
bromide;

(R)-(−)-3-[(R)-2-hydroxy-2-cyclopentyl-2-phenyl]
ethoxy-1-{3-[5-chloro-2-methoxy-4-({(R)-[2-hy-
droxy-2-(3-formamido-4-hydroxy)phenyl]
ethylamino}methyl)anilino]oxopropyl}-1-azabicyclo
[2,2,2]octylonium bromide;

(R)-(−)-3-[(R)-2-hydroxy-2-cyclopentyl-2-phenyl]
ethoxy-1-{3-[2-methoxy-4-({(R)-[2-hydroxy-2-(3-for-
mamido-4-hydroxy)phenyl]ethylamino}methyl)an-
ilino]oxopropyl-1-azabicyclo[2,2 2]octylonium
bromide;

(R)-(−)-3-[(R)-2-hydroxy-2-cyclopentyl-2-phenyl]
ethoxy-1-{3-[3-methyl-4-({(R)-[2-hydroxy-2-(3-for-
mamido-4-hydroxy)phenyl]ethylamino}methyl)an-
ilino]oxopropyl}-1-azabicyclo[2,2,2]octylonium
bromide;

(R)-(−)-3-[(R)-2-hydroxy-2-(3-methoxy)cyclopentyl-2-
phenyl]ethoxy-1-{3-[4-({(R)-[2-hydroxy-2-(3-forma-
mido-4-hydroxy)phenyl]ethylamino}methyl)anilino]
oxopropyl-1-azabicyclo[2,2,2]octylonium bromide;

(R)-(−)-3-[(R)-2-hydroxy-2-cyclopentyl-2-phenyl]
ethoxy-1-{2-[4-(2-{(R)-[2-hydroxy-2-(6-hydroxy-2H-
1,4-benzoxazin-3(4H)-one-8-yl)]
ethylamino}ethylidene)benzyloxyethyl}-1-azabicyclo
[2,2,2]octylonium bromide;

(R)-(−)-3-[(R)-2-hydroxy-2-cyclopentyl-2-phenyl]
ethoxy-1-{2-[4-((S)-2-{(R)-[2-hydroxy-2-(6-hydroxy-
2H-1,4-benzoxazin-3(4H)-one-8-yl)]
ethylamino}ethylidene)benzyloxyethyl}-1-azabicyclo
[2,2,2]octylonium bromide;

(R)-(−)-3-[(R)-2-hydroxy-2-cyclopentyl-2-phenyl]
ethoxy-1-{2-[4-((R)-2-{(R)-[2-hydroxy-2-(6-hydroxy-
2H-1,4-benzoxazin-3(4H)-one-8-yl)]
ethylamino}ethylidene)benzyloxyethyl}-1-azabicyclo
[2,2,2]octylonium bromide;

(R)-(−)-3-[(R)-2-hydroxy-2-cyclopentyl-2-phenyl]
ethoxy-1-{2-[4-(2-{(R)-[2-hydroxy-2-(6-hydroxy-2H-
1,4-benzoxazin-3(4H)-one-8-yl)]ethylamino}ethoxy)
phenoxy]ethyl}-1-azabicyclo[2,2,2]octylonium
bromide;

(R)-(−)-3-[(R)-2-hydroxy-2-cyclopentyl-2-phenyl]
ethoxy-1-{3-[2-methoxy-4-(3-{(R)-[2-hydroxy-2-(6-
hydroxy-2H-1,4-benzoxazin-3(4H)-one-8-yl)]
ethylamino}propoxy)phenoxy]propyl}-1-azabicyclo
[2,2,2]octylonium bromide;

(R)-(−)-3-[(R)-2-hydroxy-2-cyclopentyl-2-phenyl]
ethoxy-1-{3-[4-(3-{(R)-[2-hydroxy-2-(6-hydroxy-2H-
1,4-benzoxazin-3(4H)-one-8-yl)]ethylamino}propoxy)
phenoxy]propyl}-1-azabicyclo[2,2,2]octylonium
bromide;

(R)-(−)-3-[(R)-2-hydroxy-2-cyclopentyl-2-phenyl]
ethoxy-1-{3-[5-chloro-2-methoxy-4-({(R)-[2-hy-
droxy-2-(6-hydroxy-2H-1,4-benzoxazin-3(4H)-one-8-
yl)ethyl]amino}methyl)anilino]oxopropyl}-1-
azabicyclo[2,2,2]octylonium bromide;

(R)-(−)-3-[(R)-2-hydroxy-2-cyclopentyl-2-phenyl]
ethoxy-1-{3-[2-methoxy-4-({(R)-[2-hydroxy-2-(6-hy-
droxy-2H-1,4-benzoxazin-3(4H)-one-8-yl)]
ethylamino}methyl)anilino]oxopropyl}-1-azabicyclo
[2,2,2]octylonium bromide; or (R)-(−)-3-[(R)-2-hydroxy-2-cyclopentyl-2-phenyl]
ethoxy-1-{3-[3-methyl-4-({(R)-[2-hydroxy-2-(6-hy-
droxy-2H-1,4-benzoxazin-3(4H)-one-8-yl)]
ethylamino}methyl)anilino]oxopropyl}-1-azabicyclo
[2,2,2]octylonium bromide.

13. A pharmaceutical composition comprising a compound of claim 1, or a pharmaceutically acceptable salt, solvate, optical isomer and a pharmaceutically acceptable carrier thereof, wherein the composition may be in a dosage form of inhalation administration or nasal administration; and the composition further may or may not contain one or more other drugs which can be used for combination administration.

14. The pharmaceutical composition according to claim 13, wherein the pharmaceutical composition comprises a therapeutically effective amount of a steroidal anti-inflammatory drug.

15. The pharmaceutical composition according to claim 13, wherein the pharmaceutical composition comprises a therapeutically effective amount of a PDE4 inhibitor.

16. A method of preparing a compound of formula I as defined in claim 1, or a pharmaceutically acceptable salt, solvate, optical isomer thereof, comprising the steps of:

(a) reacting an intermediate 1 or salt thereof with $X_1$—$R_1$—$X_2$ to produce an intermediate 2;

(b) reacting the intermediate 2 with an intermediate 3 to produce an intermediate 4 with protecting groups;

(c) de-protecting groups from the intermediate 4 with protecting groups to obtain the compound of formula I; and (d) exchanging the compound of formula I with a basic anion exchange resin to generate a hydroxide of formula I, and then reacting with various acids to prepare quaternary ammonium salts with various acid radicals; or exchanging the compound of formula I with a specific anion exchange resin to prepare a quaternary ammonium salt with a specific acid radical; or reacting a halide of the formula I with silver oxide to generate a hydroxide of the formula I and then reacting with other acids to generate quaternary ammonium salts with various acid radicals; or reacting a halide of the formula I with a silver salt to produce a quaternary ammonium salt with a corresponding acid radical;

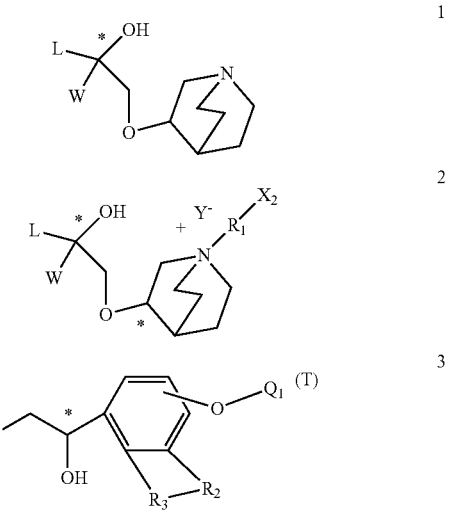

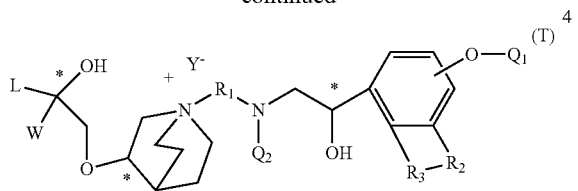

wherein, carbons marked with * in the intermediates 1, 2, 3, 4 are designated as R configuration;

$X_1$ and $X_2$ in the compound $X_1$—$R_1$—$X_2$ are leaving groups or amino groups, and the leaving groups are selected from halogen and sulfonates; Z is a leaving group or —$NHQ_2$, and the leaving group is selected from halogen and sulfonates, with the proviso that when $X_2$ is a leaving group, Z is —$NHQ_2$, and when $X_2$ is selected from amino group, Z is the leaving group; $Q_1$ is hydrogen or a hydroxy protecting group which is selected from silyl ethers, esters, and arylmethyl groups; $Q_2$ is hydrogen or an amino protecting group which is selected from benzyl, tert-butoxycarbonyl, benzyloxycarbonyl, 9-fluorenylmethoxycarbonyl (Fmoc), formyl, and acetyl; $R_1$, $R_2$, $R_3$, Y, L, W, T and Formula I are the same as defined in claim 1; and in the method, when one of the raw materials is salt, the salt is usually neutralized before or during the reaction, and such neutralization is usually carried out with a base of which molar equivalent is equal to that of the salt.

17. A method for treating a bronchi-associated disease selected from the group consisting of bronchial asthma and chronic obstructive pulmonary disease comprising administering to a person in need of such treatment an effective amount of the compound of claim 1, or a pharmaceutically acceptable salt, solvate, optical isomer thereof.

18. A method for treating a bronchi-associated disease selected from the group consisting of bronchial asthma, and chronic obstructive pulmonary disease comprising administering to a person in need of such treatment an effective amount of the composition of claim 13.

19. The compound according to claim 2, or the pharmaceutically acceptable salt, solvate, optical isomer thereof, wherein W is unsubstituted (3-6C)cycloalkyl.

* * * * *